United States Patent
Kim et al.

(10) Patent No.: US 9,034,850 B2
(45) Date of Patent: May 19, 2015

(54) GONADOTROPIN RELEASING HORMONE RECEPTOR ANTAGONIST, PREPARATION METHOD THEREOF AND PHARMACEUTICAL COMPOSITION COMPRISING THE SAME

(75) Inventors: Seon Mi Kim, Suwon-si (KR); Min Hee Lee, Seoul (KR); Jae Sun Kim, Suwon-si (KR); Hoe Chul Jung, Suwon-si (KR); So Young Lee, Suwon-si (KR); Soo Min Lee, Seoul (KR); Eun Jeong Kim, Suwon-si (KR); Eui Sun Park, Yongin-si (KR); Sung Hoon Park, Seoul (KR); Bong Yong Lee, Seoul (KR); Key An Um, Suwon-si (KR)

(73) Assignee: SK Chemicals Co., Ltd., Suwon-si (KR)

( * ) Notice: Subject to any disclaimer, the term of this patent is extended or adjusted under 35 U.S.C. 154(b) by 0 days.

(21) Appl. No.: 13/511,065

(22) PCT Filed: Nov. 19, 2010

(86) PCT No.: PCT/KR2010/008194
§ 371 (c)(1),
(2), (4) Date: Oct. 8, 2012

(87) PCT Pub. No.: WO2011/062437
PCT Pub. Date: May 26, 2011

(65) Prior Publication Data
US 2013/0137661 A1 May 30, 2013

(30) Foreign Application Priority Data

Nov. 20, 2009 (KR) .................. 10-2009-0112896
Nov. 19, 2010 (KR) .................. 10-2010-0115345

(51) Int. Cl.
| | | |
|---|---|---|
| A01N 57/00 | (2006.01) | |
| C07D 239/545 | (2006.01) | |
| A61K 31/506 | (2006.01) | |
| C07D 239/46 | (2006.01) | |
| C07D 401/04 | (2006.01) | |
| C07D 403/04 | (2006.01) | |
| C07D 405/14 | (2006.01) | |
| C07D 213/74 | (2006.01) | |
| C07D 253/075 | (2006.01) | |
| C07D 401/12 | (2006.01) | |
| C07D 401/14 | (2006.01) | |
| C07D 403/06 | (2006.01) | |
| C07D 403/12 | (2006.01) | |
| C07D 405/12 | (2006.01) | |
| C07D 409/12 | (2006.01) | |
| C07D 409/14 | (2006.01) | |
| C07D 413/12 | (2006.01) | |
| C07D 417/12 | (2006.01) | |
| C07D 487/04 | (2006.01) | |
| C07D 491/048 | (2006.01) | |
| C07F 9/6558 | (2006.01) | |

(52) U.S. Cl.
CPC .......... *C07D 239/545* (2013.01); *A61K 31/506* (2013.01); *C07D 239/46* (2013.01); *C07D 401/04* (2013.01); *C07D 403/04* (2013.01); *C07D 405/14* (2013.01); *C07D 213/74* (2013.01); *C07D 253/075* (2013.01); *C07D 401/12* (2013.01); *C07D 401/14* (2013.01); *C07D 403/06* (2013.01); *C07D 403/12* (2013.01); *C07D 405/12* (2013.01); *C07D 409/12* (2013.01); *C07D 409/14* (2013.01); *C07D 413/12* (2013.01); *C07D 417/12* (2013.01); *C07D 487/04* (2013.01); *C07D 491/048* (2013.01); *C07F 9/65583* (2013.01); *C07F 9/65586* (2013.01)

(58) Field of Classification Search
None
See application file for complete search history.

(56) References Cited

U.S. PATENT DOCUMENTS

| | | | |
|---|---|---|---|
| 5,034,404 A | 7/1991 | Uneme et al. | |
| 5,756,507 A * | 5/1998 | Goulet et al. | 514/254.08 |
| 6,673,796 B2 * | 1/2004 | Pontillo et al. | 514/242 |
| 6,750,350 B2 | 6/2004 | Chen et al. | |
| 2005/0075339 A1 | 4/2005 | Pontillo et al. | |
| 2009/0005359 A1 | 1/2009 | Cossrow et al. | |

FOREIGN PATENT DOCUMENTS

| | | |
|---|---|---|
| EP | 1110454 A2 | 6/2001 |
| JP | 5255276 A | 10/1993 |
| JP | 2003520856 A | 7/2003 |
| JP | 2005500352 A | 1/2005 |
| JP | 2005504034 A | 2/2005 |
| JP | 2005505525 A | 2/2005 |
| JP | 2007521308 A | 8/2007 |
| JP | 2007521309 A | 8/2007 |
| KR | 1020060031851 A | 4/2006 |
| KR | 1020060052790 A | 5/2006 |
| WO | 0155119 A2 | 8/2001 |

(Continued)

OTHER PUBLICATIONS

Jha, T. et al., "QSAR Study on Some Orally Active Uracil Derivatives as Human Gonadotropin-Releasing-Hormone Receptor Antagonists", Internet Electronic Journal of Molecular Design, 2008, pp. 234-250, vol. 7.
Rowbottom, M.W., et al., "Synthesis and Structure-Activity Relationships of Uracil Derived Human GnRH Receptor Antagonists: (R)-3-[2-(2-Amino)phenethyl]-1-(2,6-difluorobenzyl)-6-methyluracils Containing a Substituted Thiophene or Thiazole at C-5", Bioorganic & Medicinal Chemistry Letters, 2004, pp. 4967-4973, vol. 14.

(Continued)

*Primary Examiner* — Wu-Cheng Winston Shen
*Assistant Examiner* — Jean Cornet
(74) *Attorney, Agent, or Firm* — The Webb Law Firm

(57) ABSTRACT

Disclosed are compounds useful as gonadotrophin-releasing hormone ("GnRH") receptor antagonist.

9 Claims, No Drawings

(56) References Cited

FOREIGN PATENT DOCUMENTS

| WO | 03011293 | A2 | 2/2003 |
|---|---|---|---|
| WO | 03011841 | A1 | 2/2003 |
| WO | 03013528 | A1 | 2/2003 |
| WO | 2005007164 | A1 | 1/2005 |
| WO | 2005007165 | A1 | 1/2005 |

OTHER PUBLICATIONS

Sarma, Pks, et al., "Peptidomimetic GnRH receptor antagonists for the treatment of reproductive and proliferative diseases", Expert Opin. Ther. Patents, 2006, pp. 733-751, vol. 16-6.

* cited by examiner

GONADOTROPIN RELEASING HORMONE RECEPTOR ANTAGONIST, PREPARATION METHOD THEREOF AND PHARMACEUTICAL COMPOSITION COMPRISING THE SAME

TECHNICAL FIELD

The present invention relates to a gonadotropin-releasing hormone (GnRH) (also known as luteinizing-hormone-releasing hormone) receptor antagonist, a preparation method thereof, and a pharmaceutical composition comprising the same.

BACKGROUND ART

Gonadotropin-releasing hormone (GnRH) is a decapeptide synthesized and released from neurons within the hypothalamus which acts on its own receptors in the anterior pituitary, thus accounting for the biosynthesis and release of luteinizing hormone (LH) and follicle-stimulating hormone (FSH). Luteinizing hormone controls steroid synthesis in the male and female gonads while follicle-stimulating hormone is involved in the spermatogenesis in males and the development of ovarian follicles in females. Controlling GnRH, GnRH agonists or antagonists have attracted intensive attention for their therapeutic availability in the treatment of GnRH-related diseases, particularly, prostate cancer, breast cancer, endometriosis, leiomyoma, precocious puberty, and in the treatment of sterility.

Currently available therapeutics for the treatment of gonatrophin-related diseases use peptides which exhibit receptor antagonism by two different mechanisms. In one mechanism, they act as GnRH receptor agonists that interact with the gonadotropin-releasing hormone receptor to elicit its biologic response, which is the release of the pituitary hormones FSH and LH. However, two or three weeks after their continous administration, a profound hypogonadal effect, e.g., the depletion of gonatrophins, is achieved by receptor downregulation. Inducing superagonism at an early stage, this mechanism cannot avoid the initial concomitance of side effects.

GnRH receptor antagonists that exert direct antagonistic effects have been suggested as an alternative. When administered, they can immediately decrease the level of gonatrophins without any initial side effects. However, they suffer from the disadvantages of being of relatively low bioavailability in clinical use and stimulating histamine release. There have been reports of peptidyl antagonists which have a low histamine release, but they must be taken by parenteral administration routes, such as intravenous, subcutaneous or intramuscular injection, due to their low bioavailability.

Only recently have non-peptidyl compounds been suggested for overcoming the limitations of the peptidyl antagonists (see Expert Opin. Ther. Patents 16(6): 733-751, 2006). In spite of lots of studies in this field, there still remains a need for low-molecular weight GnRH receptor antagonists with good bioavailability. The present invention revolves around this substantial need.

DISCLOSURE

Technical Problem

It is an object of the present invention to provide a compound represented by the following Chemical Formula I, its stereoisomers, prodrugs and pharmaceutically acceptable salts, and the use thereof as a GnRH receptor antagonist:

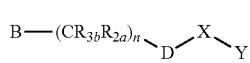

[Chemical Formula I]

wherein, B, D, X, Y, $R_{3a}$, $R_{3b}$, and n are as defined below.

The GnRH receptor antagonist of the present invention is useful for the treatment of various sex hormone-related symptoms including endometriosis, uterine fibroids, polycystic ovarian disease, hypertrichosis, precocious puberty, gonadal steroid-dependent neoplasm (prostate cancer, breast cancer, ovary cancer, etc.), gonadotropin-producing pituitary adenoma, sleep apnea, irritable bowel syndrome, premenstrual syndrome, benign prostatic hyperplasia, and sterility (e.g., assisted reproductive techniques such as in vitro fertilization). Also, the compound of the present invention may be formulated, in combination with other active ingredients, into a pharmaceutical composition.

Technical Solution

The present invention pertains to a compound useful as a GnRH receptor antagonist. The compound of the present invention has the structure of the following Chemical Formula I and its stereoisomers and pharmaceutically acceptable salts fall within the scope of the present invention.

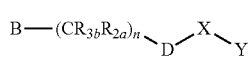

[Chemical Formula I]

[wherein,

X is a non-aromatic heterocyclic ring or a substituted, non-aromatic heterocyclic ring containing one or more N atoms;

Y represents —$(CR_{9a}R_{9b})_r$—Z—$R_4$;

B represents —$NR_1R_2$ or —$OR_1$;

r is 0, 1, 2 or 3;

n is 2, 3 or 4;

Z represents a direct bond or —O—, —S—, —$NR_{11}$—, —SO—, —$SO_2$—, —$OSO_2$—, —$SO_2O$—, —$SO_2NR_{11}$—, —$NR_{11}SO_2$—, —CO—, —COO—, —OCO—, —$CONR_{11}$—, —$NR_{11}CO$—, —$NR_{11}CONR_{11a}$—, —$OCONR_{11}$— or —$NR_{11}COO$—;

D is a ring selected from among the following structures:

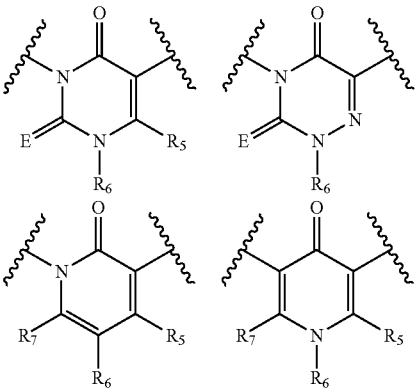

-continued

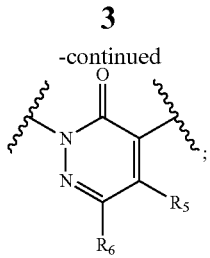

E represents —O—, —S— or —NR$_8$—;

R$_1$ and R$_2$, which may be the same or different, are independently hydrogen, (C1-C10)alkyl, substituted (C1-C10) alkyl, (C3-C10)cyclic alkyl, substituted (C3-C10)cyclic alkyl, (C6-C12)aryl, substituted (C6-C12)aryl, (C6-C12)aryl (C1-C10)alkyl, substituted (C6-C12)aryl(C1-C10)alkyl, (C1-C20)heteroaryl, substituted (C1-C20)heteroaryl, (C1-C20)heteroaryl(C1-C10)alkyl, substituted (C1-C20)heteroaryl(C1-C10)alkyl, (C1-C20)heterocycle, substituted (C1-C20) heterocycle, (C1-C20)heterocycle(C1-C10)alkyl, substituted (C1-C20)heterocycle(C1-C10)alkyl, —(CR$_{1a}$R$_{1b}$)$_s$—R$_{12}$ or —COOR$_{13}$; or R$_1$ and R$_2$ are linked to each other via a (C1-C5)alkylene to form a heterocyclic ring or a substituted heterocyclic ring wherein the —CH$_2$— moiety of the alkylene may be substituted with —C(=O)—; s is 1, 2, 3 or 4;

R$_{3a}$ and R$_{3b}$, which may be the same or different, are independent hydrogen, (C1-C10)alkyl, substituted (C1-C10) alkyl, (C3-C10)cyclic alkyl, substituted (C3-C10)cyclic alkyl, (C1-C10)alkoxy, (C1-C10)alkylthio, (C1-C10)alkylamino, (C6-C12)aryl, substituted (C6-C12)aryl, (C6-C12) aryl(C1-C10)alkyl, substituted (C6-C12)aryl(C1-C10)alkyl, (C1-C20)heteroaryl, substituted (C1-C20)heteroaryl, (C1-C20)heteroaryl(C1-C10)alkyl, substituted (C1-C20)heteroaryl(C1-C10)alkyl, (C1-C20)heterocycle, substituted (C1-C20)heterocycle, (C1-C20)heterocycle(C1-C10)alkyl, substituted (C1-C20)heterocycle(C1-C10)alkyl, —COOR$_{13}$ or —CONR$_{13}$R$_{14}$; or R$_{3a}$ and R$_{3b}$ form a homocyclic ring, a substituted homocyclic ring, a heterocyclic ring, or a substituted heterocyclic ring when connected to the carbon atom to which they are attached;

R$_{3a}$ and R$_1$ taken together with the carbon atom and the nitrogen atom to which they are respectively attached form a heterocyclic ring or a substituted heterocyclic ring;

R$_4$ is hydrogen, (C1-C10)alkyl, substituted (C1-C10)alkyl, (C3-C10)cyclic alkyl, substituted (C3-C10)cyclic alkyl, (C6-C12)aryl, substituted (C6-C12)aryl, (C6-C12)aryl(C1-C10) alkyl, substituted (C6-C12)aryl(C1-C10)alkyl, (C1-C20)heteroaryl, substituted (C1-C20)heteroaryl, (C1-C20)heteroaryl (C1-C10)alkyl, substituted (C1-C20)heteroaryl(C1-C10) alkyl, (C1-C20)heterocycle, substituted (C1-C20) heterocycle, (C1-C20)heterocycle(C1-C10)alkyl or substituted (C1-C20)heterocycle(C1-C10)alkyl;

R$_5$ is hydrogen, halogen, (C1-C6)alkyl, substituted (C1-C6)alkyl, (C3-C10)cyclic alkyl, substituted (C3-C10)cyclic alkyl, (C6-C12)aryl, substituted (C6-C12)aryl, (C6-C12)aryl (C1-C10)alkyl, substituted (C6-C12)aryl(C1-C10)alkyl, (C1-C10)alkoxy, (C1-C10)alkylthio, (C1-C10)alkylamino, cyano or nitro;

R$_6$ is hydrogen, (C1-C10)alkyl; substituted (C1-C10)alkyl; (C3-C10)cyclic alkyl, substituted (C3-C10)cyclic alkyl, (C6-C12)aryl, substituted (C6-C12)aryl, (C6-C12)aryl(C1-C10) alkyl, substituted (C6-C12)aryl(C1-C10)alkyl, (C1-C20)heteroaryl, substituted (C1-C20)heteroaryl, (C1-C20)heteroaryl (C1-C10)alkyl or substituted (C1-C20)heteroaryl(C1-C10) alkyl;

R$_7$ is hydrogen, (C1-C10)alkyl, substituted (C1-C10)alkyl, (C3-C10)cyclic alkyl or substituted (C3-C10)cyclic alkyl;

R$_8$ is hydrogen, —SO$_2$R$_{10}$, cyano, (C1-C10)alkyl, substituted (C1-C10)alkyl, (C3-C10)cyclic alkyl, substituted (C3-C10)cyclic alkyl, (C6-C12)aryl, substituted (C6-C12)aryl, (C6-C12)aryl(C1-C10)alkyl, substituted (C6-C12)aryl(C1-C10)alkyl, (C1-C20)heteroaryl, substituted (C1-C20)heteroaryl, (C1-C20)heteroaryl(C1-C10)alkyl or substituted (C1-C20)heteroaryl(C1-C10)alkyl;

R$_{1a}$, R$_{1b}$, R$_{9a}$ and R$_{9b}$, which may be the same or different, are independently hydrogen, acyl, hydroxy halogen, cyano, (C1-C10)alkyl, substituted (C1-C10)alkyl, (C3-C10)cyclic alkyl, substituted (C3-C10)cyclic alkyl, (C1-C10)alkoxy, (C1-C10)alkylthio, (C1-C10)alkylamino, (C6-C12)aryl, substituted (C6-C12)aryl, (C6-C12)aryl(C1-C10)alkyl, substituted (C6-C12)aryl(C1-C10)alkyl, (C1-C20)heteroaryl, substituted (C1-C20)heteroaryl, (C1-C20)heteroaryl(C1-C10) alkyl, substituted (C1-C20)heteroaryl(C1-C10)alkyl, (C1-C20)heterocycle, substituted (C1-C20)heterocycle, (C1-C20)heterocycle(C1-C10)alkyl, substituted (C1-C20) heterocycle(C1-C10)alkyl, —COOR$_{13}$— or —CONR$_{13}$R$_{14}$—;

a set of R$_{1a}$ and R$_{1b}$ and a set of R$_{9a}$ and R$_{9b}$, taken together with the atom(s) to which they are attached independently form a homocyclic ring, a substituted homocyclic ring, a heterocyclic ring or a substituted heterocyclic ring;

R$_{12}$ is —COON or an acid isostere;

R$_{10}$, R$_{11}$, R$_{11a}$, R$_{13}$ and R$_{14}$, which may be the same or different, are independently hydrogen, (C1-C10)alkyl, substituted (C1-C10)alkyl, (C3-C10)cyclic alkyl, substituted (C3-C10)cyclic alkyl, (C1-C10)alkoxy, (C1-C10)alkylthio, (C1-C10)alkylamino, (C6-C12)aryl, substituted (C6-C12) aryl, (C6-C12)aryl(C1-C10)alkyl, substituted (C6-C12)aryl (C1-C10)alkyl, (C1-C20)heteroaryl, substituted (C1-C20) heteroaryl, (C1-C20)heteroaryl(C1-C10)alkyl, substituted (C1-C20)heteroaryl(C1-C10)alkyl, (C1-C20)heterocycle, substituted (C1-C20)heterocycle, (C1-C20)heterocycle(C1-C10)alkyl or substituted (C1-C20)heterocycle(C1-C10) alkyl;

R$_{13}$ and R$_{14}$ taken together with the atom(s) to which they are attached, form a homocyclic ring, a substituted homocyclic ring, a heterocyclic ring or a substituted heterocyclic ring;

the heterocyclic ring, the heterocycle, the heterocyclealkyl, heteroaryl and the heteroarylalkyl, as used herein, being intended to contain one or more heteroatoms selected from among N, O and S therein;

"substituted" being intended to mean replacement with one or more substituents selected from the group consisting of hydroxy, cyano, nitro, amino, (C1-C10)alkylamino, di(C1-C10)alkylamino, (C1-C10)alkyl, (C3-C10)cyclic alkyl, (C1-C10)alkoxy, (C1-C10)alkylthio, halo(C1-C10)alkyl, (C6-C12)aryl, (C6-C12)aryl(C1-C10)alkyl, (C1-C20)heteroaryl, (C1-C20)heteroaryl(C1-C10)alkyl, (C1-C20)heterocycle, (C1-C20)heterocycle (C1-C10)alkyl, —NR$_a$R$_b$, —NR$_a$C (=O)R$_b$, —NR$_a$C(=O)NR$_a$NR$_b$, —NR$_a$C(=O)OR$_b$, —NR$_a$SO$_2$R$_b$, —C(=O)R$_a$, —C(=O)OR$_a$, —OC(=O)R$_a$, —C(=O)NR$_a$R$_b$, —OC(=O)NR$_a$R$_b$, —OR$_a$, —SR$_a$, —SOR$_a$, —S(=O)$_2$R$_a$, —OS(=O)$_2$R$_a$ and —S(=O)$_2$OR$_a$;

R$_a$ and R$_b$, which may be the same or different, are independently hydrogen, (C1-C10)alkyl, hallo(C1-C10)alkyl, (C3-C10)cyclic alkyl, (C6-C12)aryl, (C6-C12)aryl(C1-C10) alkyl, (C1-C20)heteroaryl, (C1-C20)heteroaryl(C1-C10) alkyl, (C1-C20)heterocycle, (C1-C20)heterocycle(C1-C10) alkyl or —(CH$_2$)$_z$C(=O)R$_c$;

z is an integer of 1, 2, 3 or 4;

R$_c$ is hydroxy, (C1-C10)alkyl, (C3-C10)cyclic alkyl or (C1-C10)alkoxy]

As for the nomenclature used herein, it has the meanings defined below:

The term "non-aromatic" used alone, as a suffix or as a prefix, refers to a chemical group or radical that does not contains a ring having an aromatic character such as a conjugation of 4n+2 electrons or that is saturated.

The term "alkyl" used alone or as a suffix or prefix, is intended to refer to a straight chain or branched, saturated or unsaturated, cyclic or non-cyclic aliphatic hydrocarbon having from 1 to 10 carbon atoms. Representative examples of saturated straight alkyls include methyl, ethyl, n-propyl, n-butyl, n-pentyl, and n-hexyl; isopropyl, sec-butyl, isobutyl, tert-butyl, and isopentyl are representative of saturated branched alkyls. Unsaturated alkyl contains one or more double or triple bonds between adjacent carbon atoms (also referred to as "alkenyl" or "alkynyl", respectively). Among the straight or branched alkenyls are ethylenyl, propylenyl, 1-butenyl, 2-butenyl, isobutylenyl, 1-pentenyl, 2-pentenyl, 3-methyl-1-butenyl, 2-methyl-2-butenyl, and 2,3-dimethyl-2-butenyl; straight or branched alkynyl may be represented by acetylenyl, propynyl, 1-butynyl, 2-butynyl, 1-pentynyl, 2-pentynyl, and 3-methyl-1-butynyl.

The term "cyclic alkyl" used alone or as a suffix or prefix, refers to a saturated or unsaturated, non-aromatic carbocyclic ring system containing a hydrocarbon moiety having at least 3 up to 10 carbon atoms. Representative examples of cyclic alkyl include cyclopropyl, cyclobutyl, cyclopentyl, and cyclohexyl; examples of unsaturated cyclic alkyl include cyclopentenyl and cyclohexenyl. Cyclic alkyl is also alternatively called "homocycle" or "homocyclic ring" in the specification of the present invention.

The term "aryl" used alone or as a suffix or prefix, refers to an aromatic carbocyclic radical such as phenyl or naphthyl.

The term "arylalkyl" used alone or as a suffix or prefix, refers to an alkyl radical having at least one alkyl hydrogen atom replaced with an aryl moiety, such as benzyl, —$(CH_2)_2$phenyl, —$(CH_2)_3$phenyl, —CH(phenyl)$_2$, and the like.

The term "heteroaryl", used alone or as a suffix or prefix, refers to a 5- to 10-membered heterocyclic ring, comprised of at least one heteroatom selected from nitrogen, oxygen and sulfur atoms and at least one carbon atom, having aromatic characters, which may be of a mono- or bicyclic ring system. Representative examples of heteroaryl include furyl, benzofuranyl, thiophenyl, benzothiophenyl, pyrrolyl, indolyl), isoindolyl), azaindolyl), pyridyl, quinolinyl, isoquinolinyl, oxazolyl, isooxazolyl, benzoxazolyl, pyrazolyl, imidazolyl, benzimidazolyl, thiozolyl, benzothiozolyl, isothiazolyl, pyridazinyl, pyrimidinyl, pyrazinyl, triazinyl, chinolinyl, phthalazinyl and quinazolinyl.

The term "heteroarylalkyl" used alone or as a suffix or prefix, refers to an alkyl radical having at least one alkyl hydrogen atom replaced with a heteroaryl moiety, such as —$CH_2$ pyridinyl, —$CH_2$ pyrimidinyl, etc.

The term "heterocycle" (also termed "heterocyclic ring") refers to a 5- to 7-membered monocyclic, or 7- to 10-membered bicyclic, heterocyclic ring which is either saturated, unsaturated, or aromatic, and which contains from 1 to 4 heteroatoms independently selected from among nitrogen, oxygen and sulfur atoms, and wherein the nitrogen and sulfur heteroatoms may be optionally oxidized, and the nitrogen heteroatom may be optionally quaternized, including bicyclic rings in which any of the above heterocycles are fused to a benzene ring. The heterocycle may be attached via any heteroatom or carbon atom. Heterocycles include heteroaryls as defined above. Thus, in addition to the heteroaryls listed above, heterocycles also include morpholinyl, pyrrolidinonyl, pyrrolidinyl, piperidinyl, piperazinyl, hydantoinyl, valerolactamyl, oxiranyl, oxetanyl, tetrahydrofuranyl, tetrahydropyranyl, tetrahydropyrindinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

"Heterocycloalkyl" refers to an alkyl having at least one alkyl hydrogen atom replaced with a heterocycle, such as —$CH_2$ morpholinyl.

"Homocycle" (also referred to as "homocyclic ring") refers to a saturated or unsaturated (exclusive of aromatic) carbocyclic ring, such as cyclopropane, cyclobutane, cyclopentane, cyclohexane, cycloheptane, cyclohexene, and the like.

As used herein, the term "substituted" refers to any of the above groups (i.e. alkyl, aryl, arylalkyl, heteroaryl, heteroarylalkyl, homocycle, heterocycle and/or heterocyclealkyl) wherein at least one hydrogen atom is replaced with a substituent. In the case of a keto substituent ("—C(=O)—"), two hydrogen atoms are replaced. When at least one of the substituted groups is substituted, "substituents" within the scope of the present invention include halogen, hydroxy, cyano, nitro, amino, (C1-C10)alkylamino, di(C1-C10)alkylamino, (C1-C10)alkyl, (C3-C10)cyclic alkyl, (C1-C10)alkoxy, (C1-C10)alkylthio, halo(C1-C10)alkyl, (C6-C12)aryl, (C6-C12)aryl(C1-C10)alkyl, (C1-C20)heteroaryl, (C1-C20)heteroaryl(C1-C10)alkyl, (C1-C20)heterocycle, (C1-C20)heterocycle(C1-C10)alkyl, —$NR_aR_b$, —$NR_aC(=O)R_b$, —$NR_aC(=O)NR_aNR_b$, —$NR_aC(=O)OR_b$, —$NR_aSO_2R_b$, —$C(=O)R_a$, —$C(=O)OR_a$—$OC(=O)R_a$, —$C(=O)NR_aR_b$, —$OC(=O)NR_aR_b$, —$OR_a$, —$SR_a$, —$SOR_a$, —$S(=O)_2R_a$, —$OS(=O)_2R_a$ and —$S(=O)_2OR_a$ where $R_a$ and $R_b$, which may be the same or different, are independently hydrogen, (C1-C10)alkyl, halo(C1-C10)alkyl, (C3-C10)cyclic alkyl, (C6-C12)aryl, (C6-C12)aryl(C1-C10)alkyl, (C1-C20)heteroaryl, (C1-C20)heteroaryl(C1-C10)alkyl, (C1-C20)heterocycle, (C1-C20)heterocycle(C1-C10)alkyl or $(CH_2)_zC(=O)R_c$ [z is an integer of 1, 2, 3 or 4; $R_c$ is hydroxy, (C1-C10)alkyl, (C3-C10) cyclic alkyl or (C1-C10)alkoxy]. Also, because the substituents may be further replaced with at least one of the substituents, they include substituted alkyl, substituted aryl, substituted arylalkyl, substituted heterocycle and substituted heterocyclealkyl.

"Halogen" refers to fluorine, chlorine, bromine or iodine.

"Haloalkyl" refers to an alkyl having one or more hydrogen atoms replaced with a halogen, such as trifluoromethyl.

"Alkoxy" refers to an alkyl group attached via an oxygen bridge (i.e., —O-alkyl), such as methoxy, ethoxy and the like.

"Alkylthio" refers to an alkyl group attached via a sulfur bridge (i.e., —S-alkyl), such as methylthio, ethylthio and the like.

By "alkylsulfonyl" is meant an alkyl group attached via a sulfonyl bridge (i.e., —$SO_2$-alkyl), such as methylsulfonyl, ethylsulfonyl and the like.

"Alkylamino" and "dialkylamino" refer to one and two alkyl groups, respectively, attached via a nitrogen bridge (i.e., —N-alkyl), such as, methylamino, ethylamino, dimethylamino, diethylamino and the like.

In Chemical Formula I, x is a 5- or 6-membered non-aromatic heterocyclic ring which is linked to D via N; Y is hydrogen, (C1-C10)alkyl, substituted (C1-C10)alkyl, (C3-C10)cyclic alkyl, substituted (C3-C10)cyclic alkyl, (C6-C12)aryl, substituted (C6-C12)aryl, (C6-C12)aryl(C1-C10)alkyl, substituted (C6-C12)aryl (C1-C10)alkyl, (C1-C20)heteroaryl, substituted (C1-C20) heteroaryl, (C1-C20)heteroaryl(C1-C10)alkyl, substituted (C1-C20)heteroaryl(C1-C10)alkyl, (C1-C20)heterocycle, substituted (C1-C20)heterocycle, (C1-C20)heterocycle(C1-

C10)alkyl, substituted (C1-C20)heterocycle(C1-C10)alkyl, —OR₄, —NR₄, —SO₂R₄, —COR₄ or —COOR₄; B is —NR₁R₂ or —OR₁; n is 2, 3 or 4;

D is a ring selected from among the following structures;

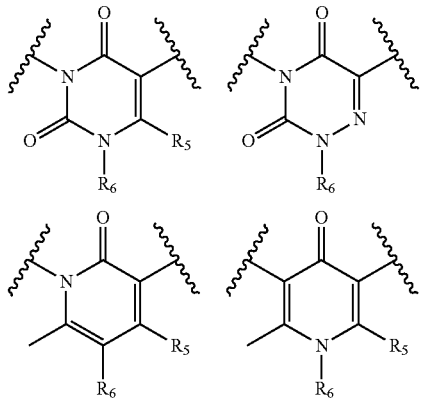

R₁ and R₂, which may be the same or different, are independently hydrogen, —(CH₂)ₛCO₂H, —(CH₂)ₛP(=O)(OEt)(OH), —(CH₂)ₛPO₃H or —(CH₂)ₛSO₃H;

s is 1, 2, 3 or 4;

R₃ₐ and R₃ᵦ, which may be the same or different, are independently hydrogen, (C1-C10)alkyl, substituted (C1-C10)alkyl, (C3-C10)cyclic alkyl, substituted (C3-C10)cyclic alkyl, (C1-C10)alkoxy, (C1-C10)alkylthio, (C6-C12)aryl, substituted (C6-C12)aryl, (C1-C20)heteroaryl, substituted (C1-C20)heteroaryl, (C1-C20)heterocycle or substituted (C1-C20)heterocycle;

R₅ is hydrogen or methyl;

R₆ is hydrogen, (C1-C10)alkyl; (C3-C10)cyclic alkyl, (C6-C12)aryl(C1-C10)alkyl or substituted (C6-C12)aryl(C1-C10)alkyl;

R₁₁ is hydrogen, (C1-C10)alkyl, substituted (C1-C10)alkyl, (C3-C10)cyclic alkyl, substituted (C3-C10)cyclic alkyl, (C6-C12)aryl, substituted (C6-C12)aryl, (C6-C12)aryl(C1-C10)alkyl, substituted (C6-C12)aryl(C1-C10)alkyl, (C1-C20)heteroaryl, substituted (C1-C20)heteroaryl, (C1-C20)heteroaryl(C1-C10)alkyl, substituted (C1-C20)heteroaryl(C1-C10)alkyl, (C1-C20) heterocycle, substituted (C1-C20) heterocycle, (C1-C20)heterocycle(C1-C10)alkyl or substituted (C1-C20)heterocycle(C1-C10)alkyl.

In an embodiment of the present invention, E is O and the representative GnRH receptor antagonists of the present invention include the compounds having the structures of the following Chemical Formulas II, III, IV and V:

[Chemical Formula II]

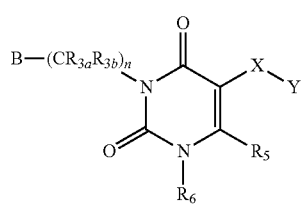

[Chemical Formula III]

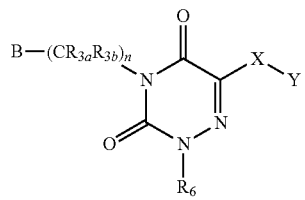

[Chemical Formula IV]

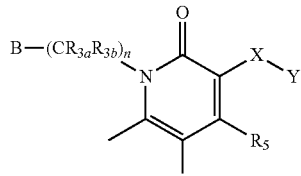

[Chemical Formula V]

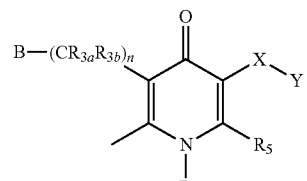

[Chemical Formula VI]

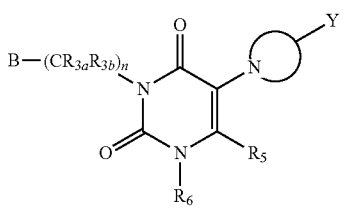

In an embodiment of the present invention, X is a uracil ring which is attached via the N atom, the GnRH receptor antagonists of the present invention being represented by the following Chemical VI:

[Chemical Formula VI]

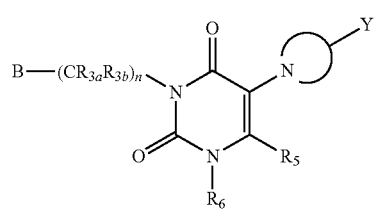

In an embodiment of the present invention, R₆ is a substituted benzyl, the GnRH receptor antagonists of the present invention being represented by the following Chemical Formula VII:

[Chemical Formula VII]

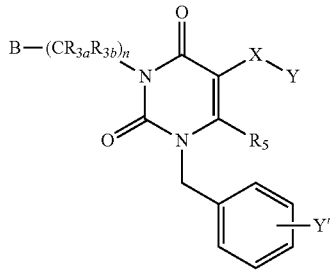

wherein Y' is at least one substituent defined above.

In a concrete embodiment of Chemical Formula VII, n is 2, $R_{3a}$ is H, and $R_{3b}$ is an aromatic ring or a substituted aromatic ring, thus the GnRH receptor antagonists of the present invention having the structures of the following Chemical Formulas VIII and IX:

[Chemical Formula VIII]

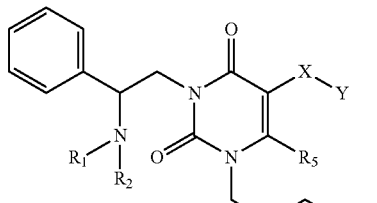

[Chemical Formula IX]

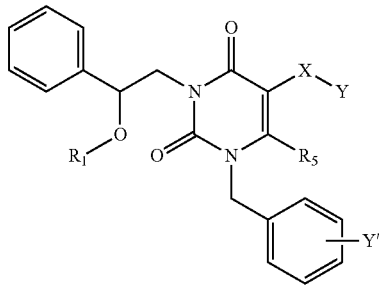

The compounds of the present invention can be prepared using well-known organic synthesis methods as illustrated in the following Example section.

A common intermediate 4 may be synthesized according to the following Reaction Scheme 1. A suitable amine is treated with equivalents of urea at 130° C. for 4 hrs with stirring, to give a compound 2 to which diketene is added together with NaI while being cooled by ice, followed by the addition of TMS-Cl with stirring at room temperature for 5 hrs to produce a cyclized uracil 3. Subsequently, treatment with bromine at room temperature for 30 min with stirring affords the intermediate 3 as a solid phase (see Bioorganic Medicinal Chemistry Letter, 2003, 13, 19, 3311)

[Reaction Scheme 1]

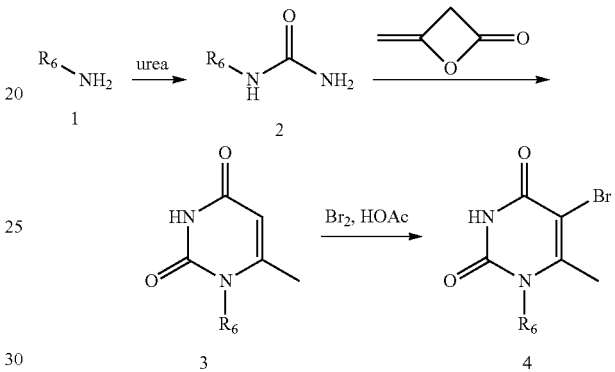

The compounds of the present invention can be prepared as illustrated in the following Reaction Schemes 2 to 5.

[Reaction Scheme 2]

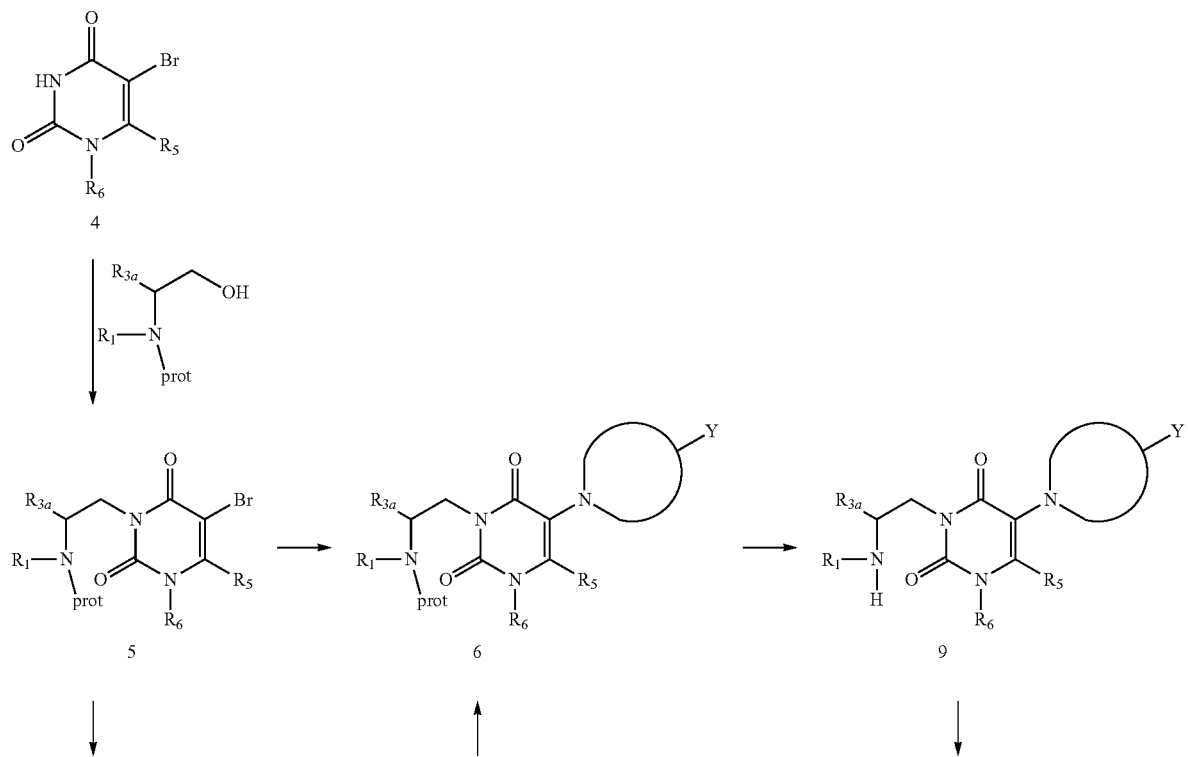

11

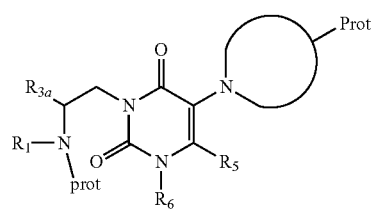

7

*Prot: Protecting group

-continued

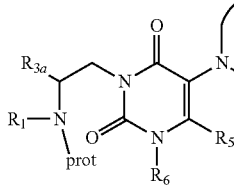

8

12

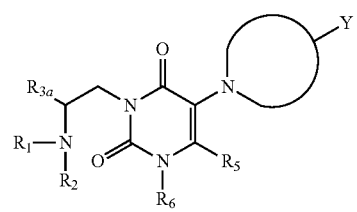

10

[Reaction Scheme 3]

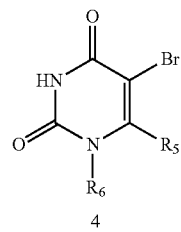

4

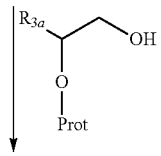

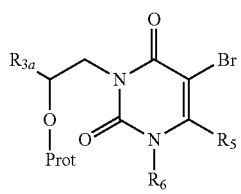

5

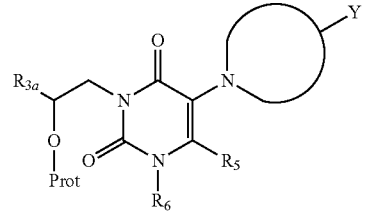

6

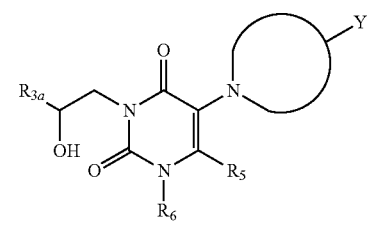

9

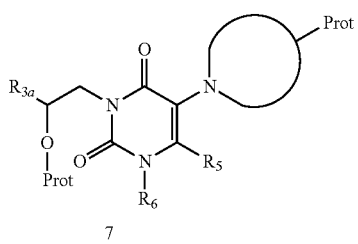

7

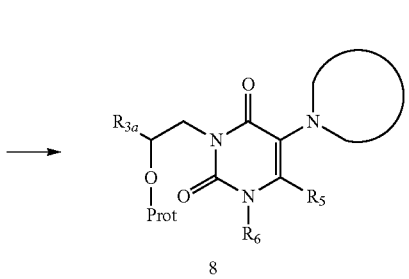

8

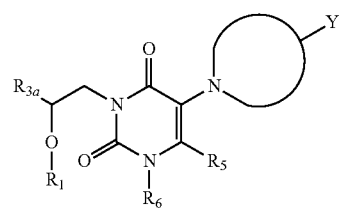

10

*Prot: Protecting group

The intermediate 4 is alkylated with a properly protected alcohol in a halide or mesylate form, or is subjected to a Mitsunobu reaction with the alcohol to give a compound 5. Then, the compound 5 is reacted with an N-containing heterocycle by microwave irradiation or by stirring at a high temperature to give a substituted compound 6. In order to introduce various substituents Y, first, the compound 5 is reacted with a properly protected, N-containing heterocycle by microwave irradiation or at a room temperature to give a compound 7 which is deprotected at the heterocycle moiety to furnish a compound 8. The introduction of various desired substituents Y may be achieved by the alkylation or reduction alkylation with the compound 8 with halide or aldehyde forms of Y. Afterwards, the compound 6 is deprotected at the B moiety, followed by reductive alkylation with an alkyl halide in the presence of base or with an aldehyde to yield a compound 10.

Alternatively, the compounds of the present invention may be also prepared upon change in reaction order, as illustrated in the following Reaction Schemes 4 and 5, with the concomitant production of various derivatives.

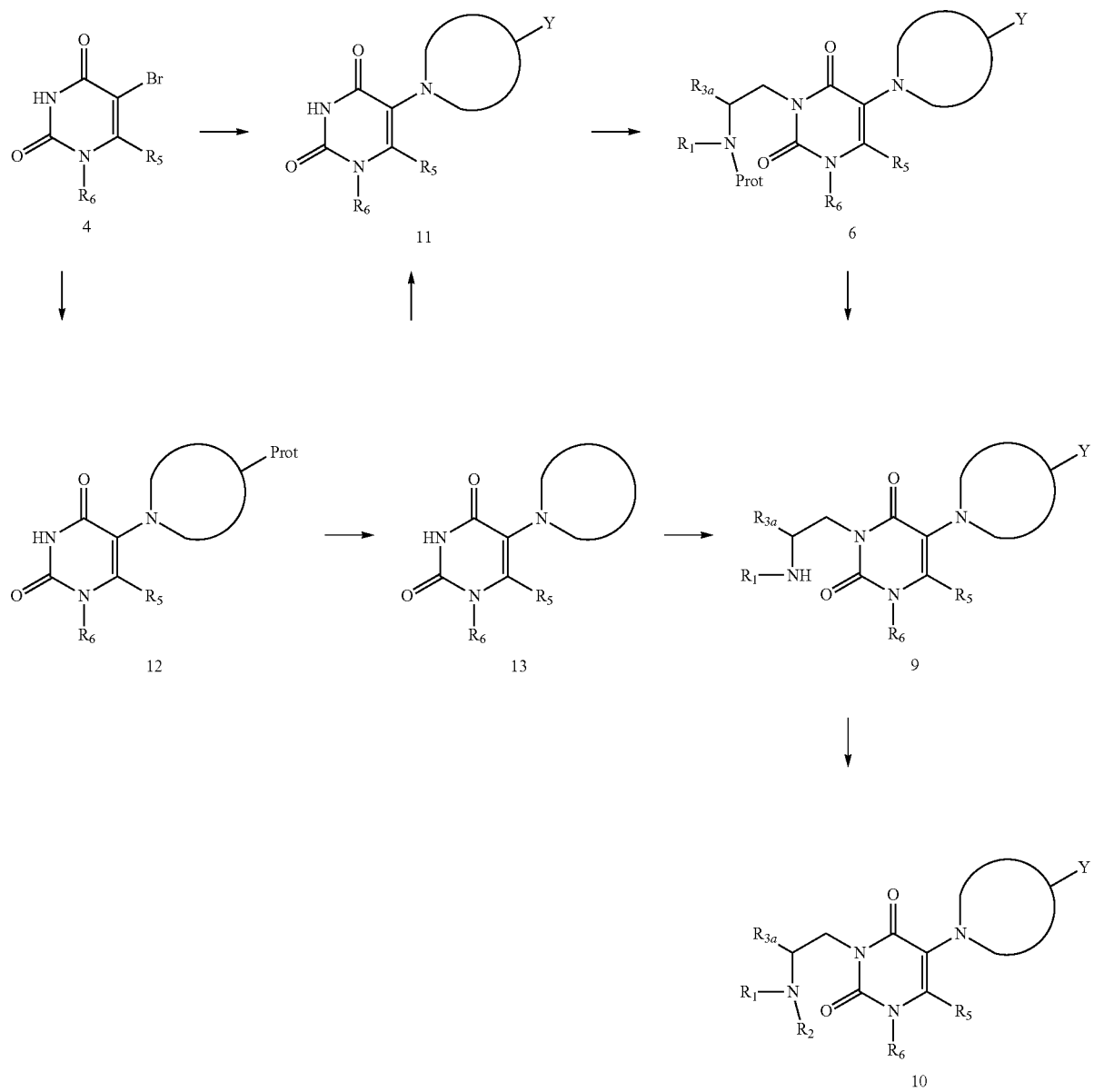
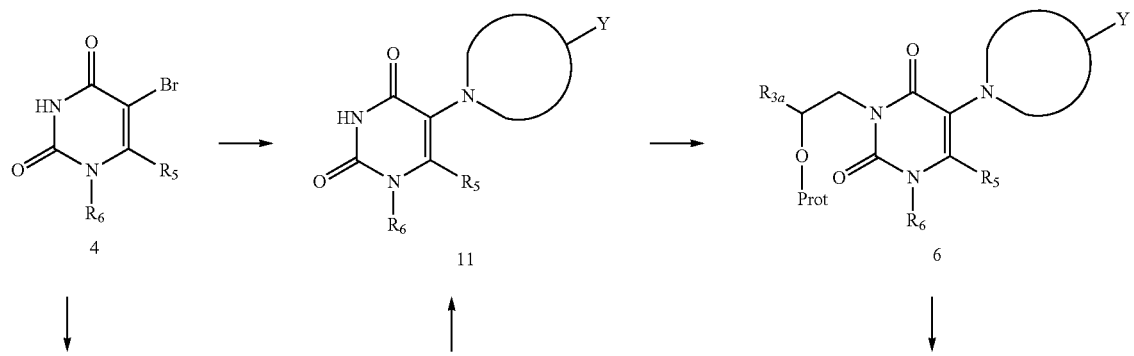
*Prot: Protecting group

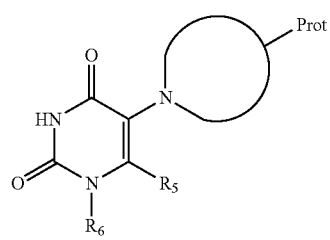 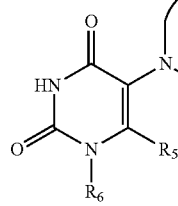 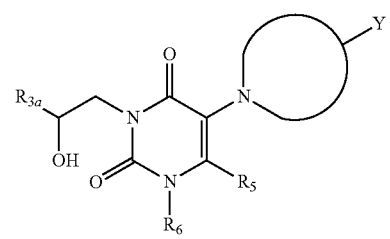

12 13 9

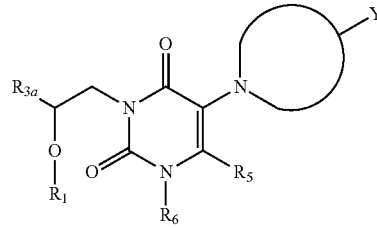

10

*Prot: Protecting group

An N-containing heterocycle is introduced into the intermediate 4 through a nucleophilic reaction by microwave irradiation or by stirring at high temperature to give a compound 11 which is further, together with an N-containing heterocycle, subjected to microwave irradiation or stirring at high temperature to give a compound 6. As for the introduction of various Y substituents, a properly protected, N-containing heterocycle is reacted with the intermediate 4 to give a compound 12 which is then deprotected to form a compound 13, followed by alkylation with a halide or aldehyde of the substituent Y.

Generally, the compounds of the present invention may be used in the form of free acids or free bases. Alternatively, the compounds of the present invention may take the form of acid or base addition salts. Acid addition salts of the free amino compounds of the present invention may be prepared, using a method known in the art, from organic or inorganic acids. Examples of the organic acids useful in the present invention include maleic acid, fumatic acid, benzoic acid, ascorbic acid, succinic acid, methane sulfonic acid, acetic acid, trifluoroacetic acid, oxalic acid, propionic acid, tartaric acid, salicylic acid, citric acid, gluconic acid, lactic acid, mandelic acid, cinnamic acid, aspartic acid, stearic acid, palmitic acid, glycolic acid, glutamic acid, and benzene sulfonic acid. Among the inorganic acid suitable in the present invention are hydrochloric acid, hydrobromic acid, sulfuric acid, phosphoric acid and nitric acid. As for the base addition salts, they include salts formed with carboxylate anions, organic and inorganic cations such as alkali metal and alkaline metal (e.g., lithium, sodium, potassium, magnesium, barium and calcium), and ammonium ions and substituted derivatives thereof (e.g., dibenzyl ammonium, benzyl ammonium, 2-hydroxyethyl ammonium, etc.). Accordingly, the term "pharmaceutically acceptable salts" of the compounds of Chemical Formula I should be understood to refer to all salt forms available in the art.

Also, the present invention pertains to prodrugs which can be in vivo converted into the compounds of Chemical Formula I by the cleavage of a covalent bond once administered to patients. Typically, prodrugs are prepared by modifying functional groups. This modification can be canceled by a typical operation or by metabolism in vivo to produce active compounds. For example, the prodrugs of the present invention in which the active compounds are bonded with hydroxy, amine or sulfyhydryl groups are metabolized to the active compounds once administered. Examples of the prodrugs of the present invention include acetate, formate and benzoate derivatives for the alcohol and amine furnctional groups of Chemical Compound I, but are not limited thereto. In addition, when carboxylic acid (—COOH) is used, the prodrugs may be in the form of esters such as methyl ester, ethyl ester and the like.

Also, the present invention pertains to stereoisomers of the compounds of Chemical Formula I. The compounds of Chemical Formula I may have a chiral center and thus exist as enantiomers or diastereomers or in the form of racemates or racemic mixtures, which all fall within the scope of the present invention. Further, the compounds of Chemical Formula I may have axial chirality, thus taking the form of atropisomers. In addition, some of the crystals of the compounds may exhibit polymorphs, which are also within the scope of the present invention. Moreover, some of the compounds of Chemical Formula I may form solvates with water or other organic solvents. The solvates fall within the scope of the present invention, as well.

Advantageous Effects compounds of the present invention are useful for the treatment of various sex hormone-related symptoms including endometriosis, uterine fibroids, polycystic ovarian disease, hypertrichosis, precocious puberty, gonadal steroid-dependent neoplasms (prostate cancer, breast cancer, ovary cancer, etc.), gonadotropin-producing pituitary adenoma, sleep apnea, irritable bowel syndrome, premenstrual syndrome, benign prostatic hyperplasia, and sterility (e.g., assisted reproductive techniques such as in vitro fertilization).

MODE FOR INVENTION

Example 1

Synthesis of 3-((R)-2-Amino-2-phenyl-ethyl)-5-(4-benzyl-piperazin-1-yl)-1-(2,6-difluoro-benzyl)-6-methyl-1H-pyrimidine-2,4-dione(1-10)

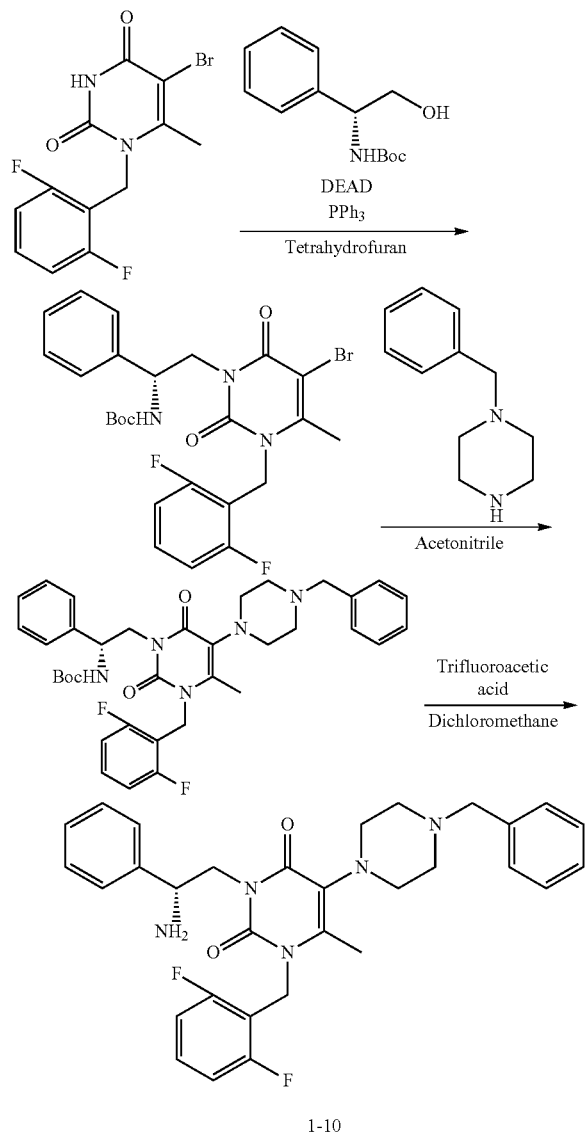

1-10

Step A. {(R)-2-[5-bromo-3-(2,6-difluoro-benzyl)-4-methyl-2,6-dioxo-3,6-dihydro-2H-pyrimidin-1-yl]-1-phenyl-ethyl}-carbamic acid tert-butyl ester 5-Bromo-1-(2,6-difluoro-benzyl)-6-methyl-1H-pyrimidine-2,4-dione (synthesized according to the method of BMCL 2004 14(19) 4967-4973) (2.77 g, 8.37 mmol), ((R)-2-hydroxy-1-phenyl-ethyl)-carbamic acid tert-butyl ester (2.08 g, 8.78 mmol), and triphenylphosphine (3.29 g, 12.5 mmol) were added to anhydrous tetrahydrofuran (70 mL) and stirred for a short time. To this solution was slowly added diethylazodicarboxylate (1.95 mL, 12.5 mmol), followed by stirring at room temperature for 12 hrs in a nitrogen atmosphere. Following concentration, the residue was purified using silica gel chromatography (eluent: hexane/ethyl acetate, 2/1) and dried in a vacuum to afford 2.26 g of the compound as a white foam (yield 49%).

Step B. {(R)-2-[5-(4-Benzyl-piperazin-1-yl)-3-(2,6-difluoro-benzyl)-4-methyl-2,6-dioxo-3,6-dihydro-2H-pyrimidin-1-yl]-1-phenyl-ethyl}-carbamic acid tert-butyl ester {(R)-2-[5-bromo-3-(2,6-difluoro-benzyl)-4-methyl-2,6-dioxo-3,6-dihydro-2H-pyrimidin-1-yl]-1-phenyl-ethyl}-carbamic acid tert-butyl ester (45 mg, 0.082 mmol), 1-benzyl-piperazine (216 mg, 1.23 mmol), and acetonitrile (500 µl) were placed in a microwave vessel and heated at 120° C. for 1 hr by microwave irradiation with stirring. Following concentration, the residue was purified using silica gel chromatography (eluent: hexane/ethyl acetate, 2/1) and dried in a vacuum to afford the 33 mg of the compound as a colorless oil (yield 62%).

Step C. 3-((R)-2-amino-2-phenyl-ethyl)-5-(4-benzyl-piperazin-1-yl)-1-(2,6-difluoro-benzyl)-6-methyl-1H-pyrimidine-2,4-dione(1-10)

To a solution of {(R)-2-[5-(4-benzyl-piperazin-1-yl)-3-(2,6-difluoro-benzyl)-4-methyl-2,6-dioxo-3,6-dihydro-2H-pyrimidin-1-yl]-1-phenyl-ethyl}-carbamic acid tert-butyl ester (33 mg, 0.051 mmol) in dichloromethane (2 mL) was slowly added trifluoroacetic acid (100 µl, 1.30 mmol), followed by stirring at room temperature for 3 hrs. The resulting solution was neutralized with an aqueous saturated sodium bicarbonate solution before the separation of an organic layer. This organic layer was concentrated, and the residue was purified using silica gel chromatography (eluent: dichloromethane/methanol, 20/1) and dried in a vacuum to afford 19 mg of the compound as a white foam. (yield 68%). $^1$H NMR (300 MHz, CDCl$_3$) δ 1.98 (2H, m), 2.23 (2H, m), 2.42 (3H, s), 2.47 (2H, m), 2.75 (2H, m), 3.55 (2H, s), 4.05 (1H, dd), 4.21 (1H, m), 4.37 (1H, m), 5.22 (2H, dd), 6.85-6.94 (2H, m), 7.20-7.41 (11H, m)

The compounds synthesized according to the procedures explained above are summarized in Table 1, below. Compounds 1-1 to 1-46 were prepared in the same manner as above, with the exception that amines were used instead of 1-benzyl-piperazine in Step B. Compounds 1-49 to 1-51 were prepared in the same manner as above, with the exception that 5-bromo-1-(2-fluoro-6-trifluoromethyl-benzyl)-6-methyl-1H-pyrimidine-2,4-dione (synthesized as instructed in PCT/US2004/021593) instead of 5-bromo-1-(2,6-difluoro-benzyl)-6-methyl-1H-pyrimidine-2,4-dione in Step A, and different amines instead of 1-benzyl-piperazine in Step B were used. Compounds 1-47 and 1-48 were prepared in the same manner as above, with the exception that 5-bromo-1-(2-fluoro-6-trifluoromethyl-benzyl)-6-methyl-1H-pyrimidine-2,4-dione, instead of 5-bromo-1-(2,6-difluoro-benzyl)-6-methyl-1H-pyrimidine-2,4-dione, and different alcohols (different amino acids were reduced LiAlH$_4$ into amino alcohols into which the protecting group was introduced), instead of ((R)-2-hydroxy-1-phenyl-ethyl)-carbamic acid tert-butyl ester, were used in Step A, and different amines were used instead of 1-benzyl-piperazine in Step B.

TABLE 1
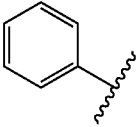 [SMILES: *c1ccccc1]
| No. | —R₃ | * | —X—Y | —R₆ | M.W. | Mass |
|---|---|---|---|---|---|---|
| 1-1 | 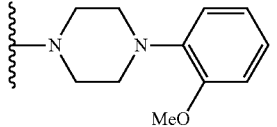 | R | 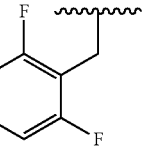 | 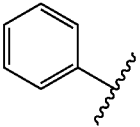 [SMILES: *c1ccccc1] | 561.62 | 562.6 |
| 1-2 | 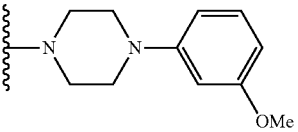 | R | 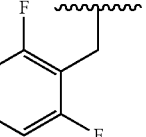 | 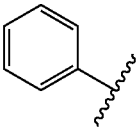 [SMILES: *c1ccccc1] | 561.62 | 562.7 |
| 1-3 | 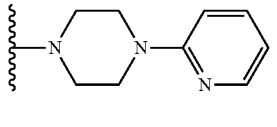 [SMILES: *N1CCN(c2ccccn2)CC1] | R | 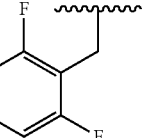 | 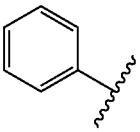 [SMILES: *c1ccccc1] | 532.58 | 533.9 |
| 1-4 | 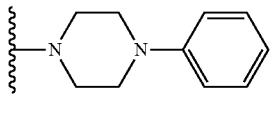 | R | 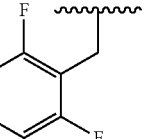 | 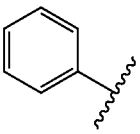 [SMILES: *c1ccccc1] | 531.6 | 532.7 |
| 1-5 | 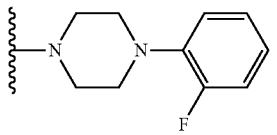 [SMILES: *N1CCN(c2ccccc2F)CC1] | R | 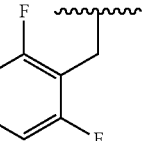 | 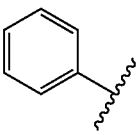 [SMILES: *c1ccccc1] | 549.59 | 550.6 |
| 1-6 | 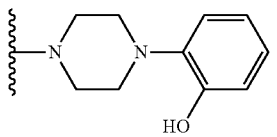 [SMILES: *N1CCN(c2ccccc2O)CC1] | R | 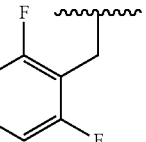 | 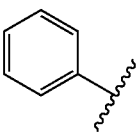 [SMILES: *c1ccccc1] | 547.6 | 548.6 |
| 1-7 | 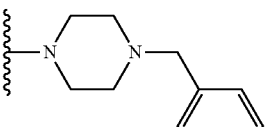 | R | 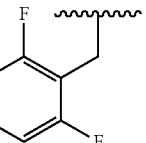 | 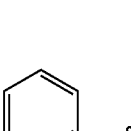 | 580.07 | 580.7 |
| 1-8 | 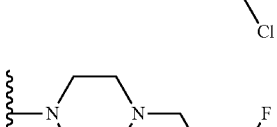 | R | 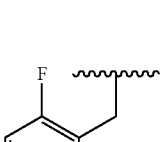 | | 563.61 | 564.6 |

TABLE 1-continued

| No. | —R₃ | * | —X—Y | —R₆ | M.W. | Mass |
|---|---|---|---|---|---|---|
| 1-9 | phenyl | R | piperazine-CH₂-(3-fluorophenyl) | 2,6-difluorobenzyl | 563.61 | 564.6 |
| 1-10 | phenyl | R | piperazine-CH₂-phenyl | 2,6-difluorobenzyl | 545.62 | 546.7 |
| 1-11 | phenyl | R | piperazine-CH₂-(4-trifluoromethylphenyl) | 2,6-difluorobenzyl | 613.62 | 614.7 |
| 1-12 | phenyl | R | piperazine-C(O)-phenyl | 2,6-difluorobenzyl | 559.61 | 560.6 |
| 1-13 | phenyl | R | piperazine-CH₂-(benzo[1,3]dioxol-5-yl) | 2,6-difluorobenzyl | 589.63 | 590.8 |
| 1-14 | phenyl | R | 1,2,3,4-tetrahydroisoquinolin-2-yl | 2,6-difluorobenzyl | 502.56 | 503.6 |
| 1-15 | phenyl | R | 3-(2-hydroxyethyl)piperazin-1-yl | 2,6-difluorobenzyl | 499.55 | 500.6 |

TABLE 1-continued
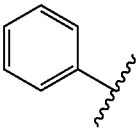 [SMILES: *c1ccccc1]
| No. | —R₃ | * | —X—Y | —R₆ | M.W. | Mass |
|---|---|---|---|---|---|---|
| 1-16 | 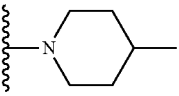 | R | 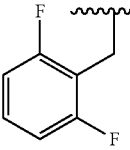 | 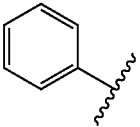 [SMILES: *c1ccccc1] | 468.54 | 469.6 |
| 1-17 | 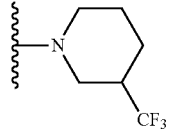 | R | 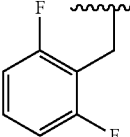 | 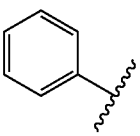 [SMILES: *c1ccccc1] | 522.51 | 523.5 |
| 1-18 | 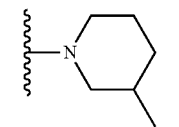 [SMILES: *N1CCCC(C)C1] | R | 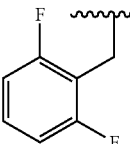 | 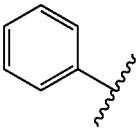 [SMILES: *c1ccccc1] | 468.54 | 469.7 |
| 1-19 | 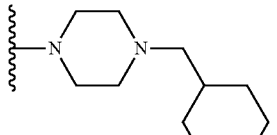 | R | 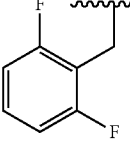 | 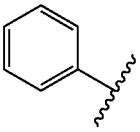 [SMILES: *c1ccccc1] | 551.67 | 552.8 |
| 1-20 | 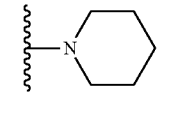 | R | 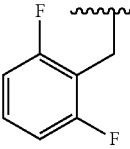 | 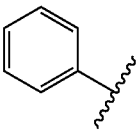 [SMILES: *c1ccccc1] | 454.51 | 455.6 |
| 1-21 | 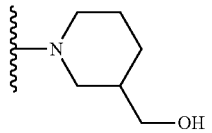 [SMILES: *N1CCCC(CO)C1] | R | 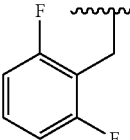 | 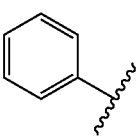 [SMILES: *c1ccccc1] | 484.54 | 485.6 |
| 1-22 | 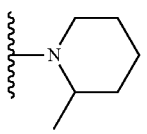 | R | 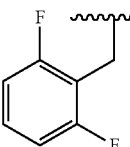 | 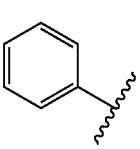 [SMILES: *c1ccccc1] | 468.54 | 469.7 |
| 1-23 | 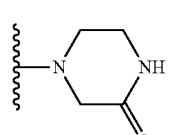 | R | 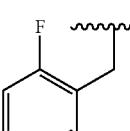 | | 469.48 | 470.4 |

TABLE 1-continued

| No. | —R₃ | * | —X—Y | —R₆ | M.W. | Mass |
|---|---|---|---|---|---|---|
| 1-24 | phenyl | R | 2,5-dihydro-1H-pyrrol-1-yl | 2,6-difluorobenzyl | 438.47 | 439.4 |
| 1-25 | phenyl | R | 4-hydroxypiperidin-1-yl | 2,6-difluorobenzyl | 470.51 | 471.5 |
| 1-26 | phenyl | R | 4-benzylpiperidin-1-yl | 2,6-difluorobenzyl | 544.63 | 545.5 |
| 1-27 | phenyl | R | 3-phenylpiperazin-1-yl | 2,6-difluorobenzyl | 531.6 | 532.4 |
| 1-28 | phenyl | R | 3-benzylpiperazin-1-yl | 2,6-difluorobenzyl | 545.62 | 546.4 |
| 1-29 | phenyl | R | 3-benzylpiperazin-1-yl | 2,6-difluorobenzyl | 545.62 | 546.4 |
| 1-30 | phenyl | R | 4-Cbz-piperazin-1-yl | 2,6-difluorobenzyl | 589.63 | 590.2 |
| 1-31 | phenyl | R | 4-(pyrazin-2-yl)piperazin-1-yl | 2,6-difluorobenzyl | 533.57 | 534.6 |

TABLE 1-continued
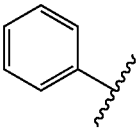 [SMILES: *c1ccccc1]
| No. | —R$_3$ | * | —X—Y | —R$_6$ | M.W. | Mass |
|---|---|---|---|---|---|---|
| 1-32 | 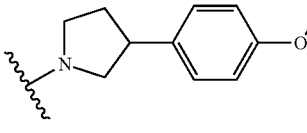 | R | 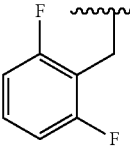 | 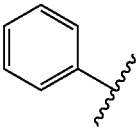 [SMILES: *c1ccccc1] | 546.61 | 547.4 |
| 1-33 | 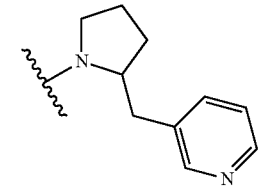 [SMILES: *N1CCCC1Cc1cccnc1] | R | 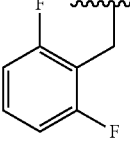 | 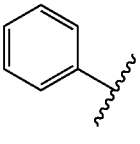 [SMILES: *c1ccccc1] | 531.6 | 532.5 |
| 1-34 | 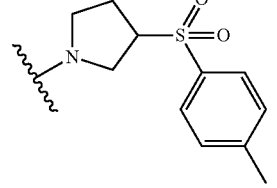 | R | 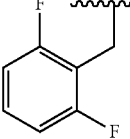 | 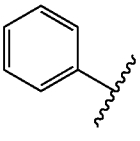 [SMILES: *c1ccccc1] | 594.67 | 595.5 |
| 1-35 | 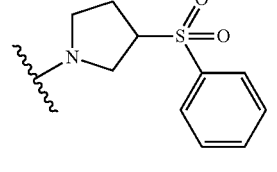 | R | 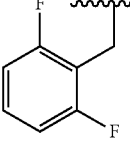 | 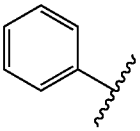 [SMILES: *c1ccccc1] | 580.65 | 581.3 |
| 1-36 | 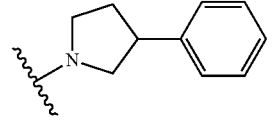 [SMILES: *N1CCC(c2ccccc2)C1] | R | 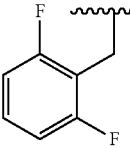 | 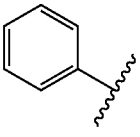 [SMILES: *c1ccccc1] | 516.58 | 517.3 |
| 1-37 | 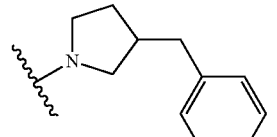 | R | 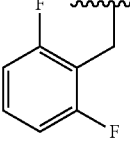 | 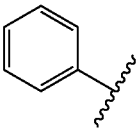 [SMILES: *c1ccccc1] | 530.61 | 531.1 |
| 1-38 | 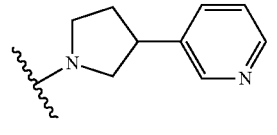 [SMILES: *N1CCC(c2cccnc2)C1] | R | 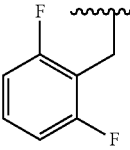 | | 517.57 | 518.3 |

TABLE 1-continued

| No. | —R₃ | * | —X—Y | —R₆ | M.W. | Mass |
|---|---|---|---|---|---|---|
| 1-39 | phenyl | R | 3-phenylpiperidin-1-yl | 2,6-difluorobenzyl | 530.61 | 531.3 |
| 1-40 | phenyl | R | 4-phenoxypiperidin-1-yl | 2,6-difluorobenzyl | 546.61 | 547.2 |
| 1-41 | phenyl | R | morpholin-4-yl | 2,6-difluorobenzyl | 456.49 | 457.2 |
| 1-42 | phenyl | R | 4-(2-fluorophenoxy)piperidin-1-yl | 2,6-difluorobenzyl | 564.6 | 565.4 |
| 1-43 | phenyl | R | 4-(4-fluorophenoxy)piperidin-1-yl | 2,6-difluorobenzyl | 564.6 | 565.4 |
| 1-44 | phenyl | R | 4-(furo[3,2-b]pyridin-yl)piperazin-1-yl | 2,6-difluorobenzyl | 572.61 | 573.4 |
| 1-45 | phenyl | R | 3-benzylpiperidin-1-yl | 2,6-difluorobenzyl | 544.63 | 545.2 |

TABLE 1-continued

| No. | —R₃ | * | —X—Y | —R₆ | M.W. | Mass |
|---|---|---|---|---|---|---|
| 1-46 | phenyl | R | N-piperidine-CH₂-(4-F-phenyl) | 2,6-difluorobenzyl | 562.63 | 563.3 |
| 1-47 | 3-fluoro-5-methylphenyl | S | N-piperazine-N-CH₂-(3-NO₂-phenyl) | 2-F-6-CF₃-benzyl | 672.64 | 673.4 |
| 1-48 | 5-fluoro-2-methoxyphenyl | S | N-piperazine-N-CH₂-(3-NO₂-phenyl) | 2-F-6-CF₃-benzyl | 688.64 | 689.3 |
| 1-49 | phenyl | R | N-(4-OH-4-benzyl-piperidine) | 2-F-6-CF₃-benzyl | 610.64 | 611.5 |
| 1-50 | phenyl | R | N-(3R-methyl-piperazine)-NH | 2-F-6-CF₃-benzyl | 519.53 | 520.4 |
| 1-51 | phenyl | R | N-(2R-methyl-piperazine)-NH | 2-F-6-CF₃-benzyl | 519.53 | 520.3 |

Compound 1-52 was prepared in the same manner as above, with the exception that 5-bromo-1,6-dimethyl-1H-pyrimidine-2,4-dione (synthesized as instructed by JMC, 1972, 15, 471-473) instead of 5-bromo-1-(2,6-difluoro-benzyl)-6-methyl-1H-pyrimidine-2,4-dione in Step A and a different amine instead of 1-benzyl-piperazine in Step B were used, and Step C was omitted.

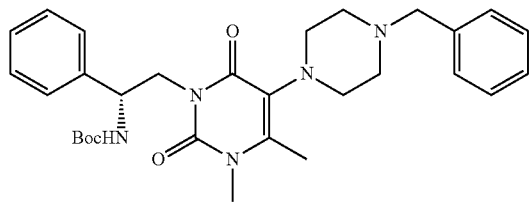

1-52

{(R)-2-[5-(4-benzyl-piperazin-1-yl)-3,4-dimethyl-2,6-dioxo-3,6-dihydro-2H-pyrimidin-1-yl]-1-phenyl-ethyl}-carbamic acid tert-butyl ester (1-52) $^1$H NMR (300 MHz, CDCl$_3$) δ 1.34 (9H, s), 2.42 (3H, s), 2.53 (2H, m), 2.94 (2H, m), 3.45 (3H, s), 3.52 (2H, m), 4.02 (1H, m), 4.29 (1H, m), 5.03 (1H, m), 5.69 (1H, m), 7.27-7.41 (10H, m)

Compound 1-53 was prepared in the same manner as above, with the exception that 5-bromo-1-(2-fluoro-6-trifluoromethyl-benzyl)-6-methyl-1H-pyrimidine-2,4-dione was used instead of 5-bromo-1-(2,6-difluoro-benzyl)-6-methyl-1H-pyrimidine-2,4-dione in Step A, and Step C was omitted.

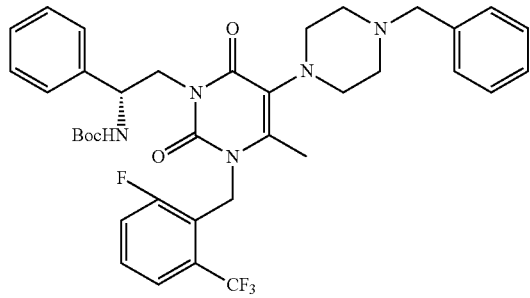

1-53

{(R)-2-[5-(4-benzyl-piperazin-1-yl)-3-(2-fluoro-6-trifluoromethyl-benzyl)-4-methyl-2,6-dioxo-3,6-dihydro-2H-pyrimidin-1-yl]-1-phenyl-ethyl}-carbamic acid tert-butyl ester (1-53)

Compound 1-54 was prepared in the same manner as above, with the exception that 5-bromo-1-(2,6-difluoro-benzyl)-1H-pyrimidine-2,4-dione, instead of 5-bromo-1-(2,6-difluoro-benzyl)-6-methyl-1H-pyrimidine-2,4-dione in Step A and a different amine, instead of 1-benzyl-piperazine were used in Step B.

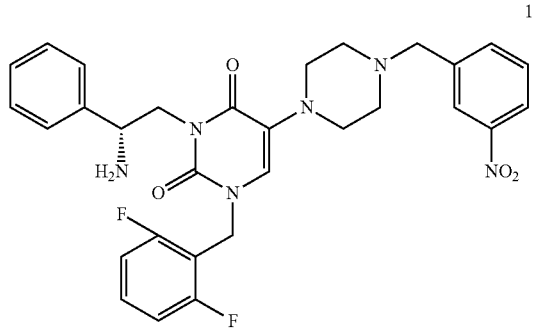

1-54

3-((R)-2-amino-2-phenyl-ethyl)-1-(2,6-difluoro-benzyl)-5-[4-(3-nitro-benzyl)-piperazin-1-yl]-1H-pyrimidine-2,4-dione(1-54) $^1$H NMR (300 MHz, CDCl$_3$) δ 2.63 (4H, m), 2.93 (4H, m), 3.65 (2H, s), 4.04 (1H, dd), 4.24 (1H, t), 4.37 (1H, dd), 5.04 (2H, dd), 6.72 (1H, s), 6.96 (2H, t), 7.20-7.41 (6H, m), 7.50 (1H, t), 7.67 (1H, d), 8.12 (1H, dd), 8.25 (1H, s). MS (ESI) m/z 577.3 (MH$^+$)

Compound 1-55 was prepared in the same manner as noted above, with the exception that 6-bromo-2-(2-fluoro-6-trifluoromethyl-benzyl)-2H-[1,2,4]triazine-3,5-dione (synthesized as instructed by US 2005/0075339 A1) was used instead of 5-bromo-1-(2,6-difluoro-benzyl)-6-methyl-1H-pyrimidine-2,4-dione in Step A, and Step C was omitted.

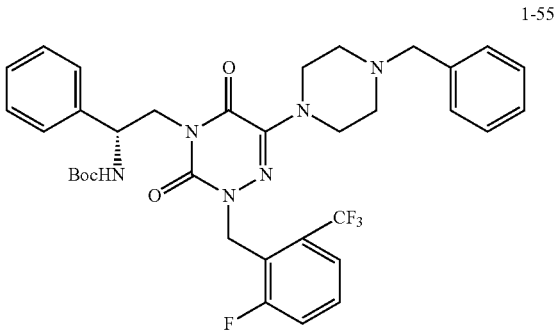 [SMILES: CC(C)(C)OC(=O)N[C@@H](Cn1c(=O)c(N2CCN(Cc3ccccc3)CC2)nn(Cc2c(F)cccc2C(F)(F)F)c1=O)c1ccccc1]

1-55

{(R)-2-[6-(4-benzyl-piperazin-1-yl)-2-(2-fluoro-6-trifluoromethyl-benzyl)-3,5-dioxo-2,5-dihydro-3H-[1,2,4]triazin-4-yl]-1-phenyl-ethyl}-carbamic acid tert-butyl ester(1-55) $^1$H NMR (300 MHz, CDCl$_3$) δ 1.38 (9H, s), 2.43 (4H, m), 3.19 (4H, bs), 3.47 (2H, s), 4.31 (1H, m), 5.09 (1H, m), 5.29 (2H, dd), 5.60 (1H, m), 7.24-7.49 (13H, m)

Compound 1-56 was prepared in the same manner as above, with the exception that 3-bromo-5-(2,6-difluorobenzyl)-4,6-dimethylpyridine-2(1H)-one (synthesized as instructed by U.S. Pat. No. 6,750,350 B2) was used instead of 5-bromo-1-(2,6-difluoro-benzyl)-6-methyl-1H-pyrimidine-2,4-dione in Step A.

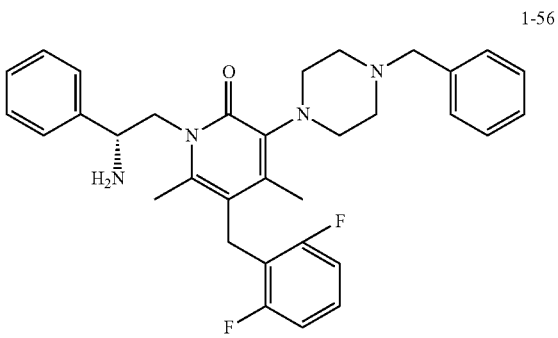 [SMILES: Cc1c(Cc2c(F)cccc2F)c(C)n(C[C@H](N)c2ccccc2)c(=O)c1N1CCN(Cc2ccccc2)CC1]

1-56

(R)-1-(2-amino-2-phenylethyl)-3-(4-benzylpiperazin-1-yl)-5-(2,6-difluorobenzyl)-4,6-dimethylpyridine-2(1H)-one (1-56) MS (ESI) m/z 543.3 (MH$^+$)

Example 2

Synthesis of {(R)-2-[3-(2-Fluoro-6-trifluoromethyl-benzyl)-4-methyl-2,6-dioxo-5-piperazin-1-yl-3,6-dihydro-2H-pyrimidin-1-yl]-1-phenyl-ethyl}-carbamic acid tert-butyl ester(2-1)

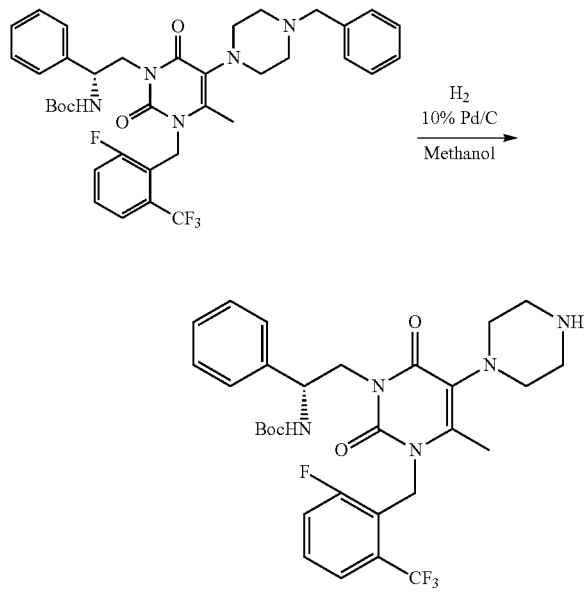 [SMILES: Cc1c(N2CCN(Cc3ccccc3)CC2)c(=O)n(C[C@H](NC(=O)OC(C)(C)C)c2ccccc2)c(=O)n1Cc1c(F)cccc1C(F)(F)F ; Cc1c(N2CCNCC2)c(=O)n(C[C@H](NC(=O)OC(C)(C)C)c2ccccc2)c(=O)n1Cc1c(F)cccc1C(F)(F)F]

Step A. {(R)-2-[3-(2-fluoro-6-trifluoromethyl-benzyl)-4-methyl-2,6-dioxo-5-piperazin-1-yl-3,6-dihydro-2H-pyrimidin-1-yl]-1-phenyl-ethyl}-carbamic acid tert-butyl ester(2-1)

To a solution of {(R)-2-[5-(4-benzyl-piperazin-1-yl)-3-(2-fluoro-6-trifluoromethyl-benzyl)-4-methyl-2,6-dioxo-3,6-dihydro-2H-pyrimidin-1-yl]-1-phenyl-ethyl}-carbamic acid tert-butyl ester (1-53) (1.89 g, 2.72 mmol) in 300 mL of methanol was added 10% palladium/carbon (350 mg) in a nitrogen atmosphere, and the reaction mixture was stirred at room temperature for 5 hrs in a hydrogen atmosphere. The palladium/carbon was removed by filtration through cellite, followed by the concentration of the filtrate. The residue was purified using silica gel chromatography (eluent: dichloromethane/methanol, 8/1) and dried in a vacuum to afford 1.3 g of the compound as a white foam (yield 95%).

The compounds synthesized according to this procedure are summarized in Table 2, below. Compound 2-2 was prepared in the same manner as above, with the exception that {(R)-2-[5-(4-benzyl-piperazin-1-yl)-3-(2,6-difluoro-benzyl)-4-methyl-2,6-dioxo-3,6-dihydro-2H-pyrimidin-1-yl]-1-phenyl-ethyl}-carbamic acid tert-butyl ester was used instead of {(R)-2-[5-(4-benzyl-piperazin-1-yl)-3-(2-fluoro-6-trifluoromethyl-benzyl)-4-methyl-2,6-dioxo-3,6-dihydro-2H-pyrimidin-1-yl]-1-phenyl-ethyl}-carbamic acid tert-butyl ester. Compound 2-3 was prepared in the same manner as above, with the exception that {(R)-2-[5-(4-benzyl-piperazin-1-yl)-3,4-dimethyl-2,6-dioxo-3,6-dihydro-2H-pyrimidin-1-yl]-1-phenyl-ethyl}-carbamic acid tert-butyl ester(1-52) was used instead of {(R)-2-[5-(4-benzyl-piperazin-1-yl)-3-(2-fluoro-6-trifluoromethyl-benzyl)-4-methyl-2,6-dioxo-3,6-dihydro-2H-pyrimidin-1-yl]-1-phenyl-ethyl}-carbamic acid tert-butyl ester.

TABLE 2

| No. | —R₆ | M.W. | Mass |
|---|---|---|---|
| 2-1 | 2-F, 6-CF₃-benzyl | 605.62 | 606.3 |
| 2-2 | 2,6-diF-benzyl | 555.62 | 556.3 |
| 2-3 | CH₃ | 443.54 | 444.3 |

Compound 2-4 was prepared in the same manner as above, with the exception that {(R)-2-[6-(4-benzyl-piperazin-1-yl)-2-(2-fluoro-6-trifluoromethyl-benzyl)-3,5-dioxo-2,5-dihydro-3H-[1,2,4]triazin-4-yl]-1-phenyl-ethyl}-carbamic acid tert-butyl ester(1-55) was used instead of {(R)-2-[5-(4-benzyl-piperazin-1-yl)-3-(2-fluoro-6-trifluoromethyl-benzyl)-4-methyl-2,6-dioxo-3,6-dihydro-2H-pyrimidin-1-yl]-1-phenyl-ethyl}-carbamic acid tert-butyl ester.

{(R)-2-[2-(2-fluoro-6-trifluoromethyl-benzyl)-3,5-dioxo-6-piperazin-1-yl-2,5-dihydro-3H-[1,2,4]triazin-4-yl]-1-phenyl-ethyl}-carbamic acid tert-butyl ester(2-4) ¹H NMR (300

MHz, CDCl₃) δ 1.37 (9H, s), 2.85 (4H, m), 3.16 (4H, m), 4.09 (1H, m), 4.32 (1H, m), 5.08 (1H, m), 5.32 (2H, dd), 5.59 (1H, m), 7.27-7.54 (8H, m)

Example 3

Synthesis of 3-((R)-2-Amino-2-phenyl-ethyl)-1-(2-fluoro-6-trifluoromethyl-benzyl)-6-methyl-5-[4-(5-trifluoromethyl-furan-2-ylmethyl)-piperazin-1-yl]-1H-pyrimidine-2,4-dione(3-66)

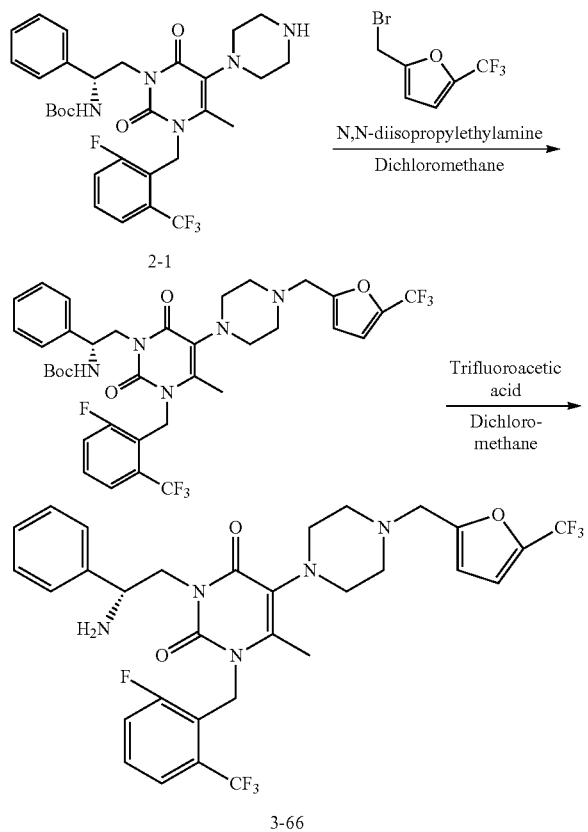

Step A. ((R)-2-{3-(2-fluoro-6-trifluoromethyl-benzyl)-4-methyl-2,6-dioxo-5-[4-(5-trifluoromethyl-furan-2-ylmethyl)-piperazin-1-yl]-3,6-dihydro-2H-pyrimidin-1-yl}-1-phenyl-ethyl)-carbamic acid tert-butyl ester To a solution of ((R)-2-{3-(2-fluoro-6-trifluoromethyl-benzyl)-4-methyl-2,6-dioxo-5-piperazin-1-yl]-3,6-dihydro-2H-pyrimidin-1-yl}-1-phenyl-ethyl)-carbamic acid tert-butyl ester (21.4 g, 35.3 mol) in 70 mL of dichloromethane was added N,N-diisopropylethyl amine (12.3 mL, 70.6 mol). The solution was cooled to 0° C. and slowly mixed with 2-bromomethyl-5-trifluoromethyl-furane (9.2 g, 38.8 mol), with stirring at room temperature for 2 hrs in a nitrogen atmosphere. The reaction solution was washed with an aqueous saturated ammonium chloride solution and concentrated. The residue was purified using silica gel chromatography (eluent: hexane/ethyl acetate, 2/1) and dried in a vacuum to afford 23.5 g of the compound as a white foam (yield 88%).

Step B. 3-((R)-2-amino-2-phenyl-ethyl)-1-(2-fluoro-6-trifluoromethyl-benzyl)-6-methyl-5-[4-(5-trifluoromethyl-furan-2-ylmethyl)-piperazin-1-yl]-1H-pyrimidine-2,4-dione(3-66)

A solution of ((R)-2-{3-(2-fluoro-6-trifluoramethyl-benzyl)-4-methyl-2,6-dioxo-5-[4-(5-trifluoromethyl-furan-2-ylmethyl)-piperazin-1-yl]-3,6-dihydro-2H-pyrimidin-1-yl}-1-phenyl-ethyl)-carbamic acid tert-butyl ester (40.0 g, 53.1 mol) in dichloromethane (700 mL) which was chilled to 0° C., trifluoroacetic acid (70 mL, 0.91 mol) was slowly added. The solution was stirred at room temperature for 3 hrs, chilled again to 0° C. and slowly neutralized with sodium bicarbonate to separate an organic layer. Sodium sulfate was added to the separated organic layer which was then stirred for 5 min and filtered. The filtrate was concentrated and dried in a vacuum to afford 33 g of the compound as a white foam (yield 95%). ¹H NMR (300 MHz, CDCl₃) δ 2.24 (2H, m), 2.31 (3H, s), 2.49 (2H, m), 2.78 (2H, m), 3.57 (2H, m), 3.61 (2H, s), 5.40 (2H, s), 6.30 (1H, d), 6.72 (1H, dd), 7.18-7.26 (4H, m), 7.29-7.42 (3H, m), 7.54 (1H, m) MS (ESI) m/z 654 (MH⁺)

The compounds listed in Table 3 were synthesized according to the procedures described above. Compounds 3-1 to 3-53 were prepared in the same manner as above, with the exception that ((R)-2-{3-(2,6-difluoro-benzyl)-4-methyl-2,6-dioxo-5-piperazin-1-yl]-3,6-dihydro-2H-pyrimidin-1-yl}-1-phenyl-ethyl)-carbamic acid tert-butyl ester(2-2), instead of ((R)-2-{3-(2-fluoro-6-trifluoromethyl-benzyl)-4-methyl-2,6-dioxo-5-piperazin-1-yl]-3,6-dihydro-2H-pyrimidin-1-yl}-1-phenyl-ethyl)-carbamic acid tert-butyl ester(2-1), and different bromomethyl compounds, instead of 2-bromomethyl-5-trifluoromethyl-furan, were used in Step A. Compounds 3-54 to 3-57 were prepared in the same manner as above, with the exception that [(R)-2-(3,4-dimethyl-2,6-dioxo-5-piperazin-1-yl-3,6-dihydro-2H-pyrimidin-1-yl)-1-phenyl-ethyl]-carbamic acid tert-butyl ester(2-3), instead of ((R)-2-{3-(2-fluoro-6-trifluoromethyl-benzyl)-4-methyl-2,6-dioxo-5-piperazin-1-yl]-3,6-dihydro-2H-pyrimidin-1-yl}-1-phenyl-ethyl)-carbamic acid tert-butyl ester(2-1), and different bromomethyl compounds, instead of 2-bromomethyl-5-trifluoromethyl-furan, were used in Step A. Compounds 3-58 to 3-98 and 3-100 to 3-107 were prepared in the same manner as above, with the exception that different bromomethyl compounds were used instead of 2-bromomethyl-5-trifluoromethyl-furan. Compound 3-99 was prepared in the same manner as noted above, with the exception that a mesylate derived from a different methyl alcohol (synthesized as instructed by EP1110454; (2001); (A2), US2009/5359 A1, U.S. Pat. No. 5,034,404; (1991); (A1)) was used instead of 2-bromomethyl-5-trifluoromethyl-furan. Compounds 3-69 and 3-70 were synthesized into the form of nitro precursors as in the corresponding compound 3-58. The nitro group was reduced into amine groups by hydrogenation in the presence of a Pd/C catalyst. Compounds 3-73, 3-74 and 3-82 were respectively prepared from the ester precursors compounds 3-71, 3-72 and 3-83 by hydrolysis. For the preparation of compound 3-85, an ester precursor was first synthesized in Step A and subjected to hydrolysis before conducting Step C. Compounds 3-90 and 3-91 were prepared from their ester precursor compound 3-83 by amidation. Compounds 3-108 and 3-109 were prepared in the same manner as above, with the exception that tert-butyl((R)-2-(3-(2-fluoro-6-(trifluoromethyl)benzyl)-4-methyl-5-((R)-3-methylpiperazin-1-yl)-2,6-dioxo-2,3-dihydropyrimidin-1(6H)-yl)-1-phenylethyl) carbamate (precursor of compound 1-50) and tert-butyl((R)-2-(3-(2-fluoro-6-(trifluoromethyl)benzyl)-4-methyl-5-((S)-3-methylpiperazin-1-yl)-2,6-dioxo-2,3-dihydropyrimidin-1(6H)-yl)-1-phenylethyl)carbamate (precursor of compound 1-51) were respectively used instead of ((R)-2-{3-(2-fluoro-6-trifluoromethyl-benzyl)-4-methyl-2,6-dioxo-5-piperazin-1-yl]-3,6-dihydro-2H-pyrimidin-1-yl}-1-phenyl-ethyl)-carbamic acid tert-butyl ester (2-1) in Step A.

TABLE 3
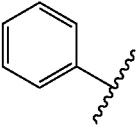 [SMILES: *c1ccccc1]
| No. | —R₃ | —Y | —A | —R₆ | M.W. | Mass |
|---|---|---|---|---|---|---|
| 3-1 | 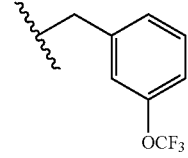 | 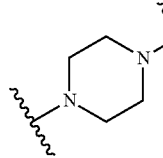 | 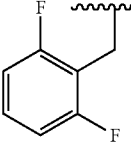 | 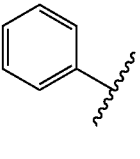 | 629.62 | 630.5 |
| 3-2 | 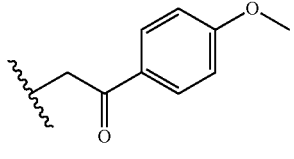 [SMILES: *CC(=O)c1ccc(OC)cc1] | 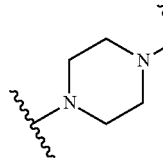 | 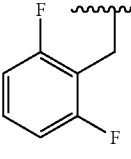 | 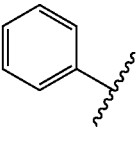 [SMILES: *c1ccccc1] | 603.66 | 604.3 |
| 3-3 | 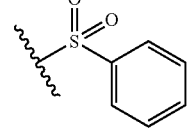 | 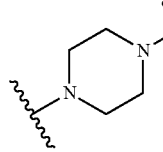 | 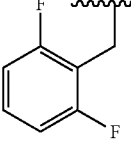 | 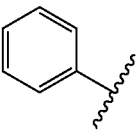 [SMILES: *c1ccccc1] | 595.66 | 596.3 |
| 3-4 | 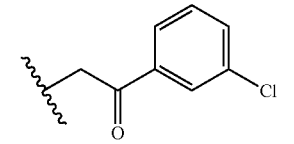 [SMILES: *CC(=O)c1cccc(Cl)c1] | 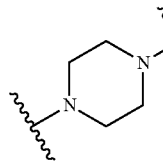 | 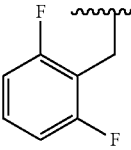 | 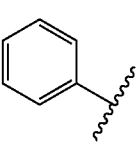 [SMILES: *c1ccccc1] | 608.08 | 609.1 |
| 3-5 | 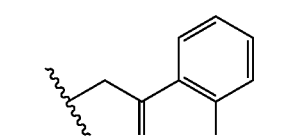 | 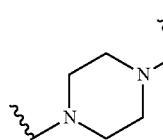 | 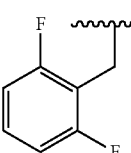 | 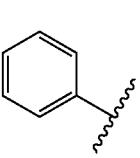 | 608.08 | 608.4 |
| 3-6 | 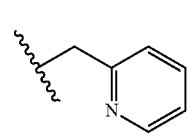 [SMILES: *Cc1ccccn1] | 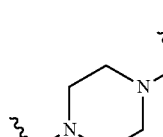 | 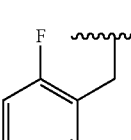 | 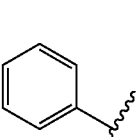 | 546.61 | 547.3 |
| 3-7 | 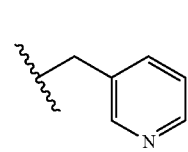 [SMILES: *Cc1cccnc1] | 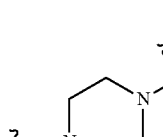 | | 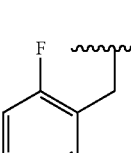 | 546.61 | 547.5 |

TABLE 3-continued
| No. | —R₃ | —Y | —A | —R₆ | M.W. | Mass |
|---|---|---|---|---|---|---|
| 3-8 | 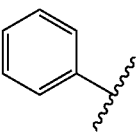 | 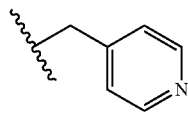 [SMILES: *Cc1ccncc1] | 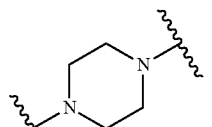 | 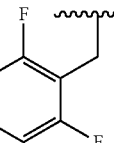 | 546.61 | 547.0 |
| 3-9 | 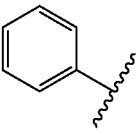 [SMILES: *c1ccccc1] | 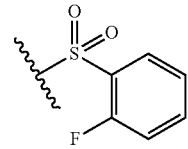 [SMILES: *S(=O)(=O)c1ccccc1F] | 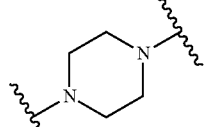 | 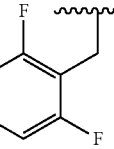 | 613.65 | 614.3 |
| 3-10 | 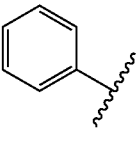 | 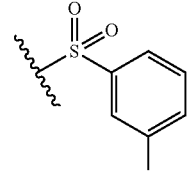 | 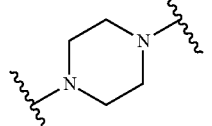 | 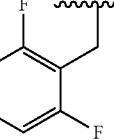 | 613.65 | 614.2 |
| 3-11 | 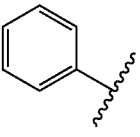 [SMILES: *c1ccccc1] | 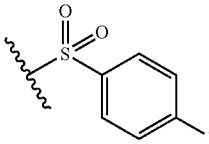 | 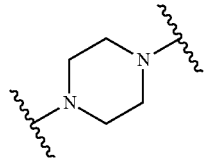 [SMILES: *N1CCN(*)CC1] | 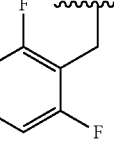 | 613.65 | 614.5 |
| 3-12 | 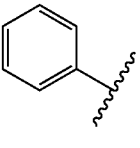 [SMILES: *c1ccccc1] | 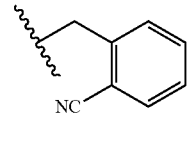 [SMILES: *Cc1ccccc1C#N] | 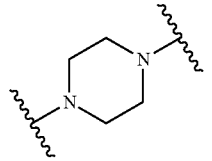 [SMILES: *N1CCN(*)CC1] | 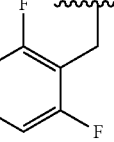 | 570.63 | 571.4 |
| 3-13 | 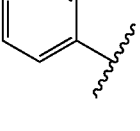 | 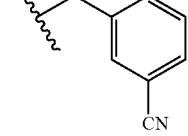 | 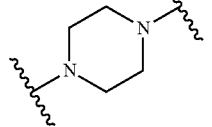 | 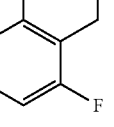 | 570.63 | 571.3 |
| 3-14 | 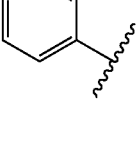 | 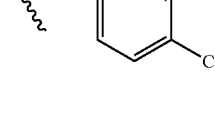 | 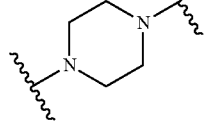 | 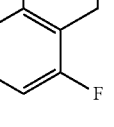 | 570.63 | 571.2 |

TABLE 3-continued

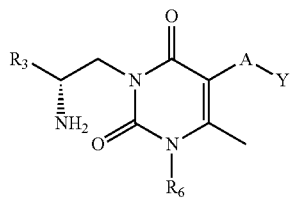

| No. | —R₃ | —Y | —A | —R₆ | M.W. | Mass |
|---|---|---|---|---|---|---|
| 3-15 | phenyl | 3-methoxybenzyl | piperazine | 2,6-difluorobenzyl | 575.65 | 576.4 |
| 3-16 | phenyl | 4-methoxybenzyl | piperazine | 2,6-difluorobenzyl | 575.65 | 576.5 |
| 3-17 | phenyl | 2-chlorobenzyl | piperazine | 2,6-difluorobenzyl | 580.07 | 580.4 |
| 3-18 | phenyl | 3-chlorobenzyl | piperazine | 2,6-difluorobenzyl | 580.07 | 580.3 |
| 3-19 | phenyl | 2-nitrobenzyl | piperazine | 2,6-difluorobenzyl | 590.62 | 591.3 |
| 3-20 | phenyl | 3-nitrobenzyl | piperazine | 2,6-difluorobenzyl | 590.62 | 591.5 |
| 3-21 | phenyl | 4-nitrobenzyl | piperazine | 2,6-difluorobenzyl | 590.62 | 591.5 |

TABLE 3-continued

| No. | —R₃ | —Y | —A | —R₆ | M.W. | Mass |
|---|---|---|---|---|---|---|
| 3-22 | phenyl | 2-methylbenzyl | piperazine | 2,6-difluorobenzyl | 559.65 | 560.5 |
| 3-23 | phenyl | 4-methylbenzyl | piperazine | 2,6-difluorobenzyl | 559.65 | 560.6 |
| 3-24 | phenyl | 2-(trifluoromethyl)benzyl | piperazine | 2,6-difluorobenzyl | 613.62 | 614.4 |
| 3-25 | phenyl | 4-fluorobenzyl | piperazine | 2,6-difluorobenzyl | 563.61 | 564.5 |
| 3-26 | phenyl | 4-(methoxycarbonyl)benzyl | piperazine | 2,6-difluorobenzyl | 603.66 | 604.4 |
| 3-27 | phenyl | 2,3-difluorobenzyl | piperazine | 2,6-difluorobenzyl | 581.60 | 582.5 |
| 3-28 | phenyl | naphthalen-2-ylmethyl | piperazine | 2,6-difluorobenzyl | 595.68 | 596.4 |

TABLE 3-continued
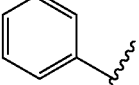
| No. | —R₃ | —Y | —A | —R₆ | M.W. | Mass |
|---|---|---|---|---|---|---|
| 3-29 | 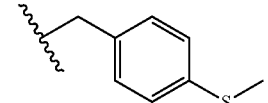 | 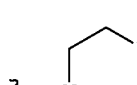 | 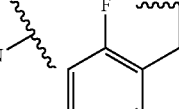 | 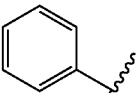 | 591.71 | 592.4 |
| 3-30 | 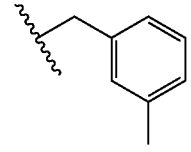 [SMILES: *Cc1cccc(C)c1] | 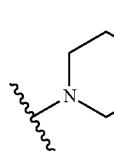 | 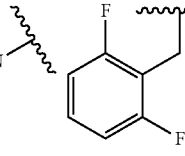 | 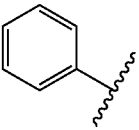 [SMILES: *c1ccccc1] | 559.66 | 560.3 |
| 3-31 | 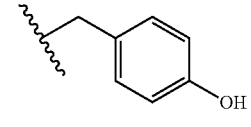 [SMILES: *Cc1ccc(O)cc1] | 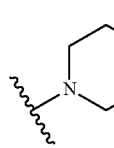 | 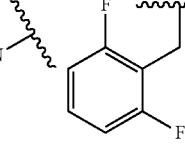 | 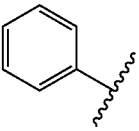 [SMILES: *c1ccccc1] | 561.63 | 562.3 |
| 3-32 | 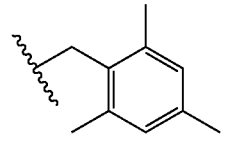 [SMILES: *Cc1c(C)cc(C)cc1C] | 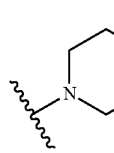 | 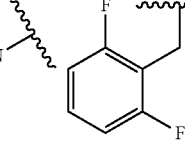 | 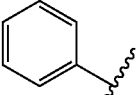 | 587.70 | 588.3 |
| 3-33 | 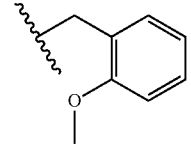 [SMILES: *Cc1ccccc1OC] | 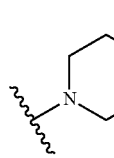 | 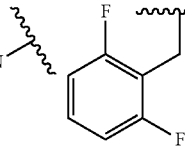 | 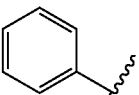 | 575.66 | 576.4 |
| 3-34 | 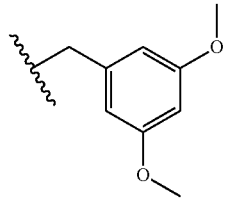 [SMILES: *Cc1cc(OC)cc(OC)c1] | 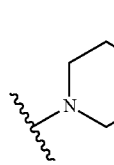 | 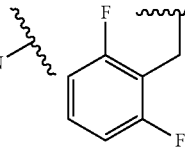 | 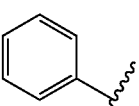 | 605.69 | 606.7 |
| 3-35 | 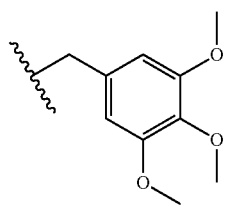 [SMILES: *Cc1cc(OC)c(OC)c(OC)c1] | 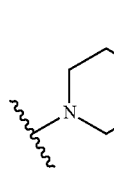 | | 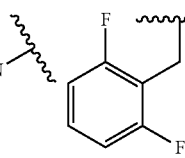 | 635.71 | 636.3 |

TABLE 3-continued

| No. | —R₃ | —Y | —A | —R₆ | M.W. | Mass |
|---|---|---|---|---|---|---|
| 3-36 | phenyl | 2,4-difluorobenzyl | piperazine | 2,6-difluorobenzyl | 581.61 | 582.4 |
| 3-37 | phenyl | 2,5-difluorobenzyl | piperazine | 2,6-difluorobenzyl | 581.61 | 582.4 |
| 3-38 | phenyl | 2,6-difluorobenzyl | piperazine | 2,6-difluorobenzyl | 581.61 | 582.4 |
| 3-39 | phenyl | 3,4-difluorobenzyl | piperazine | 2,6-difluorobenzyl | 581.61 | 582.4 |
| 3-40 | phenyl | 3,5-difluorobenzyl | piperazine | 2,6-difluorobenzyl | 581.61 | 582.4 |
| 3-41 | phenyl | 2-methoxy-3-fluorobenzyl | piperazine | 2,6-difluorobenzyl | 593.64 | 594.3 |
| 3-42 | phenyl | 3-chloro-4-fluorobenzyl | piperazine | 2,6-difluorobenzyl | 598.07 | 598.3 |

TABLE 3-continued

| No. | —R₃ | —Y | —A | —R₆ | M.W. | Mass |
|---|---|---|---|---|---|---|
| 3-43 | phenyl | 3,4,5-trifluorobenzyl | piperazine | 2,6-difluorobenzyl | 599.60 | 600.3 |
| 3-44 | phenyl | 2,3,4-trifluorobenzyl | piperazine | 2,6-difluorobenzyl | 599.60 | 600.3 |
| 3-45 | phenyl | 2,3,6-trifluorobenzyl | piperazine | 2,6-difluorobenzyl | 599.60 | 600.3 |
| 3-46 | phenyl | 2-methoxy-3,4-difluorobenzyl | piperazine | 2,6-difluorobenzyl | 611.63 | 612.5 |
| 3-47 | phenyl | 3-(trifluoromethyl)benzyl | piperazine | 2,6-difluorobenzyl | 613.63 | 614.2 |
| 3-48 | phenyl | 2-(trifluoromethoxy)benzyl | piperazine | 2,6-difluorobenzyl | 629.63 | 630.6 |
| 3-49 | phenyl | 4-(trifluoromethoxy)benzyl | piperazine | 2,6-difluorobenzyl | 629.63 | 630.2 |

TABLE 3-continued

| No. | —R₃ | —Y | —A | —R₆ | M.W. | Mass |
|---|---|---|---|---|---|---|
| 3-50 | phenyl | 2-F-3-CF₃-benzyl | piperazine | 2,6-difluorobenzyl | 631.62 | 632.4 |
| 3-51 | phenyl | 2-CF₃-6-F-benzyl | piperazine | 2,6-difluorobenzyl | 631.62 | 632.4 |
| 3-52 | phenyl | 3-CF₃-4-F-benzyl | piperazine | 2,6-difluorobenzyl | 631.62 | 632.4 |
| 3-53 | phenyl | 2-CF₃-4-F-benzyl | piperazine | 2,6-difluorobenzyl | 631.62 | 632.3 |
| 3-54 | phenyl | 3-NO₂-benzyl | piperazine | CH₃ | 478.54 | 479.74 |
| 3-55 | phenyl | 3-OCF₃-benzyl | piperazine | CH₃ | 517.54 | 518.59 |
| 3-56 | phenyl | 3-F-benzyl | piperazine | CH₃ | 451.54 | 452.28 |

TABLE 3-continued

| No. | —R₃ | —Y | —A | —R₆ | M.W. | Mass |
|---|---|---|---|---|---|---|
| 3-57 | phenyl | 3-pyridylmethyl | piperazine | CH₃ | 434.53 | 435.48 |
| 3-58 | phenyl | 3-nitrobenzyl | piperazine | 2-fluoro-6-(trifluoromethyl)benzyl | 640.63 | 641.7 |
| 3-59 | phenyl | 3-pyridylmethyl | piperazine | 2-fluoro-6-(trifluoromethyl)benzyl | 596.62 | 597.4 |
| 3-60 | phenyl | 3-(trifluoromethoxy)benzyl | piperazine | 2-fluoro-6-(trifluoromethyl)benzyl | 679.63 | 680.6 |
| 3-61 | phenyl | 3-fluorobenzyl | piperazine | 2-fluoro-6-(trifluoromethyl)benzyl | 613.62 | 614.7 |
| 3-62 | phenyl | 1-naphthylmethyl | piperazine | 2-fluoro-6-(trifluoromethyl)benzyl | 645.69 | 646.7 |
| 3-63 | phenyl | 5-fluoro-3-pyridylmethyl | piperazine | 2-fluoro-6-(trifluoromethyl)benzyl | 614.61 | 615.3 |

TABLE 3-continued

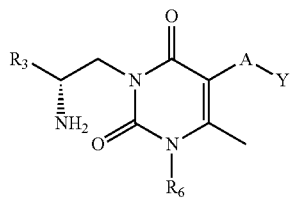

| No. | —R₃ | —Y | —A | —R₆ | M.W. | Mass |
|---|---|---|---|---|---|---|
| 3-64 | phenyl | benzothiophen-7-ylmethyl | piperazine | 2-F-6-CF₃-benzyl | 651.72 | 652.3 |
| 3-65 | phenyl | benzofurazan-4-ylmethyl | piperazine | 2-F-6-CF₃-benzyl | 637.63 | 638.3 |
| 3-66 | phenyl | (5-CF₃-furan-2-yl)methyl | piperazine | 2-F-6-CF₃-benzyl | 653.59 | 654.4 |
| 3-67 | phenyl | quinolin-8-ylmethyl | piperazine | 2-F-6-CF₃-benzyl | 646.68 | 647.4 |
| 3-68 | phenyl | benzothiazol-2-ylmethyl | piperazine | 2-F-6-CF₃-benzyl | 652.70 | 653.3 |
| 3-69 | phenyl | 2-aminobenzyl | piperazine | 2-F-6-CF₃-benzyl | 610.64 | 611.3 |
| 3-70 | phenyl | 3-aminobenzyl | piperazine | 2-F-6-CF₃-benzyl | 610.64 | 611.3 |

TABLE 3-continued

| No. | —R₃ | —Y | —A | —R₆ | M.W. | Mass |
|---|---|---|---|---|---|---|
| 3-71 | phenyl | 2-(methoxycarbonyl)benzyl | piperazine | 2-fluoro-6-(trifluoromethyl)benzyl | 653.67 | 654.17 |
| 3-72 | phenyl | 3-(methoxycarbonyl)benzyl | piperazine | 2-fluoro-6-(trifluoromethyl)benzyl | 653.67 | 654.4 |
| 3-73 | phenyl | 2-carboxybenzyl | piperazine | 2-fluoro-6-(trifluoromethyl)benzyl | 639.64 | 640.06 |
| 3-74 | phenyl | 3-carboxybenzyl | piperazine | 2-fluoro-6-(trifluoromethyl)benzyl | 639.64 | 640.37 |
| 3-75 | phenyl | 2-carbamoylbenzyl | piperazine | 2-fluoro-6-(trifluoromethyl)benzyl | 638.66 | 639.57 |
| 3-76 | phenyl | 2-cyanobenzyl | piperazine | 2-fluoro-6-(trifluoromethyl)benzyl | 620.64 | 621.5 |
| 3-77 | phenyl | 3-cyanobenzyl | piperazine | 2-fluoro-6-(trifluoromethyl)benzyl | 620.64 | 621.4 |

TABLE 3-continued
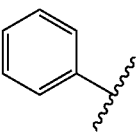
| No. | —R$_3$ | —Y | —A | —R$_6$ | M.W. | Mass |
|---|---|---|---|---|---|---|
| 3-78 | 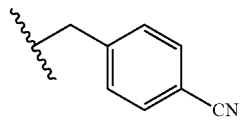 [SMILES: *Cc1ccc(C#N)cc1] | 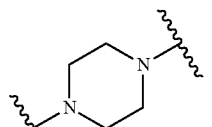 | 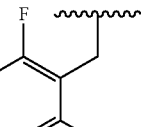 | 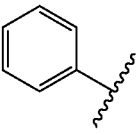 [SMILES: *c1ccccc1] | 620.64 | 621.3 |
| 3-79 | 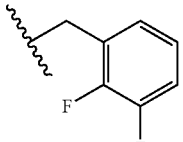 | 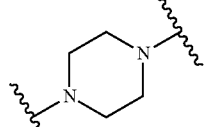 | 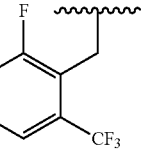 | 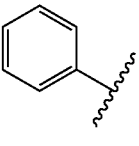 | 631.61 | 632.4 |
| 3-80 | 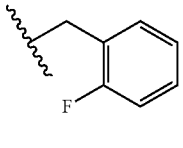 | 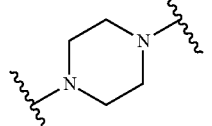 | 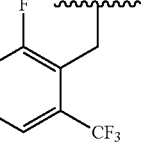 | 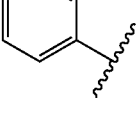 | 613.62 | 614.4 |
| 3-81 | 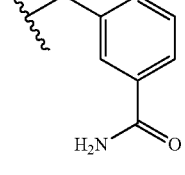 | 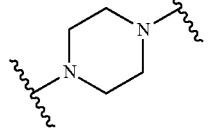 | 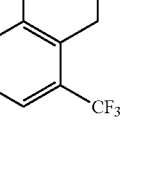 | 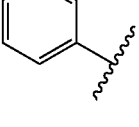 | 638.66 | 639.4 |
| 3-82 | 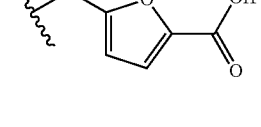 | 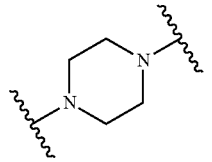 [SMILES: *N1CCN(*)CC1] | 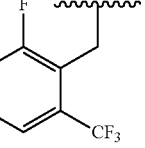 | 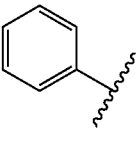 | 629.60 | 630.5 |
| 3-83 | 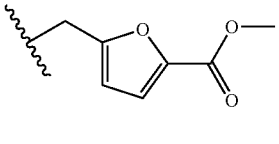 [SMILES: *Cc1ccc(C(=O)OC)o1] | 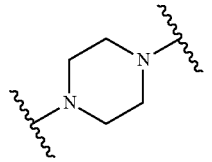 [SMILES: *N1CCN(*)CC1] | 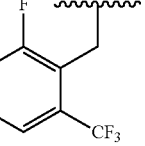 | 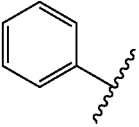 | 643.63 | 644.5 |
| 3-84 | 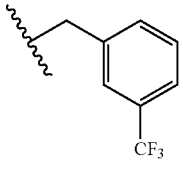 | 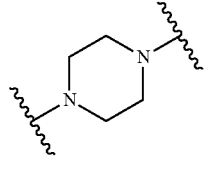 [SMILES: *N1CCN(*)CC1] | | 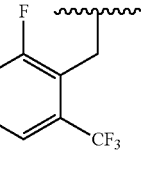 | 663.63 | 664.6 |

TABLE 3-continued

| No. | —R₃ | —Y | —A | —R₆ | M.W. | Mass |
|---|---|---|---|---|---|---|
| 3-85 | phenyl | 3-(CF₃)phenyl-CH(CO₂H)- | piperazine | 2-F-6-CF₃-benzyl | 707.64 | 708.4 |
| 3-86 | phenyl | 2-CF₃-5-methyl-furan-3-ylmethyl | piperazine | 2-F-6-CF₃-benzyl | 667.62 | 668.3 |
| 3-87 | phenyl | 6-CF₃-pyridin-3-ylmethyl | piperazine | 2-F-6-CF₃-benzyl | 664.62 | 665.3 |
| 3-88 | phenyl | 2-F-3-NO₂-benzyl | piperazine | 2-F-6-CF₃-benzyl | 658.62 | 659.5 |
| 3-89 | phenyl | 5-carbamoyl-furan-2-ylmethyl | piperazine | 2-F-6-CF₃-benzyl | 628.62 | 629.5 |
| 3-90 | phenyl | 5-(N-methylcarbamoyl)-furan-2-ylmethyl | piperazine | 2-F-6-CF₃-benzyl | 642.64 | 643.5 |
| 3-91 | phenyl | 5-(N,N-dimethylcarbamoyl)-furan-2-ylmethyl | piperazine | 2-F-6-CF₃-benzyl | 656.67 | 657.5 |

TABLE 3-continued

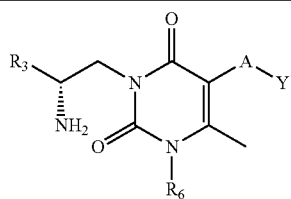

| No. | —R₃ | —Y | —A | —R₆ | M.W. | Mass |
|---|---|---|---|---|---|---|
| 3-92 | 4-F, 2-OMe-phenyl | 3-NO₂-benzyl | piperazine | 2-F, 6-CF₃-benzyl | 688.64 | 689.3 |
| 3-93 | 3-F, 5-Me-phenyl | 3-NO₂-benzyl | piperazine | 2-F, 6-CF₃-benzyl | 672.64 | 673.3 |
| 3-94 | 4-F, 2-OMe-phenyl | 3-pyridyl-methyl | piperazine | 2-F, 6-CF₃-benzyl | 644.63 | 645.3 |
| 3-95 | 3-F, 5-Me-phenyl | 3-pyridyl-methyl | piperazine | 2-F, 6-CF₃-benzyl | 628.63 | 629.3 |
| 3-96 | phenyl | 5-CF₃-1,3,4-oxadiazol-2-yl-methyl | piperazine | 2-F, 6-CF₃-benzyl | 655.57 | 656.2 |
| 3-97 | phenyl | 4-CF₃-furan-2-yl-methyl | piperazine | 2-F, 6-CF₃-benzyl | 653.59 | 654.3 |
| 3-98 | phenyl | pyrimidin-4-yl-methyl | piperazine | 2-F, 6-CF₃-benzyl | 597.61 | 598.2 |

TABLE 3-continued
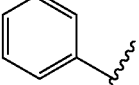
| No. | —R₃ | —Y | —A | —R₆ | M.W. | Mass |
|---|---|---|---|---|---|---|
| 3-99 | 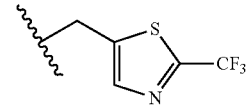 | 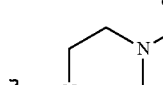 | 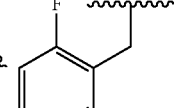 | 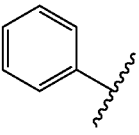 | 670.64 | 671.3 |
| 3-100 | 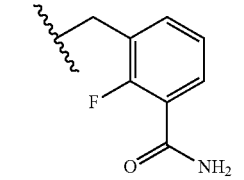 | 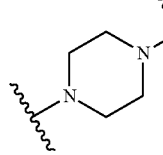 | 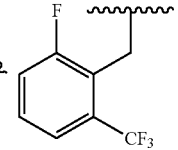 | 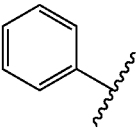 [SMILES: *c1ccccc1] | 656.65 | 657.5 |
| 3-101 | 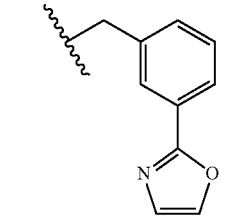 [SMILES: *Cc1cccc(-c2ncco2)c1] | 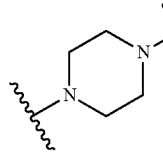 | 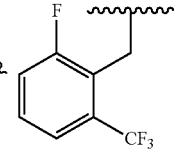 | 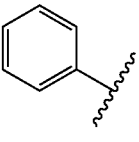 [SMILES: *c1ccccc1] | 662.68 | 663.6 |
| 3-102 | 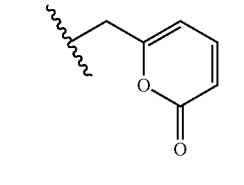 [SMILES: *Cc1cccc(=O)o1] | 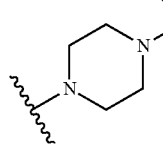 | 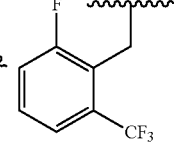 | 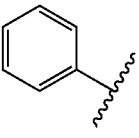 | 613.60 | 614.4 |
| 3-103 | 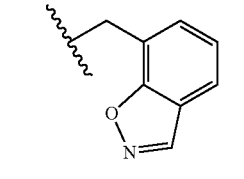 [SMILES: *Cc1cccc2cnoc12] | 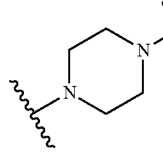 | 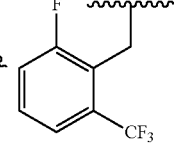 | 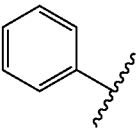 [SMILES: *c1ccccc1] | 636.64 | 637.2 |
| 3-104 | 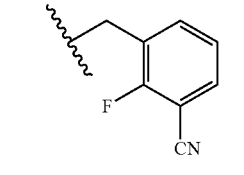 [SMILES: *Cc1cccc(C#N)c1F] | 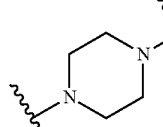 | 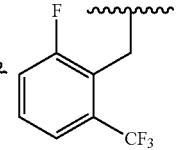 | 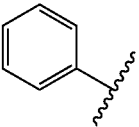 [SMILES: *c1ccccc1] | 638.63 | 639.4 |
| 3-105 | 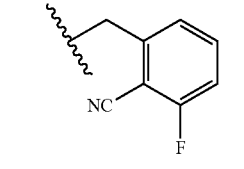 [SMILES: *Cc1cccc(F)c1C#N] | 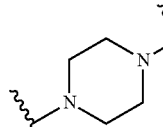 | | 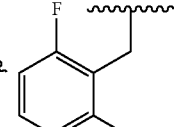 | 638.63 | 639.5 |

TABLE 3-continued

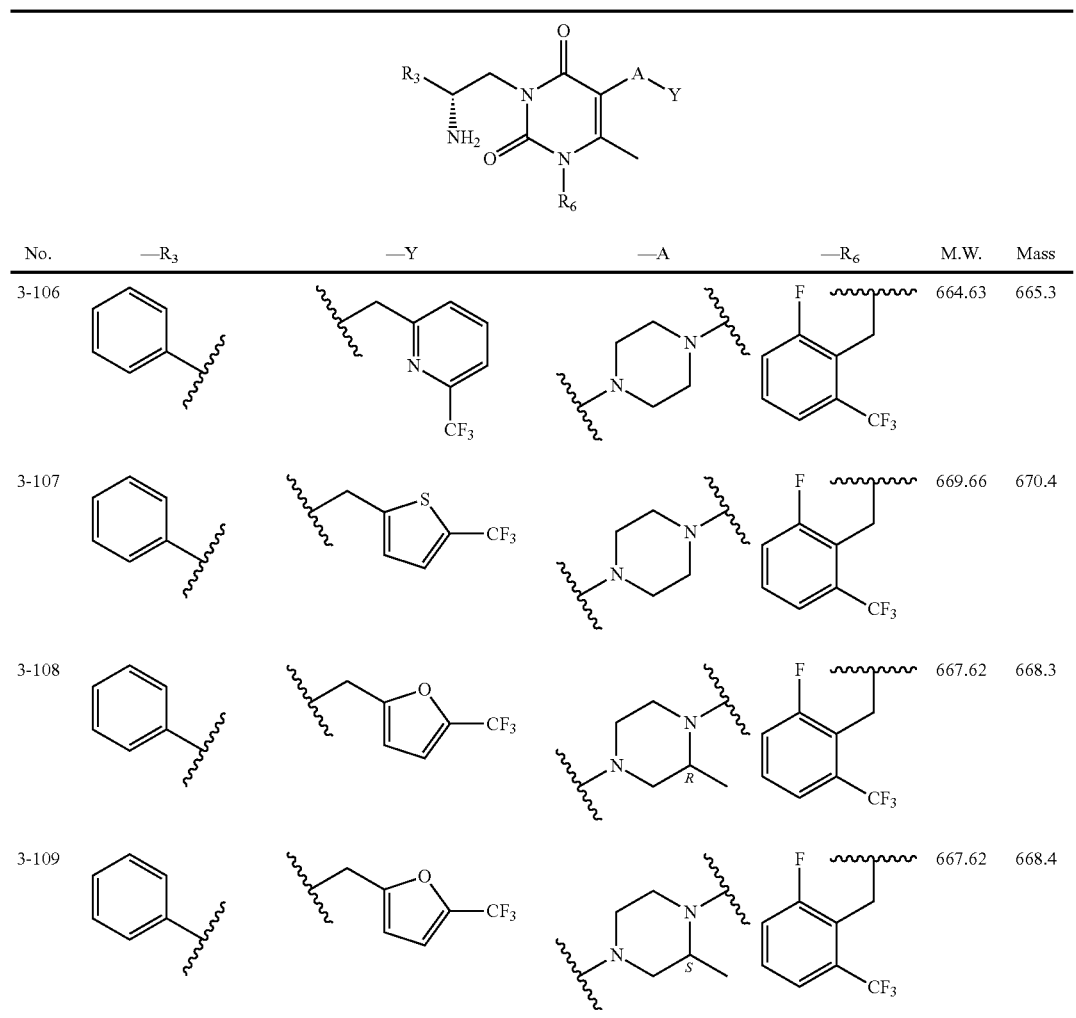

| No. | —R₃ | —Y | —A | —R₆ | M.W. | Mass |
|---|---|---|---|---|---|---|
| 3-106 | phenyl | (6-trifluoromethyl-pyridin-2-yl)methyl | piperazine | 2-fluoro-6-trifluoromethyl-benzyl | 664.63 | 665.3 |
| 3-107 | phenyl | (5-trifluoromethyl-thiophen-2-yl)methyl | piperazine | 2-fluoro-6-trifluoromethyl-benzyl | 669.66 | 670.4 |
| 3-108 | phenyl | (5-trifluoromethyl-furan-2-yl)methyl | (R)-2-methyl-piperazine | 2-fluoro-6-trifluoromethyl-benzyl | 667.62 | 668.3 |
| 3-109 | phenyl | (5-trifluoromethyl-furan-2-yl)methyl | (S)-2-methyl-piperazine | 2-fluoro-6-trifluoromethyl-benzyl | 667.62 | 668.4 |

Compound 3-110 was prepared in the same manner as above, with the exception that {(R)-2-[2-(2-fluoro-6-trifluoromethyl-benzyl)-3,5-dioxo-6-piperazin-1-yl-2,5-dihydro-3H-[1,2,4]triazin-4-yl]-1-phenyl-ethyl}-carbamic acid tert-butyl ester(2-4) was used instead of ((R)-2-{3-(2-fluoro-6-trifluoromethyl-benzyl)-4-methyl-2,6-dioxo-5-piperazin-1-yl]-3,6-dihydro-2H-pyrimidin-1-yl}-1-phenyl-ethyl)-carbamic acid tert-butyl ester(2-1) in Step A.

Compound 3-111 was prepared in the same manner as above, with the exception that {(R)-2-[2-(2-fluoro-6-trifluoromethyl-benzyl)-3,5-dioxo-6-piperazin-1-yl-2,5-dihydro-3H-[1,2,4]triazin-4-yl]-1-phenyl-ethyl}-carbamic acid tert-butyl ester(2-4), instead of ((R)-2-{3-(2-fluoro-6-trifluoromethyl-benzyl)-4-methyl-2,6-dioxo-5-piperazin-1-yl]-3,6-dihydro-2H-pyrimidin-1-yl}-1-phenyl-ethyl)-carbamic acid tert-butyl ester(2-1), and a different bromomethyl compound, instead of 2-bromomethyl-5-trifluoromethyl-furan, were used in Step A.

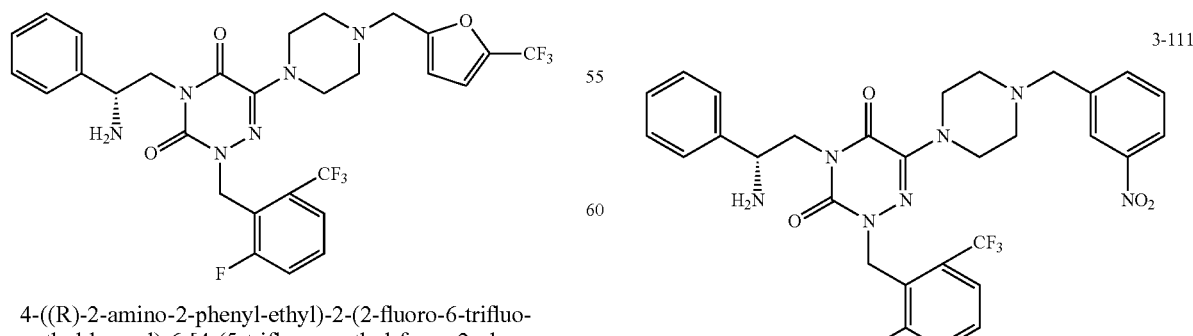

4-((R)-2-amino-2-phenyl-ethyl)-2-(2-fluoro-6-trifluoromethyl-benzyl)-6-[4-(5-trifluoromethyl-furan-2-ylmethyl)-piperazin-1-yl]-2H-[1,2,4]triazine-3,5-dione(3-110)
MS (ESI) m/z 641.3 (MH⁺)

4-((R)-2-amino-2-phenyl-ethyl)-2-(2-fluoro-6-trifluoromethyl-benzyl)-6-[4-(3-nitro-benzyl)-piperazin-1-yl]-2H-[1,2,4]triazine-3,5-dione(3-111) MS (ESI) m/z 628.4 (MH$^+$)

Example 4

Synthesis of 3-((R)-2-Amino-2-phenyl-ethyl)-1-(2,6-difluoro-benzyl)-6-methyl-5-[4-(2-hydroxy-benzyl)-piperazin-1-yl]-1H-pyrimidine-2,4-dione (4-1)

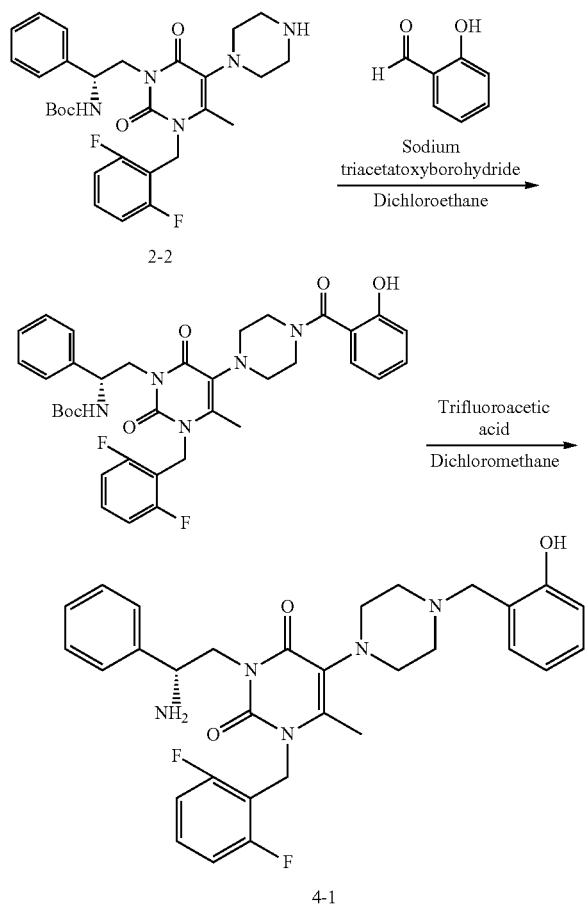

Step A. ((R)-2-{3-(2,6-difluoro-benzyl)-5-[4-(2-hydroxy-benzyl)-piperazin-1-yl]-4-methyl-2,6-dioxo-3,6-dihydro-2H-pyrimidin-1-yl}-1-phenyl-ethyl)-carbamic acid tert-butyl ester To a solution of ((R)-2-{3-(2,6-difluoro-benzyl)-4-methyl-2,6-dioxo-5-piperazin-1-yl]-3,6-dihydro-2H-pyrimidin-1-yl}-1-phenyl-ethyl)-carbamic acid tert-butyl ester (30 mg, 0.054 mmol) in 1 mL of dichloroethane was added 2-hydroxy-benzaldehyde(6.9 μl, 0.066 mmol), with stirring at room temperature for 10 min. Again, NaBH(OAc)$_3$ (14 mg, 0.066 mmol) was added, with stirring for 2 hrs. After being concentrated, the reaction solution was neutralized with an aqueous saturated sodium bicarbonate solution before extraction with dichloromethane. The organic layer thus formed was separated and mixed with sodium sulfate, with stirring for 5 min, after which the mixture was filtered. The filtrate was concentrated, and the residue was purified using silica gel chromatography (eluent: dichloromethane/methanol, 20/1) and dried in a vacuum to afford 17 mg of the compound as a colorless oil (yield 48%).

Step B. 3-((R)-2-amino-2-phenyl-ethyl)-1-(2,6-difluoro-benzyl)-6-methyl-5-[4-(2-hydroxy-benzyl)-piperazin-1-yl]-1H-pyrimidine-2,4-dione (4-1)

To a solution of ((R)-2-[3-(2,6-difluoro-benzyl)-5-[4-(2-hydroxy-benzyl)-piperazin-1-yl]-4-methyl-2,6-dioxo-3,6-dihydro-2H-pyrimidin-1-yl]-1-phenyl-ethyl)-carbamic acid tert-butyl ester (17 mg, 0.026 mmol) in dichloromethane (2 mL) which was chilled to 0° C., trifluoroacetic acid (200 μl, 2.6 mmol) was slowly added. This solution was stirred at room temperature for 3 hrs, chilled again to 0° C., and slowly neutralized with an aqueous saturated sodium bicarbonate solution to separate an organic layer. Sodium sulfate was added to the separated organic layer which was then stirred for 5 min and filtered. The filtrate was concentrated, and the residue was purified using silica gel chromatography (eluent: dichloromethane/methanol, 10/1) and dried in a vacuum to afford 11 mg of the compound as a white foam (yield 75%). $^1$H NMR (300 MHz, CDCl$_3$) δ 2.27 (2H, m), 2.42 (3H, s), 2.54 (2H, m), 2.91 (2H, m), 3.63 (2H, m), 3.72 (2H, s), 4.04 (1H, dd), 4.19 (1H, dd), 4.35 (1H, dd), 5.21 (2H, dd), 6.75-6.98 (5H, m), 7.15-7.34 (5H, m), 7.39 (2H, m), MS (ESI) m/z 562.4 (MH$^+$)

Compounds synthesized according to the procedures are summarized in Table 4, below. Compounds 4-1 to 4-12 were prepared in the same manner as in the procedures above, with the exception that different aldehyde compounds were used instead of 2-hydroxy-benzaldehyde in Step A. Compounds 4-13 to 4-55 were prepared in the same manner as in the procedures above, with the exception that ((R)-2-{3-(2-fluoro-6-trifluoromethyl-benzyl)-4-methyl-2,6-dioxo-5-piperazin-1-yl}-3,6-dihydro-2H-pyrimidin-1-yl}-1-phenyl-ethyl)-carbamic acid tert-butyl ester(2-1), instead of ((R)-2-{3-(2,6-difluoro-benzyl)-4-methyl-2,6-dioxo-5-piperazin-1-yl]-3,6-dihydro-2H-pyrimidin-1-yl}-1-phenyl-ethyl)-carbamic acid tert-butyl ester(2-2), and different aldehyde compounds, instead of 2-hydroxy-benzaldehyde, were used in Step A.

TABLE 4

| No. | —Y | —R$_6$ | M.W. | Mass |
|---|---|---|---|---|
| 4-1 | 2-hydroxybenzyl | 2,6-difluorobenzyl | 561.63 | 562.4 |
| 4-2 | 3-hydroxybenzyl | 2,6-difluorobenzyl | 561.63 | 562.4 |

TABLE 4-continued

| No. | —Y | —R6 | M.W. | Mass |
|---|---|---|---|---|
| 4-3 | 2,3-dimethylbenzyl | 2,6-difluorobenzyl | 573.68 | 574.4 |
| 4-4 | 2,4-dimethylbenzyl | 2,6-difluorobenzyl | 573.68 | 574.5 |
| 4-5 | 2,5-dimethylbenzyl | 2,6-difluorobenzyl | 573.68 | 574.5 |
| 4-6 | 2,6-dimethylbenzyl | 2,6-difluorobenzyl | 573.68 | 574.4 |
| 4-7 | 3,4-dimethylbenzyl | 2,6-difluorobenzyl | 573.68 | 574.5 |
| 4-8 | 3,5-dimethylbenzyl | 2,6-difluorobenzyl | 573.68 | 574.5 |
| 4-9 | 2-hydroxy-3-methylbenzyl | 2,6-difluorobenzyl | 575.65 | 576.4 |
| 4-10 | 2-hydroxy-5-methylbenzyl | 2,6-difluorobenzyl | 575.65 | 576.4 |
| 4-11 | 4-hydroxy-3-methylbenzyl | 2,6-difluorobenzyl | 575.65 | 576.5 |
| 4-12 | 3,4-dimethoxybenzyl | 2,6-difluorobenzyl | 605.69 | 606.4 |
| 4-13 | 1H-imidazol-4-ylmethyl | 2-fluoro-6-(trifluoromethyl)benzyl | 585.60 | 586.3 |
| 4-14 | (2-fluoropyridin-3-yl)methyl | 2-fluoro-6-(trifluoromethyl)benzyl | 614.61 | 615.3 |
| 4-15 | (6-methylpyridin-3-yl)methyl | 2-fluoro-6-(trifluoromethyl)benzyl | 610.64 | 611.4 |
| 4-16 | (2-methoxypyridin-3-yl)methyl | 2-fluoro-6-(trifluoromethyl)benzyl | 626.64 | 627.4 |
| 4-17 | 1H-imidazol-2-ylmethyl | 2-fluoro-6-(trifluoromethyl)benzyl | 585.60 | 586.4 |
| 4-18 | (2-aminopyridin-3-yl)methyl | 2-fluoro-6-(trifluoromethyl)benzyl | 611.63 | 612.3 |
| 4-19 | (2-chloropyridin-3-yl)methyl | 2-fluoro-6-(trifluoromethyl)benzyl | 631.06 | 631.4 |
| 4-20 | (6-chloropyridin-3-yl)methyl | 2-fluoro-6-(trifluoromethyl)benzyl | 631.06 | 631.4 |
| 4-21 | (2-methylpyridin-3-yl)methyl | 2-fluoro-6-(trifluoromethyl)benzyl | 610.64 | 611.4 |
| 4-22 | (5-methylpyridin-3-yl)methyl | 2-fluoro-6-(trifluoromethyl)benzyl | 610.64 | 611.4 |

TABLE 4-continued

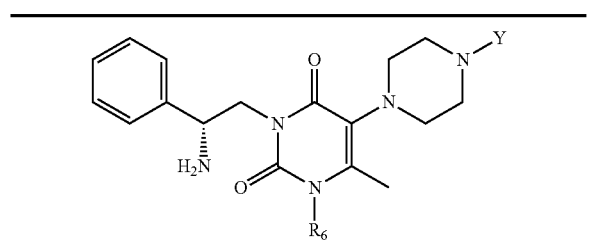

| No. | —Y | —R$_6$ | M.W. | Mass |
|---|---|---|---|---|
| 4-23 | 5-methoxypyridin-2-yl-methyl | 2-F-6-CF$_3$-benzyl | 626.64 | 627.3 |
| 4-24 | 4-methoxypyridin-3-yl-methyl | 2-F-6-CF$_3$-benzyl | 626.64 | 627.4 |
| 4-25 | 1-methylimidazol-2-yl-methyl | 2-F-6-CF$_3$-benzyl | 599.62 | 600.4 |
| 4-26 | 4-hydroxy-3-nitrobenzyl | 2-F-6-CF$_3$-benzyl | 656.63 | 657.2 |
| 4-27 | 3-fluoro-4-hydroxybenzyl | 2-F-6-CF$_3$-benzyl | 629.62 | 630.5 |
| 4-28 | 2-fluoro-4-hydroxybenzyl | 2-F-6-CF$_3$-benzyl | 629.62 | 630.6 |
| 4-29 | 2-oxo-1H-pyridin-5-yl-methyl | 2-F-6-CF$_3$-benzyl | 612.62 | 613.10 |
| 4-30 | pyrazin-2-yl-methyl | 2-F-6-CF$_3$-benzyl | 597.61 | 598.5 |
| 4-31 | 2-oxo-1H-pyridin-3-yl-methyl | 2-F-6-CF$_3$-benzyl | 612.62 | 613.6 |

TABLE 4-continued

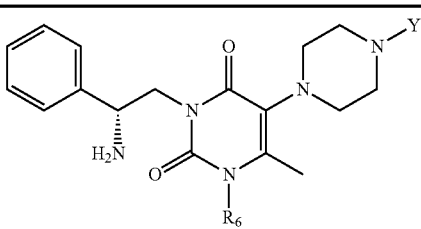

| No. | —Y | —R$_6$ | M.W. | Mass |
|---|---|---|---|---|
| 4-32 | thiazol-5-yl-methyl | 2-F-6-CF$_3$-benzyl | 602.65 | 603.4 |
| 4-33 | thiazol-4-yl-methyl | 2-F-6-CF$_3$-benzyl | 602.65 | 603.4 |
| 4-34 | thiazol-2-yl-methyl | 2-F-6-CF$_3$-benzyl | 602.65 | 603.4 |
| 4-35 | oxazol-4-yl-methyl | 2-F-6-CF$_3$-benzyl | 586.58 | 587.5 |
| 4-36 | isoxazol-3-yl-methyl | 2-F-6-CF$_3$-benzyl | 586.58 | 587.5 |
| 4-37 | 1-methylpyrazol-3-yl-methyl | 2-F-6-CF$_3$-benzyl | 599.62 | 600.5 |
| 4-38 | 1-methylpyrazol-4-yl-methyl | 2-F-6-CF$_3$-benzyl | 599.62 | 600.4 |
| 4-39 | 1-methylpyrazol-5-yl-methyl | 2-F-6-CF$_3$-benzyl | 599.62 | 600.5 |
| 4-40 | furan-2-yl-methyl | 2-F-6-CF$_3$-benzyl | 585.59 | 586.4 |
| 4-41 | furan-3-yl-methyl | 2-F-6-CF$_3$-benzyl | 585.59 | 586.4 |

TABLE 4-continued

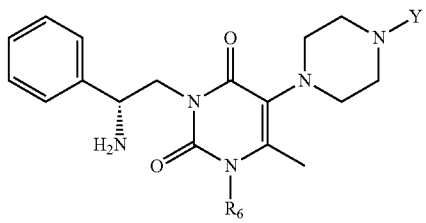

| No. | —Y | —R6 | M.W. | Mass |
|---|---|---|---|---|
| 4-42 | furan-Cl | 2-F-6-CF3-benzyl | 620.04 | 620.4 |
| 4-43 | thiophene | 2-F-6-CF3-benzyl | 601.66 | 602.4 |
| 4-44 | 3-(methylsulfonyl)benzyl | 2-F-6-CF3-benzyl | 673.72 | 674.6 |
| 4-45 | 5-cyanofuran-2-yl-methyl | 2-F-6-CF3-benzyl | 610.60 | 611.5 |
| 4-46 | 3-acetylbenzyl | 2-F-6-CF3-benzyl | 637.67 | 638.5 |
| 4-47 | 2-CF3-pyridin-3-yl-methyl | 2-F-6-CF3-benzyl | 664.62 | 665.1 |
| 4-48 | 4-hydroxy-3-CF3-benzyl | 2-F-6-CF3-benzyl | 679.63 | 680.4 |
| 4-49 | benzofuran-4-yl-methyl | 2-F-6-CF3-benzyl | 635.65 | 636.5 |
| 4-50 | 5-methylfuran-2-yl-methyl | 2-F-6-CF3-benzyl | 599.62 | 600.6 |

TABLE 4-continued

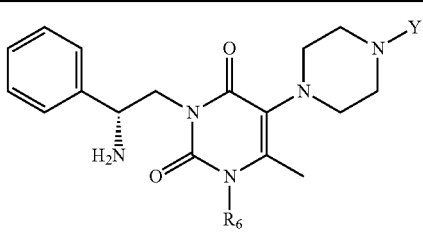

| No. | —Y | —R6 | M.W. | Mass |
|---|---|---|---|---|
| 4-51 | 3-acetoxybenzyl | 2-F-6-CF3-benzyl | 653.67 | 654.5 |
| 4-52 | 5-tert-butylfuran-2-yl-methyl | 2-F-6-CF3-benzyl | 641.70 | 642.3 |
| 4-53 | methyl 5-(methyl)-1H-pyrrole-2-carboxylate | 2-F-6-CF3-benzyl | 642.64 | 643.6 |
| 4-54 | pyrrolizinone | 2-F-6-CF3-benzyl | 638.66 | 639.5 |
| 4-55 | 3-(methylsulfinyl)benzyl | 2-F-6-CF3-benzyl | 657.72 | 658.6 |

Example 5

Synthesis of 1-(2-Fluoro-6-trifluoromethyl-benzyl)-6-methyl-5-[4-(3-nitro-benzyl)-piperazin-1-yl-1H-pyrimidine-2,4-dione(5-2)

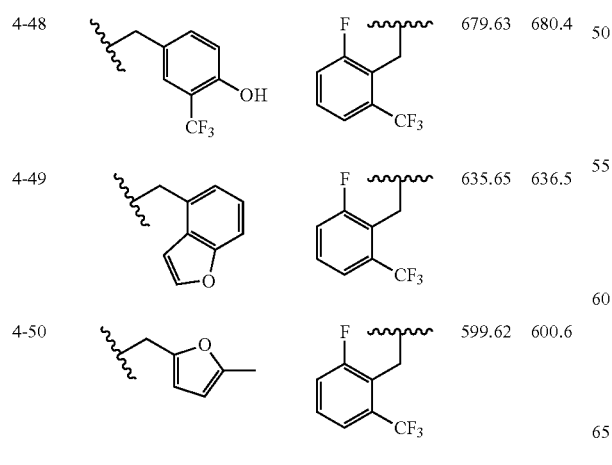

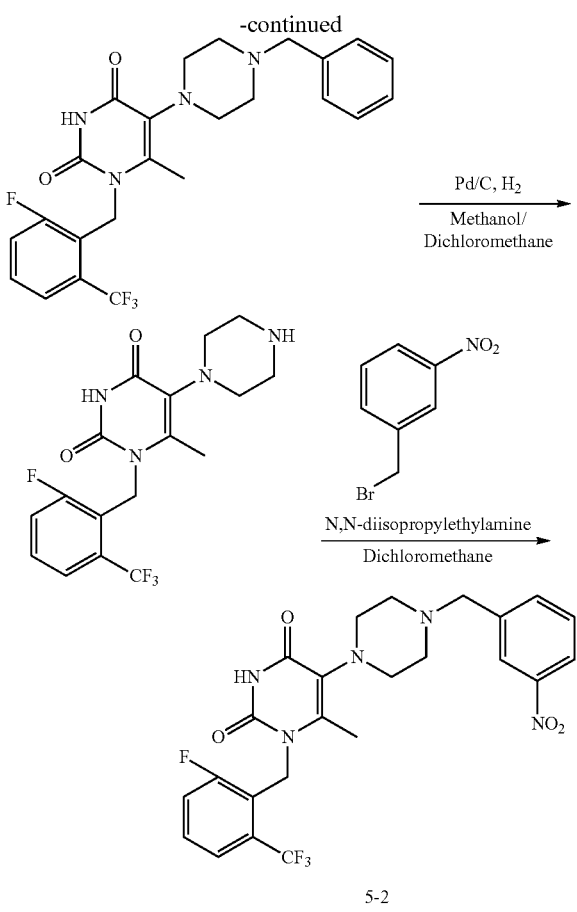

centration, the residue was purified using silica gel chromatography (eluent: hexane/ethyl acetate/dichloromethane, 1/2/1) and dried in a vacuum to afford the 1.48 g of the compound as a white solid (yield 79%). $^1$H NMR (300 MHz, CDCl$_3$) δ 2.15 (2H, m), 2.31 (3H, s), 2.50 (2H, m), 2.78 (2H, m), 3.52 (3H, s), 3.58 (2H, m), 5.36 (2H, s), 7.19-7.41 (7H, m), 7.53 (1H, d)

Step B. 1-(2-fluoro-6-trifluoromethyl-benzyl)-6-methyl-5-piperazin-1-yl-1H-pyrimidine-2,4-dione To a solution of 5-(4-benzyl-piperazin-1-yl)-1-(2-fluoro-6-trifluoromethyl-benzyl)-6-methyl-1H-pyrimidine-2,4-dione (1.48 g, 3.11 mmol) in 10 mL of methanol/dichloromethane (1/1) was added 10% palladium/carbon (280 mg), after which the solution was stirred at room temperature for 5 hrs in a hydrogen atmosphere. Following the removal of palladium/carbon therefrom by filtration through cellite, the solution was concentrated. The residue was purified using amine silica gel chromatography (eluent: dichloromethane/methanol, 30/1→10/1) and dried in a vacuum to afford 934 mg of the compound as a white solid. (yield 79%). $^1$H NMR (300 MHz, CDCl$_3$) δ 2.32 (3H, s), 2.52 (2H, m), 2.83 (2H, m), 2.96 (2H, m), 3.43 (2H, m), 5.37 (2H, s), 7.22 (1H, d), 7.40 (1H, dd), 7.54 (1H, d)

Step C. 1-(2-fluoro-6-trifluoromethyl-benzyl)-6-methyl-5-[4-(3-nitro-benzyl)-piperazin-1-yl-1H-pyrimidine-2,4-dione(5-2)

A solution of 1-(2-fluoro-6-trifluoromethyl-benzyl)-6-methyl-5-piperazin-1-yl-1H-pyrimidine-2,4-dione (1.93 g, 5.00 mmol), N,N-diisopropylethylamine (4.5 mL, 25.0 mmol), and 3-nitro-benzyl bromide (1.60 g, 7.50 mmol) in 50 mL of 1,2-dichloroethane was stirred at 50° C. for 2 hrs in a nitrogen atmosphere, cooled to room temperature, washed with an aqueous saturated ammonium chloride solution, and concentrated. The residue was purified using silica gel chromatography (eluent: dichloromethane/methanol, 30/1) and dried in a vacuum to afford 2.30 g of the compound as a yellowish foam (yield 77%).

Compounds synthesized according to the above procedures are summarized in Table 5, below. Compounds 5-1, 5-3 and 5-4 were prepared in the same manner as in the above procedures, with the exception that different amines were used instead of 3-nitro-benzyl bromide in Step C.

Step A. 5-(4-benzyl-piperazin-1-yl)-1-(2-fluoro-6-trifluoromethyl-benzyl)-6-methyl-1H-pyrimidine-2,4-dione 5-bromo-1-(2-fluoro-6-trifluoromethyl-benzyl)-6-methyl-1H-pyrimidine-2,4-dione (1.50 g, 3.94 mmol), 1-benzyl-piperazine (5.5 mL, 31.5 mmol), and acetonitrile (1 mL) were placed in a microwave vessel and heated at 120° C. for 1.5 hr by microwave irradiation with stirring. Following con-

TABLE 5

| No. | —R$_6$ | —Y | M.W. | Mass |
|---|---|---|---|---|
| 5-1 | (2-fluoro-6-trifluoromethyl-benzyl) | (3-fluoro-benzyl) | 494.46 | 495.4 |

TABLE 5-continued
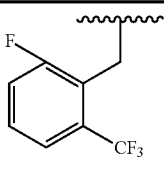
| No. | —R₆ | —Y | M.W. | Mass |
|---|---|---|---|---|
| 5-2 | 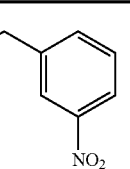 | 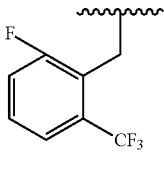 | 521.46 | 522.1 |
| 5-3 | 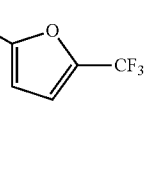 | 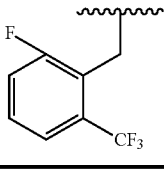 | 534.43 | 535.2 |
| 5-4 | 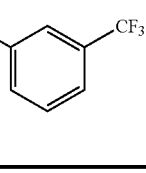 | 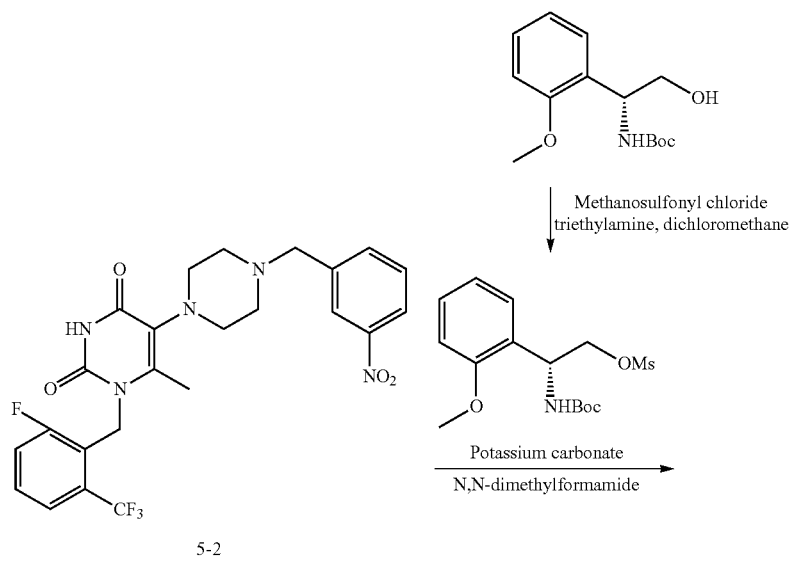 | 544.46 | 545.4 |
Example 6
Synthesis of 3-[(R)-2-Amino-2-(2-methoxy-phenyl)-ethyl]-1-(2-fluoro-6-trifluoromethyl-benzyl)-6-methyl-5-[4-(3-nitro-benzyl)-piperazin-1-yl]-1H-pyrimidine-2,4-dione (6-2)
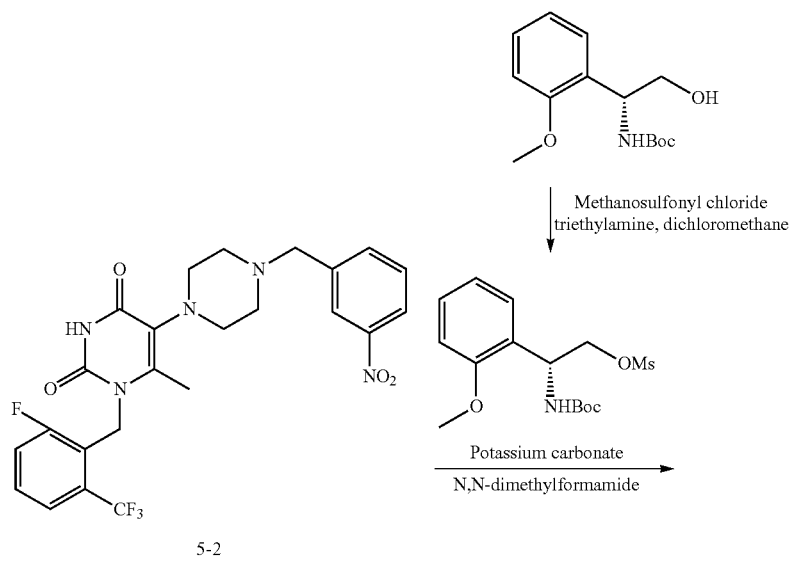
5-2

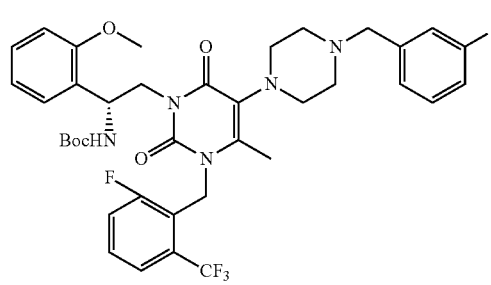 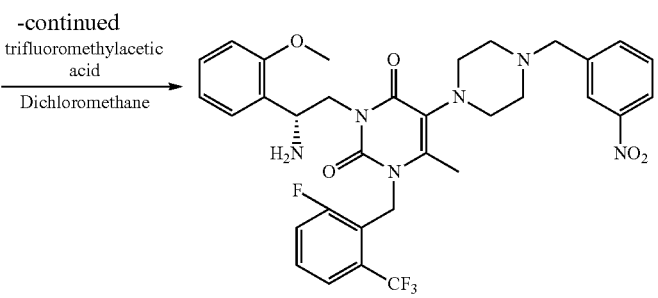

6-2

Step A. [(R)-2-{3-(2-fluoro-6-trifluoromethyl-benzyl)-4-methyl-5-[4-(3-nitro-benzyl)-piperazin-1-yl]-2,6-dioxo-3,6-dihydro-2H-pyrimidin-1-yl}-1-(2-methoxy-phenyl)-ethyl]-carbamic acid tert-butyl ester To a solution of [(R)-2-hydroxy-1-(2-methoxy-phenyl)-ethyl]-carbamic acid tert-butyl ester(5-2) (90 mg, 0.336 mmol) in dichloromethane (2 mL) were added triethylamine (61 μl, 0.44 mmol) and methanesulfonyl chloride (27 μl, 0.35 mmol) in the order. The solution was stirred at room temperature for 20 min and washed with an aqueous saturated sodium bicarbonate solution to separate an organic layer. The organic layer was dried with sodium sulfate and filtered. After concentration, the filtrate was dried for 30 min in a vacuum to give methanesulfonic acid (R)-2-tert-butoxycarbonylamino-2-2-methoxy-phenyl)-ethyl ester. Methanesulfonic acid (R)-2-tert-butoxycarbonylamino-2-2-methoxy-phenyl)-ethyl ester, 1-(2-fluoro-6-trifluoromethyl-benzyl)-6-methyl-5-[4-(3-nitro-benzyl)-piperazin-1-yl-1H-pyrimidine-2,4-dione (5-2) (50 mg, 0.096 mmol), and potassium carbonate (66 mg, 0.48 mmol) were dissolved at 70° C. for 12 hrs in DMF (1.5 ml) in a nitrogen atmosphere, with stirring. The solution was cooled to room temperature, diluted with dichloromethane, and washed with an aqueous saturated sodium bicarbonate solution. The organic layer thus formed was separated and concentrated, and the residue was purified using silica gel chromatography (eluent: hexane/ethyl acetate, 2/1) and dried in a vacuum to afford 31 mg of the compound as a yellowish foam (yield 42%).

Step B. 3-[(R)-2-amino-2-(2-methoxy-phenyl)-ethyl]-1-(2-fluoro-6-trifluoromethyl-benzyl)-6-methyl-5-[4-(3-nitro-benzyl)-piperazin-1-yl]-1H-pyrimidine-2,4-dione (6-2)

To a solution of [(R)-2-{3-(2-fluoro-6-trifluoromethyl-benzyl)-4-methyl-5-[4-(3-nitro-benzyl)-piperazin-1-yl]-2,6-dioxo-3,6-dihydro-2H-pyrimidin-1-yl}-1-(2-methoxy-phenyl)-ethyl]-carbamic acid tert-butyl ester (31 mg, 1.08 mmol) in dichloromethane (2 mL) was slowly added trifluoroacetic acid (100 μl, 1.30 mmol), followed by stirring at room temperature for 3 hrs. The solution was neutralized by slowly adding an aqueous saturated sodium bicarbonate. The organic layer thus formed was separated and concentrated, after which the residue was purified using silica gel chromatography (eluent: dichloromethane/methanol, 15/1) and dried in a vacuum to afford 22 mg of the compound as a white foam (yield 81%). $^1$H NMR (300 MHz, CDCl$_3$) δ 2.19 (2H, m), 2.30 (3H, s), 2.47 (2H, m), 2.73 (2H, d), 3.59 (4H, m), 3.86 (3H, s), 4.15 (1H, m), 4.38 (1H, t), 4.47 (1H, dd), 5.39 (2H, dd), 6.86 (2H, m), 7.16-7.26 (3H, m), 7.38 (1H, m), 7.48 (1H, t), 7.53 (1H, d), 7.75 (1H, d), 8.08 (1H, dd), 8.17 (1H, s)

Compounds synthesized according to the above procedures are summarized in Table 6, below. Compounds 6-1 to 6-6 were prepared in the same manner as in the above procedures, with the exception that different alcohols were used instead of [(R)-2-hydroxy-1-(2-methoxy-phenyl)-ethyl]-carbamic acid tert-butyl ester in Step A. Compounds 6-7 to 6-17, 6-19, and 6-20 were prepared in the same manner as in the above procedures, with the exception that 1-(2-fluoro-6-trifluoromethyl-benzyl)-6-methyl-5-[4-(5-trifluoromethyl-furan-2-ylmethyl)-piperazin-1-yl]-1H-pyrimidine-2,4-dione (5-3), instead of 1-(2-fluoro-6-trifluoromethyl-benzyl)-6-methyl-5-[4-(3-nitro-benzyl)-piperazin-1-yl-1H-pyrimidine-2,4-dione(5-2), and different alcohols, instead of [(R)-2-hydroxy-1-(2-methoxy-phenyl)-ethyl]-carbamic acid tert-butyl ester, were used in Step A. In this regard, the alcohols were prepared by reducing their precursors, that is, amino acids, into amino alcohols in the presence of lithium aluminum hydride (LiAlH$_4$) and introducing the protecting group Boc into the amine moiety. In the case of compounds 6-10 and 6-11, 4-(1-amino-2-hydroxy-ethyl)-benzo acid methyl ester was used as the alcohol and subjected to hydrolysis between Steps A and B. Compound 6-18 was prepared in the same manner as in the above procedures, with the exception that 1-(2-fluoro-6-trifluoromethyl-benzyl)-6-methyl-5-[4-(3-trifluoromethylbenzyl)-piperazin-1-yl]-1H-pyrimidine-2,4-dione(5-4), instead of 1-(2-fluoro-6-trifluoromethyl-benzyl)-6-methyl-5-[4-(3-nitro-benzyl)-piperazin-1-yl-1H-pyrimidine-2,4-dione(5-2), and a different alcohol, instead of [(R)-2-hydroxy-1-(2-methoxy-phenyl)-ethyl]-carbamic acid tert-butyl ester, were used in Step A.

TABLE 6

| No. | —R₃ | * | —Y | M.W. | Mass |
|---|---|---|---|---|---|
| 6-1 | 2-methylphenyl | RS | 3-nitrobenzyl | 654.65 | 655.5 |
| 6-2 | 2-methoxyphenyl | R | 3-nitrobenzyl | 670.65 | 671.3 |
| 6-3 | 2-fluorophenyl | RS | 3-nitrobenzyl | 658.62 | 659.7 |
| 6-4 | 3-methylphenyl | RS | 3-nitrobenzyl | 654.65 | 655.6 |
| 6-5 | 4-fluorophenyl | R | 3-nitrobenzyl | 658.62 | 659.6 |
| 6-6 | 3-fluorophenyl | RS | 3-nitrobenzyl | 658.62 | 659.6 |
| 6-7 | 2-methoxyphenyl | R | 5-(trifluoromethyl)furan-2-ylmethyl | 683.62 | 684.4 |

TABLE 6-continued

| No. | —R₃ | * | —Y | M.W. | Mass |
|---|---|---|---|---|---|
| 6-8 | (5-fluoro-2-methoxyphenyl)methyl | R | (5-trifluoromethylfuran-2-yl)methyl | 701.61 | 702.4 |
| 6-9 | (3-fluoro-5-methylphenyl)methyl | R | (5-trifluoromethylfuran-2-yl)methyl | 685.61 | 686.5 |
| 6-10 | (3-carboxyphenyl)methyl | R | (5-trifluoromethylfuran-2-yl)methyl | 697.60 | 698.5 |
| 6-11 | (4-carboxyphenyl)methyl | R | (5-trifluoromethylfuran-2-yl)methyl | 697.60 | 698.6 |
| 6-12 | methyl | R | (5-trifluoromethylfuran-2-yl)methyl | 591.52 | 592.3 |
| 6-13 | isobutyl | R | (5-trifluoromethylfuran-2-yl)methyl | 633.60 | 634.4 |
| 6-14 | isobutyl | S | (5-trifluoromethylfuran-2-yl)methyl | 633.60 | 634.3 |
| 6-15 | methoxymethyl | R | (5-trifluoromethylfuran-2-yl)methyl | 621.55 | 622.6 |

TABLE 6-continued

| No. | —R₃ | * | —Y | M.W. | Mass |
|---|---|---|---|---|---|
| 6-16 | methoxymethyl | S | (5-trifluoromethyl-furan-2-yl)methyl | 621.55 | 622.6 |
| 6-17 | 2-(methylthio)ethyl | RS | (5-trifluoromethyl-furan-2-yl)methyl | 651.64 | 652.4 |
| 6-18 | (2-methoxyphenyl)methyl | R | (3-trifluoromethyl-phenyl)methyl | 693.65 | 694.4 |
| 6-19 | furan-2-ylmethyl | R | (5-trifluoromethyl-furan-2-yl)methyl | 643.55 | 644.4 |
| 6-20 | thiophen-3-ylmethyl | S | (5-trifluoromethyl-furan-2-yl)methyl | 659.62 | 660.2 |

Example 7

Synthesis of {(R)-2-[3-(2,6-Difluoro-benzyl)-2,6-dioxo-5-(2-oxo-piperazin-1-yl)-3,6-dihydro-2H-pyrimidin-1-yl]-1-phenyl-ethyl}-carbamic acid tert-butyl ester (7)

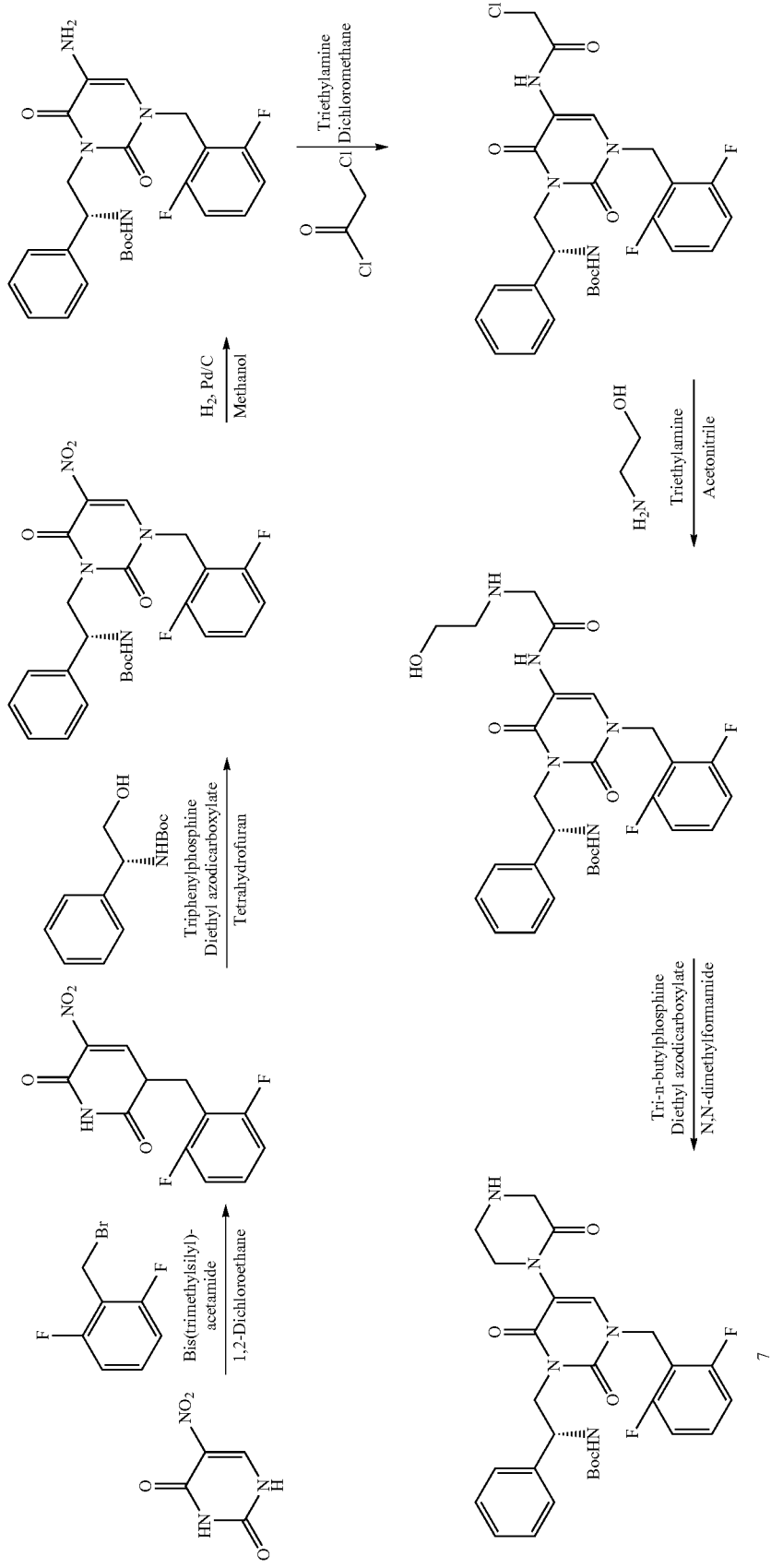

Step A. 1-(2,6-difluoro-benzyl)-5-nitro-1H-pyrimidine-2,4-dione

To a solution of 5-nitro-1H-pyrimidine-2,4-dione (1.0 g, 6.4 mmol) in 1,2-dicholoroethane (15 mL) was added bis(trimethylsilyl)acetamide (3.1 mL, 12.8 mmol), followed by stirring at 80° C. for 30 min in a nitrogen atmosphere. The solution was chilled to 0° C., mixed with 2,6-difluorobenzyl bromide (1.45 g, 7.0 mmol) and stirred at 85° C. for 12 hrs. The addition of methanol (7 mL) to the solution cooled to room temperature resulted in the formation of white solids. This suspension was neutralized with an aqueous saturated ammonium chloride and mixed with dichloromethane to separate an organic layer. This organic layer was concentrated and the residue was purified using silica gel chromatography (eluent: dichloromethane/methanol, 50/1) and dried in a vacuum to afford 230 mg of the compound as a pale yellowish foam (yield 30%). $^1$H NMR (300 MHz, DMSO-$d_6$) δ 5.17 (2H, s), 7.13 (2H, m), 7.47 (1H, m), 9.44 (1H, s), 12.0 (1H, s)

Step B. {(R)-2-[3-(2,6-difluoro-benzyl)-5-nitro-2,6-dioxo-3,6-dihydro-2H-pyrimidin-1-yl]-1-phenyl-ethyl}-carbamic acid tert-butyl ester 1-(2,6-difluoro-benzyl)-5-nitro-1H-pyrimidine-2,4-dione (82 mg, 0.29 mmol), ((R)-2-hydroxy-1-phenyl-ethyl)-carbamic acid tert-butyl ester (69 mg, 0.29 mmol), and triphenylphosphine (114 mg, 0.44 mmol) were dissolved in anhydrous tetrahydrofuran (2 mL). To this solution was added diethyl azodicarboxylate (200 μl, 0.44 mmol), followed by stirring at room temperature for 4 hrs. The solution was concentrated, after which the residue was purified using silica gel chromatography (eluent: hexane/ethyl acetate/dichloromethane, 3/1/1) and dried in a vacuum to afford 67 mg of the compound as a colorless oil (yield 67%). $^1$H NMR (300 MHz, CDCl$_3$) δ 1.30 (9H, s), 3.40 (1H, d), 4.50 (1H, m), 5.08-5.27 (4H, m), 7.02 (2H, t), 7.26-7.47 (6H, m), 8.78 (1H, s)

Step C. {(R)-2-[5-amino-3-(2,6-difluoro-benzyl)-2,6-dioxo-3,6-dihydro-2H-pyrimidin-1-yl]-1-phenyl-ethyl}-carbamic acid tert-butyl ester To a solution of {(R)-2-[3-(2,6-difluoro-benzyl)-5-nitro-2,6-dioxo-3,6-dihydro-2H-pyrimidin-1-yl]-1-phenyl-ethyl}-carbamic acid tert-butyl ester (173 mg, 0.34 mmol) in methanol (5 mL) was added 10% palladium/carbon (36 mg) in a nitrogen atmosphere, followed by stirring at room temperature for 1 hr in a hydrogen atmosphere. After removal of the palladium/carbon by filtration through celite, the filtrate was concentrated. The residue was purified using silica gel chromatography (eluent: hexane/ethyl acetate/dichloromethane, 1/1/1) and dried in a vacuum to afford 109 mg of the compound as a colorless oil (yield 66%).

Step D. {(R)-2-[5-(2-chloro-acetylamino)-3-(2,6-difluoro-benzyl)-2,6-dioxo-3,6-dihydro-2H-pyrimidin-1-yl]-1-phenyl-ethyl}-carbamic acid tert-butyl ester To a solution of {(R)-2-[5-amino-3-(2,6-difluoro-benzyl)-2,6-dioxo-3,6-dihydro-2H-pyrimidin-1-yl]-1-phenyl-ethyl}-carbamic acid tert-butyl ester (50 mg, 0.11 mmol) in dichloromethane (2 mL) were added triethylamine (29 μl, 0.22 mmol) and chloro-acetyl chloride (9.3 μl, 0.12 mmol) in that order, followed by stirring at room temperature for 2 hrs. Again, chloro-acetyl chloride (5.0 μl, 0.06 mmol) was added to the solution which was then stirred at room temperature for 1 hr. The solution was washed with an aqueous saturated sodium bicarbonate solution to separate an organic layer which was then concentrated. The residue was purified using silica gel chromatography (eluent: hexane/ethyl acetate, 2/1) and dried in a vacuum to afford 44 mg of the compound as a colorless oil (yield 76%).

Step E. ((R)-2-{3-(2,6-difluoro-benzyl)-5-[2-(2-hydroxy-ethylamino)-acetylamino]-2,6-dioxo-3,6-dihydro-2H-pyrimidin-1-yl}-1-phenyl-ethyl)-carbamic acid tert-butyl ester To a solution of {(R)-2-[5-(2-chloro-acetylamino)-3-(2,6-difluoro-benzyl)-2,6-dioxo-3,6-dihydro-2H-pyrimidin-1-yl]-1-phenyl-ethyl}-carbamic acid tert-butyl ester (44 mg, 0.08 mmol) in acetonitrile (2 mL) were added triethylamine (30 μl, 0.22 mmol) and 2-amino-ethanol (60 μl, 0.96 mmol) in that order. The solution was stirred at 60° C. for 4 hrs, cooled to room temperature, and washed with an aqueous saturated sodium bicarbonate solution to separate an organic layer. The organic layer was concentrated, and the residue was purified using silica gel chromatography (eluent: dichloromethane/methanol, 10/1) and dried in a vacuum to afford 37 mg of the compound as a colorless oil (yield 80%).

Step F. {(R)-2-[3-(2,6-difluoro-benzyl)-2,6-dioxo-5-(2-oxo-piperazin-1-yl)-3,6-dihydro-2H-pyrimidin-1-yl]-1-phenyl-ethyl}-carbamic acid tert-butyl ester(7)

To a solution of ((R)-2-{3-(2,6-difluoro-benzyl)-5-[2-(2-hydroxy-ethylamino)-acetylamino]-2,6-dioxo-3,6-dihydro-2H-pyrimidin-1-yl}-1-phenyl-ethyl)-carbamic acid tert-butyl ester (20 mg, 0.035 mmol) and tri-n-butylphosphine (14 mg, 0.053 mmol) in anhydrous DMF (2 mL) was added diethyl azodicarboxylate (16 μl, 0.053 mmol), followed by stirring at room temperature for 1 hr. The solution was concentrated, and the residue was purified using silica gel chromatography (eluent: dichloromethane/methanol, 10/1) and dried in a vacuum to afford 12 mg of the compound as a colorless oil (yield 63%). $^1$H NMR (300 MHz, CDCl$_3$) δ 1.30 (9H, s), 3.20 (1H, t), 3.56 (2H, m), 3.66 (2H, s), 4.05 (1H, dd), 4.46 (1H, t), 5.04 (3H, m), 5.56 (1H, m), 6.96 (2H, t), 7.23-7.40 (6H, m), 7.47 (1H, s) MS (ESI) m/z 456.3 (MH$^+$)

Example 8

Synthesis of 3-((R)-2-Amino-2-phenyl-ethyl)-5-(4-benzyl-2-oxo-piperazin-1-yl)-1-(2,6-difluoro-benzyl)-1H-pyrimidine-2,4-dione (8-1)

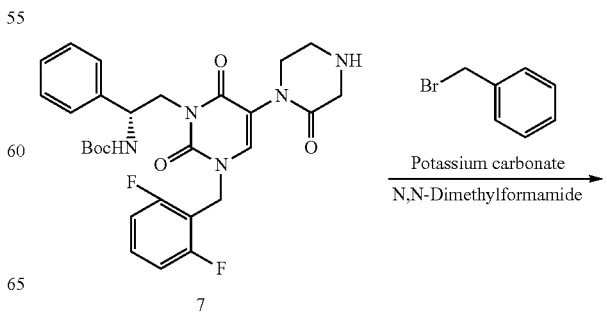

7

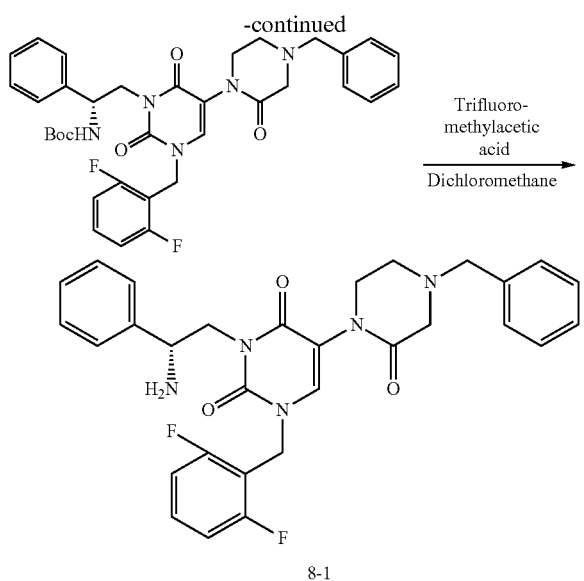

Step A. {(R)-2-[5-(4-benzyl-2-oxo-piperazin-1-yl)-3-(2,6-difluoro-benzyl)-2,6-dioxo-3,6-dihydro-2H-pyrimidin-1-yl]-1-phenyl-ethyl}-carbamic acid tert-butyl ester To a solution of {(R)-2-[3-(2,6-difluoro-benzyl)-2,6-dioxo-5-(2-oxo-piperazin-1-yl)-3,6-dihydro-2H-pyrimidin-1-yl]-1-phenyl-ethyl}-carbamic acid tert-butyl ester (7) (20 mg, 0.036 mmol) in DMF (1 mL) were added potassium carbonate (12 mg, 0.09 mmol) and benzyl bromide (7 mg, 0.040 mmol) in that order, followed by stirring at room temperature for 1 hr. The solution was diluted with dichloromethane and washed with distilled water. The organic layer thus formed was separated and concentrated, and the residue was purified using silica gel chromatography (eluent: dichloromethane/methanol, 30/1) and dried in a vacuum to afford 22 mg of the compound as a white solid (yield 96%). $^1$H NMR (300 MHz, CDCl$_3$) δ 1.32 (9H, s), 2.86 (2H, t), 3.32 (2H, s), 3.58 (2H, m), 3.73 (2H, s), 4.04 (1H, m), 4.46 (1H, t), 5.05 (3H, m), 5.53 (1H, m), 6.98 (2H, t), 7.24-7.38 (6H, m), 7.56 (2H, m), 7.71 (1H, d), 8.20 (1H, dd), 8.26 (1H, s)

Step B. 3-((R)-2-amino-2-phenyl-ethyl)-5-(4-benzyl-2-oxo-piperazin-1-yl)-1-(2,6-difluoro-benzyl)-1H-pyrimidine-2,4-dione (8-1)

To a solution of {(R)-2-[5-(4-benzyl-2-oxo-piperazin-1-yl)-3-(2,6-difluoro-benzyl)-2,6-dioxo-3,6-dihydro-2H-pyrimidin-1-yl]-1-phenyl-ethyl}-carbamic acid tert-butyl ester (22 mg, 0.034 mmol) in dichloromethane (2 mL) was slowly added trifluoroacetic acid (100 μl, 1.30 mmol), followed by stirring at room temperature for 3 hrs. This resulting solution was neutralized with an aqueous saturated sodium bicarbonate solution to separate an organic layer. This organic layer was concentrated, and the residue was purified using amine-silica gel chromatography (eluent: dichloromethane/methanol, 20/1) and dried in a vacuum to afford 18 mg of the compound as a white foam (yield 99%). $^1$H NMR (300 MHz, CDCl$_3$) δ 2.78 (2H, t), 3.30 (2H, s), 3.49 (2H, t), 3.60 (2H, s), 4.01 (1H, dd), 4.19 (1H, t), 4.34 (1H, dd), 5.00 (2H, s), 6.96 (2H, t), 7.18-7.44 (11H, m), 7.45 (1H, s)

Compounds synthesized according to the above procedures are summarized in Table 8, below. Compound 8-2 was prepared in the same manner as in the procedures, with the exception that 3-nitrobenzyl bromide was used instead of benzyl bromide in Step A.

TABLE 8

| No. | —Y | M.W. | Mass |
|---|---|---|---|
| 8-1 | benzyl | 545.58 | 546.3 |
| 8-2 | 3-nitrobenzyl | 590.58 | 591.3 |

Example 9

Synthesis of 3-((R)-2-Amino-2-phenyl-ethyl)-1-(2-fluoro-6-trifluoromethyl-benzyl)-6-methyl-5-[4-(3-nitro-benzyl)-3-oxo-piperazin-1-yl]-1H-pyrimidine-2,4-dione (9-1)

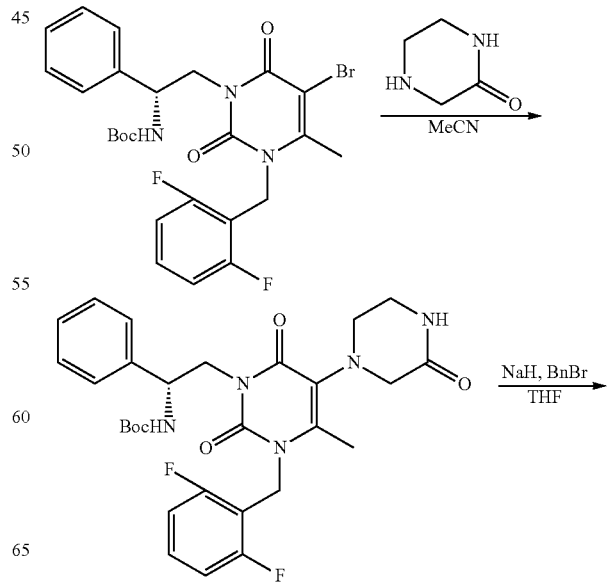

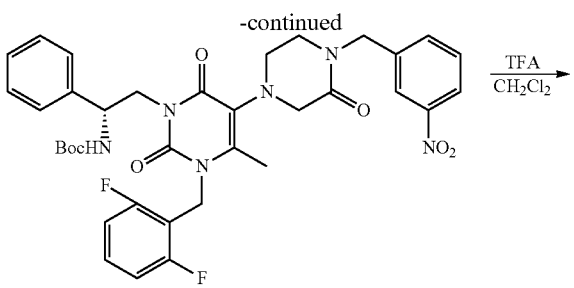

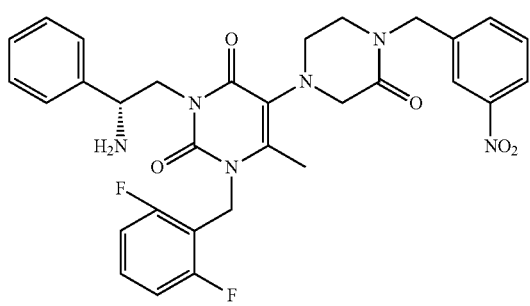

Step A. {(R)-2-[3-(2,6-difluoro-benzyl)-4-methyl-2, 6-dioxo-5-(3-oxo-piperazin-1-yl)-3,6-dihydro-2H-pyrimidin-1-yl]-1-phenyl-ethyl}-carbamic acid tert-butyl ester {(R)-2-[5-bromo-3-(2,6-difluoro-benzyl)-4-methyl-2,6-dioxo-3,6-dihydro-2H-pyrimidin-1-yl]-1-phenyl-ethyl}-carbamic acid tert-butyl ester (100 mg, 0.182 mmol) and piperazine-2-one (187 mg, 1.82 mmol) were placed into a microwave flask along the wall of which 1 mL of acetonitrile was then added. The solution was stirred at 140° C. for 3 hrs while being irradiated with microwaves. After concentration in a vacuum, the concentrate was purified by column chromatography eluting with a dichloromethane/methanol (35/1) eluent to afford 60 mg of the compound as a yellowish solid (yield 58%). $^1$H NMR (300 MHz, CDCl$_3$) δ 1.36 (9H, s), 2.43 (3H, s), 2.86 (1H, m), 3.27 (2H, m), 3.50 (1H, m), 3.74 (1H, m), 4.07 (2H, m), 4.27 (1H, m), 5.04 (1H, m), 5.29 (2H, dd), 5.68 (1H, m), 6.30 (1H, m), 6.90 (2H, t), 7.22-7.37 (6H, m)

Step B. ((R)-2-{3-(2,6-difluoro-benzyl)-4-methyl-5-[4-(3-nitro-benzyl)-3-oxo-piperazin-1-yl]-2,6-dioxo-3,6-dihydro-2H-pyrimidin-1-yl}-1-phenyl-ethyl)-carbamic acid tert-butyl ester {(R)-2-[3-(2,6-difluoro-benzyl)-4-methyl-2,6-dioxo-5-(3-oxo-piperazin-1-yl)-3,6-dihydro-2H-pyrimidin-1-yl]-1-phenyl-ethyl}-carbamic acid tert-butyl ester (50 mg, 0.0878 mmol) was dissolved in 1 mL of THF, with nitrogen purge. While on ice, 60% NaH (10 mg, 0.263 mmol) was added to the solution which was then stirred at room temperature for 10 min. Again, while being cooled on ice, 3-nitrobenzyl bromide (23 mg, 0.105 mmol) was added, followed by stirring at room temperature for 1 hr. A little amount of a saturated ammonium chloride solution was added before extraction with dichloromethane. After concentration, the resulting residue was purified by column chromatography eluting with an EtOAc/hexane/dichloromethane (2/1/0.5) eluent to afford 28 mg of the compound (42%).

Step C. 3-((R)-2-amino-2-phenyl-ethyl)-1-(2,6-difluoro-benzyl)-6-methyl-5-[4-(3-nitro-benzyl)-3-oxo-piperazin-1-yl]-1H-pyrimidine-2,4-dione To a solution of ((R)-2-{3-(2,6-difluoro-benzyl)-4-methyl-5-[4-(3-nitro-benzyl)-3-oxo-piperazin-1-yl]-2,6-dioxo-3,6-dihydro-2H-pyrimidin-1-yl}-1-phenyl-ethyl)-carbamic acid tert-butyl ester (28 mg, 0.0371 mmol) in 1 mL of dichloromethane was added trifluoroacetic acid (0.1 ml, 1.29 mmol) under ice cooling, followed by stirring at room temperature for 2 hrs. The solution was neutralized with sat. NaHCO$_3$, extracted with dichloromethane and concentrated in a vacuum. The residue was purified by column chromatography eluting with a dichloromethane/methanol (20/1) eluent to afford 11 mg of compound 9-1 (45%). $^1$H NMR (300 MHz, CDCl$_3$) δ 2.42 (3H, s), 2.81 (1H, m), 3.12 (1H, m), 3.30-3.49 (2H, m), 3.72 (1H, m), 4.02-4.22 (3H, m), 4.33 (1H, dd), 4.55 (1H, m), 4.91 (1H, m), 5.23 (2H, dd), 6.92 (2H, t), 7.20-7.37 (6H, m), 7.53 (1H, t), 7.65 (1H, d), 8.13 (1H, s), 8.15 (1H, m).

Compounds synthesized according to the above procedures are summarized in Table 9, below. Compound 9-2 was prepared in the same manner as in the above procedures, with the exception that benzyl bromide was used instead of 3-nitro-benzyl bromide in Step B.

TABLE 9

| No. | —Y | M.W. | Mass |
|---|---|---|---|
| 9-1 | ~CH$_2$-(3-NO$_2$-C$_6$H$_4$) | 604.60 | 605.0 |
| 9-2 | ~CH$_2$-C$_6$H$_5$ | 559.61 | 560.5 |

Example 10

Synthesis of 4-(3-{4-[3-((R)-2-Amino-2-phenyl-ethyl)-1-(2-fluoro-6-trifluoromethyl-benzyl)-6-methyl-2,4-dioxo-1,2,3,4-tetrahydro-pyrimidin-5-yl]-piperazin-1-ylmethyl}-benzoylamino)-butyric acid (10-6)

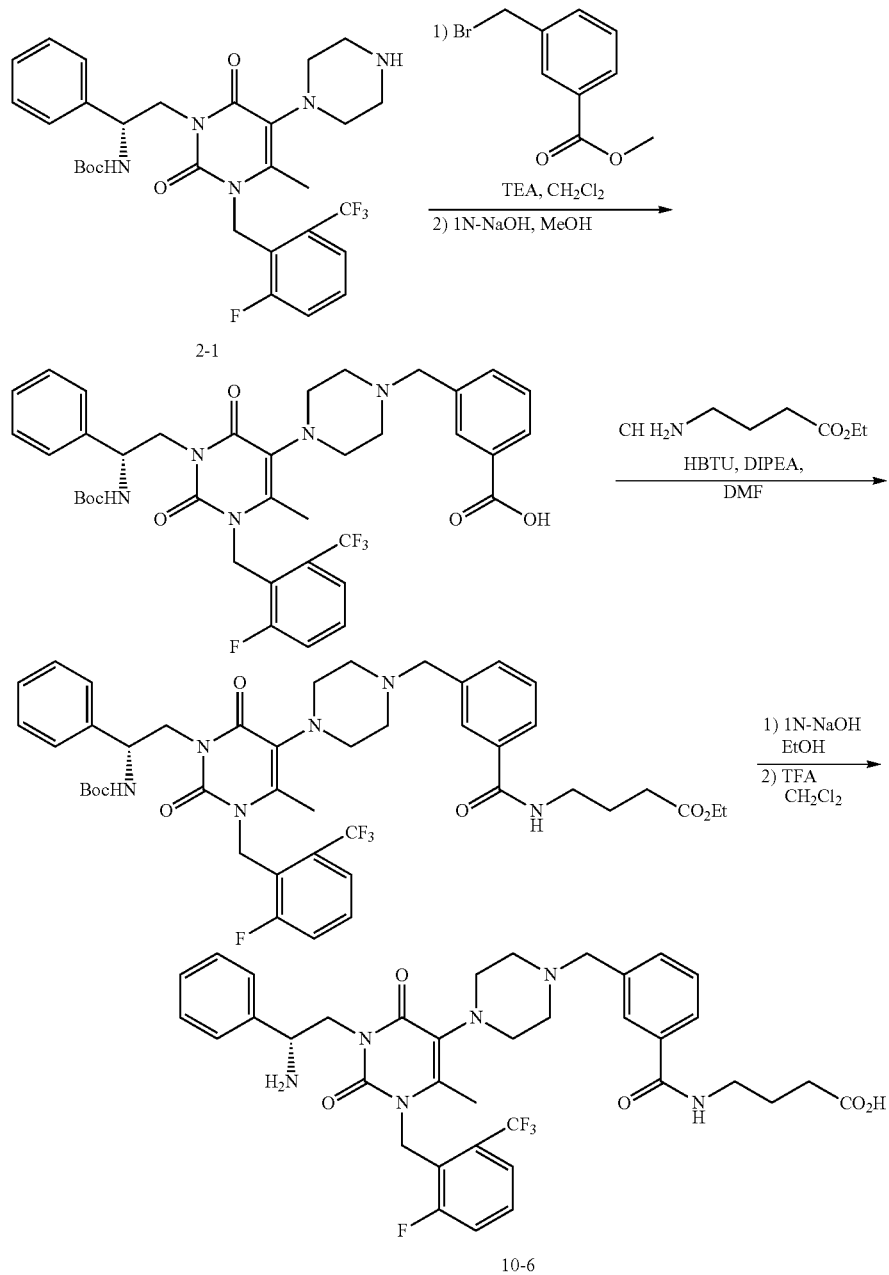

Step A. 3-{4-[3-((R)-2-tert-butoxycarbonylamino-2-phenyl-ethyl)-1-(2-fluoro-6-trifluoromethyl-benzyl)-6-methyl-2,4-dioxo-1,2,3,4-tetrahydro-pyrimidin-5-yl]-piperazin-1-ylmethyl}-benzoic acid To a solution of {(R)-2-[3-(2-fluoro-6-trifluoromethyl-benzyl)-4-methyl-2,6-dioxo-5-piperazin-1-yl-3,6-dihydro-2H-pyrimidin-1-yl]-1-phenyl-ethyl}-carbamic acid tert-butyl ester(2-1) (363 mg, 0.586 mmol) in dichloromethane (3 mL) were added triethylamine (0.18 ml, 1.29 mmol) and 3-bromomethyl-benzoic acidmethyl ester (152 mg, 0.644 mmol) in that order, followed by stirring at room temperature for 1 hr. The solution was neutralized with an aqueous saturated sodium bicarbonate solution before extraction with dichloromethane. The organic layer thus formed was concentrated, and the residue was purified sing silica gel chromatography (eluent: hexane/ethyl acetate, 2/1) and dried in a vacuum to afford 394 mg of a yellowish solid (yield 89%). This solid was dissolved in methanol (5 mL) to which 1N-NaOH (3.1 mL, 3.14 mmol) was then added, followed by stirring at 60° C. for 1.5 hrs. The solution was cooled, concentrated in a vacuum, and acidified to pH 3 with 0.2N HCl. After extraction with ethyl acetate (50 mL), the extract was dried and filtered to afford the compound as a yellowish solid (443 mg, quant. yield).

Step B. 4-(3-{4-[3-((R)-2-tert-butoxycarbonylamino-2-phenyl-ethyl)-1-(2-fluoro-6-trifluoromethyl-benzyl)-6-methyl-2,4-dioxo-1,2,3,4-tetrahydro-pyrimidin-5-yl]-piperazin-1-ylmethyl}-benzoylamino)-butyric acid ethyl ester To a solution of 3-{4-[3-((R)-2-tert-butoxycarbonylamino-2-phenyl-ethyl)-1-(2-fluoro-6-trifluoromethyl-benzyl)-6-methyl-2,4-dioxo-1,2,3,4-tetrahydro-pyrimidin-5-yl]-piperazin-1-ylmethyl}-benzoic acid (40 mg, 0.0541 mmol) and 4-amino-butyric acid ethyl ester chloride (19 mg, 0.108 mmol) in DMF (0.5 mL) was added N,N-diisopropyl-ethylamine(38 µl, 0.216 mmol), after which HBTU (51 mg, 0.162 mmol) was added to the solution, with stirring. The solution was concentrated at room temperature for 6 hrs, with stirring. The residue was diluted in EtOAc and washed with an aqueous saturated sodium bicarbonate solution, an aqueous saturated ammonium chloride solution, and an aqueous saturated sodium chloride solution in that order. After being separated, the organic layer was dried over sodium sulfate, filtered and concentrated. The residue was purified using silica gel chromatography (eluent: dichloromethane/methanol, 30/1) and dried in a vacuum to afford 46 mg of the compound as a yellowish solid (yield 99%). $^1$H NMR (300 MHz, CDCl$_3$) δ 1.24 (3H, t), 1.34 (9H, s), 1.98 (2H, pentet), 2.31 (2H, m), 2.34 (3H, s), 2.44 (2H, t), 2.53 (2H, m), 2.82 (2H, m), 3.53 (2H, q), 3.64 (4H, m), 4.06 (1H, m), 4.12 (2H, q), 4.24 (1H, t), 5.00 (1H, m), 5.45 (2H, dd), 5.78 (1H, m), 6.30 (0.2H, t), 6.77 (0.8H, t), 7.20-7.41 (8H, m), 7.53 (2H, t), 7.83 (1H, d), 7.71 (1H, d), 7.75 (1H, s)

Step C. 4-(3-{4-[3-((R)-2-amino-2-phenyl-ethyl)-1-(2-fluoro-6-trifluoromethyl-benzyl)-6-methyl-2,4-dioxo-1,2,3,4-tetrahydro-pyrimidin-5-yl]-piperazin-1-ylmethyl}-benzoylamino)-butyric acid (10-6)

To a solution of 4-(3-{4-[3-((R)-2-tert-butoxycarbonylamino-2-phenyl-ethyl)-1-(2-fluoro-6-trifluoromethyl-benzyl)-6-methyl-2,4-dioxo-1,2,3,4-tetrahydro-pyrimidin-5-yl]-piperazin-1-ylmethyl}-benzoylamino)-butyric acid ethyl ester (46 mg, 0.0539 mmol) in ethanol (1 mL) was added 1N-NaOH (0.3 ml, 0.32 mmol), followed by stirring at room temperature for 30 min. The solution was diluted with water and acidified with 0.3N—HCl. Then, the solution extracted with a mixture of dichloromethane/methanol, dried over sodium sulfate, and filtered. After concentration, the residue was purified using silica gel chromatography (eluent: dichloromethane/methanol, 20/1) and dried in a vacuum to give 42 mg of an intermediate. This was dissolved in dichloromethane (1.5 mL), chilled to 0° C. and mixed at room temperature for 30 min with TFA (0.15 ml), with stirring. The solution was adjusted into a neural pH with an aqueous saturated sodium bicarbonate solution before extraction with EtOAc/methanol. The organic layer thus formed was washed again with an aqueous saturated sodium chloride solution and concentrated. The residue was purified by prepLC (distilled water containing MeOH/0.1% formic acid) to afford 10 mg of compound 10-6 (yield 26%). $^1$H NMR (300 MHz, CD$_3$OD) δ 1.96 (2H, pentet), 2.39 (2H, t), 2.42 (3, s), 2.57-2.78 (4H, m), 3.13 (2H, m), 3.45 (2H, t), 3.64 (2H, m), 4.01 (2H, s), 4.36 (2H, d), 4.65 (1H, m), 5.38 (2H, dd), 7.33-7.49 (6H, m), 7.51 (2H, m), 7.62 (2H, d), 7.83 (1H, d), 7.90 (1H, s), MS (ESI) m/z 725.7 (MH$^+$).

Compounds synthesized according to the above procedures are summarized in Table 10, below. For preparation of compounds 10-1, 10-2, 10-4 and 10-5, different esters were used instead of 3-bromomethyl-benzoic acidmethyl ester in Step A. In this context, compounds 10-1, 10-2, and 10-3 were respectively prepared from the intermediates obtained in Step B during the synthesis of compounds 10-4, 10-5 and 10-6, with the omission of the hydrolysis process in Step C.

TABLE 10

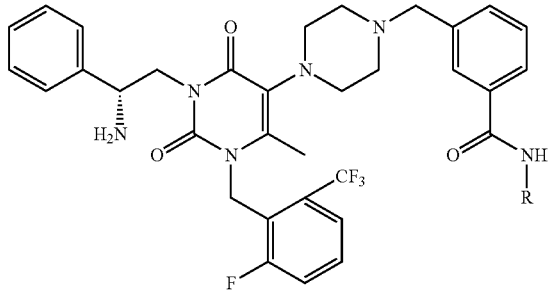

| No. | —R | M.W. | Mass |
|---|---|---|---|
| 10-1 | | 710.72 | 711.8 |
| 10-2 | | 738.72 | 739.5 |
| 10-3 | | 752.80 | 753.6 |

TABLE 10-continued
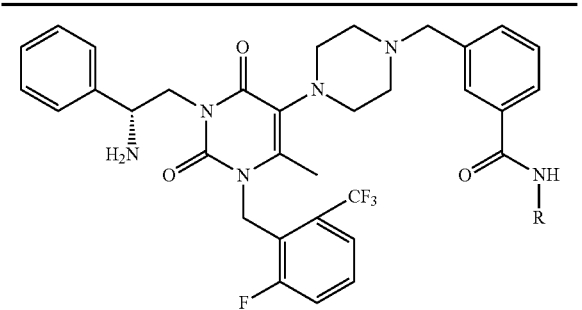
| No. | —R | M.W. | Mass |
|---|---|---|---|
| 10-4 | (CH2COOH) | 696.69 | 697.6 |
| 10-5 | (CH2CH2COOH) | 710.72 | 711.7 |
TABLE 10-continued
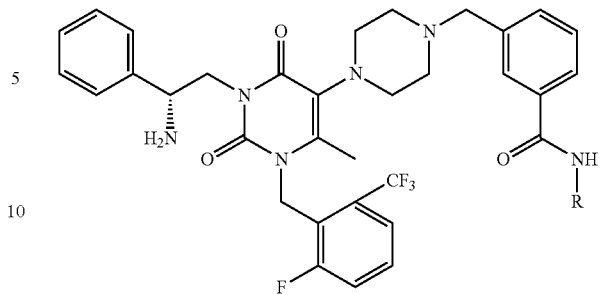
| No. | —R | M.W. | Mass |
|---|---|---|---|
| 10-6 | (CH2CH2CH2COOH) | 724.74 | 725.7 |
Example 11
Synthesis of 4-((R)-2-{3-(2-Fluoro-6-trifluorom-ethyl-benzyl)-4-methyl-5-[4-(3-nitro-benzyl)-piper-azin-1-yl]-2,6-dioxo-3,6-dihydro-2H-pyrimidin-1-yl}-1-phenyl-ethylamino)-butyric acid (11-1)
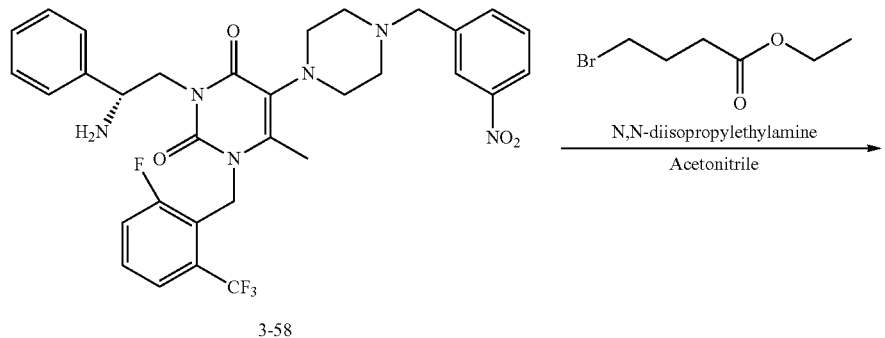
3-58
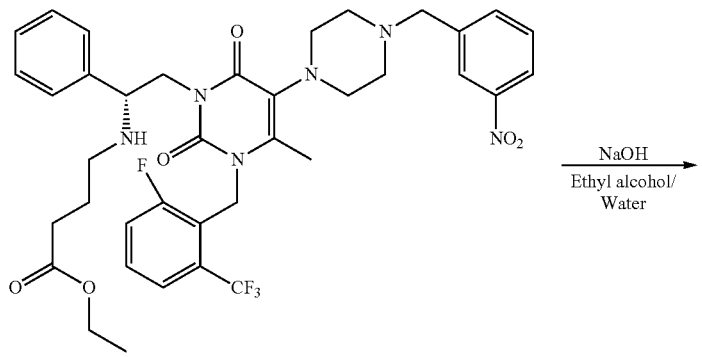

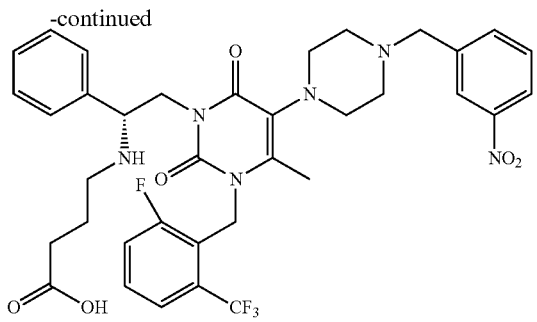

11-1

Step A. 4-((R)-2-{3-(2-Fluoro-6-trifluoromethyl-benzyl)-4-methyl-5-[4-(3-nitro-benzyl)-piperazin-1-yl]-2,6-dioxo-3,6-dihydro-2H-pyrimidin-1-yl}-1-phenyl-ethylamino)-butyric acid ethyl ester To a solution of 3-((R)-2-amino-2-phenyl-ethyl)-1-(2-fluoro-6-trifluoromethyl-benzyl)-6-methyl-5-[4-(3-nitro-benzyl)-piperazin-1-yl]-1H-pyrimidine-2,4-dione (3-58) (55 mg, 0.086 mmol) in acetonitrile (2 mL) were added N,N-diisopropylethylamine (37 µl, 0.271 mmol) and 4-bromo-butyric acid ethyl ester (15 µl, 0.086 mmol) in the order, followed by stirring at 95° C. for 12 hrs. The solution was cooled to room temperature, diluted with dichloromethane and washed with an aqueous saturated sodium bicarbonate solution. The organic layer thus formed was separated and concentrated. The residue was purified using silica gel chromatography (eluent: dichloromethane/methanol, 30/1) and dried in a vacuum to afford 21 mg of the compound as a colorless oil (yield 33%). $^1$H NMR (300 MHz, CDCl$_3$) δ 1.19 (3H, t), 1.65 (2H, m), 2.24 (4H, m), 2.33 (3H, s), 2.37-2.50 (4H, m), 2.74 (2H, m), 3.60 (4H, m), 4.02-4.09 (4H, m), 4.16 (1H, m), 5.40 (2H, dd), 7.20-7.40 (7H, m), 7.49 (1H, t), 7.53 (1H, d), 7.76 (1H, d), 8.10 (1H, dd), 8.18 (1H, s)

Step B. 4-((R)-2-[(3-(2-fluoro-6-trifluoromethyl-benzyl)-4-methyl-5-[4-(3-nitro-benzyl)-piperazin-1-yl]-2,6-dioxo-3,6-dihydro-2H-pyrimidin-1-yl]-1-phenyl-ethylamino)-butyric acid (11-1)

To a solution of 4-((R)-2-{3-(2-fluoro-6-trifluoromethyl-benzyl)-4-methyl-5-[4-(3-nitro-benzyl)-piperazin-1-yl]-2,6-dioxo-3,6-dihydro-2H-pyrimidin-1-yl}-1-phenyl-ethylamino)-butyric acid ethyl ester (21 mg, 0.028 mmol) in ethanol (1 mL)/distilled water (700 µl) was slowly added 1N NaOH (280 µl, 0.28 mmol). This solution was stirred at 60° C. for 3 hrs and concentrated. The residue was neutralized with 0.2N HCl and diluted with dichloromethane, after which the organic layer thus formed was separated. Following concentration of the organic layer, the residue was purified using silica gel chromatography (eluent: dichloromethane/methanol, 10/1) and dried in a vacuum to afford 18 mg of the compound as a colorless oil (yield 90%). $^1$H NMR (300 MHz, CDCl$_3$) δ 1.69 (2H, m), 2.23 (2H, m), 2.39 (3H, s), 2.42-2.78 (8H, m), 3.62 (4H, m), 4.05 (1H, dd), 4.29 (1H, dd), 4.42 (1H, dd), 5.41 (2H, s), 7.22 (1H,), 7.28-7.42 (6H, m), 7.47 (1H, t), 7.53 (1H, d), 7.74 (1H, d), 8.10 (1H, dd), 8.21 (1H, s).

Compounds synthesized according to the above procedures are summarized in Table 11, below. Compound 11-2 was prepared in the same manner as in the above procedures, with the exception that 3-((R)-2-amino-2-phenyl-ethyl)-1-(2-fluoro-6-trifluoromethyl-benzyl)-6-methyl-5-[4-(3-trifluoromethyl-benzyl)-piperazin-1-yl]-1H-pyrimidine-2,4-dione (3-84) was used instead of 3-((R)-2-amino-2-phenyl-ethyl)-1-(2-fluoro-6-trifluoromethyl-benzyl)-6-methyl-5-[4-(3-nitro-benzyl)-piperazin-1-yl]-1H-pyrimidine-2,4-dione(3-58) in Step A. Compounds 11-3, 11-7, 11-8, 11-10 and 11-11 were prepared in the same manner as in the above procedures, with the exception that 3-((R)-2-amino-2-phenyl-ethyl)-1-(2-fluoro-6-trifluoromethyl-benzyl)-6-methyl-5-[4-(5-trifluoromethyl-furan-2-ylmethyl)-piperazin-1-yl]-1H-pyrimidine-2,4-dione (3-66), instead of 3-((R)-2-amino-2-phenyl-ethyl)-1-(2-fluoro-6-trifluoromethyl-benzyl)-6-methyl-5-[4-(3-nitro-benzyl)-piperazin-1-yl]-1H-pyrimidine-2,4-dione (3-58), and different bromide compounds, instead of 4-bromo-butyric acid ethyl ester, were used in Step A. Compound 11-4 was prepared in the same manner as in the above procedures, with the exception that, instead of 3-((R)-2-amino-2-phenyl-ethyl)-1-(2-fluoro-6-trifluoromethyl-benzyl)-6-methyl-5-[4-(3-nitro-benzyl)-piperazin-1-yl]-1H-pyrimidine-2,4-dione(3-58), 3-[(R)-2-amino-2-(3-fluoro-5-methyl-phenyl)-ethyl]-1-(2-fluoro-6-trifluoromethyl-benzyl)-6-methyl-5-[4-(5-trifluoromethyl-furan-2-ylmethyl)-piperazin-1-yl]-1H-pyrimidine-2,4-dione(6-9) was used in Step A. Compound 11-5 was prepared in the same manner as in the above procedures, with the exception that, instead of 3-((R)-2-amino-2-phenyl-ethyl)-1-(2-fluoro-6-trifluoromethyl-benzyl)-6-methyl-5-[4-(3-nitro-benzyl)-piperazin-1-yl]-1H-pyrimidine-2,4-dione(3-58), 3-[(R)-2-amino-2-(5-fluoro-2-methoxy-phenyl)-ethyl]-1-(2-fluoro-6-trifluoromethyl-benzyl)-6-methyl-5-[4-(5-trifluoromethyl-furan-2-ylmethyl)-piperazin-1-yl]-1H-pyrimidine-2,4-dione (6-8) was used in Step A. Compound 11-6 was prepared in the same manner as in the above procedures, with the exception that, instead of 3-((R)-2-amino-2-phenyl-ethyl)-1-(2-fluoro-6-trifluoromethyl-benzyl)-6-methyl-5-[4-(3-nitro-benzyl)-piperazin-1-yl]-1H-pyrimidine-2,4-dione(3-58), 3-[(R)-2-amino-2-(2-methoxy-phenyl)-ethyl]-1-(2-fluoro-6-trifluoromethyl-benzyl)-6-methyl-5-[4-(5-trifluoromethyl-furan-2-ylmethyl)-piperazin-1-yl]-1H-pyrimidine-2,4-dione (6-7) was used in Step A. Compound 11-9 was prepared in the same manner as in the above procedures, with the exception that, instead of 4-bromo-butyric acid ethyl ester, a different bromide compound was used in Step A. Compound 11-12 was prepared in the same manner as in the above procedures, with the exception that, instead of 3-((R)-2-amino-2-phenyl-ethyl)-1-(2-fluoro-6-trifluoromethyl-benzyl)-6-methyl-5-[4-(3-nitro-benzyl)-piperazin-1-yl]-1H-pyrimidine-2,4-dione (3-58), 3-((R)-2-amino-2-phenyl-ethyl)-1-(2-fluoro-6-trifluoromethyl-benzyl)-6-methyl-5-[4-(3-(oxazol-2-yl)benzyl)-piperazin-1-yl]-1H-pyrimidine-2,4-dione (3-101) was used in Step A. Compound 11-13 was prepared in the same manner as in the above procedures, with the exception that, instead of 3-((R)-2-amino-2-phenyl-ethyl)-1-(2-fluoro-6-trifluoromethyl-benzyl)-6-methyl-5-[4-(3-nitro-benzyl)-piperazin-1-yl]-1H-pyrimidine-2,4-dione(3-58), (R)-3-((4-(3-(2-amino-2-phenylethyl)-1-(2-fluoro-6-(trifluoromethyl) benzyl)-6-methyl-2,4-dioxo-1,2,3,4-tetrahydropyrimidin-5-yl)piperazin-1-yl)methyl)-2-fluorobenzonitrile (3-104) was used in Step A. Compound 11-14 was prepared in the same manner as in the above procedures, with the exception that, instead of 3-((R)-2-amino-2-phenyl-ethyl)-1-(2-fluoro-6-trifluoromethyl-benzyl)-6-methyl-5-[4-(3-nitro-benzyl)-piperazin-1-yl]-1H-pyrimidine-2,4-dione (3-58), (R)-2-((4-(3-(2-amino-2-phenylethyl)-1-(2-fluoro-6-(trifluoromethyl) benzyl)-6-methyl-2,4-dioxo-1,2,3,4-tetrahydropyrimidin-5-yl)piperazin-1-yl)methyl)-6-fluorobenzonitrile (3-105) was used in Step A. Compound 11-15 was prepared in the same manner as in the above procedures, with the exception that, instead of 3-((R)-2-amino-2-phenyl-ethyl)-1-(2-fluoro-6-trifluoromethyl-benzyl)-6-methyl-5-[4-(3-nitro-benzyl)-piperazin-1-yl]-1H-pyrimidine-2,4-dione(3-58), 3-[(R)-2-amino-2-(2-methoxy-phenyl)-ethyl]-1-(2-fluoro-6-trifluoromethyl-benzyl)-6-methyl-5-[4-(3-trifluoromethyl-benzyl)-piperazin-1-yl]-1H-pyrimidine-2,4-dione (6-18) was used in Step A. Compound 11-16 was prepared in the same manner as in the above procedures, with the exception that, instead of 3-((R)-2-amino-2-phenyl-ethyl)-1-(2-fluoro-6-trifluoromethyl-benzyl)-6-methyl-5- [4-(3-nitro-benzyl)-piperazin-1-ethyl-benzyl)-6-methyl-5- [4-(3-nitro-benzyl)-piperazin-1-yl]-1H-pyrimidine-2,4-dione(3-58), 3-((R)-2-amino-2-phenylethyl)-1-(2-fluoro-6-(trifluoromethyl)benzyl)-6-methyl-5-HR)-3-methyl-4-((5-(trifluoromethyl)furan-2-yl)methyl) piperazin-1-yl)pyrimidine-2,4(1H,3H)-dione (3-108) was used in Step A. Compound 11-17 was prepared in the same manner as in the above procedures, with the exception that, instead of 3-((R)-2-amino-2-phenyl-ethyl)-1-(2-fluoro-6-trifluoromethyl-benzyl)-6-methyl-5-[4-(3-nitro-benzyl)-piperazin-1-yl]-1H-pyrimidine-2,4-dione(3-58), 3-((R)-2-amino-2-phenylethyl)-1-(2-fluoro-6-(trifluoromethyl)benzyl)-6-methyl-5-((S)-3-methyl-4-((5-(trifluoromethyl)furan-2-yl) methyl)piperazin-1-yl)pyrimidine-2,4(1H,3H)-dione (3-109) was used in Step A. Compound 11-18 was prepared in the same manner as in the above procedures, with the exception that, instead of 3-((R)-2-amino-2-phenyl-ethyl)-1-(2-fluoro-6-trifluoromethyl-benzyl)-6-methyl-5-[4-(3-nitro-benzyl)-piperazin-1-yl]-1H-pyrimidine-2,4-dione(3-58), (S)-3-(2-amino-2-(furan-2-yl)ethyl)-1-(2-fluoro-6-(trifluoromethyl)benzyl)-6-methyl-5-(4-((5-(trifluoromethyl)furan-2-yl)methyl)piperazin-1-yl)pyrimidine-2,4(1H,3H)-dione (6-19) was used in Step A. Compound 11-19 was prepared in the same manner as in the above procedures, with the exception that, instead of 3-((R)-2-amino-2-phenyl-ethyl)-1-(2-fluoro-6-trifluoromethyl-benzyl)-6-methyl-5-[4-(3-nitro-benzyl)-piperazin-1-yl]-1H-pyrimidine-2,4-dione(3-58), (R)-3-(2-amino-2-(thiophen-3-yl)ethyl)-1-(2-fluoro-6-(trifluoromethyl)benzyl)-6-methyl-5-(4-((5-(trifluoromethyl)furan-2-yl)methyl)piperazin-1-yl)pyrimidine-2,4(1H,3H)-dione (6-20) was used in Step A.

TABLE 11

| No. | —R₃ | —Y | —A | —NH—R₁ | M.W. | Mass |
|---|---|---|---|---|---|---|
| 11-1 | phenyl | 3-nitrobenzyl | piperazinyl | NH-(CH₂)₃-COOH | 726.72 | 727.4 |
| 11-2 | phenyl | 3-trifluoromethylbenzyl | piperazinyl | NH-(CH₂)₃-COOH | 749.72 | 750.3 |
| 11-3 | phenyl | (5-trifluoromethylfuran-2-yl)methyl | piperazinyl | NH-(CH₂)₃-COOH | 739.68 | 740.3 |

TABLE 11-continued
| No. | —R₃ | —Y | —A | —NH—R₁ | M.W. | Mass |
|---|---|---|---|---|---|---|
| 11-4 | 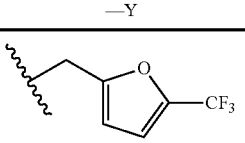 | 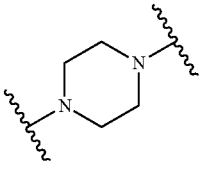 [SMILES: *N1CCN(*)CC1] | 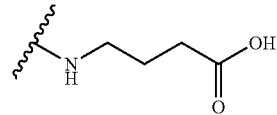 | 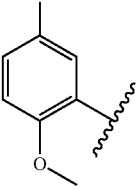 | 771.7 | 772.3 |
| 11-5 | 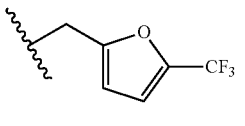 [SMILES: *Cc1ccc(C(F)(F)F)o1] | 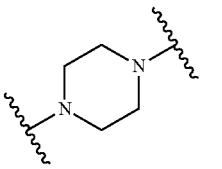 [SMILES: *N1CCN(*)CC1] | 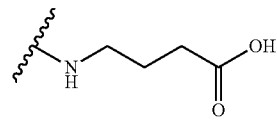 [SMILES: *NCCCC(=O)O] | 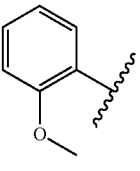 [SMILES: *c1ccccc1OC] | 787.7 | 788.3 |
| 11-6 | 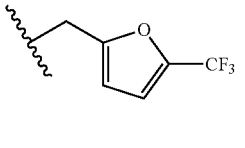 | 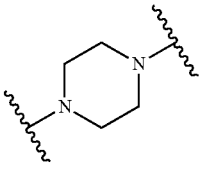 [SMILES: *N1CCN(*)CC1] | 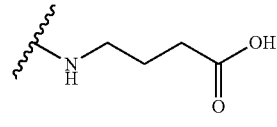 [SMILES: *NCCCC(=O)O] | 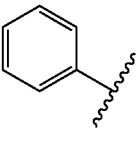 | 769.71 | 770.2 |
| 11-7 | 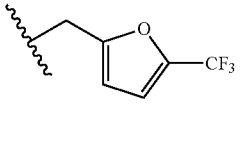 [SMILES: *Cc1ccc(C(F)(F)F)o1] | 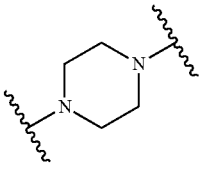 [SMILES: *N1CCN(*)CC1] | 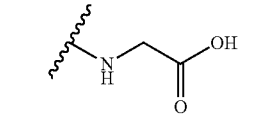 [SMILES: *NCC(=O)O] | 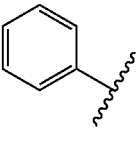 [SMILES: *c1ccccc1] | 711.63 | 712.6 |
| 11-8 | 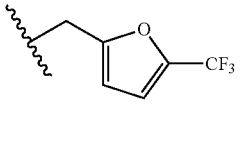 | 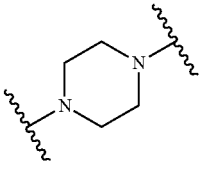 [SMILES: *N1CCN(*)CC1] | 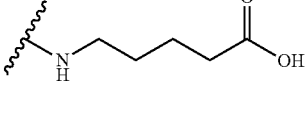 | 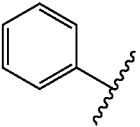 | 753.71 | 754.5 |
| 11-9 | 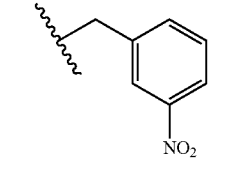 [SMILES: *Cc1cccc([N+](=O)[O-])c1] | 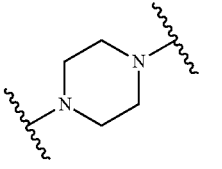 [SMILES: *N1CCN(*)CC1] | 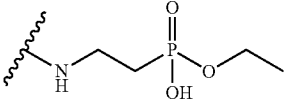 [SMILES: *NCCP(=O)(O)OCC] | 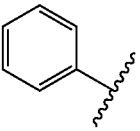 [SMILES: *c1ccccc1] | 776.71 | 777.5 |
| 11-10 | 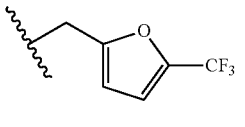 [SMILES: *Cc1ccc(C(F)(F)F)o1] | 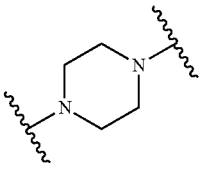 [SMILES: *N1CCN(*)CC1] | 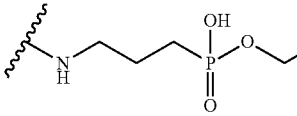 | 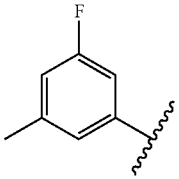 | 803.70 | 804.4 |

TABLE 11-continued
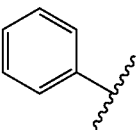 [SMILES: *c1ccccc1]
| No. | —R₃ | —Y | —A | —NH—R₁ | M.W. | Mass |
|---|---|---|---|---|---|---|
| 11-11 | 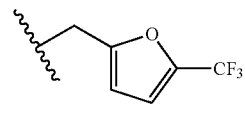 [SMILES: *Cc1ccc(C(F)(F)F)o1] | 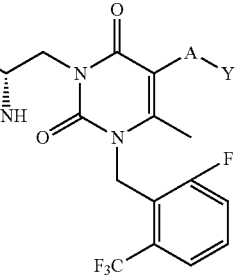 | 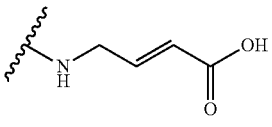 | 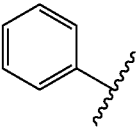 [SMILES: *c1ccccc1] | 737.66 | 738.4 |
| 11-12 | 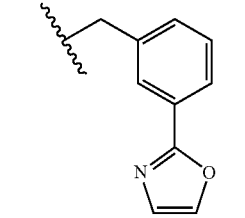 [SMILES: *Cc1cccc(-c2ncco2)c1] | 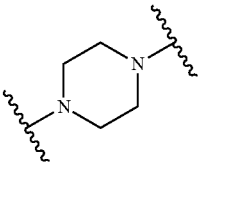 [SMILES: *N1CCN(*)CC1] | 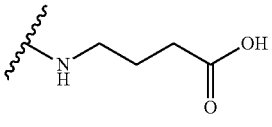 [SMILES: *NCCCC(=O)O] | 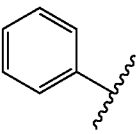 [SMILES: *c1ccccc1] | 748.77 | 749.5 |
| 11-13 | 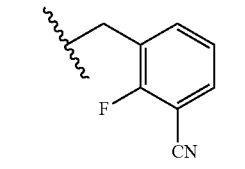 [SMILES: *Cc1cccc(C#N)c1F] | 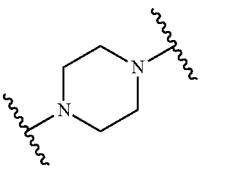 [SMILES: *N1CCN(*)CC1] | 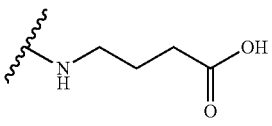 [SMILES: *NCCCC(=O)O] | 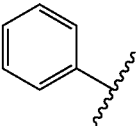 | 724.72 | 724.3 |
| 11-14 | 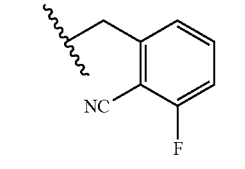 [SMILES: *Cc1cccc(F)c1C#N] | 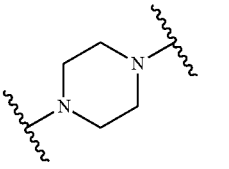 [SMILES: *N1CCN(*)CC1] | 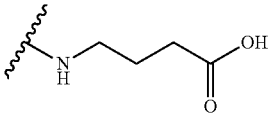 [SMILES: *NCCCC(=O)O] | 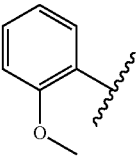 [SMILES: *c1ccccc1OC] | 724.72 | 724.3 |
| 11-15 | 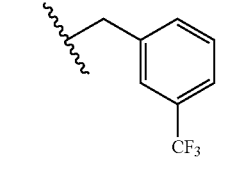 | 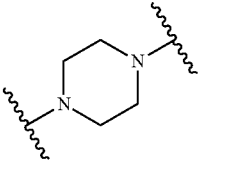 [SMILES: *N1CCN(*)CC1] | 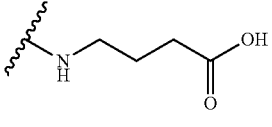 [SMILES: *NCCCC(=O)O] | 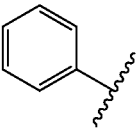 [SMILES: *c1ccccc1] | 779.74 | 780.2 |
| 11-16 | 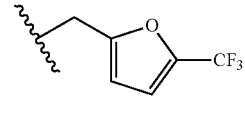 | 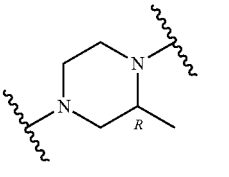 | 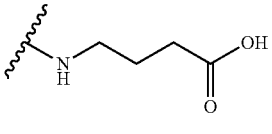 [SMILES: *NCCCC(=O)O] | | 753.71 | 754.4 |

TABLE 11-continued

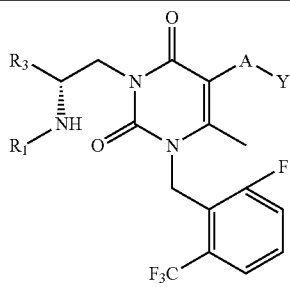

| No. | —R₃ | —Y | —A | —NH—R₁ | M.W. | Mass |
|-----|-----|----|----|--------|------|------|
| 11-17 | phenyl | furan-CF₃ | 2-methylpiperazine (S) | NH-(CH₂)₃-COOH | 753.71 | 754.3 |
| 11-18 | furan-2-yl | furan-CF₃ | piperazine | NH-(CH₂)₃-COOH | 729.64 | 730.2 |
| 11-19 | thiophen-3-yl | furan-CF₃ | piperazine | NH-(CH₂)₃-COOH | 745.71 | 746.2 |

As for compound 11-20, it was isolated by filtering off related compounds generated in the final hydrolysis process during the synthesis of compound 11-3 using column chromatography.

11-20

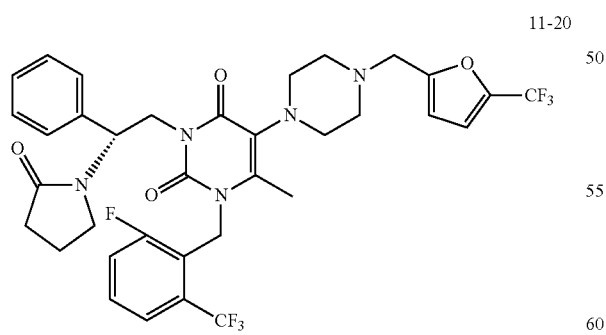

$^1$H NMR (300 MHz, CDCl$_3$) δ 1.82 (2H, m), 2.18-2.28 (4H, m), 2.32 (3H, s), 2.55 (2H, m), 2.80 (3H, m), 3.56-3.68 (5H, m), 4.13 (1H, m), 4.85 (1H, t), 5.16 (1H, m), 5.62 (1H, m), 5.77 (1H, m), 6.30 (1H, d), 6.72 (1H, m), 7.18-7.41 (7H, m), 7.52 (1H, m) MS (ESI) m/z 722.3 (MH$^+$)

Example 12

Synthesis of [2-((R)-2-{3-(2-fluoro-6-trifluoromethyl-benzyl)-4-methyl-5-[4-(3-nitro-benzyl)-piperazin-1-yl]-2,6-dioxo-3,6-dihydro-2H-pyrimidin-1-yl}-1-phenyl-ethylamino)-ethyl]-phosphonic acid (12-3)

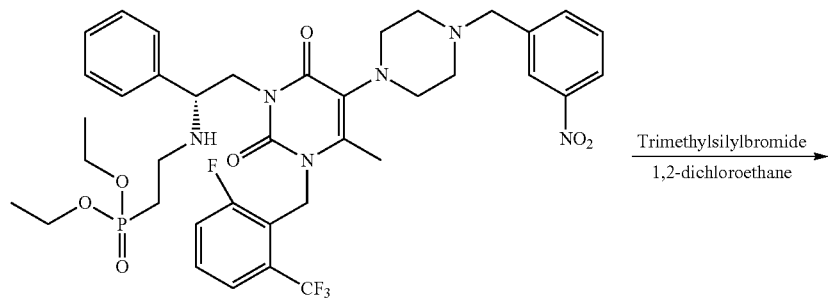

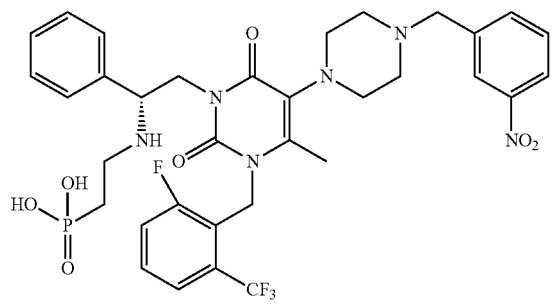

12-3

Step A. [2-((R)-2-[3-(2-fluoro-6-trifluoromethyl-benzyl)-4-methyl-5-[4-(3-nitro-benzyl)-piperazin-1-yl]-2,6-dioxo-3,6-dihydro-2H-pyrimidin-1-yl]-1-phenyl-ethylamino)-ethyl]-phosphonic acid (12-3)

To a solution of [2-((R)-2-{3-(2-fluoro-6-trifluoromethyl-benzyl)-4-methyl-5-[4-(3-nitro-benzyl)-piperazin-1-yl]-2,6-dioxo-3,6-dihydro-2H-pyrimidin-1-yl}-1-phenyl-ethylamino)-ethyl]-phosphonic acid diethyl ester (20 mg, 0.025 mmol) in 1,2-dicholoroethane was slowly added trimethylsilylbromide (20 μl, 0.149 mmol). The solution was stirred at 45° C. for 5 hrs in a nitrogen atmosphere and concentrated. The residue was dissolved for 30 min in a mixture of methyl acetate (2 mL) and distilled water (2 mL) with stirring, after which the aqueous layer was separated. The aqueous layer was allowed to pass through a cotton filter, freeze-dried, and then purified by prep-LC (eluent: distilled water containing methanol/0.1% formic acid, 2/3) to afford 8 mg of the compound as a white solid (yield 43%). $^1$H NMR (300 MHz, CD$_3$OD) δ 1.82 (2H, m), 2.28-2.60 (4H, m), 2.40 (3H, s), 2.83 (2H, d), 3.03 (2H, m), 3.58 (2H, m), 3.72 (2H, s), 4.43 (2H, d), 4.63 (1H, t), 5.41 (2H, s), 7.33-7.64 (9H, m), 7.79 (1H, d), 8.18 (1H, d), 8.30 (1H, s).

Compounds synthesized according to the above procedures are summarized in table 12, below. Compound 12-1 was prepared in the same manner as in the above procedures, with the exception that, instead of [2-((R)-2-[3-(2-fluoro-6-trifluoromethyl-benzyl)-4-methyl-5-[4-(3-nitro-benzyl)-piperazin-1-yl]-2,6-dioxo-3,6-dihydro-2H-pyrimidin-1-yl]-1-phenyl-ethylamino)-ethyl]-phosphonic acid diethyl ester, [2-((R)-2-{3-(2-fluoro-6-trifluoromethyl-benzyl)-4-methyl-2,6-dioxo-5-[4-(5-trifluoromethyl-furan-2-ylmethyl)-piperazin-1-yl]-3,6-dihydro-2H-pyrimidin-1-yl}-1-phenyl-ethylamino)-ethyl]-phosphonic acid diethyl ester was used in Step A. Compound 12-2 was prepared in the same manner as in the above procedures, with the exception that, instead of [2-((R)-2-{3-(2-fluoro-6-trifluoromethyl-benzyl)-4-methyl-5-[4-(3-nitro-benzyl)-piperazin-1-yl]-2,6-dioxo-3,6-dihydro-2H-pyrimidin-1-yl}-1-phenyl-ethylamino)-ethyl]-phosphonic acid diethyl ester, [3-((R)-2-{3-(2-fluoro-6-trifluoromethyl-benzyl)-4-methyl-2,6-dioxo-5-[4-(5-trifluoromethyl-furan-2-ylmethyl)-piperazin-1-yl]-3,6-dihydro-2H-pyrimidin-1-yl}-1-phenyl-ethylamino)-propyl]-phosphonic acid diethyl ester was used in Step A.

TABLE 12

[Structure shown with phenyl, piperazine-Y, pyrimidinedione core, methyl, 2-fluoro-6-trifluoromethyl-benzyl, and R₁—NH— substituent]

| No. | —NH—R₁ | —Y | M.W. | Mass |
|---|---|---|---|---|
| 12-1 | [NH-CH₂CH₂-P(O)(OH)₂] | [CH₂-furan-CF₃] | 761.62 | 762.6 |
| 12-2 | [NH-CH₂CH₂CH₂-P(O)(OH)₂] | [CH₂-furan-CF₃] | 775.65 | 776.5 |
| 12-3 | [NH-CH₂CH₂-P(O)(OH)₂] | [CH₂-phenyl-NO₂] | 748.66 | 749.6 |

Example 13

Synthesis of 3-((R)-2-{3-(2-fluoro-6-trifluoromethyl-benzyl)-4-methyl-5-[4-(3-nitro-benzyl)-piperazin-1-yl]-2,6-dioxo-3,6-dihydro-2H-pyrimidin-1-yl}-1-phenyl-ethylamino)-propane-1-sulfonic acid (13-1)

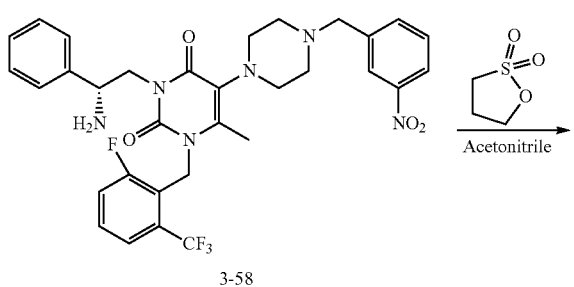

3-58

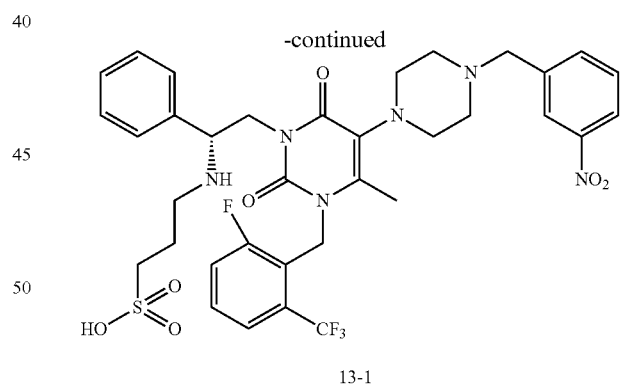

13-1

Step A. 3-((R)-2-{3-(2-fluoro-6-trifluoromethyl-benzyl)-4-methyl-5-[4-(3-nitro-benzyl)-piperazin-1-yl]-2,6-dioxo-3,6-dihydro-2H-pyrimidin-1-yl}-1-phenyl-ethylamino)-propane-1-sulfonic acid (13-1)

3-((R)-2-amino-2-phenyl-ethyl)-1-(2-fluoro-6-trifluoromethyl-benzyl)-6-methyl-5-[4-(3-nitro-benzyl)-piperazin-1-yl]-1H-pyrimidine-2,4-dione (3-58) (23 mg, 0.036 mmol) and 1,3-propanone (7 μL, 0.072 mmol) were dissolved at 90° C. for 12 hrs in acetonitrile (2 mL) with stirring. After concentration of the solution, the residue was purified using silica gel chromatography (eluent: dichloromethane/methanol, 8/1) and dried in a vacuum to afford 25 mg of the compound as a white solid (yield 93%). $^1$H NMR (300 MHz, CDCl$_3$) δ 2.16 (3H, m), 2.35 (3H, s), 2.35-2.50 (3H, m), 2.64 (2H, m), 2.83 (1H, m), 3.05 (2H, m), 3.23 (1H, m), 3.39-3.53 (4H, m), 4.08 (1H, dd), 4.76 (2H, m), 5.36 (2H, dd), 7.18 (1H, dd), 7.33-7.40 (4H, m), 7.45-7.56 (4H, m), 7.67 (1H, d), 8.10 (2H, m)

Compounds synthesized according to the above procedures are summarized in Table 13, below. Compound 13-2 was prepared in the same manner as in the above procedures, with the exception that, instead of 3-((R)-2-amino-2-phenyl-ethyl)-1-(2-fluoro-6-trifluoromethyl-benzyl)-6-methyl-5-[4-(3-nitro-benzyl)-piperazin-1-yl]-1H-pyrimidine-2,4-dione (3-58), 3-((R)-2-amino-2-phenyl-ethyl)-1-(2-fluoro-6-trifluoromethyl-benzyl)-6-methyl-5-[4-(5-trifluoromethyl-furan-2-ylmethyl)-piperazin-1-yl]-1H-pyrimidine-2,4-dione (3-66) was used in Step A.

TABLE 13

| No. | —Y | M.W. | Mass |
|---|---|---|---|
| 13-1 | 3-nitrobenzyl | 762.77 | 763.6 |
| 13-2 | 5-(trifluoromethyl)furan-2-ylmethyl | 775.73 | 776.7 |

Example 14

Synthesis of 3-((R)-2-{3-(2-fluoro-6-trifluoromethyl-benzyl)-4-methyl-5-[4-(3-nitro-benzyl)-piperazin-1-yl]-2,6-dioxo-3,6-dihydro-2H-pyrimidin-1-yl}-1-phenyl-ethylamino)-propionic acid (14-1)

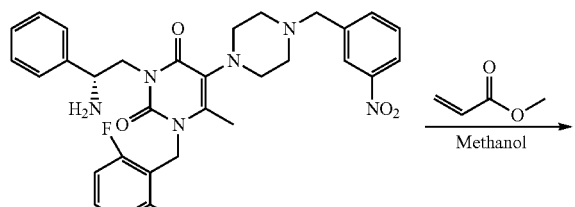

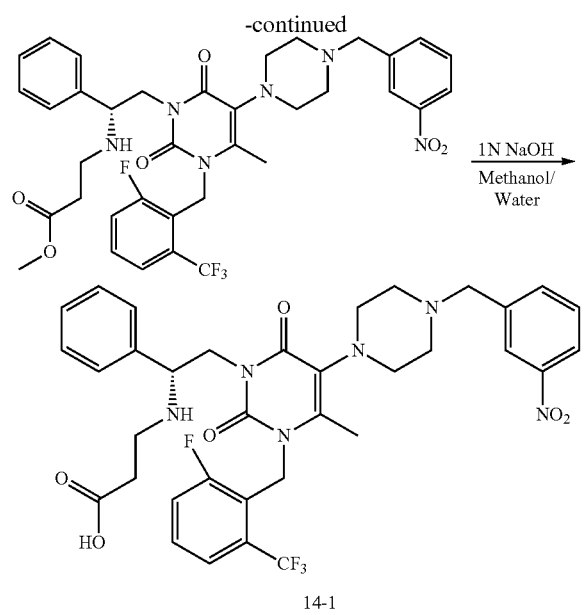

Step A. 3-((R)-2-{3-(2-fluoro-6-trifluoromethyl-benzyl)-4-methyl-5-[4-(3-nitro-benzyl)-piperazin-1-yl]-2,6-dioxo-3,6-dihydro-2H-pyrimidin-1-yl}-1-phenyl-ethylamino)-propionic acid methyl ester In a closed tube, 3-((R)-2-amino-2-phenyl-ethyl)-1-(2-fluoro-6-trifluoromethyl-benzyl)-6-methyl-5-[4-(3-nitro-benzyl)-piperazin-1-yl]-1H-pyrimidine-2,4-dione (3-58) (20 mg, 0.031 mmol), methyl acrylate (9 µl, 0.093 mmol), and methanol (2 mL) were mixed at 70° C. for 4 hrs with stirring. The resulting solution was concentrated, and the residue was purified using silica gel chromatography (eluent: dichloromethane/methanol, 20/1) and dried in a vacuum to afford 17 mg of the compound as a colorless oil (yield 74%). $^1$H NMR (300 MHz, CDCl$_3$) δ 2.17 (2H, m), 2.33 (3H, s), 2.38 (2H, t), 2.40-2.77 (6H, m), 3.58 (7H, m), 4.02-4.20 (3H, m), 5.39 (2H, d), 7.20-7.55 (9H, m), 7.77 (1H, d), 8.10 (1H, d), 8.17 (1H, s)

Step B. 3-((R)-2-{3-(2-fluoro-6-trifluoromethyl-benzyl)-4-methyl-5-[4-(3-nitro-benzyl)-piperazin-1-yl]-2,6-dioxo-3,6-dihydro-2H-pyrimidin-1-yl}-1-phenyl-ethylamino)-propionic acid (14-1)

To a solution of 3-((R)-2-[3-(2-fluoro-6-trifluoromethyl-benzyl)-4-methyl-5-[4-(3-nitro-benzyl)-piperazin-1-yl]-2,6-dioxo-3,6-dihydro-2H-pyrimidin-1-yl]-1-phenyl-ethylamino)-propionic acid methyl ester (17 mg, 0.023 mmol) in methanol (1 mL)/distilled water (500 µl) was slowly added 1N NaOH (400 µl, 0.40 mmol), followed by stirring at 50° C. for 12 hrs. The solution was concentrated, and the residue was neutralized with an aqueous saturated ammonium chloride and diluted in dichloromethane to separate an organic layer. It was purified using silica gel chromatography (eluent: dichloromethane/methanol, 10/1) and dried in a vacuum to afford 15 mg of the compound as a white solid (yield 99%). $^1$H NMR (300 MHz, CDCl$_3$) δ 2.20-2.32 (3H, m), 2.40 (3H, s), 2.40-2.83 (7H, m), 3.61 (2H, m), 3.63 (2H, s), 4.02 (1H, dd), 4.25 (1H, dd), 4.49 (1H, dd), 5.44 (2H, dd), 7.26 (1H, m), 7.37-7.58 (8H, m), 7.76 (1H, d), 8.13 (1H, d), 8.24 (1H, s).

Compounds synthesized according to the above procedures are summarized in Table 14, below. Compound 14-2 was prepared in the same manner as in the above procedures, with the exception that, instead of 3-((R)-2-amino-2-phenyl-ethyl)-1-(2-fluoro-6-trifluoromethyl-benzyl)-6-methyl-5-[4-

(3-nitro-benzyl)-piperazin-1-yl]-1H-pyrimidine-2,4-dione (3-58), 3-((R)-2-amino-2-phenyl-ethyl)-1-(2-fluoro-6-trifluoromethyl-benzyl)-6-methyl-5-[4-(5-trifluoromethyl-furan-2-ylmethyl)-piperazin-1-yl]-1H-pyrimidine-2,4-dione (3-66) was used in Step A.

TABLE 14

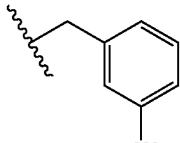

| No. | —Y | M.W. | Mass |
|-----|-----|------|------|
| 14-1 | <image at 3-nitrobenzyl position> | 712.69 | 713.5 |

TABLE 14-continued

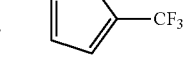

| No. | —Y | M.W. | Mass |
|-----|-----|------|------|
| 14-2 | <image of 5-trifluoromethyl-furan-2-ylmethyl> | 725.65 | 726.6 |

Example 15

Synthesis of 3-[(R)-2-Amino-2-(2-hydroxy-phenyl)-ethyl]-1-(2-fluoro-6-trifluoromethyl-benzyl)-6-methyl-5-[4-(5-trifluoromethyl-furan-2-ylmethyl)-piperazin-1-yl]-1H-pyrimidine-2,4-dione (15)

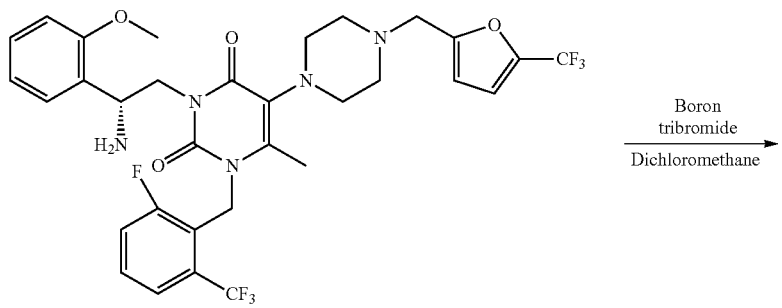

6-7

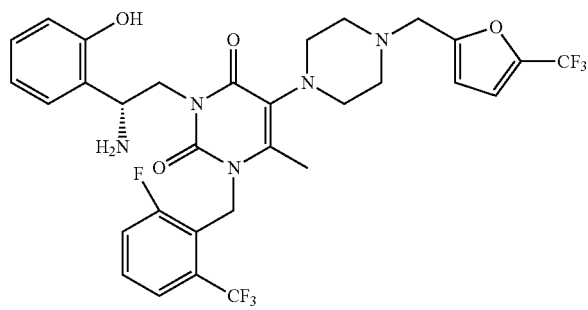

15-1

Step A. 3-[(R)-2-amino-2-(2-hydroxy-phenyl)-ethyl]-1-(2-fluoro-6-trifluoromethyl-benzyl)-6-methyl-5-[4-(5-trifluoromethyl-furan-2-ylmethyl)-piperazin-1-yl]-1H-pyrimidine-2,4-dione(15)

A solution of 3-[(R)-2-amino-2-(2-methoxy-phenyl)-ethyl]-1-(2-fluoro-6-trifluoromethyl-benzyl)-6-methyl-5-[4-(5-trifluoromethyl-furan-2-ylmethyl)-piperazin-1-yl]-1H-pyrimidine-2,4-dione (6-7) (75 mg, 0.110 mmol) in anhydrous dichloromethane (3 mL) was chilled to 0° C. In a nitrogen atmosphere, boron tribromide (550 µl, 0.550 mmol) was slowly added to the solution which was then heated to 40° C. and stirred for 12 hrs. The addition of methanol (5 mL) was followed by stirring at room temperature for 30 min. After the concentration of the solution, the residue was diluted in dichloromethane, and the organic layer thus formed was separated and concentrated. The residue was pured using silica gel chromatography (eluent: dichloromethane/methanol, 10/1) and dried in a vacuum to afford 68 mg of the compound as a pale yellowish foam (yield 92%) $^1$H NMR (300 MHz, CDCl$_3$) δ 2.21-2.35 (2H, m), 2.32 (3H, s), 2.52 (2H, m), 2.80 (2H, m), 3.57 (2H, m), 3.62 (2H, s), 4.23 (1H, d), 4.49 (1H, m), 4.64 (1H, m), 5.39 (2H, dd), 6.33 (1H, m), 6.73-6.83 (3H, m), 7.04-7.23 (3H, m), 7.40 (1H, q), 7.54 (1H, d).

Compounds synthesized according to the above procedures are summarized in Table 15, below. Compound 15-2 was prepared in the same manner as in the above procedures, with the exception that, instead of 3-[(R)-2-amino-2-(2-methoxy-phenyl)-ethyl]-1-(2-fluoro-6-trifluoromethyl-benzyl)-6-methyl-5-[4-(5-trifluoromethyl-furan-2-ylmethyl)-piperazin-1-yl]-1H-pyrimidine-2,4-dione(6-7), 3-[(R)-2-amino-2-(2-methoxy-phenyl)-ethyl]-1-(2-fluoro-6-trifluoromethyl-benzyl)-6-methyl-5-[4-(3-nitro-benzyl)-piperazin-1-yl]-1H-pyrimidine-2,4-dione (6-2) was used in Step A.

TABLE 15

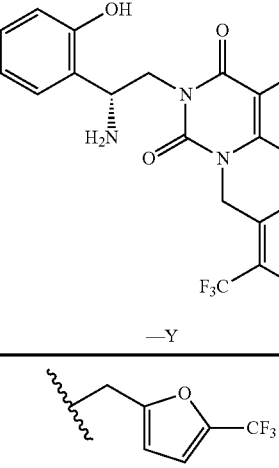

| No. | —Y | M.W. | Mass |
|---|---|---|---|
| 15-1 | (furan-CF$_3$ group) | 669.59 | 670.4 |
| 15-2 | (3-nitrobenzyl group) | 656.63 | 657.7 |

Example 16

Synthesis of 4-[(R)-2-{3-(2-fluoro-6-trifluoromethyl-benzyl)-4-methyl-2,6-dioxo-5-[4-(5-trifluoromethyl-furan-2-ylmethyl)-piperazin-1-yl]-3,6-dihydro-2H-pyrimidin-1-yl}-1-(2-hydroxy-phenyl)-ethylamino]-butyric acid (16-1)

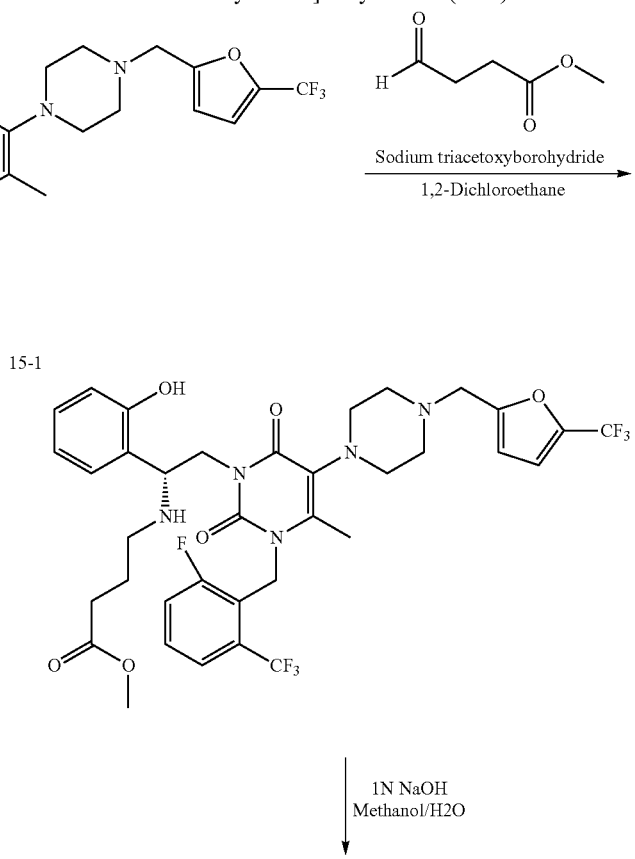

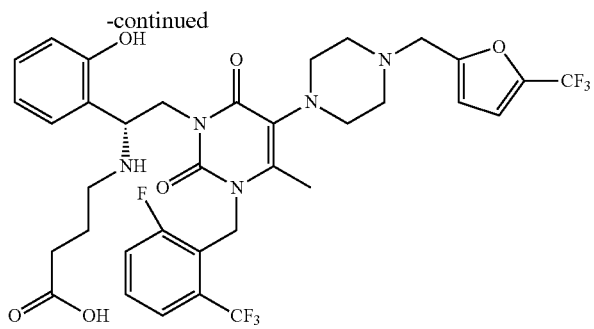

16-1

Step A. 4-[(R)-2-{3-(2-fluoro-6-trifluoromethyl-benzyl)-4-methyl-2,6-dioxo-5-[4-(5-trifluoromethyl-furan-2-ylmethyl)-piperazin-1-yl]-3,6-dihydro-2H-pyrimidin-1-yl}-1-(2-hydroxy-phenyl)-ethylamino]-butyric acid methyl ester To a solution of 3-[(R)-2-amino-2-(2-hydroxy-phenyl)-ethyl]-1-(2-fluoro-6-trifluoromethyl-benzyl)-6-methyl-5-[4-(5-trifluoromethyl-furan-2-ylmethyl)-piperazin-1-yl]-1H-pyrimidine-2,4-dione (15-1) (67 mg, 0.100 mmol) in 1,2-dicholoroethane (2 mL) were 4-oxo-butyric acid methyl ester (17 mg, 0.150 mmol) and sodium triacetoxyborohydride (42 mg, 0.200 mmol) in the order, followed by stirring at room temperature for 1.5 hrs. The solution was neutralized with an aqueous saturated sodium bicarbonate solution to separate an organic layer. After concentration of the organic layer, the residue was purified using silica gel chromatography(eluent: dichloromethane/methanol, 30/1) and dried in a vacuum to afford 40 mg of the compound as a colorless oil (yield 53%).
$^1$H NMR (300 MHz, CDCl$_3$) δ 1.79 (2H, m), 2.20-2.33 (4H, m), 2.32 (3H, s), 2.48 (2H, m), 2.60 (2H, t), 2.80 (2H, m), 3.58 (2H, m), 3.61 (2H, s), 3.63 (3H, s), 4.06-4.15 (2H, m), 4.42 (1H, dd), 5.42 (2H, dd), 6.30 (1H, d), 6.72-6.78 (3H, m), 7.06-7.15 (2H, m), 7.26 (1H, m), 7.41 (1H, m), 7.55 (1H, d)

Step B. 4-[(R)-2-{3-(2-fluoro-6-trifluoromethyl-benzyl)-4-methyl-2,6-dioxo-5-[4-(5-trifluoromethyl-furan-2-ylmethyl)-piperazin-1-yl]-3,6-dihydro-2H-pyrimidin-1-yl}-1-(2-hydroxy-phenyl)-ethylamino]-butyric acid (16-1)

To a solution of 4-[(R)-2-{3-(2-fluoro-6-trifluoromethyl-benzyl)-4-methyl-2,6-dioxo-5-[4-(5-trifluoromethyl-furan-2-ylmethyl)-piperazin-1-yl]-3,6-dihydro-2H-pyrimidin-1-yl}-1-(2-hydroxy-phenyl)-ethylamino]-butyric acid methyl ester (40 mg, 0.052 mmol) in methanol (1 mL) was slowly added 1N NaOH (520 µl, 0.52 mmol). The solution was stirred at 60° C. for 12 hrs and concentrated. The residue was neutralized with an aqueous saturated ammonium chloride solution and diluted in dichloromethane/methanol (10/1) to separate an organic layer. Following concentration of the organic layer, the residue was purified using silica gel chromatography (eluent: dichloromethane/methanol, 7/1) and dried in a vacuum to afford 18 mg of the compound as a white solid (yield 39%).

Compounds synthesized according to the above procedures are summarized in Table 16, below. Compound 16-2 was prepared in the same manner as in the above procedures, with the exception that, instead of 3-[(R)-2-amino-2-(2-hydroxy-phenyl)-ethyl]-1-(2-fluoro-6-trifluoromethyl-benzyl)-6-methyl-5-[4-(5-trifluoromethyl-furan-2-ylmethyl)-piperazin-1-yl]-1H-pyrimidine-2,4-dione(15-1), 3-(R)-((4-3-(2-amino-2-phenylethyl)-1-(2-fluoro-6-trifluoromethyl-benzyl)-6-methyl-2,4-dioxo-1,2,3,4-tetrahydropyrimidin-5-yl)-piperazin-1-yl)-methyl)-2-fluorobenzamide (3-100) was used in Step A.

TABLE 16

| No. | —Y | —R | M.W. | Mass |
|---|---|---|---|---|
| 16-1 | furan-CF$_3$ | 2-OH-phenyl | 755.7 | 756.3 |
| 16-2 | 2-F-3-CONH$_2$-benzyl | phenyl | 742.73 | 743.5 |

As for compound 16-3, it was isolated by filtering off related compounds generated in the final hydrolysis process during the synthesis of compound 16-2 through column chromatography.

16-3
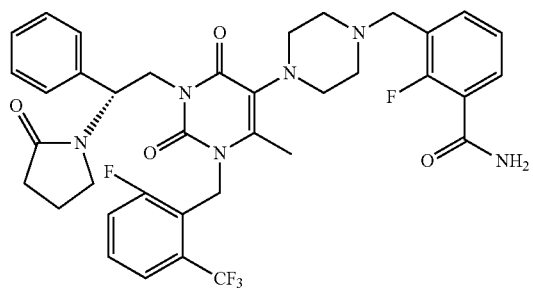
$^1$H NMR (300 MHz, CDCl$_3$) δ 1.82 (2H, m), 2.18-2.30 (4H, m), 2.34 (3H, s), 2.54 (2H, m), 2.80 (3H, m), 3.56-3.65 (5H, m), 4.13 (1H, m), 4.84 (1H, t), 5.17 (1H, m), 5.61 (1H, m), 5.78 (1H, m), 5.84 (1H, m), 6.70 (1H, m), 7.18-7.41 (8H, m), 7.52 (1H, m), 7.64 (1H, m), 8.00 (1H, m) MS (ESI) m/z 725.6 (MH$^+$)
Example 17
Synthesis of [2-((R)-1-tert-butoxycarbonylamino-2-{3-(2-fluoro-6-trifluoromethyl-benzyl)-4-methyl-2,6-dioxo-5-[4-(5-trifluoromethyl-furan-2-ylmethyl)-piperazin-1-yl]-3,6-dihydro-2H-pyrimidin-1-yl}-ethyl)-phenoxy]-acetic acid (17-3)
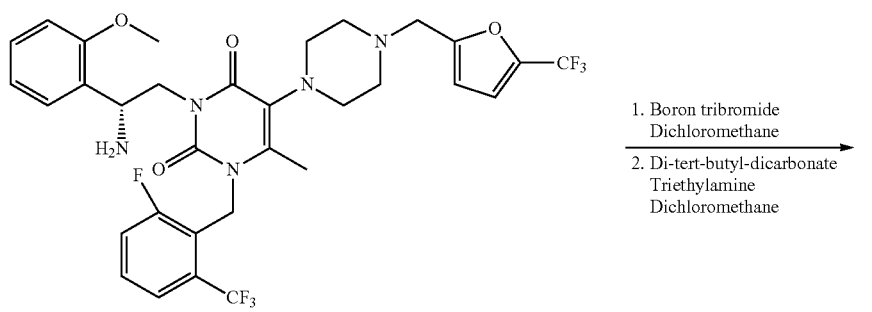
6-7
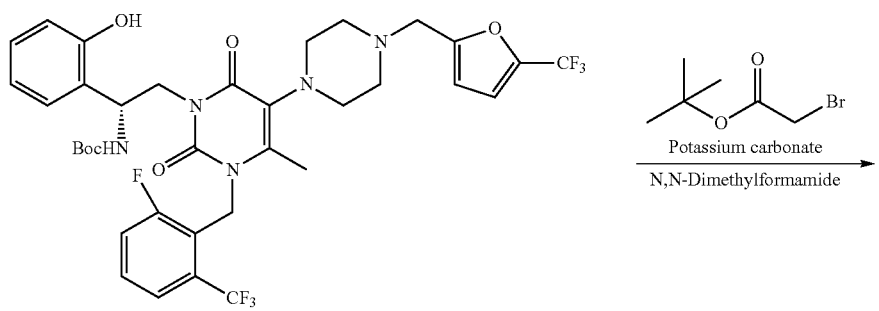
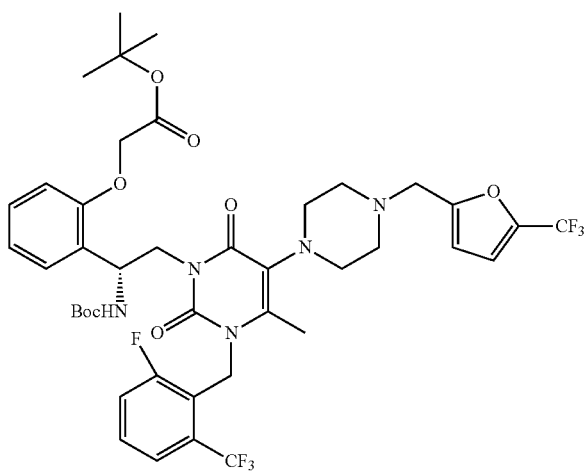

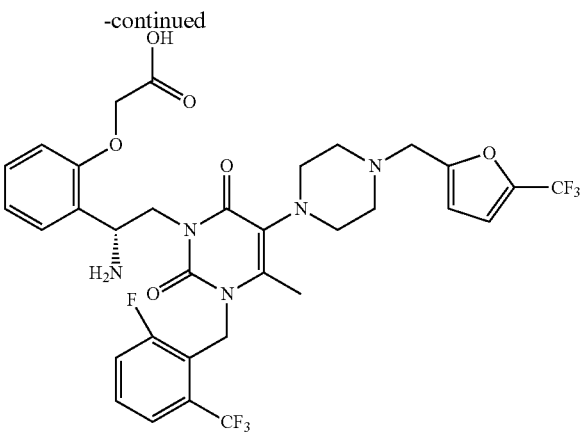

17-3

Step A. (R)-2-{3-(2-fluoro-6-trifluoromethyl-benzyl)-4-methyl-2,6-dioxo-5-[4-(5-trifluoromethyl-furan-2-ylmethyl)-piperazin-1-yl]-3,6-dihydro-2H-pyrimidin-1-yl}-1-(2-hydroxy-phenyl)-ethyl]-carbamic acid tert-butyl ester A solution of 3-[(R)-2-amino-2-(2-methoxy-phenyl)-ethyl]-1-(2-fluoro-6-trifluoromethyl-benzyl)-6-methyl-5-[4-(5-trifluoromethyl-furan-2-ylmethyl)-piperazin-1-yl]-1H-pyrimidine-2,4-dione (6-7) (250 mg, 0.364 mmol) in anhydrous dichloromethane (10 mL) was chilled to −78° C. In a nitrogen atmosphere, boron tribromide (1.8 mL, 1.82 mmol) was slowly added to the solution which was then slowly heated to 40° C. and stirred for 12 hrs. Methanol (10 mL) was added to the solution which was then stirred at room temperature for 20 min. After concentration of the solution, the residue was diluted in dichloromethane and washed with an aqueous saturated sodium bicarbonate solution. The organic layer thus formed was dried over sodium sulfate and filtered. The filtrate was concentrated to produce a brownish foam ($^1$H NMR (300 MHz, CDCl$_3$) δ 2.20-2.33 (2H, m), 2.32 (3H, s), 2.49 (2H, m), 2.79 (2H, m), 3.50-3.62 (2H, s), 3.61 (2H, s), 4.19 (1H, dd), 4.42 (1H, dd), 4.51 (1H, dd), 5.42 (2H, dd), 6.29 (1H, d), 6.73-6.83 (3H, m), 7.05-7.26 (3H, m), 7.41 (1H, m), 7.55 (1H, d)). To a solution of the brownish foam in dichloromethane (10 mL) were added triethylamine (66 μl, 0.545 mmol) and di-tert-butyl-dicarbonate (80 μl, 0.400 mmol) in that order, followed by stirring at 40° C. for 3 hrs. The solution was washed with an aqueous saturated ammonium chloride to separate an organic layer. After concentration of the organic layer, the residue was purified using silica gel chromatography (eluent: hexane/ethyl acetate/dichloromethane, 1.5/1/1) and dried in a vacuum to afford 200 mg of the compound as a colorless oil (yield 71%).

Step B. [2-((R)-1-tert-butoxycarbonylamino-2-{3-(2-fluoro-6-trifluoromethyl-benzyl)-4-methyl-2,6-dioxo-5-[4-(5-trifluoromethyl-furan-2-ylmethyl)-piperazin-1-yl]-3,6-dihydro-2H-pyrimidin-1-yl}-ethyl)-phenoxy]-acetic acid tert-butyl ester A solution of [(R)-2-{3-(2-fluoro-6-trifluoromethyl-benzyl)-4-methyl-2,6-dioxo-5-[4-(5-trifluoromethyl-furan-2-ylmethyl)-piperazin-1-yl]-3,6-dihydro-2H-pyrimidin-1-yl}-1-(2-hydroxy-phenyl)-ethyl]-carbamic acid tert-butyl ester (100 mg, 0.13 mmol), potassium carbonate (36 mg, 0.26 mmol), and bromo-acetic acid tert-butyl ester (38 μl, 0.26 mmol) were dissolved at 70° C. for 4 hrs in DMF (1 mL) with stirring, and then chilled to room temperature. The solution was diluted in dichloromethane and washed with an aqueous saturated sodium bicarbonate solution. The organic layer thus formed was separated and concentrated, and the residue was purified using silica gel chromatography (eluent: hexane/ethyl acetate, 2/1) and dried in a vacuum to afford 51 mg of the compound as a white oil (yield 44%).

Step C. [2-((R)-1-tert-butoxycarbonylamino-2-{3-(2-fluoro-6-trifluoromethyl-benzyl)-4-methyl-2,6-dioxo-5-[4-(5-trifluoromethyl-furan-2-ylmethyl)-piperazin-1-yl]-3,6-dihydro-2H-pyrimidin-1-yl}-ethyl)-phenoxy]-acetic acid (17-3)

To a solution of [2-((R)-1-tert-butoxycarbonylamino-2-{3-(2-fluoro-6-trifluoromethyl-benzyl)-4-methyl-2,6-dioxo-5-[4-(5-trifluoromethyl-furan-2-ylmethyl)-piperazin-1-yl]-3,6-dihydro-2H-pyrimidin-1-yl}-ethyl)-phenoxy]-acetic acid tert-butyl ester (51 mg, 0.058 mmol) in dichloromethane (2 mL) was added trifluoroacetic acid (500 μl, 6.50 mmol), followed by stirring at room temperature for hrs. The solution was neutralized with an aqueous saturated sodium bicarbonate solution and the organic layer thus formed was separated. After concentration of the organic layer, the residue was purified using silica gel chromatography (eluent: dichloromethane/methanol, 7/1) and dried in a vacuum to afford 36 mg of the compound as a white solid (yield 86%). $^1$H NMR (300 MHz, CDCl$_3$) δ 2.00-2.50 (4H, m), 2.25 (3H, s), 2.67 (2H, m), 3.30-3.62 (4H, m), 4.10-4.60 (4H, m), 4.81 (1H, m), 5.20-5.50 (2H, m), 6.34 (1H, m), 6.70 (1H, m), 6.77-6.87 (2H, m), 7.10-7.20 (3H, m), 7.34 (1H, m), 7.49 (1H, d)

Compounds synthesized according to the above procedures are summarized in Table 17, below. Compound 17-1 was prepared in the same manner as in the above procedures, with the exception that, instead of 3-[(R)-2-amino-2-(2-methoxy-phenyl)-ethyl]-1-(2-fluoro-6-trifluoromethyl-benzyl)-6-methyl-5-[4-(5-trifluoromethyl-furan-2-ylmethyl)-piperazin-1-yl]-1H-pyrimidine-2,4-dione (6-7), 3-[(R)-2-amino-2-(2-methoxy-phenyl)-ethyl]-1-(2-fluoro-6-trifluoromethyl-benzyl)-6-methyl-5-[4-(3-nitro-benzyl)-piperazin-1-yl]-1H-pyrimidine-2,4-dione (6-2) was used in Step A. Compound 17-2 was prepared in the same manner as in the above procedures, with the exception that, instead of bromo-acetic acid tert-butyl ester, a different bromide compound was used in Step B.

TABLE 17
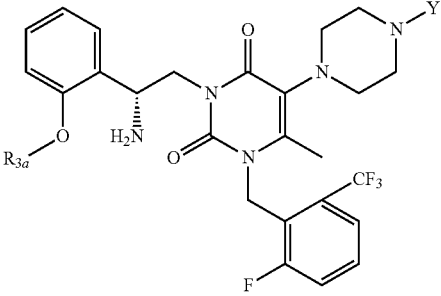
| No. | —R$_{3a}$ | —Y | M.W. | Mass |
|---|---|---|---|---|
| 17-1 | 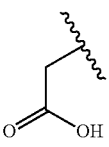 [SMILES: *CC(=O)O] | 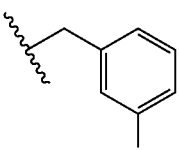 | 714.66 | 715.5 |
| 17-2 | 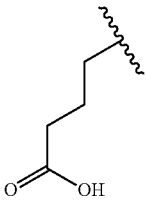 [SMILES: *CCCC(=O)O] | 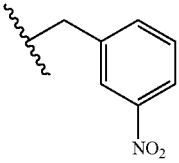 [SMILES: *Cc1cccc([N+](=O)[O-])c1] | 742.72 | 743.5 |
| 17-3 | 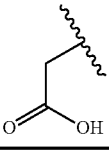 | 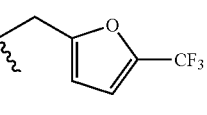 | 727.63 | 728.2 |
Example 18
Synthesis 3-((R)-2-amino-2-phenyl-ethyl)-1-(2-fluoro-6-trifluoromethyl-benzyl)-5-{4-[3-(1H-tetrazol-5-yl)-benzyl]-piperazin-1-yl}-1H-pyrimidine-2,4-dione(18)
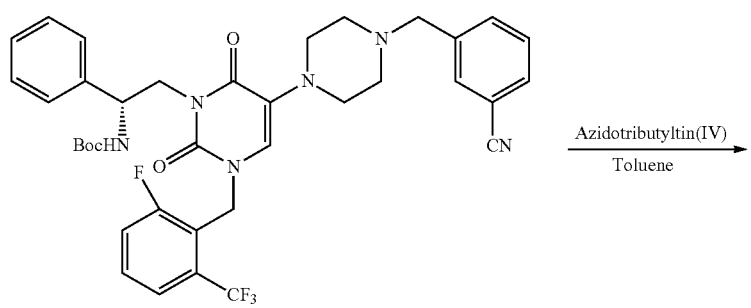

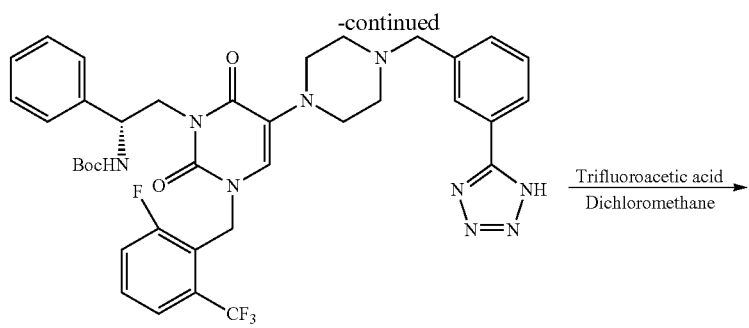

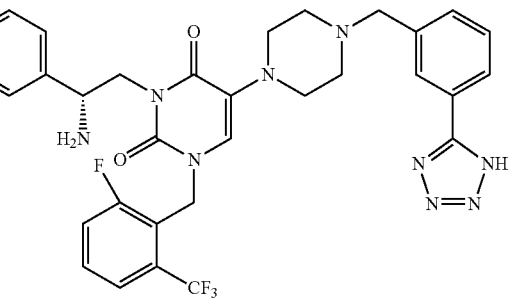

18

Step A. [(R)-2-(3-(2-fluoro-6-trifluoromethyl-benzyl)-2,6-dioxo-5-{4-[3-(1H-tetrazol-5-yl)-benzyl]-piperazin-1-yl}-3,6-dihydro-2H-pyrimidin-1-yl)-1-phenyl-ethyl]-carbamic acid tert-butyl ester {(R)-2-[5-[4-(3-cyano-benzyl)-piperazin-1-yl]-3-(2-fluoro-6-trifluoromethyl-benzyl)-2,6-dioxo-3,6-dihydro-2H-pyrimidin-1-yl]-1-phenyl-ethyl}-carbamic acid tert-butyl ester (35 mg, 0.049 mmol), and azidotributyl tin (IV) (16 μl, 0.059 mmol) were dissolved at 120° C. for 10 hrs in toluene (1 mL) with stirring. The solution was cooled to room temperature, followed by the addition of azidotributyl tin (IV) (20 μl, 0.074 mmol) thereto and stirring at 120° C. for an additional 2 hrs. The solution was cooled to room temperature, diluted in dichloromethane, and washed with an aqueous saturated ammonium chloride solution and an aqueous saturated sodium chloride solution in the order. The organic layer thus formed was separated and concentrated, and the residue was purified using silica gel chromatography (eluent: dichloromethane/methanol, 6/1) and dried in a vacuum to afford 20 mg of the compound as a colorless oil (yield 54%).

Step B. 3-((R)-2-amino-2-phenyl-ethyl)-1-(2-fluoro-6-trifluoromethyl-benzyl)-5-{4-[3-(1H-tetrazol-5-yl)-benzyl]-piperazin-1-yl}-1H-pyrimidine-2,4-dione (18)

To a solution of [(R)-2-(3-(2-fluoro-6-trifluoromethyl-benzyl)-2,6-dioxo-5-{4-[3-(1H-tetrazol-5-yl)-benzyl]-piperazin-1-yl}-3,6-dihydro-2H-pyrimidin-1-yl)-1-phenyl-ethyl]-carbamic acid tert-butyl ester (20 mg, 0.027 mmol) in dichloromethane (2 mL) was added trifluoroacetic acid (100 μL, 1.30 mmol), followed by stirring at room temperature for 4 hrs. The solution was neutralized with an aqueous saturated sodium bicarbonate solution to separate an organic layer. After concentration of the organic layer, the residue was purified using prep-LC (eluent: distilled water containing methanol/0.1% formic acid, 3/7→95/5, every 15 min) and dried in a vacuum to afford 5 mg of the compound as a pale yellowish oil (yield 30%). $^1$H NMR (300 MHz, CD$_3$OD) δ 2.40 (3H, s), 2.51-2.64 (4H, m), 3.07 (2H, m), 3.61 (2H, m), 3.94 (2H, s), 4.34 (2H, m), 4.62 (1H, t), 5.38 (2H, d), 7.32-7.56 (9H, m), 7.62 (1H, d), 8.01-8.04 (2H, m) MS (ESI) m/z 664.5 (MH$^+$)

Example 19

Synthesis of 3-((R)-2-amino-2-phenyl-ethyl)-1-(2,6-difluoro-benzyl)-5-(2-oxo-pyrrolidin-1-yl)-1H-pyrimidine-2,4-dione (19)

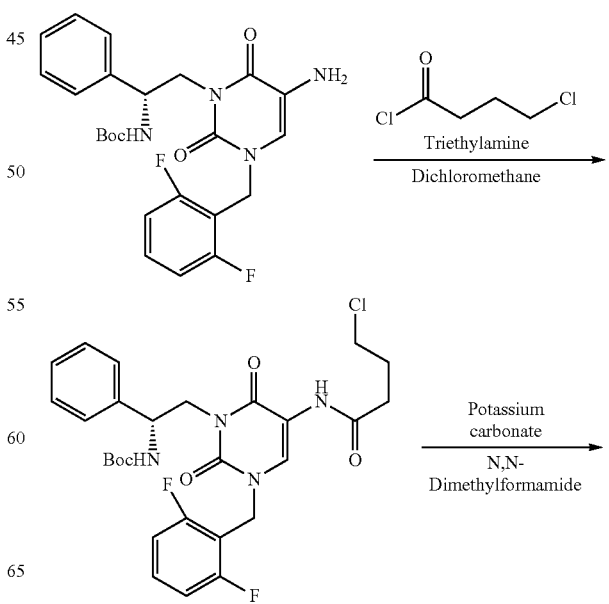

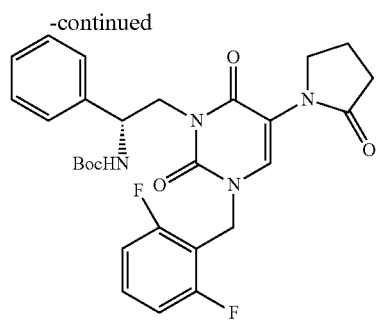

↓ Trifluoroacetic acid
  Dichloromethane

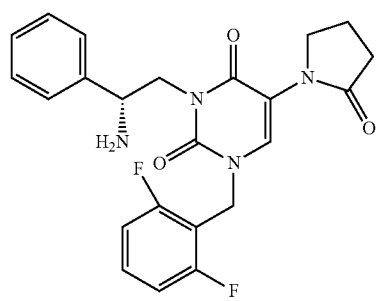

19

Step A. {(R)-2-[5-(4-chloro-butyrylamino)-3-(2,6-difluoro-benzyl)-2,6-dioxo-3,6-dihydro-2H-pyrimidin-1-yl]-1-phenyl-ethyl}-carbamic acid tert-butyl ester To a solution of {(R)-2-[5-amino-3-(2,6-difluoro-benzyl)-2,6-dioxo-3,6-dihydro-2H-pyrimidin-1-yl]-1-phenyl-ethyl}-carbamic acid tert-butyl ester (42 mg, 0.089 mmol) in dichloromethane (2 mL) were added triethylamine (25 μl, 0.178 mmol) and 4-chloro-butyryl chloride (11 μl, 0.097 mmol) in the order. The solution was stirred at room temperature for 2 hrs and concentrated. The residue was purified using silica gel chromatography (eluent: hexane/ethyl acetate/dichloromethane, 2/1/1) and dried in a vacuum to afford 40 mg of the compound as a colorless oil (yield 78%). $^1$H NMR (300 MHz, CDCl$_3$) δ 1.33 (9H, s), 2.17 (2H, p), 2.57 (2H, t), 3.63 (2H, t), 4.10 (1H, m), 4.34 (1H, t), 4.99-5.14 (3H, m), 5.47 (1H, d), 6.96 (2H, m), 7.24-7.39 (6H, m), 7.72 (1H, s), 8.65 (1H, s)

Step B. {(R)-2-[3-(2,6-difluoro-benzyl)-2,6-dioxo-5-(2-oxo-pyrrolidin-1-yl)-3,6-dihydro-2H-pyrimidin-1-yl]-1-phenyl-ethyl}-carbamic acid tert-butyl ester {(R)-2-[5-(4-chloro-butyrylamino)-3-(2,6-difluoro-benzyl)-2,6-dioxo-3,6-dihydro-2H-pyrimidin-1-yl]-1-phenyl-ethyl}-carbamic acid tert-butyl ester (30 mg, 0.052 mmol) and potassium carbonate (30 mg, 0.217 mmol) were dissolved at room temperature for 6 hrs in DMF (1 mL) with stirring. The solution was diluted with dichloromethane and washed with water to separate an organic layer. After concentration of the organic layer, the residue was purified using silica gel chromatography (eluent: dichloromethane/methanol, 30/1) and dried in a vacuum to afford 25 mg of the compound as a colorless oil (yield 90%). $^1$H NMR (300 MHz, CDCl$_3$) δ 1.34 (9H, s), 2.15 (2H, p), 2.51 (2H, t), 3.80 (2H, m), 4.03 (1H, m), 4.27 (1H, m), 4.98-5.13 (3H, m), 5.57 (1H, d), 6.97 (2H, m), 7.22-7.40 (6H, m), 7.62 (1H, s)

Step C. 3-((R)-2-amino-2-phenyl-ethyl)-1-(2,6-difluoro-benzyl)-5-(2-oxo-pyrrolidin-1-yl)-1H-pyrimidine-2,4-dione(19)

To a solution of {(R)-2-[3-(2,6-difluoro-benzyl)-2,6-dioxo-5-(2-oxo-pyrrolidin-1-yl)-3,6-dihydro-2H-pyrimidin-1-yl]-1-phenyl-ethyl}-carbamic acid tert-butyl ester (25 mg, 0.046 mmol) in dichloromethane (1 mL) was added trifluoroacetic acid (100 μl, 1.30 mmol), followed by stirring at room temperature for 3 hrs. The solution was neutralized with an aqueous saturated sodium bicarbonate solution to separate an organic layer. After concentration of the organic layer, the residue was purified using silica gel chromatography (eluent: dichloromethane/methanol, 20/1) and dried in a vacuum to afford 15 mg of compound 19 (yield 75%). $^1$H NMR (300 MHz, CDCl$_3$) δ 2.13 (2H, p), 2.50 (2H, t), 3.74 (2H, m), 4.02 (1H, dd), 4.20 (1H, dd), 4.34 (1H, dd), 5.04 (2H, s), 6.96 (2H, m), 7.23-7.39 (6H, m), 7.57 (1H, s)

Example 20

Synthesis of 1-(2-fluoro-6-trifluoromethyl-benzyl)-3-((R)-2-hydroxy-2-phenyl-ethyl)-6-methyl-5-[4-(5-trifluoromethyl-furan-2-ylmethyl)-piperazin-1-yl]-1H-pyrimidine-2,4-dione (20)

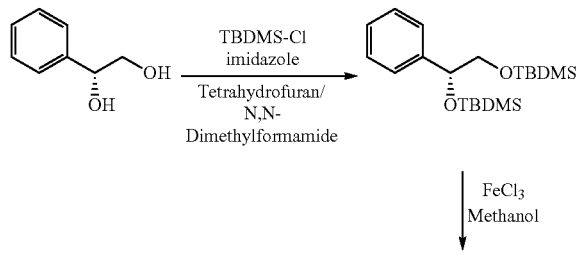

↓ FeCl$_3$
  Methanol

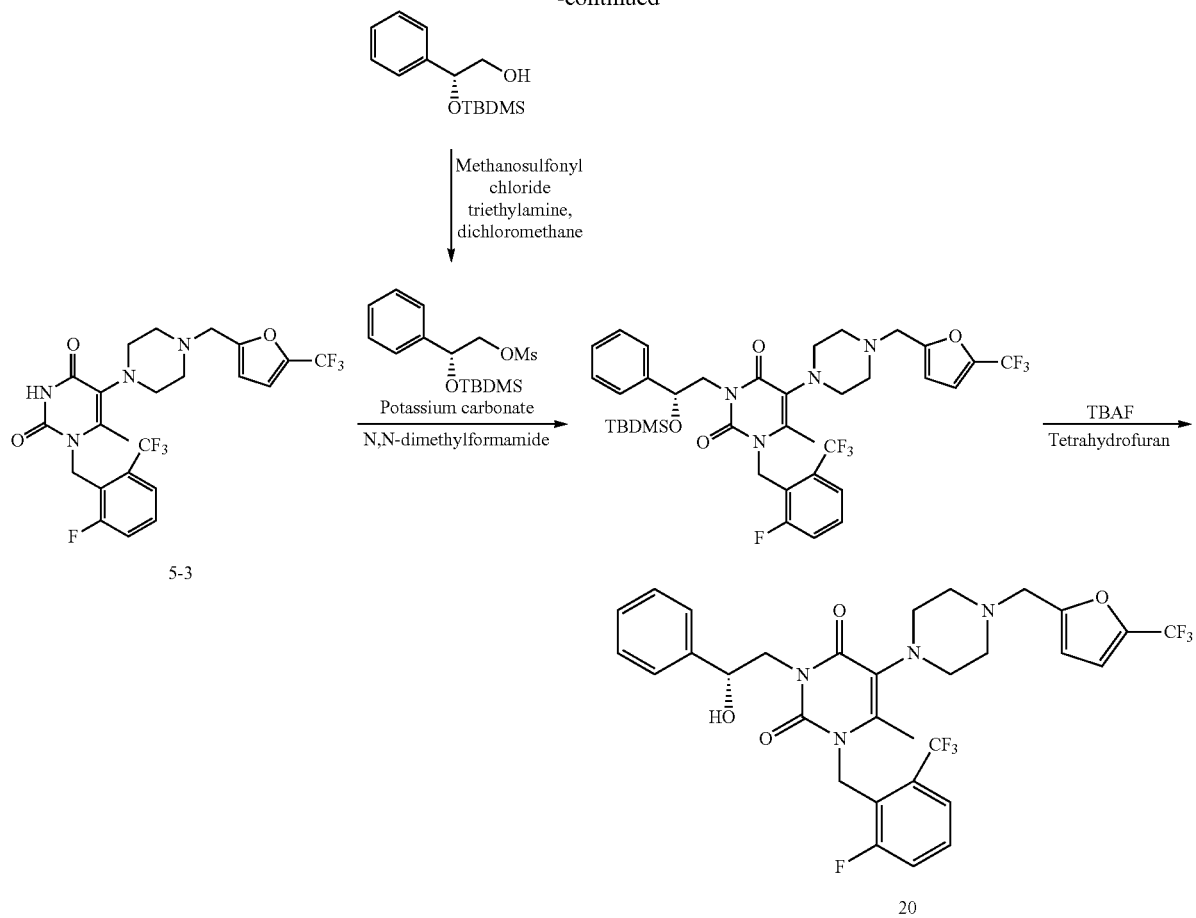

Step A. [(R)-1,2-bis-(tert-butyl-dimethyl-silanyloxy)-ethyl]-benzene (R)-1-phenyl-ethane-1,2-diol (276 mg, 2 mmol) and tert-butyldimethylsilyl chloride (663 mg, 4.4 mmol) was mixed and dissolved in DMF(5 mL)/THF(1.5 mL). To the solution was added imidazole (408 mg, 6 mmol), followed by stirring at room temperature for 12 hrs. After concentration of the solution, the residue was diluted in ethylether (20 cc) and washed with an aqueous saturated sodium bicarbonate solution, distilled water and an aqueous saturated sodium chloride solution in the order. To the organic layer thus formed, sodium sulfate was added. Stirring for 5 min was followed by filtration. The filtrate was concentrated and the residue was dried in a vacuum to afford 450 mg of the compound as a colorless oil (yield 62%).

Step B. 2-(tert-butyl-dimethyl-silanyloxy)-2-phenyl-ethanol

To a solution of [(R)-1,2-bis-(tert-butyl-dimethyl-silanyloxy)-ethyl]-benzene (625 mg, 1.7 mmol) in methanol (3 mL) was slowly added ferric chloride III) (276 mg, 1.7 mmol) with stirring at room temperature. When the reaction was monitored to be completed about 25 min after the addition, an aqueous saturated sodium bicarbonate solution was added. The solution was extracted with ethyl ether and the organic layer thus formed was separated. To the organic layer was added sodium sulfate, followed by stirring for 5 min and filtering. The filtrate was concentrated and dried in a vacuum, and the residue was purified using silica gel chromatography (eluent: hexane/ethyl acetate, 16/1) and dried in a vacuum to afford 270 mg of the compound as a colorless oil (yield 63%).

Step C. 3-[(R)-2-(tert-butyl-dimethyl-silanyloxy)-2-phenyl-ethyl]-1-(2-fluoro-6-trifluoromethyl-benzyl)-6-methyl-5-[4-(5-trifluoromethyl-furan-2-ylmethyl)-piperazin-1-yl]-1H-pyrimidine-2,4-dione To a solution of 2-(tert-butyl-dimethyl-silanyloxy)-2-phenyl-ethanol (85 mg, 0.337 mmol) in dichloromethane (2 mL) were added triethylamine (61 µl, 0.44 mmol) and methanesulfonyl chloride (27 µl, 0.35 mmol) in the order, followed by stirring at room temperature for 20 min. The solution was washed with an aqueous saturated sodium bicarbonate solution to separate an organic layer. The organic layer was dried over sodium sulfate and filtrated. The filtrate was concentrated and dried for 30 min in a vacuum to give methanesulfonic acid (R)-2-(tert-butyl-dimethyl-silanyloxy)-2-phenyl-ethyl ester. Methanesulfonic acid (R)-2-(tert-butyl-dimethyl-silanyloxy)-2-phenyl-ethyl ester, 1-(2-fluoro-6-trifluoromethyl-benzyl)-6-methyl-5-[4-(5-trifluoromethyl-furan-2-ylmethyl)-piperazin-1-yl]-1H-pyrimidine-2,4-dione (5-3) (60 mg, 0.112 mmol) and potassium carbonate (77 mg, 0.560 mmol) were dissolved at 70° C. for 12 hrs in DMF (1 ml) in a nitrogen atmosphere with stirring. The solution was cooled to room temperature, washed with an aqueous saturated sodium bicarbonate solution and concentrated. The residue was purified using silica gel chromatography (eluent: hexane/ethyl acetate, 5/1) and dried in a vacuum to afford 83 mg of the compound as a white solid (yield 97%). $^1$H NMR (300 MHz, CDCl$_3$) δ −0.23 (3H, s), −0.11 (3H, s), 0.80 (9H, s), 2.25 (2H, m), 2.33 (3H, s), 2.47 (2H, m), 2.80 (2H, m), 3.50-3.70 (2H, m), 3.62 (2H, s), 3.83 (1H, dd), 4.36 (1H, dd), 5.13 (1H, dd), 5.26-5.50 (2H, m), 6.30 (1H, d), 6.73 (1H, m), 7.16-7.43 (7H, m), 7.53 (1H, d)

Step D. 1-(2-fluoro-6-trifluoromethyl-benzyl)-3-((R)-2-hydroxy-2-phenyl-ethyl)-6-methyl-5-[4-(5-trifluoromethyl-furan-2-ylmethyl)-piperazin-1-yl]-1H-pyrimidine-2,4-dione(20)

To a solution of 3-[(R)-2-(tert-butyl-dimethyl-silanyloxy)-2-phenyl-ethyl]-1-(2-fluoro-6-trifluoromethyl-benzyl)-6-methyl-5-[4-(5-trifluoromethyl-furan-2-ylmethyl)-piperazin-1-yl]-1H-pyrimidine-2,4-dione (83 mg, 0.108 mmol) in tetrahydrofuran (2 mL) was added tetrabutylammoniumfluoride (220 µl in 1.0 M tetrahydrofuran, 0.220 mmol), followed by stirring at room temperature for 12 hrs in a nitrogen atmosphere. The solution was washed with an aqueous saturated sodium bicarbonate solution and extracted with dichloromethane to separate an organic layer. After concentration of the organic layer, the residue was purified using silica gel chromatography (eluent: hexane/ethyl acetate/dichloromethane, 1/1/1) and dried in a vacuum to afford 50 mg of the compound as a white foam (70%). $^1$H NMR (300 MHz, CDCl$_3$) δ 2.26 (2H, m), 2.34 (3H, s), 2.51 (2H, m), 2.81 (2H, m), 3.60 (2H, m), 3.63 (2H, s), 3.88 (1H, d), 4.26 (1H, s), 4.28 (1H, d), 5.02 (1H, m), 5.41 (2H, s), 6.31 (1H, d), 6.73 (1H, m), 7.20-7.48 (7H, m), 7.55 (1H, d)

Example 21

Synthesis 4-((R)-2-{3-(2-fluoro-6-trifluoromethyl-benzyl)-4-methyl-2,6-dioxo-5-[4-(5-trifluoromethyl-furan-2-ylmethyl)-piperazin-1-yl]-3,6-dihydro-2H-pyrimidin-1-yl}-1-phenyl-ethylamino)-2-hydroxy-butyric acid(21)

Step A. Synthesis of 4-bromo-2-hydroxy-butyric acid methyl ester

To a solution of 5-(2-bromo-ethyl)-2,2-dimethyl-[1,3]dioxolan-4-one (synthesized as instructed in Tetrahedron Letters, 1997, 38, 28, 4935) (93 mg, 0.416 mmol) in toluene (0.5 mL) were added p-TsOH.H$_2$O (8 mg, 0.0415 mmol) and methanol (0.5 mL), followed stirring overnight at room temperature. The solution was concentrated in a vacuum, diluted with dichloromethane and washed with an aqueous saturated sodium bicarbonate solution. The organic layer thus formed was dried over sodium sulfate and filtered. The filtrate was concentrated to produce 68 mg of the compound as an oil. $^1$H NMR (300 MHz, CDCl$_3$) δ 1.98 (1H, m), 2.34 (1H, m), 2.96 (1H, d), 3.56 (2H, m), 3.82 (3H, s), 4.37 (1H, pentet).

Step B. Synthesis of 4-(2-{3-(2-fluoro-6-trifluoromethyl-benzyl)-4-methyl-2,6-dioxo-5-[4-(5-trifluoromethyl-furan-2-ylmethyl)-piperazin-1-yl]-3,6-dihydro-2H-pyrimidin-1-yl}-1-phenyl-ethylamino)-2-hydroxy-butyric acid (21)

To a solution of 3-((R)-2-amino-2-phenyl-ethyl)-1-(2-fluoro-6-trifluoromethyl-benzyl)-6-methyl-5-[4-(5-trifluoromethyl-furan-2-ylmethyl)-piperazin-1-yl]-1H-pyrimidine-2,4-dione(3-66) (60 mg, 0.0918 mmol) and 4-bromo-2-hydroxy-butyric acid methyl ester (54 mg, 0.275 mmol) in acetonitrile (1.5 mL) was added N,N-diisopropylethylamine (24 µl, 0.182 mmol), followed by stirring overnight at 90° C. The solution was cooled after which the solvent was removed in a vacuum. The residue was diluted in an aqueous saturated sodium bicarbonate solution and extracted with dichloromethane. The organic layer thus formed was dried over sodium sulfate and filtered. After concentration of the filtrate, the residue was purified by PrepTLC with EtOAc/hexane/dichloromethane(2/1/1) to produce 15 mg of an intermediate (yield 21%). To a solution of the intermediate in methanol (0.5 mL) was added 1N-NaOH (0.12 ml, 0.117 mmol), followed by stirring at room temperature for 3 hrs. 0.2N—HCl was gradually added to form white precipitates. The suspen-

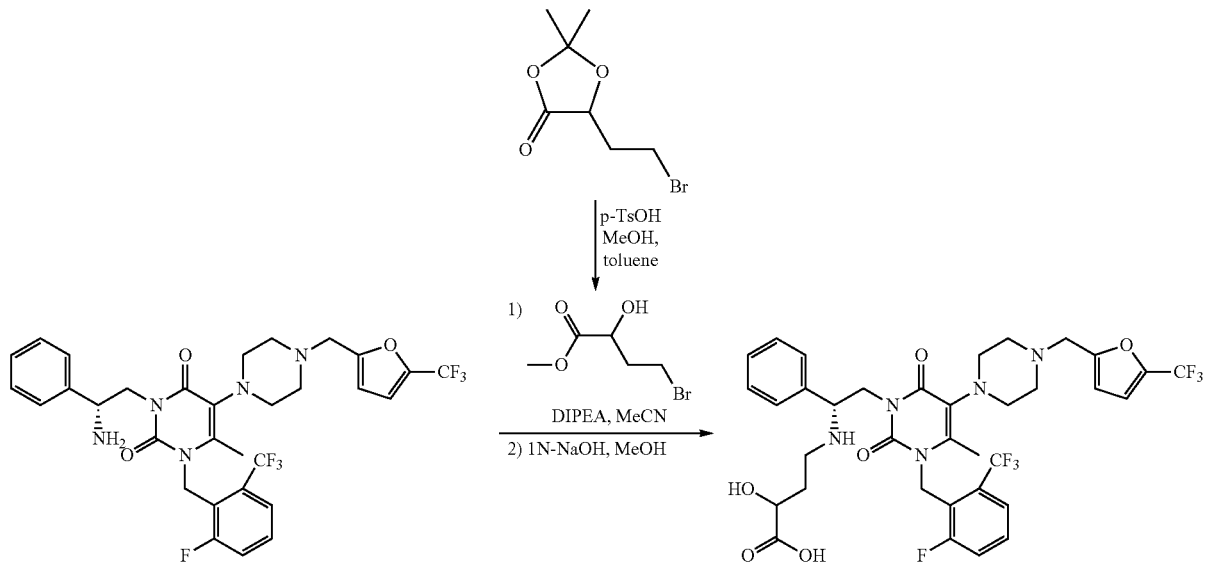

sion was extracted three times with a mixture of. dichloromethane/methanol, and the organic layers thus formed were pooled, dried over sodium sulfate and filtrated. After concentration of the filtrate, the residue was purified using silica gel chromatography eluting with dichloromethane/methanol (10/1) to afford 7 mg of compound (yield 48%). $^1$H NMR (300 MHz, CD$_3$OD) δ 1.88-2.04 (2H, m), 2.31 (2H, t), 2.39 (3H, s), 2.46 (1H, d), 2.58 (1H, d), 2.84 (2H, m), 2.92 (2H, m), 3.54 (2H, m), 3.66 (2H, s), 3.91 (2H, q), 4.34 (2H, m), 4.46 (1H, m), 4.60 (1H, m), 5.38 (2H, s), 6.49 (1H, d), 6.93 (1H, d), 7.32-7.41 (6H, m), 7.51 (2H, m), 7.61 (2H, d). MS (ESI) m/z 756.5 (MH$^+$).

Example 22

Synthesis of 3-((R)-2-amino-2-phenyl-ethyl)-1-(2-fluoro-6-trifluoromethyl-benzyl)-5-[3-hydroxymethyl-4-(5-trifluoromethyl-furan-2-ylmethyl)-piperazin-1-yl]-6-methyl-1H-pyrimidine-2,4-dione (22)

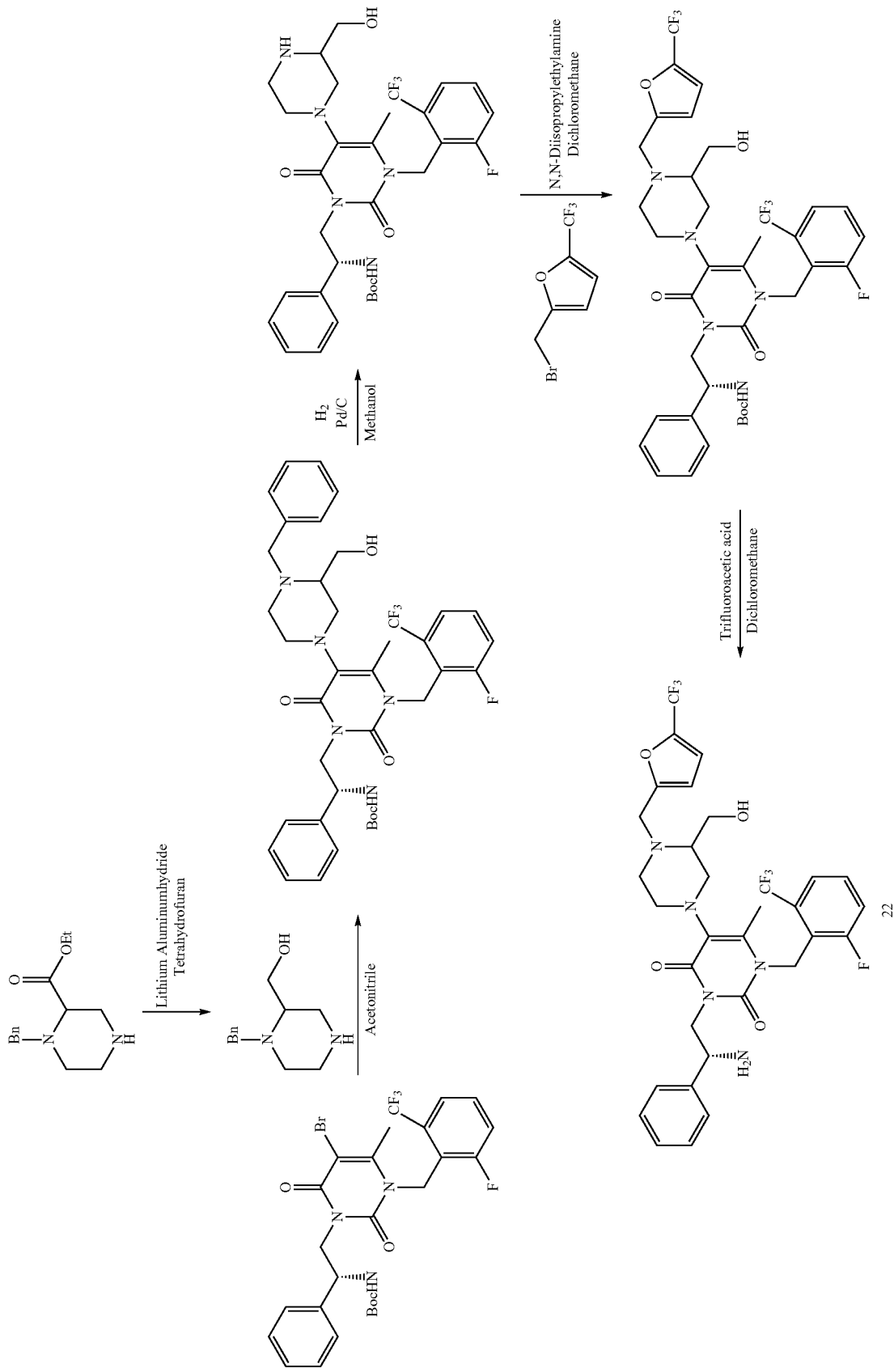

Step A. {(R)-2-[5-(4-benzyl-3-hydroxymethyl-piperazin-1-yl)-3-(2-fluoro-6-trifluoromethyl-benzyl)-4-methyl-2,6-dioxo-3,6-dihydro-2H-pyrimidin-1-yl]-1-phenyl-ethyl}-carbamic acid tert-butyl ester To a solution of 1-benzyl-piperazinee-2-carboxylic acid ethyl ester (synthesized as instructed in Synthesis 11 1992 1065-1067/4 1991 318-319) (500 mg, 2.01 mmol) in anhydrous tetrahydrofuran (10 mL) was slowly added lithium aluminum hydride (LiAlH$_4$) (4 mL in 1.0 M THF, 4.02 mmol) at 0° C. in a nitrogen atmosphere. The solution was stirred at room temperature for 2 hrs and then chilled to 0° C. Slow addition of water (100 μl), 1N NaOH (1000), and water (300 μl) in the order produced a white slurry. To this was added a small amount of potassium carbonate, followed by stirring at room temperature for 20 min. After filtration through a cotton filter, the filtrate was purified using silica gel chromatography (eluent: dichloromethane/methanol, 10/1) and dried in a vacuum to afford 290 mg of (1-benzyl-piperazin-2-yl)-methanol (white solid, yield 70%). $^1$H NMR (300 MHz, CDCl$_3$) δ 2.28 (1H, m), 2.49 (1H, m), 2.87 (2H, m), 3.01 (2H, m), 3.34 (1H, d), 3.49-3.65 (2H, d), 4.02 (1H, dd), 4.07 (1H, d), 7.25-7.32 (5H, m))

(1-Benzyl-piperazin-2-yl)-methanol (200 mg, 0.97 mmol), {(R)-2-[5-bromo-3-(2-fluoro-6-trifluoromethyl-benzyl)-4-methyl-2,6-dioxo-3,6-dihydro-2H-pyrimidin-1-yl]-1-phenyl-ethyl}-carbamic acid tert-butyl ester (50 mg, 0.083 mmol), and acetonitrile (1 mL) were placed in a microwave vessel and stirred at 120° C. for 3 hrs with microwave irradiation. After concentration of the solution, the residue was purified using silica gel chromatography (eluent: hexane/ethyl acetate/dichloromethane, 1/1/1) and dried in a vacuum to afford 20 mg of a colorless oil (yield 33%) 을 얻었다. $^1$H NMR (300 MHz, CDCl$_3$) δ 1.37 (9H, s), 2.23 (1H, m), 2.34 (3H, s), 2.41-2.66 (2H, m), 2.85 (1H, m), 3.16 (1H, m), 3.49 (1H, m), 3.72 (1H, m), 3.93-4.15 (3H, m), 4.21 (1H, m), 5.03 (1H, m), 5.42 (2H, dd), 5.74 (1H, m), 7.21 (2H, m), 7.18-7.26 (10H, m), 7.54 (1H, d)

Step B. {(R)-2-[(3-(2-fluoro-6-trifluoromethyl-benzyl)-5-(3-hydroxymethyl-piperazin-1-yl)-4-methyl-2,6-dioxo-3,6-dihydro-2H-pyrimidin-1-yl]-1-phenyl-ethyl}-carbamic acid tert-butyl ester To a solution of {(R)-2-[5-(4-benzyl-3-hydroxymethyl-piperazin-1-yl)-3-(2-fluoro-6-trifluoramethyl-benzyl)-4-methyl-2,6-dioxo-3,6-dihydro-2H-pyrimidin-1-yl]-1-phenyl-ethyl}-carbamic acid tert-butyl ester (20 mg, 0.028 mmol) in methanol (2 mL) was added 10% palladium/carbon (5 mg) in a nitrogen atmosphere, followed stirring the solution at room temperature for 3 hrs in a hydrogen atmosphere. The solution was allowed to pass through a cotton filter to remove the palladium/carbon, and the filtrate was concentrated and dried in a vacuum to produce {(R)-2-[3-(2-fluoro-6-trifluoromethyl-benzyl)-5-(3-hydroxymethyl-piperazin-1-yl)-4-methyl-2,6-dioxo-3,6-dihydro-2H-pyrimidin-1-yl]-1-phenyl-ethyl}-carbamic acid tert-butyl ester.

Step C. ((R)-2-{3-(2-fluoro-6-trifluoromethyl-benzyl)-5-[3-hydroxymethyl-4-(5-trifluoromethyl-furan-2-ylmethyl)-piperazin-1-yl]-4-methyl-2,6-dioxo-3,6-dihydro-2H-pyrimidin-1-yl}-1-phenyl-ethyl)-carbamic acid tert-butyl ester To a solution of {(R)-2-[3-(2-fluoro-6-trifluoromethyl-benzyl)-5-(3-hydroxymethyl-piperazin-1- yl)-4-methyl-2,6-dioxo-3,6-dihydro-2H-pyrimidin-1-yl]-1-phenyl-ethyl}-carbamic acid tert-butyl ester (0.028 mmol) in dichloromethane (2 mL) were added N,N-diisopropylethylamine (10 μl, 0.056 mol) and 2-bromomethyl-5-trifluoromethyl-furan (7.6 mg, 0.034 mmol) in the order, followed by stirring at room temperature for 6 hrs. After concentration of the solution, the residue was purified using silica gel chromatography (eluent: hexane/ethyl acetate/dichloromethane, 1/2/1) and dried in a vacuum to afford 17 mg of a white oil (yield 77%).

Step D. 3-((R)-2-amino-2-phenyl-ethyl)-1-(2-fluoro-6-trifluoromethyl-benzyl)-5-[3-hydroxymethyl-4-(5-trifluoromethyl-furan-2-ylmethyl)-piperazin-1-yl]-6-methyl-1H-pyrimidine-2,4-dione (22)

To a solution of ((R)-2-{3-(2-fluoro-6-trifluoromethyl-benzyl)-5-[3-hydroxymethyl-4-(5-trifluoromethyl-furan-2-ylmethyl)-piperazin-1-yl]-4-methyl-2,6-dioxo-3,6-dihydro-2H-pyrimidin-1-yl}-1-phenyl-ethyl)-carbamic acid tert-butyl ester (17 mg, 0.022 mmol) in dichloromethane (1 mL) was added trifluoroacetic acid (100 μl, 1.30 mmol), followed by at room temperature for 1 hr. The solution was neutralized with an aqueous saturated sodium bicarbonate solution. After concentration of the organic layer thus formed, the residue was purified using silica gel chromatography (eluent: dichloromethane/methanol, 10/1) and dried in a vacuum to afford 12 mg of the compound as a white foam (yield 81%). $^1$H NMR (300 MHz, CDCl$_3$) δ 2.29 (3H, s), 2.50 (3H, m), 2.86 (2H, m), 3.50-3.76 (3H, m), 3.95 (2H, m), 4.04 (2H, m), 4.21 (1H, t), 4.36 (1H, dd), 5.40 (2H, dd), 6.30 (1H, s), 6.73 (1H, s), 7.22 (2H, m), 7.33 (2H, t), 7.40 (3H, m), 7.54 (1H, d) MS (ESI) m/z 684.4 (MH$^+$)

Example 23

Synthesis of 3-((R)-2-amino-2-phenyl-ethyl)-1-(2,6-difluoro-benzyl)-6-methyl-5-(4-phenethyl-piperazin-1-yl)-1H-pyrimidine-2,4-dione (23-1)

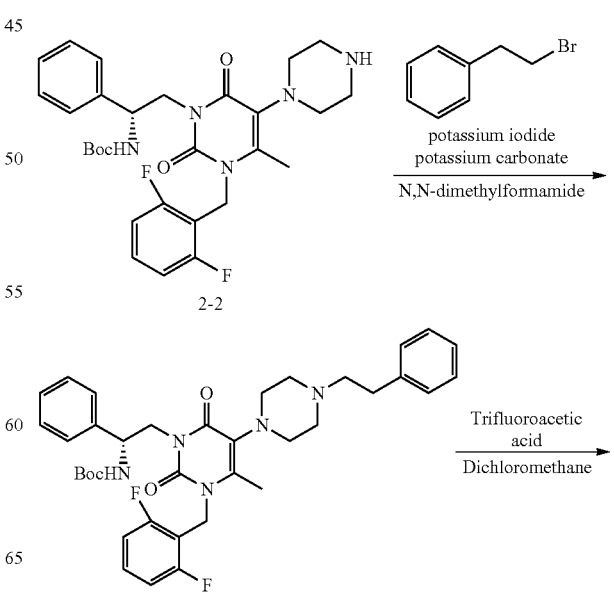

-continued

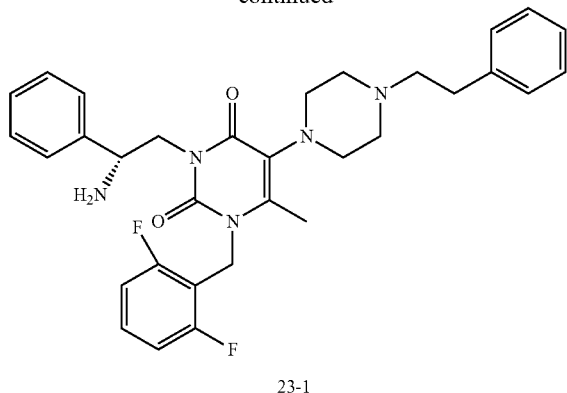

23-1

Step A. {(R)-2-[3-(2,6-difluoro-benzyl)-4-methyl-2,6-dioxo-5-(4-phenethyl-piperazin-1-yl)-3,6-dihydro-2H-pyrimidin-1-yl]-1-phenyl-ethyl}-carbamic acid tert-butyl ester To a solution of {(R)-2-[3-(2,6-difluoro-benzyl)-4-methyl-2,6-dioxo-5-piperazin-1-yl-3,6-dihydro-2H-pyrimidin-1-yl]-1-phenyl-ethyl}-carbamic acid tert-butyl ester (2-2) (30 mg, 0.054 mmol) in DMF (1 mL) were added potassium carbonate (15 mg, 0.108 mmol), KI (1.3 mg, 0.0081 mmol), and (2-bromo-ethyl)-benzene (11.0 mg, 0.059 mmol) in the order, followed by stirring at 80° C. for 4 hrs. The solution was diluted in dichloromethane and washed with distilled water. After concentration of the organic layer thus formed, the residue was purified using silica gel chromatography (eluent: hexane/ethyl acetate/dichloromethane, 1/1/1) and dried in a vacuum to afford 25 mg of the compound as a colorless oil (yield 70%). $^1$H NMR (300 MHz, CDCl$_3$) δ 1.35 (9H, s), 2.22 (2H, m), 2.44 (3H, s), 2.49 (2H, m), 2.63 (2H, t), 2.82 (2H, t), 2.88 (2H, m), 3.62 (2H, m), 4.04 (1H, dd), 4.25 (1H, t), 5.01 (1H, m), 5.01-5.36 (2H, dd), 5.84 (1H, m), 6.89 (2H, t), 7.17-7.40 (11H, m)

Step B. 3-((R)-2-amino-2-phenyl-ethyl)-1-(2,6-difluoro-benzyl)-6-methyl-5-(4-phenethyl-piperazin-1-yl)-1H-pyrimidine-2,4-dione (23-1)

To a solution of {(R)-2-[3-(2,6-difluoro-benzyl)-4-methyl-2,6-dioxo-5-(4-phenethyl-piperazin-1-yl)-3,6-dihydro-2H-pyrimidin-1-yl]-1-phenyl-ethyl}-carbamic acid tert-butyl ester (25 mg, 0.038 mmol) in dichloromethane (2 mL) was added trifluoroacetic acid (70 mL, 0.91 mol), followed by stirring at room temperature for 3 hrs. The solution was neutralized with an aqueous saturated sodium bicarbonate solution to separate an organic layer. After concentration of the organic layer, the residue was purified using silica gel chromatography (eluent: dichloromethane/methanol, 10/1) and dried in a vacuum to afford 12 mg of the compound as a white foam (yield 57%). $^1$H NMR (300 MHz, CDCl$_3$) δ 2.20 (2H, m), 2.42 (3H, s), 2.50 (2H, m), 2.61 (2H, dd), 2.81 (2H, dd), 2.89 (2H, m), 3.58 (2H, m), 4.05 (1H, dd), 4.20 (1H, t), 4.36 (1H, dd), 5.22 (2H, dd), 5.84 (1H, m), 6.89 (2H, t), 7.19-7.41 (11H, m)

Compounds synthesized according to the above procedures are summarized in Table 23, below. Compounds 23-2 to 23-9 were prepared in the same manner as in the above procedures, with the exception that, instead of (2-bromo-ethyl)-benzene, different bromide compounds were used in Step A.

TABLE 23

| No. | —R$_3$ | —Y | —R$_6$ | M.W. | Mass |
|---|---|---|---|---|---|
| 23-1 | phenyl | phenethyl | 2,6-difluorobenzyl | 559.65 | 560.3 |
| 23-2 | phenyl | 2-fluorophenethyl | 2,6-difluorobenzyl | 577.64 | 578.3 |
| 23-3 | phenyl | 2-methoxyphenethyl | 2,6-difluorobenzyl | 589.68 | 590.5 |

TABLE 23-continued
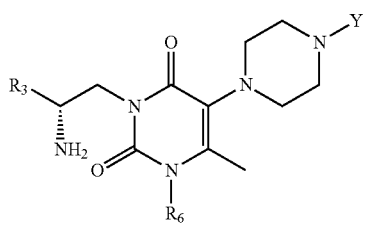
| No. | —R₃ | —Y | —R₆ | M.W. | Mass |
|---|---|---|---|---|---|
| 23-4 | phenyl | 3-(4-fluorophenyl)propyl | 2,6-difluorobenzyl | 577.64 | 578.4 |
| 23-5 | phenyl | 3-(3-methoxyphenyl)propyl | 2,6-difluorobenzyl | 589.68 | 590.5 |
| 23-6 | phenyl | 3-(4-methylphenyl)propyl | 2,6-difluorobenzyl | 573.68 | 574.4 |
| 23-7 | phenyl | 3-(4-nitrophenyl)propyl | 2,6-difluorobenzyl | 604.65 | 605.2 |
| 23-8 | phenyl | 3-phenylpropyl | 2,6-difluorobenzyl | 573.68 | 574.5 |
| 23-9 | phenyl | 2-(2,3-dihydro-1,4-benzodioxin-2-yl)ethyl | 2,6-difluorobenzyl | 603.66 | 604.3 |

Example 24

Synthesis of 4-[(R)-2-{3-(2-fluoro-6-trifluoromethyl-benzyl)-4-methyl-2,6-dioxo-5-[4-(5-trifluoromethyl-furan-2-ylmethyl)-piperazin-1-yl]-3,6-dihydro-2H-pyrimidin-1-yl}-1-(2-hydroxy-phenyl)-ethylamino]-butyric acid (24-1)

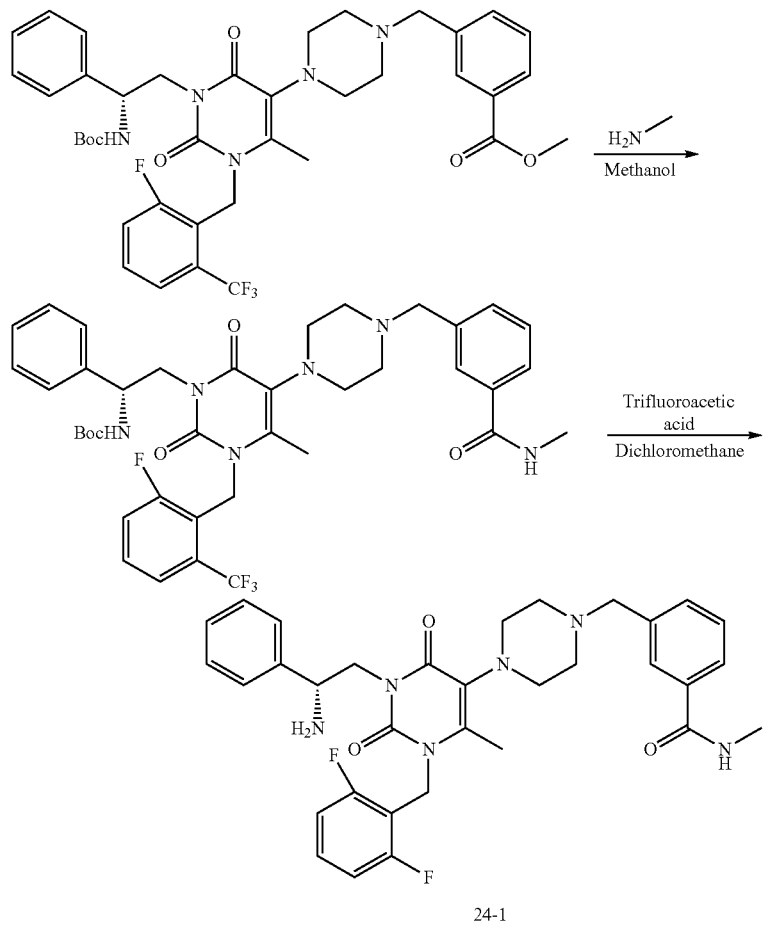

24-1

Step A. (R)-tert-butyl (2-(3-(2-fluoro-6-(trifluoromethyl)benzyl)-4-methyl-5-(4-(3-(methylcarbamoyl)benzyl)piperazin-1-yl)-2,6-dioxo-2,3-dihydropyrimidin-1(6H)-yl)-1-phenylethyl)carbamate (R)-methyl 3-((4-(3-(2-((tert-butoxycarbonyl)amino)-2-phenylethyl)-1-(2-fluoro-6-(trifluoromethyl)benzyl)-6-methyl-2,4-dioxo-1,2,3,4-tetrahydropyrimidin-5-yl)piperazin-1-yl)methyl)benzoate (a precursor of compound 3-72) (35 mg) and a 2.0 M methylamine methanol solution (5 mL) were stirred at 90° C. for 12 hrs in a sealed-tube. The solution was concentrated, and the residue was purified using silica gel chromatography (eluent: dichloromethane/methanol, 30/1) and dried in a vacuum to afford 28 mg of the compound as a colorless oil (yield 78%). $^1$H NMR (300 MHz, CDCl$_3$) δ 1.35 (9H, s), 2.19 (2H, m), 2.35 (3H, s), 2.50 (2H, m), 2.77 (2H, m), 3.04 (3H, d), 3.56 (2H, s), 3.64 (2H, m), 4.07 (1H, m), 4.28 (1H, m), 5.04 (1H, m), 5.41 (2H, m), 5.77 (1H, d), 6.28 (1H, m), 7.17-7.42 (8H, m), 7.48-7.56 (2H, m), 7.68-7.71 (1H, m), 7.73 (1H, s)

Step B. (R)-3-((4-(3-(2-amino-2-phenylethyl)-1-(2-fluoro-6-(trifluoromethyl)benzyl)-6-methyl-2,4-dioxo-1,2,3,4-tetrahydropyrimidin-5-yl)piperazin-1-yl)methyl)-N-methylbenzamide(24-1)

To a solution of (R)-tert-butyl (2-(3-(2-fluoro-6-(trifluoromethyl)benzyl)-4-methyl-5-(4-(3-(methylcarbamoyl)benzyl)piperazin-1-yl)-2,6-dioxo-2,3-dihydropyrimidin-1(6H)-yl)-1-phenylethyl)carbamate (28 mg) in dichloromethane (2 mL) was added trifluoroacetic acid (100 μl), followed by stirring at room temperature for 3 hrs. The solution was neutralized with an aqueous saturated sodium bicarbonate solution after which an organic layer was separated. The organic layer was concentrated and the residue was purified using silica gel chromatography (eluent: dichloromethane/methanol, 7/1) and dried in a vacuum to afford 15 mg of the compound as a white foam (yield 63%). $^1$H NMR (300 MHz, CDCl$_3$) δ 2.18 (2H, m), 2.33 (3H, s), 2.47 (2H, m), 2.75 (2H, m), 3.04 (3H, d), 3.55 (2H, s), 3.61 (2H, m), 4.06 (1H, m), 4.19 (1H, m), 4.37 (1H, m), 5.40 (2H, s), 6.32 (1H, m), 7.19-7.25 (2H, m), 7.29-7.43 (6H, m), 7.47 (1H, m), 7.54 (1H, m), 7.70 (1H, m), 7.73 (1H, s)

Compounds synthesized according to the above procedures are summarized in Table 24, below. Compound 24-2 was prepared in the same manner as in the above procedures, with the exception that, instead of the methylamine solution, an ethylamine solution was used in Step A.

TABLE 24
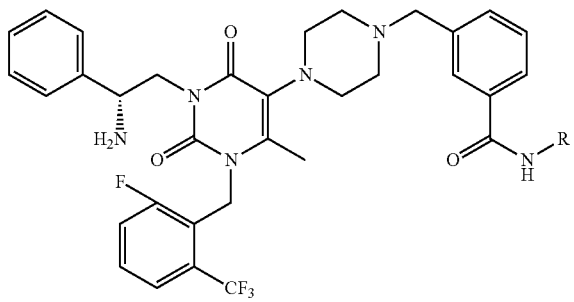
| No. | —R | M.W. | Mass |
|---|---|---|---|
| 24-1 | Me | 652.68 | 653.4 |
| 24-2 | ethyl | 666.71 | 667.3 |
Example 25
Synthesis of (R)-3-(2-amino-2-phenylethyl)-1-(2-fluoro-6-(trifluoromethyl)benzyl)-6-methyl-5-(4-(4,4,5,5,5-pentafluoropentyl)piperazin-1-yl)pyrimidine-2,4(1H,3H)-dione(25-1)
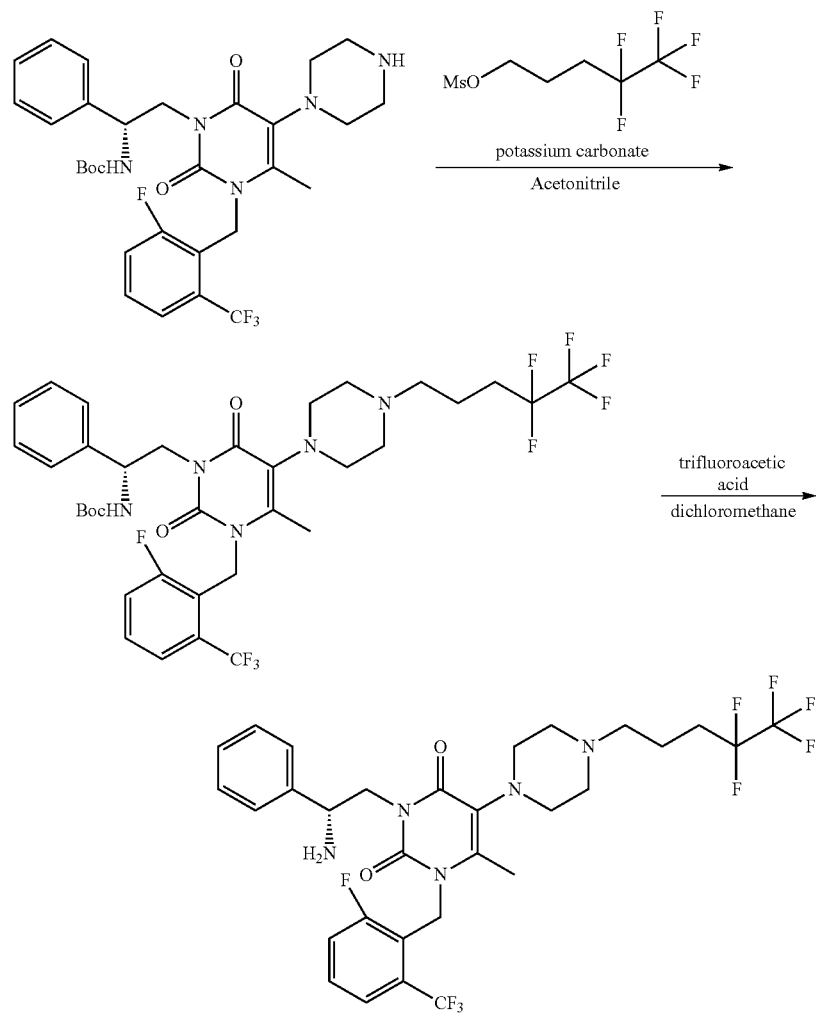
25-1

Step A. (R)-tert-butyl-(2-(3-(2-fluoro-6-(trifluoromethyl)benzyl)-4-methyl-2,6-dioxo-5-(4-(4,4,5,5,5-pentafluoropentyl)-piperazin-1-yl)-2,3-dihydropyrimidin-1(6H)-yl)-1-phenylethyl)carbamate To a solution of 100 μl (0.416 mmol) of 4,4,5,5,5-pentafluoropentan-1-ol in 2 mL of dichloromethane were added 69 μl (1.2 eq) of triethylamine and 36 μl (1.1 eq) of methanesulfonyl chloride in the order, followed by stirring at room temperature for 30 min. The solution was washed with an aqueous saturated sodium bicarbonate solution, dried over sodium sulfate, filtrated and concentrated to produce a colorless oil. 60 μl of the oil, 30 mg of (R)-tert-butyl (2-(3-(2-fluoro-6-(trifluoromethyl)benzyl)-4-methyl-2,6-dioxo-5-(piperazin-1-yl)-2,3-dihydropyrimidin-1(6H)-yl)-1-phenylethyl)carbamate (0.049 mmol), and 21 mg (0.149 mmol) of potassium carbonate were dissolved at 80° C. for 7 hrs in 2 mL of acetonitrile, with stirring. The solution was concentrated, diluted with dichloromethane, and washed with an aqueous saturated sodium bicarbonate solution. After concentration of the organic layer thus formed, the residue was purified by prep-TLC (eluent: hexane/ethyl acetate, 1/1) and dried in a vacuum to afford 8 mg of the compound as a colorless oil (yield 21%). $^1$H NMR (300 MHz, CDCl$_3$) δ 1.36 (9H, s), 1.77 (2H, m), 2.14 (4H, m), 2.36 (3H, s), 2.42 (2H, m), 2.53 (2H, m), 2.75 (2H, m), 3.61 (2H, m), 4.05 (1H, m), 4.28 (1H, m), 5.01 (1H, m), 5.33 (1H, m), 5.51 (1H, m), 5.82 (1H, d), 7.19-7.44 (7H, m), 7.55 (1H, m)

Step B. (R)-3-(2-amino-2-phenylethyl)-1-(2-fluoro-6-(trifluoromethyl)benzyl)-6-methyl-5-(4-(4,4,5,5,5-pentafluoropentyl)piperazin-1-yl)pyrimidine-2,4(1H,3H)-dione(25-1)

To a solution of (R)-tert-butyl-(2-(3-(2-fluoro-6-(trifluoromethyl)benzyl)-4-methyl-2,6-dioxo-5-(4-(4,4,5,5,5-pentafluoropentyl)-piperazin-1-yl)-2,3-dihydropyrimidin-1(6H)-yl)-1-phenylethyl)carbamate (8 mg) in dichloromethane (2 mL) was added trifluoroacetic acid (100 μl), followed by stirring at room temperature for 2 hrs. The solution was neutralized with an aqueous saturated sodium bicarbonate solution to separate an organic layer. After concentration of the organic layer, the residue was purified using silica gel chromatography (eluent: dichloromethane/methanol, 10/1) and dried in a vacuum to afford 4 mg of the compound as a colorless oil (yield 58%). $^1$H NMR (300 MHz, CDCl$_3$) δ 1.75 (2H, m), 2.12 (4H, m), 2.33 (3H, s), 2.40 (2H, t), 2.49 (2H, m), 2.76 (2H, m), 3.56 (2H, m), 4.06 (1H, m), 4.21 (1H, m), 4.37 (1H, m), 5.41 (2H, s), 7.20-7.26 (2H, m), 7.30-7.43 (5H, m), 7.55 (1H, m)

Compounds synthesized according to the above procedures are summarized in Table 25, below. Compound 25-2 was synthesized in the same manner as in the above procedures, with the exception that, instead of 4,4,5,5,5-pentafluoropentan-1-ol, 2-(2-bromoethoxy)-1,1,1-trifluoroethane was used in Step A thus to omit the production process of a mesylate.

TABLE 25

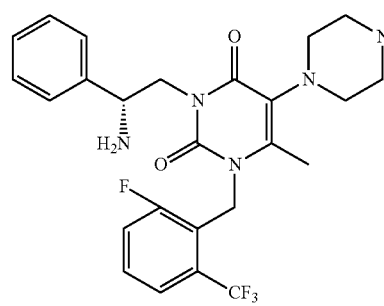

| No. | —R | M.W. | Mass |
|---|---|---|---|
| 25-1 | 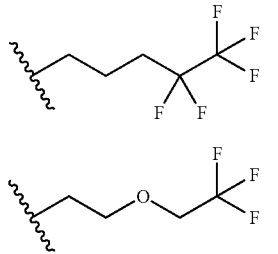 | 665.59 | 666.5 |
| 25-2 | | 631.58 | 632.5 |

Experimental Example 1

Assay for GnRH Receptor Membrane Binding

A membrane Target system (Perkin Elmer), isolated from CHO-K1 cells stably transfected with a GnRH receptor, was employed. A reaction was initiated by the addition of a 0.2 nM [$^{125}$I]-labeled labeled D-Trp$^6$-LHRH peptide and the GnRH receptor membrane target system at a density of 1 μg/250 μl/well, together with competitors at various concentrations of from 0.1 nM to 100 nM, to a binding buffer composed of 25 mM Hepes (pH 7.4), 10 mM MgCl$_2$, 1 mM CaCl$_2$, 0.5% BSA, pH 7.4. After incubation at 27° C. for 1 hr, the reaction mix was transferred to a filter (Fitermat A, PerkinElmer) using a vacuum pump and the reaction was terminated by washing many times with 50 mM tris-HCl buffer. The radioactivity on the filter was measured using Microbeta2 trilux (PerkinElmer). The competitors were analyzed for binding inhibition rate (%) on the basis of the measured radioactivity and calculated for IC$_{50}$ values using a nonlinear least square regression method with Prism (GraphPad, Inc.). In Table 26 are summarized compounds that were found to have an IC$_{50}$ of less than 100 nM as measured by the GnRH receptor membrane binding assay.

TABLE 26

| Example Table No | Cpd. No. |
|---|---|
| 1 | 1-7~11, 1-13, 1-16, 1-18, 1-26, 1-47~49 |
| 3 | 3-1, 3-7, 3-12~15, 3-27~27, 3-29, 3-31, 3-32, 3-37~39, 3-43~45, 3-47, 3-49, 3-50, 3-52, 3-58~66, 3-68~81, 3-83~95, 3-100~111 |
| 4 | 4-4, 4-6, 4-9, 4-14~23, 4-26~30, 4-32~36, 4-39~55 |
| 6 | 6-1~9, 6-18~20 |
| 10 | 10-1, 10-2, 10-4~6 |
| 11 | 11-1~6, 11-8, 11-10, 11-11~19 |
| 12 | 12-1~3 |
| 13 | 13-1~2 |
| 14 | 14-1~2 |

TABLE 26-continued

| Example Table No | Cpd. No. |
|---|---|
| 15 | 15-1~2 |
| 16 | 16-1~2 |
| 17 | 17-1~3 |
| 18 | 18 |
| 20 | 20 |
| 21 | 21 |
| 22 | 22 |
| 24 | 24-1~2 |

Experimental Example 2

Screening of Gene Expression for Evaluating Antagonistic Effect on GnRH Receptor A double-transformed cell line (HEK293 transformed with pcDNA3.1/GnRH receptor and pGL4/NFAT promoter) was employed. To conduct a GnRH-R reporter assay, the double-transformed cell line was diluted at a density of $3 \times 10^4$ cells/well in a medium (DMEM, 10% FBS, 1% Penicillin-Streptomycin), plated into polylysine-coated white-clear bottom 96-well plates and incubated for 24 hrs. After the medium was changed with a serum-free medium (DMEM, 1% Penicillin-Streptomycin), the cells were incubated for an additional 12 hrs before reaction. The cells were incubated for 1 hr with a GnRH antagonist to be tested and then for an additional 6 hrs with a ligand (leuprolide acetate, Sigma), followed by reaction with a Luciferase assay system (Promega, Cat. No. E1500). Luminescence was measured using a luminometer (PerkinElmer, VICTOR3™, 1420 Multilabel Counter).

Each sample was analyzed at a 6-dose level to obtain the binding inhibitory rates (%) of the competitors on the basis of the measured luminescence. $IC_{50}$ values were calculated using a nonlinear least square regression method with Prism (GraphPad, Inc.). Some of the compounds of Chemical Formula I have an $IC_{50}$ value less than 1 µM while others show $IC_{50}$ values less than 100 µM. In Table 27, examples of such compounds are listed.

TABLE 27

| Test Compound | $IC_{50}$ Value (nM) |
|---|---|
| 11-2 | 9.9 |
| 11-4 | 4.9 |
| Control Compound 1 | 1.6 |

Experimental Example 3

Assay for Oral Absorptivity

1) Preparation of Specimen for Measuring Drug Level upon Oral Administration

For use as experimental animals, SD rats (Charles River Japan, male, 8 weeks old, 220-270 g) was starved overnight. Test compounds (25~30 mg) were dissolved in polyethyleneglycol 400 (PEG400) 20%, and a 0.5% carboxy methyl cellulose (CMC) solution 80% to produce solutions of 4 µmmol/mL. The rats were weighed. The test compounds were orally administered at a dose of 40 µmol/kg (ca. 25~30 mg/kg) to the rats using a sonde and a 3 mL syringe. Blood samples were taken 20, 40, 60, 120, 240, and 360 min after the oral administration. Plasmas separated from the blood samples by centrifugation were used as specimens.

2) Measurement of Drug Level 0.09 mL of methanol was added to 0.03 mL of the plasma obtained in 1), followed by vortexing to precipitate and remove proteins. 0.005 mL of the supernatant was injected to LC/MS/MS.

LC

Apparatus: Shiseido Nanospace SI-2

Column: Shiseido capcelpack C18, MG3, 5 um, 2.0 mm I.D×50 mm

Mobile Phase: a mixture of 3:7 10 mM ammonium formate (pH 4.0): acetonitrile.

Column Temp.: 45

Flow Rate: 0.25 ml/min

MS/MS

Apparatus: API4000

Ionization: ESI

TABLE 28

| Test Compound | $C_{max}$ (ng/mL) |
|---|---|
| 11-2 | 5098.0 |
| 11-4 | 4144.0 |
| Control Compound 1 | 442.9 |

TABLE 29

| Test Compound | AUC8 hr (ng/mL*hr) |
|---|---|
| 11-2 | 29388.2 |
| 11-4 | 19587.3 |
| Control Compound 1 | 757.6 |

The control 1 in Tables 27 to 29 was the compound of Example 1 disclosed in U.S. Pat. No. 7,056,927 B2.

Taken together, the data obtained in the experimental examples demonstrate that the compounds of the present invention have much better blood profiles upon oral administration, compared to the control. For example, the compounds of the present invention have a maximal plasma level (Cmax) 9 to 12 times greater than that of the control, showing good blood migration properties. In addition, the AUC (area under the curve) obtained by analyzing drug levels in blood was found to 26 to 38-fold increase, showing excellent sustainability. Accordingly, the compounds of the present invention may be anticipated to exert sufficient pharmaceutical effects even upon oral administration as well as showing the possibility thereof as sustainable agents.

INDUSTRIAL APPLICABILITY

Exhibiting the potential activity of GnRH receptor antagonists, the compounds of the present invention are useful for the treatment of various sex hormone-related symptoms including endometriosis, uterine fibroids, polycystic ovarian disease, hypertrichosis, precocious puberty, gonadal steroid-dependent neoplasm (prostate cancer, breast cancer, ovary cancer, etc.), gonadotropin-producing pituitary adenoma, sleep apnea, irritable bowel syndrome, premenstrual syndrome, benign prostatic hyperplasia, and sterility (e.g., assisted reproductive techniques such as in vitro fertilization).

The invention claimed is:
1. A compound, represented by the following Chemical Formula I:

   [Chemical Formula I]

wherein,

X is a 5- or 6-membered non-aromatic heterocyclic ring containing one or more N atoms which is linked to D via N or 5- or 6-membered substituted non-aromatic heterocyclic containing one or more N atoms are linked to D via a N Y represents $-(CR_{9a}R_{9b})_r-Z-R_4$;

B represents $-NR_1R_2$ or $-OR_1$;

r is 0, 1, 2 or 3;

n is 2, 3 or 4;

Z represents a direct bond or $-O-$, $-S-$, $-NR_{11}-$, $-SO-$, $-SO_2-$, $-OSO_2-$, $-SO_2O-$, $-SO_2NR_{11}-$, $-NR_{11}SO_2-$, $-CO-$, $-COO-$, $-OCO-$, $-CONR_{11}-$, $-NR_{11}CO-$, $-NR_{11}CONR_{11a}-$, $-OCONR_{11}-$ or $-NR_{11}COO-$;

D is

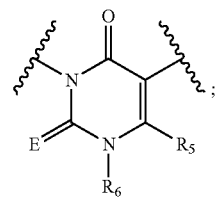

E represents $-O-$, $-S-$ or $-NR_8-$;

$R_1$ and $R_2$, which may be the same or different, are independently hydrogen, (C1-C10)alkyl, substituted (C1-C10)alkyl, (C3-C10)cyclic alkyl, substituted (C3-C10)cyclic alkyl, (C6-C12)aryl, substituted (C6-C12)aryl, (C6-C12)aryl(C1-C10)alkyl, substituted (C6-C12)aryl(C1-C10)alkyl, (C1-C20)heteroaryl, substituted (C1-C20)heteroaryl, (C1-C20)heteroaryl(C1-C10)alkyl, substituted (C1-C20)heteroaryl(C1-C10)alkyl, (C1-C20)heterocycle, substituted (C1-C20)heterocycle, (C1-C20)heterocycle (C1-C10)alkyl, substituted (C1-C20)heterocycle(C1-C10)alkyl, $-(CR_{1a}R_{1b})_s-R_{12}$ or $-COOR_{13}$; or $R_1$ and $R_2$ are linked to each other via a (C1-C5)alkylene to form a heterocyclic ring or a substituted heterocyclic ring wherein the $-CH_2-$ moiety of the alkylene may be substituted with $-C(=O)-$; s is 1, 2, 3 or 4;

$R_{3a}$ and $R_{3b}$, which may be the same or different, are independent hydrogen, (C1-C10)alkyl, substituted (C1-C10)alkyl, (C3-C10)cyclic alkyl, substituted (C3-C10)cyclic alkyl, (C1-C10)alkoxy, (C1-C10)alkylthio, (C1-C10)alkylamino, (C6-C12)aryl, substituted (C6-C12)aryl, (C6-C12)aryl(C1-C10)alkyl, substituted (C6-C12)aryl(C1-C10)alkyl, (C1-C20)heteroaryl, substituted (C1-C20)heteroaryl, (C1-C20)heteroaryl(C1-C10)alkyl, substituted (C1-C20)heteroaryl(C1-C10)alkyl, (C1-C20)heterocycle, substituted (C1-C20)heterocycle, (C1-C20)heterocycle(C1-C10)alkyl, substituted (C1-C20)heterocycle(C1-C10)alkyl, $-COOR_{13}$ or $-CONR_{13}R_{14}$; or $R_{3a}$ and $R_{3b}$ taken together with the carbon atom to which they are attached, form a homocyclic ring, a substituted homocyclic ring, a heterocyclic ring, or a substituted heterocyclic ring;

$R_{3a}$ and $R_1$ taken together with the carbon atom and the nitrogen atom to which they are respectively attached form a heterocyclic ring or a substituted heterocyclic ring;

$R_4$ is hydrogen, (C1-C10)alkyl, substituted (C1-C10)alkyl, (C3-C10)cyclic alkyl, substituted (C3-C10)cyclic alkyl, (C6-C12)aryl, substituted (C6-C12)aryl, (C6-C12)aryl(C1-C10)alkyl, substituted (C6-C12)aryl(C1-C10)alkyl, (C1-C20)heteroaryl, substituted (C1-C20)heteroaryl, (C1-C20)heteroaryl(C1-C10)alkyl, substituted (C1-C20)heteroaryl(C1-C10)alkyl, (C1-C20)heterocycle, substituted (C1-C20)heterocycle, (C1-C20)heterocycle(C1-C10)alkyl or substituted (C1-C20)heterocycle(C1-C10)alkyl;

$R_5$ is hydrogen, halogen, (C1-C6)alkyl, substituted (C1-C6)alkyl, (C3-C10)cyclic alkyl, substituted (C3-C10)cyclic alkyl, (C6-C12)aryl, substituted (C6-C12)aryl, (C6-C12)aryl(C1-C10)alkyl, substituted (C6-C12)aryl(C1-C10)alkyl, (C1-C10)alkoxy, (C1-C10)alkylthio, (C1-C10)alkylamino, cyano or nitro;

$R_6$ is hydrogen, (C1-C10)alkyl; substituted (C1-C10)alkyl; (C3-C10)cyclic alkyl, substituted (C3-C10)cyclic alkyl, (C6-C12)aryl, substituted (C6-C12)aryl, (C6-C12)aryl(C1-C10)alkyl, substituted (C6-C12)aryl(C1-C10)alkyl, (C1-C20)heteroaryl, substituted (C1-C20)heteroaryl, (C1-C20)heteroaryl(C1-C10)alkyl or substituted (C1-C20)heteroaryl(C1-C10)alkyl;

$R_8$ is hydrogen, $-SO_2R_{10}$, cyano, (C1-C10)alkyl, substituted (C1-C10)alkyl, (C3-C10)cyclic alkyl, substituted (C3-C10)cyclic alkyl, (C6-C12)aryl, substituted (C6-C12)aryl, (C6-C12)aryl(C1-C10)alkyl, substituted (C6-C12)aryl(C1-C10)alkyl, (C1-C20)heteroaryl, substituted (C1-C20)heteroaryl, (C1-C20)heteroaryl(C1-C10)alkyl or substituted (C1-C20)heteroaryl(C1-C10)alkyl;

$R_{1a}$, $R_{1b}$, $R_{9a}$ and $R_{9b}$, which may be the same or different, are independently hydrogen, acyl, hydroxy halogen, cyano, (C1-C10)alkyl, substituted (C1-C10)alkyl, (C3-C10)cyclic alkyl, substituted (C3-C10)cyclic alkyl, (C1-C10)alkoxy, (C1-C10)alkylthio, (C1-C10)alkylamino, (C6-C12)aryl, substituted (C6-C12)aryl, (C6-C12)aryl(C1-C10)alkyl, substituted (C6-C12)aryl(C1-C10)alkyl, (C1-C20)heteroaryl, substituted (C1-C20)heteroaryl, (C1-C20)heteroaryl(C1-C10)alkyl, substituted (C1-C20)heteroaryl(C1-C10)alkyl, (C1-C20)heterocycle, substituted (C1-C20)heterocycle, (C1-C20)heterocycle(C1-C10)alkyl, substituted (C1-C20)heterocycle(C1-C10)alkyl, $-COOR_{13}-$ or $-CONR_{13}R_{14}-$;

a set of $R_{1a}$ and $R_{1b}$ and a set of $R_{9a}$ and $R_{9b}$, taken together with the atom(s) to which they are attached independently form a homocyclic ring, a substituted homocyclic ring, a heterocyclic ring or a substituted heterocyclic ring;

$R_{12}$ is $-COOH$ or an acid isostere;

$R_{10}$, $R_{11}$, $R_{11a}$, $R_{13}$ and $R_{14}$, which may be the same or different, are independently hydrogen, (C1-C10)alkyl, substituted (C1-C10)alkyl, (C3-C10)cyclic alkyl, substituted (C3-C10)cyclic alkyl, (C1-C10)alkoxy, (C1-C10)alkylthio, (C1-C10)alkylamino, (C6-C12)aryl, substituted (C6-C12)aryl, (C6-C12)aryl(C1-C10)alkyl, substituted (C6-C12)aryl(C1-C10)alkyl, (C1-C20)heteroaryl, substituted (C1-C20)heteroaryl, (C1-C20)heteroaryl(C1-C10)alkyl, substituted (C1-C20)heteroaryl (C1-C10)alkyl, (C1-C20)heterocycle, substituted (C1-C20)heterocycle, (C1-C20)heterocycle(C1-C10)alkyl or substituted (C1-C20)heterocycle(C1-C10)alkyl;

$R_{13}$ and $R_{14}$ taken together with the atom(s) to which they are attached, form a homocyclic ring, a substituted homocyclic ring, a heterocyclic ring or a substituted heterocyclic ring;

the heterocyclic ring, the heterocycle, the heterocyclealkyl, heteroaryl and the heteroarylalkyl, as used herein, being intended to contain one or more heteroatoms selected from among N, O and S therein;

"substituted" being intended to mean replacement with one or more substituents selected from the group consisting of hydroxy, cyano, nitro, amino, (C1-C10)alkylamino, di(C1-C10)alkylamino, (C1-C10)alkyl, (C3-C10)cyclic alkyl, (C1-C10)alkoxy, (C1-C10)alkylthio, halo(C1-C10)alkyl, (C6-C12)aryl, (C6-C12)aryl(C1-C10)alkyl, (C1-C20)heteroaryl, (C1-C20)heteroaryl(C1-C10)alkyl, (C1-C20)heterocycle, (C1-C20)heterocycle(C1-C10)alkyl, $-NR_aR_b$, $-NR_aC(=O)R_b$, $-NR_aC(=O)NR_aNR_b$, $-NR_aC(=O)OR_b$, $-NR_aSO_2R_b$, $-C(=O)R_a$, $-C(=O)OR_a$, $-OC(=O)R_a$, $-C(=O)NR_aR_b$, $-OC(=O)NR_aR_b$, $-OR_a$, $-SR_a$, $-SOR_a$, $-S(=O)_2R_a$, $-OS(=O)_2R_a$ and $-S(=O)_2OR_a$;

$R_a$ and $R_b$, which may be the same or different, are independently hydrogen, $(C_1-C10)$alkyl, hallo(C1-C10)alkyl, (C3-C10)cyclic alkyl, (C6-C12)aryl, (C6-C12)aryl(C1-C10)alkyl, (C1-C20)heteroaryl, (C1-C20)heterocycle(C1-C10)alkyl, (C1-C20)heterocycle, (C1-C20)heterocycle(C1-C10)alkyl or $-(CH_2)_zC(=O)R_c$;

z is an integer of 1, 2, 3 or 4; and $R_c$ is hydroxy, (C1-C10)alkyl, (C3-C10)cyclic alkyl or (C1-C10)alkoxy], or a streoisomer thereof, or a pharmaceutically acceptable salt thereof.

2. The compound according to claim 1, wherein

Y is hydrogen, (C1-C10)alkyl, substituted (C1-C10)alkyl, (C3-C10)cyclic alkyl, substituted (C3-C10)cyclic alkyl, (C6-C12)aryl, substituted (C6-C12)aryl, (C6-C12)aryl(C1-C10)alkyl, substituted (C6-C12)aryl(C1-C10)alkyl, (C1-C20)heteroaryl, substituted (C1-C20)heteroaryl, $(C_1-C20)$heteroaryl(C1-C10)alkyl, substituted (C1-C20)heteroaryl(C1-C10)alkyl, (C1-C20)heterocycle, substituted (C1-C20)heterocycle, (C1-C20)heterocycle(C1-C10)alkyl, substituted (C1-C20)heterocycle(C1-C10)alkyl, $-OR_4$, $-NR_4$, $-SO_2R_4$, $-COR_4$ or $-COOR_4$;

B is $-NR_1R_2$ or $-OR_1$;

n is 2, 3 or 4;

D is

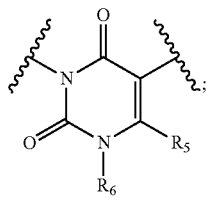

$R_1$ and $R_2$, which may be the same or different, is independently hydrogen, $-(CH_2)_sCO_2H$, $-(CH_2)_sP(=O)(OEt)(OH)$, $-(CH_2)_sPO_3H$ or $-(CH_2)_sSO_3H$;

s is 1, 2, 3 or 4;

$R_{3a}$ and $R_{3b}$, which may be the same or different, are independently hydrogen, (C1-C10)alkyl, substituted (C1-C10)alkyl, (C3-C10)cyclic alkyl, substituted (C3-C10)cyclic alkyl, (C1-C10)alkoxy, (C1-C10)alkylthio, (C6-C12)aryl, substituted (C6-C12)aryl, (C1-C20)heteroaryl, substituted (C1-C20)heteroaryl, (C1-C20)heterocycle or substituted (C1-C20)heterocycle;

$R_5$ is hydrogen or methyl;

$R_6$ is hydrogen, (C1-C10)alkyl; (C3-C10)cyclic alkyl, (C6-C12)aryl(C1-C10)alkyl or substituted (C6-C12)aryl (C1-C10)alkyl; and $R_{11}$ is hydrogen, (C1-C10)alkyl, substituted (C1-C10)alkyl, (C3-C10)cyclic alkyl, substituted (C3-C10)cyclic alkyl, (C6-C12)aryl, substituted (C6-C12)aryl, (C6-C12)aryl(C1-C10)alkyl, substituted (C6-C12)aryl(C1-C10)alkyl, (C1-C20)heteroaryl, substituted (C1-C20)heteroaryl, (C1-C20)heteroaryl(C1-C10)alkyl, substituted (C1-C20)heteroaryl(C1-C10)alkyl, (C1-C20)heterocycle, substituted (C1-C20)heterocycle, (C1-C20)heterocycle(C1-C10)alkyl or substituted (C1-C20)heterocycle(C1-C10)alkyl, or the streoisomer thereof or the pharmaceutically acceptable salt thereof.

3. The compound according to claim 1, having a structure selected from the compounds of the following Chemical Formula II:

[Chemical Formula II]

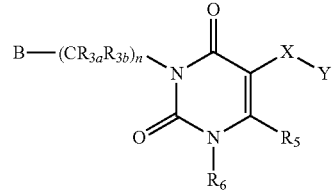

wherein B, $R_1$, $R_2$, $R_{3a}$, $R_{3b}$, $R_5$, $R_6$, B, X, Y and n are as defined in claim 1, or the stereoisomer thereof or the pharmaceutically acceptable salt thereof.

4. The compound according to claim 1, selected from the group consisting of:

3-((R)-2-amino-2-phenyl-ethyl)-1-(2,6-difluoro-benzyl)-5-[4-(2-methoxy-phenyl)-piperazin-1-yl]-6-methyl-1H-pyrimidine-2,4-dione;

3-((R)-2-amino-2-phenyl-ethyl)-1-(2,6-difluoro-benzyl)-5-[4-(3-methoxy-phenyl)-piperazin-1-yl]-6-methyl-1H-pyrimidine-2,4-dione;

3-((R)-2-amino-2-phenyl-ethyl)-5-(4-benzyl-piperazin-1-yl)-1-(2,6-difluoro-benzyl)-6-methyl-1H-pyrimidine-2,4-dione;

3-((R)-2-amino-2-phenyl-ethyl)-5-[4-(4-chloro-benzyl)-piperazin-1-yl]-1-(2,6-difluoro-benzyl)-6-methyl-1H-pyrimidine-2,4-dione;

3-((R)-2-amino-2-phenyl-ethyl)-1-(2,6-difluoro-benzyl)-5-[4-(2-fluoro-benzyl)-piperazin-1-yl]-6-methyl-1H-pyrimidine-2,4-dione;

3-((R)-2-amino-2-phenyl-ethyl)-1-(2,6-difluoro-benzyl)-6-methyl-5-(4-pyridin-2-yl-piperazin-1-yl)-1H-pyrimidine-2,4-dione;

3-((R)-2-amino-2-phenyl-ethyl)-1-(2,6-difluoro-benzyl)-5-[4-(3-fluoro-benzyl)-piperazin-1-yl]-6-methyl-1H-pyrimidine-2,4-dione;

3-((R)-2-amino-2-phenyl-ethyl)-1-(2,6-difluoro-benzyl)-6-methyl-5-[4-(4-trifluoromethyl-benzyl)-piperazin-1-yl]-1H-pyrimidine-2,4-dione;

3-((R)-2-amino-2-phenyl-ethyl)-5-(4-benzoyl-piperazin-1-yl)-1-(2,6-difluoro-benzyl)-6-methyl-1H-pyrimidine-2,4-dione;

3-((R)-2-amino-2-phenyl-ethyl)-1-(2,6-difluoro-benzyl)-6-methyl-5-(4-methyl-piperidin-1-yl)-1H-pyrimidine-2,4-dione;
3-((R)-2-amino-2-phenyl-ethyl)-1-(2,6-difluoro-benzyl)-6-methyl-5-(3-trifluoromethyl-piperidin-1-yl)-1H-pyrimidine-2,4-dione;
3-((R)-2-amino-2-phenyl-ethyl)-1-(2,6-difluoro-benzyl)-6-methyl-5-(3-methyl-piperidin-1-yl)-1H-pyrimidine-2,4-dione;
3-((R)-2-amino-2-phenyl-ethyl)-1-(2,6-difluoro-benzyl)-6-methyl-5-(4-phenyl-piperazin-1-yl)-1H-pyrimidine-2,4-dione;
3-((R)-2-amino-2-phenyl-ethyl)-5-(4-cyclohexylmethyl-piperazin-1-yl)-1-(2,6-difluoro-benzyl)-6-methyl-1H-pyrimidine-2,4-dione;
3-((R)-2-amino-2-phenyl-ethyl)-1-(2,6-difluoro-benzyl)-5-[4-(2-fluoro-phenyl)-piperazin-1-yl]-6-methyl-1H-pyrimidine-2,4-dione;
3-((R)-2-amino-2-phenyl-ethyl)-1-(2,6-difluoro-benzyl)-5-[4-(2-hydroxy-phenyl)-piperazin-1-yl]-6-methyl-1H-pyrimidine-2,4-dione;
3-((R)-2-amino-2-phenyl-ethyl)-1-(2,6-difluoro-benzyl)-6-methyl-5-piperidin-1-yl-1H-pyrimidine-2,4-dione;
3-((R)-2-amino-2-phenyl-ethyl)-1-(2,6-difluoro-benzyl)-5-[3-(2-hydroxy-ethyl)-piperazin-1-yl]-6-methyl-1H-pyrimidine-2,4-dione;
3-((R)-2-amino-2-phenyl-ethyl)-5-(4-benzo[1,3]dioxol-5-ylmethyl-piperazin-1-yl)-1-(2,6-difluoro-benzyl)-6-methyl-1H-pyrimidine-2,4-dione;
3-((R)-2-amino-2-phenyl-ethyl)-1-(2,6-difluoro-benzyl)-6-methyl-5-(2-methyl-piperidin-1-yl)-1H-pyrimidine-2,4-dione;
3-((R)-2-amino-2-phenyl-ethyl)-1-(2,6-difluoro-benzyl)-5-(3-hydroxymethyl-piperidin-1-yl)-6-methyl-1H-pyrimidine-2,4-dione;
3-((R)-2-amino-2-phenyl-ethyl)-1-(2,6-difluoro-benzyl)-6-methyl-5-(3-oxo-piperazin-1-yl)-1H-pyrimidine-2,4-dione;
3-((R)-2-amino-2-phenyl-ethyl)-1-(2,6-difluoro-benzyl)-5-(2,5-dihydro-pyrrol-1-yl)-6-methyl-1H-pyrimidine-2,4-dione;
3-((R)-2-amino-2-phenyl-ethyl)-1-(2,6-difluoro-benzyl)-6-methyl-5-[4-(3-trifluoromethoxy-benzyl)-piperazin-1-yl]-1H-pyrimidine-2,4-dione;
3-((R)-2-amino-2-phenyl-ethyl)-1-(2,6-difluoro-benzyl)-6-methyl-5-piperazin-1-yl-1H-pyrimidine-2,4-dione;
3-((R)-2-amino-2-phenyl-ethyl)-1-(2,6-difluoro-benzyl)-5-{4-[2-(4-methoxy-phenyl)-2-oxo-ethyl]-piperazin-1-yl}-6-methyl-1H-pyrimidine-2,4-dione;
3-((R)-2-amino-2-phenyl-ethyl)-1-(2,6-difluoro-benzyl)-6-methyl-5-(4-phenethyl-piperazin-1-yl)-1H-pyrimidine-2,4-dione;
3-((R)-2-amino-2-phenyl-ethyl)-5-(4-benzenesulfonyl-piperazin-1-yl)-1-(2,6-difluoro-benzyl)-6-methyl-1H-pyrimidine-2,4-dione;
3-((R)-2-amino-2-phenyl-ethyl)-1-(2,6-difluoro-benzyl)-5-{4-[2-(2-fluoro-phenyl)-ethyl]-piperazin-1-yl}-6-methyl-1H-pyrimidine-2,4-dione;
3-((R)-2-amino-2-phenyl-ethyl)-1-(2,6-difluoro-benzyl)-5-{4-[2-(2-methoxy-phenyl)-ethyl]-piperazin-1-yl}-6-methyl-1H-pyrimidine-2,4-dione;
3-((R)-2-amino-2-phenyl-ethyl)-1-(2,6-difluoro-benzyl)-5-{4-[2-(4-fluoro-phenyl)-ethyl]-piperazin-1-yl}-6-methyl-1H-pyrimidine-2,4-dione;
3-((R)-2-amino-2-phenyl-ethyl)-1-(2,6-difluoro-benzyl)-5-{4-[2-(3-methoxy-phenyl)-ethyl]-piperazin-1-yl}-6-methyl-1H-pyrimidine-2,4-dione;
3-((R)-2-amino-2-phenyl-ethyl)-1-(2,6-difluoro-benzyl)-6-methyl-5-[4-(2-p-tollyl-ethyl)-piperazin-1-yl]-1H-pyrimidine-2,4-dione;
3-((R)-2-amino-2-phenyl-ethyl)-1-(2,6-difluoro-benzyl)-6-methyl-5-{4-[2-(4-nitro-phenyl)-ethyl]-piperazin-1-yl}-1H-pyrimidine-2,4-dione;
3-((R)-2-amino-2-phenyl-ethyl)-1-(2,6-difluoro-benzyl)-6-methyl-5-[4-(3-phenyl-propyl)-piperazin-1-yl]-1H-pyrimidine-2,4-dione;
3-((R)-2-amino-2-phenyl-ethyl)-1-(2,6-difluoro-benzyl)-5-[4-(2,3-dihydrobenzo[1,4]dioxin-2-ylmethyl)-piperazin-1-yl]-6-methyl-1H-pyrimidine-2,4-dione;
3-((R)-2-amino-2-phenyl-ethyl)-5-{4-[2-(2-chloro-phenyl)-2-oxo-ethyl]-piperazin-1-yl}-1-(2,6-difluoro-benzyl)-6-methyl-1H-pyrimidine-2,4-dione;
3-((R)-2-amino-2-phenyl-ethyl)-5-{4-[2-(3-chloro-phenyl)-2-oxo-ethyl]-piperazin-1-yl}-1-(2,6-difluoro-benzyl)-6-methyl-1H-pyrimidine-2,4-dione;
3-((R)-2-amino-2-phenyl-ethyl)-1-(2,6-difluoro-benzyl)-6-methyl-5-(4-pyridin-2-ylmethyl-piperazin-1-yl)-1H-pyrimidine-2,4-dione;
3-((R)-2-amino-2-phenyl-ethyl)-1-(2,6-difluoro-benzyl)-6-methyl-5-(4-pyridin-3-ylmethyl-piperazin-1-yl)-1H-pyrimidine-2,4-dione;
3-((R)-2-amino-2-phenyl-ethyl)-1-(2,6-difluoro-benzyl)-6-methyl-5-(4-pyridin-4-ylmethyl-piperazin-1-yl)-1H-pyrimidine-2,4-dione;
3-((R)-2-amino-2-phenyl-ethyl)-1-(2,6-difluoro-benzyl)-5-[4-(2-fluoro-benzenesulfonyl)-piperazin-1-yl]-6-methyl-1H-pyrimidine-2,4-dione;
3-((R)-2-amino-2-phenyl-ethyl)-1-(2,6-difluoro-benzyl)-5-[4-(3-fluoro-benzenesulfonyl)-piperazin-1-yl]-6-methyl-1H-pyrimidine-2,4-dione;
3-((R)-2-amino-2-phenyl-ethyl)-1-(2,6-difluoro-benzyl)-5-[4-(4-fluoro-benzenesulfonyl)-piperazin-1-yl]-6-methyl-1H-pyrimidine-2,4-dione;
3-((R)-2-amino-2-phenyl-ethyl)-1-(2,6-difluoro-benzyl)-5-(4-hydroxy-piperidin-1-yl)-6-methyl-1H-pyrimidine-2,4-dione;
3-((R)-2-amino-2-phenyl-ethyl)-5-(4-benzyl-piperidin-1-yl)-1-(2,6-difluoro-benzyl)-6-methyl-1H-pyrimidine-2,4-dione;
3-((R)-2-amino-2-phenyl-ethyl)-1-(2,6-difluoro-benzyl)-6-methyl-5-(3-phenyl-piperazin-1-yl)-1H-pyrimidine-2,4-dione;
3-((R)-2-amino-2-phenyl-ethyl)-5-(R)-(3-benzyl-piperazin-1-yl)-1-(2,6-difluoro-benzyl)-6-methyl-1H-pyrimidine-2,4-dione;
3-((R)-2-amino-2-phenyl-ethyl)-5-(S)-(3-benzyl-piperazin-1-yl)-1-(2,6-difluoro-benzyl)-6-methyl-1H-pyrimidine-2,4-dione;
2-{4-[3-((R)-2-amino-2-phenyl-ethyl)-1-(2,6-difluoro-benzyl)-6-methyl-2,4-dioxo-1,2,3,4-tetrahydro-pyrimidin-5-yl]-piperazin-1-ylmethyl}-benzonitrile;
3-{4-[3-((R)-2-amino-2-phenyl-ethyl)-1-(2,6-difluoro-benzyl)-6-methyl-2,4-dioxo-1,2,3,4-tetrahydro-pyrimidin-5-yl]-piperazin-1-ylmethyl}-benzonitrile;
4-{4-[3-((R)-2-amino-2-phenyl-ethyl)-1-(2,6-difluoro-benzyl)-6-methyl-2,4-dioxo-1,2,3,4-tetrahydro-pyrimidin-5-yl]-piperazin-1-ylmethyl}-benzonitrile;
3-((R)-2-amino-2-phenyl-ethyl)-1-(2,6-difluoro-benzyl)-5-[4-(3-methoxy-benzyl)-piperazin-1-yl]-6-methyl-1H-pyrimidine-2,4-dione;
3-((R)-2-amino-2-phenyl-ethyl)-1-(2,6-difluoro-benzyl)-5-[4-(4-methoxy-benzyl)-piperazin-1-yl]-6-methyl-1H-pyrimidine-2,4-dione;

3-((R)-2-amino-2-phenyl-ethyl)-5-[4-(2-chloro-benzyl)-piperazin-1-yl]-1-(2,6-difluoro-benzyl)-6-methyl-1H-pyrimidine-2,4-dione;

3-((R)-2-amino-2-phenyl-ethyl)-5-[4-(3-chloro-benzyl)-piperazin-1-yl]-1-(2,6-difluoro-benzyl)-6-methyl-1H-pyrimidine-2,4-dione;

3-((R)-2-amino-2-phenyl-ethyl)-1-(2,6-difluoro-benzyl)-6-methyl-5-[4-(2-nitro-benzyl)-piperazin-1-yl]-1H-pyrimidine-2,4-dione;

3-((R)-2-amino-2-phenyl-ethyl)-1-(2,6-difluoro-benzyl)-6-methyl-5-[4-(3-nitro-benzyl)-piperazin-1-yl]-1H-pyrimidine-2,4-dione;

3-((R)-2-amino-2-phenyl-ethyl)-1-(2,6-difluoro-benzyl)-6-methyl-5-[4-(4-nitro-benzyl)-piperazin-1-yl]-1H-pyrimidine-2,4-dione;

3-((R)-2-amino-2-phenyl-ethyl)-1-(2,6-difluoro-benzyl)-6-methyl-5-[4-(2-methyl-benzyl)-piperazin-1-yl]-1H-pyrimidine-2,4-dione;

3-((R)-2-amino-2-phenyl-ethyl)-1-(2,6-difluoro-benzyl)-6-methyl-5-[4-(4-methyl-benzyl)-piperazin-1-yl]-1H-pyrimidine-2,4-dione;

3-((R)-2-amino-2-phenyl-ethyl)-1-(2,6-difluoro-benzyl)-6-methyl-5-[4-(2-trifluoromethyl-benzyl)-piperazin-1-yl]-1H-pyrimidine-2,4-dione;

3-((R)-2-amino-2-phenyl-ethyl)-1-(2,6-difluoro-benzyl)-5-[4-(4-fluoro-benzyl)-piperazin-1-yl]-6-methyl-1H-pyrimidine-2,4-dione;

4-{4-[3-((R)-2-amino-2-phenyl-ethyl)-1-(2,6-difluoro-benzyl)-6-methyl-2,4-dioxo-1,2,3,4-tetrahydro-pyrimidin-5-yl]-piperazin-1-ylmethyl}-benzoic acid methyl ester;

3-((R)-2-amino-2-phenyl-ethyl)-1-(2,6-difluoro-benzyl)-5-[4-(2,3-difluoro-benzyl)-piperazin-1-yl]-6-methyl-1H-pyrimidine-2,4-dione;

4-[3-((R)-2-amino-2-phenyl-ethyl)-1-(2,6-difluoro-benzyl)-6-methyl-2,4-dioxo-1,2,3,4-tetrahydro-pyrimidin-5-yl]-piperazine-1-carboxylic acid benzyl ester;

3-((R)-2-amino-2-phenyl-ethyl)-1-(2,6-difluoro-benzyl)-6-methyl-5-(2,3,5,6-tetrahydro-[1,2']bipyrazinyl-4-yl)-1H-pyrimidine-2,4-dione;

3-((R)-2-amino-2-phenyl-ethyl)-1-(2,6-difluoro-benzyl)-5-[3-(4-methoxy-phenyl)-pyrrolidin-1-yl]-6-methyl-1H-pyrimidine-2,4-dione;

3-((R)-2-amino-2-phenyl-ethyl)-1-(2,6-difluoro-benzyl)-6-methyl-5-(2-pyridin-3-ylmethyl-pyrrolidin-1-yl)-1H-pyrimidine-2,4-dione;

3-((R)-2-amino-2-phenyl-ethyl)-1-(2,6-difluoro-benzyl)-6-methyl-5-[3-(toluene-4-sulfonyl)-pyrrolidin-1-yl]-1H-pyrimidine-2,4-dione;

3-((R)-2-amino-2-phenyl-ethyl)-5-(3-benzenesulfonyl-pyrrolidin-1-yl)-1-(2,6-difluoro-benzyl)-6-methyl-1H-pyrimidine-2,4-dione;

3-((R)-2-amino-2-phenyl-ethyl)-1-(2,6-difluoro-benzyl)-6-methyl-5-(3-phenyl-pyrrolidin-1-yl)-1H-pyrimidine-2,4-dione;

3-((R)-2-amino-2-phenyl-ethyl)-5-(3-benzyl-pyrrolidin-1-yl)-1-(2,6-difluoro-benzyl)-6-methyl-1H-pyrimidine-2,4-dione;

3-((R)-2-amino-2-phenyl-ethyl)-1-(2,6-difluoro-benzyl)-6-methyl-5-(3-pyridin-3-yl-pyrrolidin-1-yl)-1H-pyrimidine-2,4-dione;

3-((R)-2-amino-2-phenyl-ethyl)-1-(2,6-difluoro-benzyl)-6-methyl-5-(3-phenyl-piperidin-1-yl)-1H-pyrimidine-2,4-dione;

3-((R)-2-amino-2-phenyl-ethyl)-1-(2,6-difluoro-benzyl)-6-methyl-5-(4-phenoxy-piperidin-1-yl)-1H-pyrimidine-2,4-dione;

3-((R)-2-amino-2-phenyl-ethyl)-1-(2,6-difluoro-benzyl)-6-methyl-5-morpholin-4-yl-1H-pyrimidine-2,4-dione;

3-((R)-2-amino-2-phenyl-ethyl)-1-(2,6-difluoro-benzyl)-5-[4-(2-fluoro-phenoxy)-piperidin-1-yl]-6-methyl-1H-pyrimidine-2,4-dione;

3-((R)-2-amino-2-phenyl-ethyl)-1-(2,6-difluoro-benzyl)-5-[4-(4-fluoro-phenoxy)-piperidin-1-yl]-6-methyl-1H-pyrimidine-2,4-dione;

3-((R)-2-amino-2-phenyl-ethyl)-1-(2,6-difluoro-benzyl)-5-(4-furo[3,2-c]pyridin-4-yl-piperazin-1-yl)-6-methyl-1H-pyrimidine-2,4-dione;

3-((R)-2-amino-2-phenyl-ethyl)-1-(2,6-difluoro-benzyl)-6-methyl-5-(4-naphthalen-2-ylmethyl-piperazin-1-yl)-1H-pyrimidine-2,4-dione;

3-((R)-2-amino-2-phenyl-ethyl)-1-(2,6-difluoro-benzyl)-6-methyl-5-[4-(4-methylsulfanyl-benzyl)-piperazin-1-yl]-1H-pyrimidine-2,4-dione;

3-((R)-2-amino-2-phenyl-ethyl)-1-(2,6-difluoro-benzyl)-6-methyl-5-[4-(3-methyl-benzyl)-piperazin-1-yl]-1H-pyrimidine-2,4-dione;

3-((R)-2-amino-2-phenyl-ethyl)-1-(2,6-difluoro-benzyl)-5-[4-(2-hydroxy-benzyl)-piperazin-1-yl]-6-methyl-1H-pyrimidine-2,4-dione;

3-((R)-2-amino-2-phenyl-ethyl)-1-(2,6-difluoro-benzyl)-5-[4-(3-hydroxy-benzyl)-piperazin-1-yl]-6-methyl-1H-pyrimidine-2,4-dione;

3-((R)-2-amino-2-phenyl-ethyl)-1-(2,6-difluoro-benzyl)-5-[4-(4-hydroxy-benzyl)-piperazin-1-yl]-6-methyl-1H-pyrimidine-2,4-dione;

3-((R)-2-amino-2-phenyl-ethyl)-1-(2,6-difluoro-benzyl)-5-[4-(2,3-dimethyl-benzyl)-piperazin-1-yl]-6-methyl-1H-pyrimidine-2,4-dione;

3-((R)-2-amino-2-phenyl-ethyl)-1-(2,6-difluoro-benzyl)-5-[4-(2,4-dimethyl-benzyl)-piperazin-1-yl]-6-methyl-1H-pyrimidine-2,4-dione;

3-((R)-2-amino-2-phenyl-ethyl)-1-(2,6-difluoro-benzyl)-5-[4-(2,5-dimethyl-benzyl)-piperazin-1-yl]-6-methyl-1H-pyrimidine-2,4-dione;

3-((R)-2-amino-2-phenyl-ethyl)-1-(2,6-difluoro-benzyl)-5-[4-(2,6-dimethyl-benzyl)-piperazin-1-yl]-6-methyl-1H-pyrimidine-2,4-dione;

3-((R)-2-amino-2-phenyl-ethyl)-1-(2,6-difluoro-benzyl)-5-[4-(3,4-dimethyl-benzyl)-piperazin-1-yl]-6-methyl-1H-pyrimidine-2,4-dione;

3-((R)-2-amino-2-phenyl-ethyl)-1-(2,6-difluoro-benzyl)-5-[4-(3,5-dimethyl-benzyl)-piperazin-1-yl]-6-methyl-1H-pyrimidine-2,4-dione;

3-((R)-2-amino-2-phenyl-ethyl)-1-(2,6-difluoro-benzyl)-5-[4-(2-hydroxy-3-methyl-benzyl)-piperazin-1-yl]-6-methyl-1H-pyrimidine-2,4-dione;

3-((R)-2-amino-2-phenyl-ethyl)-1-(2,6-difluoro-benzyl)-5-[4-(2-hydroxy-5-methyl-benzyl)-piperazin-1-yl]-6-methyl-1H-pyrimidine-2,4-dione;

3-((R)-2-amino-2-phenyl-ethyl)-1-(2,6-difluoro-benzyl)-5-[4-(4-hydroxy-3-methyl-benzyl)-piperazin-1-yl]-6-methyl-1H-pyrimidine-2,4-dione;

3-((R)-2-amino-2-phenyl-ethyl)-1-(2,6-difluoro-benzyl)-6-methyl-5-[4-(2,4,6-trimethyl-benzyl)-piperazin-1-yl]-1H-pyrimidine-2,4-dione;

3-((R)-2-amino-2-phenyl-ethyl)-1-(2,6-difluoro-benzyl)-5-[4-(2-methoxy-benzyl)-piperazin-1-yl]-6-methyl-1H-pyrimidine-2,4-dione;

3-((R)-2-amino-2-phenyl-ethyl)-1-(2,6-difluoro-benzyl)-5-[4-(3,5-dimethoxy-benzyl)-piperazin-1-yl]-6-methyl-1H-pyrimidine-2,4-dione;

3-((R)-2-amino-2-phenyl-ethyl)-1-(2,6-difluoro-benzyl)-5-[4-(3,4-dimethoxy-benzyl)-piperazin-1-yl]-6-methyl-1H-pyrimidine-2,4-dione;
3-((R)-2-amino-2-phenyl-ethyl)-1-(2,6-difluoro-benzyl)-6-methyl-5-[4-(3,4,5-trimethoxy-benzyl)-piperazin-1-yl]-1H-pyrimidine-2,4-dione;
3-((R)-2-amino-2-phenyl-ethyl)-1-(2,6-difluoro-benzyl)-5-[4-(2,4-difluoro-benzyl)-piperazin-1-yl]-6-methyl-1H-pyrimidine-2,4-dione;
3-((R)-2-amino-2-phenyl-ethyl)-1-(2,6-difluoro-benzyl)-5-[4-(2,5-difluoro-benzyl)-piperazin-1-yl]-6-methyl-1H-pyrimidine-2,4-dione;
3-((R)-2-amino-2-phenyl-ethyl)-1-(2,6-difluoro-benzyl)-5-[4-(2,4-difluoro-benzyl)-piperazin-1-yl]-6-methyl-1H-pyrimidine-2,4-dione;
3-((R)-2-amino-2-phenyl-ethyl)-1-(2,6-difluoro-benzyl)-5-[4-(3,4-difluoro-benzyl)-piperazin-1-yl]-6-methyl-1H-pyrimidine-2,4-dione;
3-((R)-2-amino-2-phenyl-ethyl)-1-(2,6-difluoro-benzyl)-5-[4-(3,5-difluoro-benzyl)-piperazin-1-yl]-6-methyl-1H-pyrimidine-2,4-dione;
3-((R)-2-amino-2-phenyl-ethyl)-1-(2,6-difluoro-benzyl)-5-[4-(3-fluoro-2-methoxy-benzyl)-piperazin-1-yl]-6-methyl-1H-pyrimidine-2,4-dione;
3-((R)-2-amino-2-phenyl-ethyl)-5-[4-(3-chloro-4-fluoro-benzyl)-piperazin-1-yl]-1-(2,6-difluoro-benzyl)-6-methyl-1H-pyrimidine-2,4-dione;
3-((R)-2-amino-2-phenyl-ethyl)-1-(2,6-difluoro-benzyl)-6-methyl-5-[4-(3,4,5-trifluoro-benzyl)-piperazin-1-yl]-1H-pyrimidine-2,4-dione;
3-((R)-2-amino-2-phenyl-ethyl)-1-(2,6-difluoro-benzyl)-6-methyl-5-[4-(2,3,4-trifluoro-benzyl)-piperazin-1-yl]-1H-pyrimidine-2,4-dione;
3-((R)-2-amino-2-phenyl-ethyl)-1-(2,6-difluoro-benzyl)-6-methyl-5-[4-(2,3,6-trifluoro-benzyl)-piperazin-1-yl]-1H-pyrimidine-2,4-dione;
3-((R)-2-amino-2-phenyl-ethyl)-1-(2,6-difluoro-benzyl)-5-[4-(2,3-difluoro-6-methoxy-benzyl)-piperazin-1-yl]-6-methyl-1H-pyrimidine-2,4-dione;
3-((R)-2-amino-2-phenyl-ethyl)-1-(2,6-difluoro-benzyl)-6-methyl-5-[4-(3-trifluoromethyl-benzyl)-piperazin-1-yl]-1H-pyrimidine-2,4-dione;
3-((R)-2-amino-2-phenyl-ethyl)-1-(2,6-difluoro-benzyl)-6-methyl-5-[4-(2-trifluoromethoxy-benzyl)-piperazin-1-yl]-1H-pyrimidine-2,4-dione;
3-((R)-2-amino-2-phenyl-ethyl)-1-(2,6-difluoro-benzyl)-6-methyl-5-[4-(4-trifluoromethoxy-benzyl)-piperazin-1-yl]-1H-pyrimidine-2,4-dione;
3-((R)-2-amino-2-phenyl-ethyl)-1-(2,6-difluoro-benzyl)-5-[4-(2-fluoro-3-trifluoromethyl-benzyl)-piperazin-1-yl]-6-methyl-1H-pyrimidine-2,4-dione;
3-((R)-2-amino-2-phenyl-ethyl)-1-(2,6-difluoro-benzyl)-5-[4-(2-fluoro-6-trifluoromethyl-benzyl)-piperazin-1-yl]-6-methyl-1H-pyrimidine-2,4-dione;
3-((R)-2-amino-2-phenyl-ethyl)-1-(2,6-difluoro-benzyl)-5-[4-(4-fluoro-3-trifluoromethyl-benzyl)-piperazin-1-yl]-6-methyl-1H-pyrimidine-2,4-dione;
3-((R)-2-amino-2-phenyl-ethyl)-1-(2,6-difluoro-benzyl)-5-[4-(4-fluoro-2-trifluoromethyl-benzyl)-piperazin-1-yl]-6-methyl-1H-pyrimidine-2,4-dione;
3-((R)-2-amino-2-phenyl-ethyl)-5-(3-benzyl-piperidin-1-yl)-1-(2,6-difluoro-benzyl)-6-methyl-1H-pyrimidine-2,4-dione;
3-((R)-2-amino-2-phenyl-ethyl)-1-(2,6-difluoro-benzyl)-5-[3-(4-fluoro-benzyl)-piperidin-1-yl]-6-methyl-1H-pyrimidine-2,4-dione;
3-((R)-2-amino-2-phenyl-ethyl)-1,6-dimethyl-5-[4-(3-nitro-benzyl)-piperazin-1-yl]-1H-pyrimidine-2,4-dione;
3-((R)-2-amino-2-phenyl-ethyl)-1,6-dimethyl-5-[4-(3-trifluoromethoxy-benzyl)-piperazin-1-yl]-1H-pyrimidine-2,4-dione;
3-((R)-2-amino-2-phenyl-ethyl)-5-[4-(3-fluoro-benzyl)-piperazin-1-yl]-1,6-dimethyl-1H-pyrimidine-2,4-dione;
3-((R)-2-amino-2-phenyl-ethyl)-1,6-dimethyl-5-(4-pyridin-3-ylmethyl-piperazin-1-yl)-1H-pyrimidine-2,4-dione;
3-((R)-2-amino-2-phenyl-ethyl)-1-(2-fluoro-6-trifluoromethyl-benzyl)-6-methyl-5-[4-(3-nitro-benzyl)-piperazin-1-yl]-1H-pyrimidine-2,4-dione;
3-((R)-2-amino-2-phenyl-ethyl)-1-(2-fluoro-6-trifluoromethyl-benzyl)-6-methyl-5-(4-pyridin-3-ylmethyl-piperazin-1-yl)-1H-pyrimidine-2,4-dione;
3-((R)-2-amino-2-phenyl-ethyl)-1-(2-fluoro-6-trifluoromethyl-benzyl)-6-methyl-5-[4-(3-trifluoromethoxy-benzyl)-piperazin-1-yl]-1H-pyrimidine-2,4-dione;
3-((R)-2-amino-2-phenyl-ethyl)-5-[4-(3-fluoro-benzyl)-piperazin-1-yl]-1-(2-fluoro-6-trifluoromethyl-benzyl)-6-methyl-1H-pyrimidine-2,4-dione;
3-((R)-2-amino-2-phenyl-ethyl)-1-(2-fluoro-6-trifluoromethyl-benzyl)-6-methyl-5-(4-naphthalen-1-ylmethyl-piperazin-1-yl)-1H-pyrimidine-2,4-dione;
3-((R)-2-amino-2-phenyl-ethyl)-5-[4-(5-fluoro-pyridin-3-ylmethyl)-piperazin-1-yl]-1-(2-fluoro-6-trifluoromethyl-benzyl)-6-methyl-1H-pyrimidine-2,4-dione;
3-((R)-2-amino-2-phenyl-ethyl)-5-(4-benzo[b]thiophen-7-ylmethyl-piperazin-1-yl)-1-(2-fluoro-6-trifluoromethyl-benzyl)-6-methyl-1H-pyrimidine-2,4-dione;
3-((R)-2-amino-2-phenyl-ethyl)-5-(4-benzo[1,2,5]oxadiazol-4-ylmethyl-piperazin-1-yl)-1-(2-fluoro-6-trifluoromethyl-benzyl)-6-methyl-1H-pyrimidine-2,4-dione;
3-((R)-2-amino-2-phenyl-ethyl)-1-(2-fluoro-6-trifluoromethyl-benzyl)-6-methyl-5-[4-(5-trifluoromethyl-furan-2-ylmethyl)-piperazin-1-yl]-1H-pyrimidine-2,4-dione;
3-((R)-2-amino-2-phenyl-ethyl)-1-(2-fluoro-6-trifluoromethyl-benzyl)-6-methyl-5-(4-quinolin-8-ylmethyl-piperazin-1-yl)-1H-pyrimidine-2,4-dione;
3-((R)-2-amino-2-phenyl-ethyl)-5-(4-benzothiazol-2-ylmethyl-piperazin-1-yl)-1-(2-fluoro-6-trifluoromethyl-benzyl)-6-methyl-1H-pyrimidine-2,4-dione;
3-((R)-2-amino-2-phenyl-ethyl)-1-(2-fluoro-6-trifluoromethyl-benzyl)-5-[4-(3H-imidazol-4-ylmethyl)-piperazin-1-yl]-6-methyl-1H-pyrimidine-2,4-dione;
3-((R)-2-amino-2-phenyl-ethyl)-5-[4-(2-fluoro-pyridin-3-ylmethyl)-piperazin-1-yl]-1-(2-fluoro-6-trifluoromethyl-benzyl)-6-methyl-1H-pyrimidine-2,4-dione;
3-((R)-2-amino-2-phenyl-ethyl)-1-(2-fluoro-6-trifluoromethyl-benzyl)-6-methyl-5-[4-(6-methyl-pyridin-3-ylmethyl)-piperazin-1-yl]-1H-pyrimidine-2,4-dione;
3-((R)-2-amino-2-phenyl-ethyl)-1-(2-fluoro-6-trifluoromethyl-benzyl)-5-[4-(2-methoxy-pyridin-3-ylmethyl)-piperazin-1-yl]-6-methyl-1H-pyrimidine-2,4-dione;
3-((R)-2-amino-2-phenyl-ethyl)-1-(2-fluoro-6-trifluoromethyl-benzyl)-5-[4-(1H-imidazol-2-ylmethyl)-piperazin-1-yl]-6-methyl-1H-pyrimidine-2,4-dione;
3-((R)-2-amino-2-phenyl-ethyl)-5-[4-(2-amino-pyridin-3-ylmethyl)-piperazin-1-yl]-1-(2-fluoro-6-trifluoromethyl-benzyl)-6-methyl-1H-pyrimidine-2,4-dione;

5-[4-(2-amino-benzyl)-piperazin-1-yl]-3-((R)-2-amino-2-phenyl-ethyl)-1-(2-fluoro-6-trifluoromethyl-benzyl)-6-methyl-1H-pyrimidine-2,4-dione;

5-[4-(3-amino-benzyl)-piperazin-1-yl]-3-((R)-2-amino-2-phenyl-ethyl)-1-(2-fluoro-6-trifluoromethyl-benzyl)-6-methyl-1H-pyrimidine-2,4-dione;

3-((R)-2-amino-2-phenyl-ethyl)-1-(2,6-difluoro-benzyl)-5-(2-oxo-pyrrolidin-1-yl)-1H-pyrimidine-2,4-dione;

2-{4-[3-((R)-2-amino-2-phenyl-ethyl)-1-(2-fluoro-6-trifluoromethyl-benzyl)-6-methyl-2,4-dioxo-1,2,3,4-tetrahydro-pyrimidin-5-yl]-piperazin-1-ylmethyl}-benzoic acid methyl ester;

3-{4-[3-((R)-2-amino-2-phenyl-ethyl)-1-(2-fluoro-6-trifluoromethyl-benzyl)-6-methyl-2,4-dioxo-1,2,3,4-tetrahydro-pyrimidin-5-yl]-piperazin-1-ylmethyl}-benzoic acid methyl ester;

2-{4-[3-((R)-2-amino-2-phenyl-ethyl)-1-(2-fluoro-6-trifluoromethyl-benzyl)-6-methyl-2,4-dioxo-1,2,3,4-tetrahydro-pyrimidin-5-yl]-piperazin-1-ylmethyl}-benzoic acid;

3-{4-[3-((R)-2-amino-2-phenyl-ethyl)-1-(2-fluoro-6-trifluoromethyl-benzyl)-6-methyl-2,4-dioxo-1,2,3,4-tetrahydro-pyrimidin-5-yl]-piperazin-1-ylmethyl}-benzoic acid;

2-{4-[3-((R)-2-amino-2-phenyl-ethyl)-1-(2-fluoro-6-trifluoromethyl-benzyl)-6-methyl-2,4-dioxo-1,2,3,4-tetrahydro-pyrimidin-5-yl]-piperazin-1-ylmethyl}-benzamide;

3-((R)-2-amino-2-phenyl-ethyl)-1-(2,6-difluoro-benzyl)-5-[4-(3-nitro-benzyl)-piperazin-1-yl]-1H-pyrimidine-2,4-dione;

3-((R)-2-amino-2-phenyl-ethyl)-1-(2,6-difluoro-benzyl)-5-(2-oxo-piperazin-1-yl)-1H-pyrimidine-2,4-dione;

3-((R)-2-amino-2-phenyl-ethyl)-5-(4-benzyl-2-oxo-piperazin-1-yl)-1-(2,6-difluoro-benzyl)-1H-pyrimidine-2,4-dione;

3-((R)-2-amino-2-phenyl-ethyl)-1-(2,6-difluoro-benzyl)-5-[4-(3-nitro-benzyl)-2-oxo-piperazin-1-yl]-1H-pyrimidine-2,4-dione;

3-((R)-2-amino-2-phenyl-ethyl)-5-[4-(2-chloro-pyridin-3-ylmethyl)-piperazin-1-yl]-1-(2-fluoro-6-trifluoromethyl-benzyl)-6-methyl-1H-pyrimidine-2,4-dione;

3-((R)-2-amino-2-phenyl-ethyl)-5-[4-(6-chloro-pyridin-3-ylmethyl)-piperazin-1-yl]-1-(2-fluoro-6-trifluoromethyl-benzyl)-6-methyl-1H-pyrimidine-2,4-dione;

3-((R)-2-amino-2-phenyl-ethyl)-1-(2-fluoro-6-trifluoromethyl-benzyl)-6-methyl-5-[4-(2-methyl-pyridin-3-ylmethyl)-piperazin-1-yl]-1H-pyrimidine-2,4-dione;

3-((R)-2-amino-2-phenyl-ethyl)-1-(2-fluoro-6-trifluoromethyl-benzyl)-6-methyl-5-[4-(5-methyl-pyridin-3-ylmethyl)-piperazin-1-yl]-1H-pyrimidine-2,4-dione;

3-((R)-2-amino-2-phenyl-ethyl)-1-(2-fluoro-6-trifluoromethyl-benzyl)-5-[4-(6-methoxy-pyridin-3-ylmethyl)-piperazin-1-yl]-6-methyl-1H-pyrimidine-2,4-dione;

3-((R)-2-amino-2-phenyl-ethyl)-1-(2-fluoro-6-trifluoromethyl-benzyl)-5-[4-(4-methoxy-pyridin-3-ylmethyl)-piperazin-1-yl]-6-methyl-1H-pyrimidine-2,4-dione;

3-((R)-2-amino-2-phenyl-ethyl)-1-(2-fluoro-6-trifluoromethyl-benzyl)-6-methyl-5-[4-(1-methyl-1H-imidazol-2-ylmethyl)-piperazin-1-yl]-1H-pyrimidine-2,4-dione;

3-((R)-2-amino-2-phenyl-ethyl)-1-(2-fluoro-6-trifluoromethyl-benzyl)-5-[4-(4-hydroxy-3-nitro-benzyl)-piperazin-1-yl]-6-methyl-1H-pyrimidine-2,4-dione;

3-((R)-2-amino-2-phenyl-ethyl)-5-[4-(2-fluoro-4-hydroxy-benzyl)-piperazin-1-yl]-1-(2-fluoro-6-trifluoromethyl-benzyl)-6-methyl-1H-pyrimidine-2,4-dione;

3-((R)-2-amino-2-phenyl-ethyl)-5-[4-(3-fluoro-4-hydroxy-benzyl)-piperazin-1-yl]-1-(2-fluoro-6-trifluoromethyl-benzyl)-6-methyl-1H-pyrimidine-2,4-dione;

3-((R)-2-amino-2-phenyl-ethyl)-5-(4-benzyl-3-oxo-piperazin-1-yl)-1-(2-fluoro-6-trifluoromethyl-benzyl)-6-methyl-1H-pyrimidine-2,4-dione;

3-((R)-2-amino-2-phenyl-ethyl)-1-(2-fluoro-6-trifluoromethyl-benzyl)-6-methyl-5-[4-(3-nitro-benzyl)-3-oxo-piperazin-1-yl]-1H-pyrimidine-2,4-dione;

3-((R)-2-amino-2-phenyl-ethyl)-1-(2-fluoro-6-trifluoromethyl-benzyl)-6-methyl-5-[4-(6-oxo-1,6-dihydro-pyridin-3-ylmethyl)-piperazin-1-yl]-1H-pyrimidine-2,4-dione;

3-((R)-2-amino-2-phenyl-ethyl)-1-(2-fluoro-6-trifluoromethyl-benzyl)-6-methyl-5-(4-pyrazin-2-ylmethyl-piperazin-1-yl)-1H-pyrimidine-2,4-dione;

3-((R)-2-amino-2-phenyl-ethyl)-1-(2-fluoro-6-trifluoromethyl-benzyl)-6-methyl-5-[4-(2-oxo-1,2-dihydro-pyridin-3-ylmethyl)-piperazin-1-yl]-1H-pyrimidine-2,4-dione;

3-((R)-2-amino-2-phenyl-ethyl)-1-(2-fluoro-6-trifluoromethyl-benzyl)-6-methyl-5-(4-thiozol-5-ylmethyl-piperazin-1-yl)-1H-pyrimidine-2,4-dione;

3-((R)-2-amino-2-phenyl-ethyl)-1-(2-fluoro-6-trifluoromethyl-benzyl)-6-methyl-5-(4-thiozol-4-ylmethyl-piperazin-1-yl)-1H-pyrimidine-2,4-dione;

3-((R)-2-amino-2-phenyl-ethyl)-1-(2-fluoro-6-trifluoromethyl-benzyl)-6-methyl-5-(4-thiozol-2-ylmethyl-piperazin-1-yl)-1H-pyrimidine-2,4-dione;

3-[(R)-2-amino-2-(5-fluoro-2-methoxy-phenyl)-ethyl]-1-(2-fluoro-6-trifluoromethyl-benzyl)-6-methyl-5-[4-(3-nitro-benzyl)-piperazin-1-yl]-1H-pyrimidine-2,4-dione;

3-[(S)-2-amino-2-(3-fluoro-5-methyl-phenyl)-ethyl]-1-(2-fluoro-6-trifluoromethyl-benzyl)-6-methyl-5-[4-(3-nitro-benzyl)-piperazin-1-yl]-1H-pyrimidine-2,4-dione;

3-[(S)-2-amino-2-(5-fluoro-2-methoxy-phenyl)-ethyl]-1-(2-fluoro-6-trifluoromethyl-benzyl)-6-methyl-5-[4-(3-nitro-benzyl)-piperazin-1-yl]-1H-pyrimidine-2,4-dione;

3-[(R)-2-amino-2-(3-fluoro-5-methyl-phenyl)-ethyl]-1-(2-fluoro-6-trifluoromethyl-benzyl)-6-methyl-5-[4-(3-nitro-benzyl)-piperazin-1-yl]-1H-pyrimidine-2,4-dione;

4-((R)-2-{3-(2-fluoro-6-trifluoromethyl-benzyl)-4-methyl-5-[4-(3-nitro-benzyl)-piperazin-1-yl]-2,6-dioxo-3,6-dihydro-2H-pyrimidin-1-yl}-1-phenyl-ethylamino)-butyric acid;

3-((R)-2-amino-2-phenyl-ethyl)-1-(2-fluoro-6-trifluoromethyl-benzyl)-6-methyl-5-(4-oxazol-4-ylmethyl-piperazin-1-yl)-1H-pyrimidine-2,4-dione;

3-((R)-2-amino-2-phenyl-ethyl)-1-(2-fluoro-6-trifluoromethyl-benzyl)-6-methyl-5-(4-isooxazol-3-ylmethyl-piperazin-1-yl)-1H-pyrimidine-2,4-dione;

3-((R)-2-amino-2-phenyl-ethyl)-1-(2-fluoro-6-trifluoromethyl-benzyl)-6-methyl-5-[4-(1-methyl-1H-pyrazol-3-ylmethyl)-piperazin-1-yl]-1H-pyrimidine-2,4-dione;

3-((R)-2-amino-2-phenyl-ethyl)-1-(2-fluoro-6-trifluoromethyl-benzyl)-6-methyl-5-[4-(1-methyl-1H-pyrazol-4-ylmethyl)-piperazin-1-yl]-1H-pyrimidine-2,4-dione;

3-((R)-2-amino-2-phenyl-ethyl)-1-(2-fluoro-6-trifluoromethyl-benzyl)-6-methyl-5-[4-(2-methyl-2H-pyrazol-3-ylmethyl)-piperazin-1-yl]-1H-pyrimidine-2,4-dione;

3-[(R)-2-amino-2-(5-fluoro-2-methoxy-phenyl)-ethyl]-1-(2-fluoro-6-trifluoromethyl-benzyl)-6-methyl-5-(4-pyridin-3-ylmethyl-piperazin-1-yl)-1H-pyrimidine-2,4-dione;

3-[(R)-2-amino-2-(3-fluoro-5-methyl-phenyl)-ethyl]-1-(2-fluoro-6-trifluoromethyl-benzyl)-6-methyl-5-(4-pyridin-3-ylmethyl-piperazin-1-yl)-1H-pyrimidine-2,4-dione;

2-{4-[3-((R)-2-amino-2-phenyl-ethyl)-1-(2-fluoro-6-trifluoromethyl-benzyl)-6-methyl-2,4-dioxo-1,2,3,4-tetrahydro-pyrimidin-5-yl]-piperazin-1-ylmethyl}-benzonitrile;

3-{4-[3-((R)-2-amino-2-phenyl-ethyl)-1-(2-fluoro-6-trifluoromethyl-benzyl)-6-methyl-2,4-dioxo-1,2,3,4-tetrahydro-pyrimidin-5-yl]-piperazin-1-ylmethyl}-benzonitrile;

4-{4-[3-((R)-2-amino-2-phenyl-ethyl)-1-(2-fluoro-6-trifluoromethyl-benzyl)-6-methyl-2,4-dioxo-1,2,3,4-tetrahydro-pyrimidin-5-yl]-piperazin-1-ylmethyl}-benzonitrile;

3-((R)-2-amino-2-phenyl-ethyl)-5-[4-(2,3-difluoro-benzyl)-piperazin-1-yl]-1-(2-fluoro-6-trifluoromethyl-benzyl)-6-methyl-1H-pyrimidine-2,4-dione;

3-((R)-2-amino-2-phenyl-ethyl)-5-[4-(2-fluoro-benzyl)-piperazin-1-yl]-1-(2-fluoro-6-trifluoromethyl-benzyl)-6-methyl-1H-pyrimidine-2,4-dione;

3-((R)-2-amino-2-phenyl-ethyl)-1-(2-fluoro-6-trifluoromethyl-benzyl)-5-(4-furan-2-ylmethyl-piperazin-1-yl)-6-methyl-1H-pyrimidine-2,4-dione;

3-((R)-2-amino-2-phenyl-ethyl)-1-(2-fluoro-6-trifluoromethyl-benzyl)-5-(4-furan-3-ylmethyl-piperazin-1-yl)-6-methyl-1H-pyrimidine-2,4-dione;

3-((R)-2-amino-2-phenyl-ethyl)-5-[4-(5-chloro-furan-2-ylmethyl)-piperazin-1-yl]-1-(2-fluoro-6-trifluoromethyl-benzyl)-6-methyl-1H-pyrimidine-2,4-dione;

3-((R)-2-amino-2-phenyl-ethyl)-1-(2-fluoro-6-trifluoromethyl-benzyl)-6-methyl-5-(4-thiophen-2-ylmethyl-piperazin-1-yl)-1H-pyrimidine-2,4-dione;

3-{4-[3-((R)-2-amino-2-phenyl-ethyl)-1-(2-fluoro-6-trifluoromethyl-benzyl)-6-methyl-2,4-dioxo-1,2,3,4-tetrahydro-pyrimidin-5-yl]-piperazin-1-ylmethyl}-benzamide;

3-(2-amino-2-o-tollyl-ethyl)-1-(2-fluoro-6-trifluoromethyl-benzyl)-6-methyl-5-[4-(3-nitro-benzyl)-piperazin-1-yl]-1H-pyrimidine-2,4-dione;

3-[(R)-2-amino-2-(2-methoxy-phenyl)-ethyl]-1-(2-fluoro-6-trifluoromethyl-benzyl)-6-methyl-5-[4-(3-nitro-benzyl)-piperazin-1-yl]-1H-pyrimidine-2,4-dione;

3-[2-amino-2-(2-fluoro-phenyl)-ethyl]-1-(2-fluoro-6-trifluoromethyl-benzyl)-6-methyl-5-[4-(3-nitro-benzyl)-piperazin-1-yl]-1H-pyrimidine-2,4-dione;

3-(2-amino-2-m-tollyl-ethyl)-1-(2-fluoro-6-trifluoromethyl-benzyl)-6-methyl-5-[4-(3-nitro-benzyl)-piperazin-1-yl]-1H-pyrimidine-2,4-dione;

3-[(R)-2-amino-2-(4-fluoro-phenyl)-ethyl]-1-(2-fluoro-6-trifluoromethyl-benzyl)-6-methyl-5-[4-(3-nitro-benzyl)-piperazin-1-yl]-1H-pyrimidine-2,4-dione;

3-[2-amino-2-(3-fluoro-phenyl)-ethyl]-1-(2-fluoro-6-trifluoromethyl-benzyl)-6-methyl-5-[4-(3-nitro-benzyl)-piperazin-1-yl]-1H-pyrimidine-2,4-dione;

[2-((R)-2-{3-(2-fluoro-6-trifluoromethyl-benzyl)-4-methyl-5-[4-(3-nitro-benzyl)-piperazin-1-yl]-2,6-dioxo-3,6-dihydro-2H-pyrimidin-1-yl}-1-phenyl-ethylamino)-ethyl]-phosphonic acid monoethyl ester;

[3-((R)-2-{3-(2-fluoro-6-trifluoromethyl-benzyl)-4-methyl-2,6-dioxo-5-[4-(5-trifluoromethyl-furan-2-ylmethyl)-piperazin-1-yl]-3,6-dihydro-2H-pyrimidin-1-yl}-1-phenyl-ethylamino)-propyl]-phosphonic acid monoethyl ester;

5-{4-[3-((R)-2-amino-2-phenyl-ethyl)-1-(2-fluoro-6-trifluoromethyl-benzyl)-6-methyl-2,4-dioxo-1,2,3,4-tetrahydro-pyrimidin-5-yl]-piperazin-1-ylmethyl}-furan-2-carboxylic acid;

3-[(R)-2-amino-2-(2-methoxy-phenyl)-ethyl]-1-(2-fluoro-6-trifluoromethyl-benzyl)-6-methyl-5-[4-(5-trifluoromethyl-furan-2-ylmethyl)-piperazin-1-yl]-1H-pyrimidine-2,4-dione;

3-[(R)-2-amino-2-(5-fluoro-2-methoxy-phenyl)-ethyl]-1-(2-fluoro-6-trifluoromethyl-benzyl)-6-methyl-5-[4-(5-trifluoromethyl-furan-2-ylmethyl)-piperazin-1-yl]-1H-pyrimidine-2,4-dione;

3-[(R)-2-amino-2-(3-fluoro-5-methyl-phenyl)-ethyl]-1-(2-fluoro-6-trifluoromethyl-benzyl)-6-methyl-5-[4-(5-trifluoromethyl-furan-2-ylmethyl)-piperazin-1-yl]-1H-pyrimidine-2,4-dione;

[2-((R)-2-{3-(2-fluoro-6-trifluoromethyl-benzyl)-4-methyl-2,6-dioxo-5-[4-(5-trifluoromethyl-furan-2-ylmethyl)-piperazin-1-yl]-3,6-dihydro-2H-pyrimidin-1-yl}-1-phenyl-ethylamino)-ethyl]-phosphonic acid;

[3-((R)-2-{3-(2-fluoro-6-trifluoromethyl-benzyl)-4-methyl-2,6-dioxo-5-[4-(5-trifluoromethyl-furan-2-ylmethyl)-piperazin-1-yl]-3,6-dihydro-2H-pyrimidin-1-yl}-1-phenyl-ethylamino)-propyl]-phosphonic acid;

3-((R)-2-amino-2-phenyl-ethyl)-1-(2-fluoro-6-trifluoromethyl-benzyl)-5-[4-(3-methanesulfonyl-benzyl)-piperazin-1-yl]-6-methyl-1H-pyrimidine-2,4-dione;

5-{4-[3-((R)-2-amino-2-phenyl-ethyl)-1-(2-fluoro-6-trifluoromethyl-benzyl)-6-methyl-2,4-dioxo-1,2,3,4-tetrahydro-pyrimidin-5-yl]-piperazin-1-ylmethyl}-furan-2-carboxylic acid methyl ester;

5-{4-[3-((R)-2-amino-2-phenyl-ethyl)-1-(2-fluoro-6-trifluoromethyl-benzyl)-6-methyl-2,4-dioxo-1,2,3,4-tetrahydro-pyrimidin-5-yl]-piperazin-1-ylmethyl}-furan-2-carbonitrile;

5-[4-(3-acetyl-benzyl)-piperazin-1-yl]-3-((R)-2-amino-2-phenyl-ethyl)-1-(2-fluoro-6-trifluoromethyl-benzyl)-6-methyl-1H-pyrimidine-2,4-dione;

5-{4-[3-((R)-2-amino-2-phenyl-ethyl)-1-(2-fluoro-6-trifluoromethyl-benzyl)-6-methyl-2,4-dioxo-1,2,3,4-tetrahydro-pyrimidin-5-yl]-piperazin-1-ylmethyl}-furan-2-carboxylic acid amide;

5-{4-[3-((R)-2-amino-2-phenyl-ethyl)-1-(2-fluoro-6-trifluoromethyl-benzyl)-6-methyl-2,4-dioxo-1,2,3,4-tetrahydro-pyrimidin-5-yl]-piperazin-1-yl-methyl}-furan-2-carboxylic acid methylamide;

5-{4-[3-((R)-2-amino-2-phenyl-ethyl)-1-(2-fluoro-6-trifluoromethyl-benzyl)-6-methyl-2,4-dioxo-1,2,3,4-tetrahydro-pyrimidin-5-yl]-piperazin-1-yl-methyl}-furan-2-carboxylic acid dimethylamide;

4-((R)-2-{3-(2-fluoro-6-trifluoromethyl-benzyl)-4-methyl-2,6-dioxo-5-[4-(5-trifluoromethyl-furan-2-ylmethyl)-piperazin-1-yl]-3,6-dihydro-2H-pyrimidin-1-yl}-1-phenyl-ethylamino)-butyric acid;

[2-((R)-2-{3-(2-fluoro-6-trifluoromethyl-benzyl)-4-methyl-5-[4-(3-nitro-benzyl)-piperazine-yl]-2,6-dioxo-3,6-dihydro-2H-pyrimidin-1-yl}-1-phenyl-ethylamino)-ethyl]-phosphonic acid;

(3-{4-[3-((R)-2-amino-2-phenyl-ethyl)-1-(2-fluoro-6-trifluoromethyl-benzyl)-6-methyl-2,4-dioxo-1,2,3,4-tetrahydro-pyrimidin-5-yl]-piperazin-1-ylmethyl}-benzoylamino)-acetic acid methyl ester;
3-(3-{4-[3-((R)-2-amino-2-phenyl-ethyl)-1-(2-fluoro-6-trifluoromethyl-benzyl)-6-methyl-2,4-dioxo-1,2,3,4-tetrahydro-pyrimidin-5-yl]-piperazin-1-ylmethyl}-benzoylamino)-propionic acid ethyl ester;
4-(3-{4-[3-((R)-2-amino-2-phenyl-ethyl)-1-(2-fluoro-6-trifluoromethyl-benzyl)-6-methyl-2,4-dioxo-1,2,3,4-tetrahydro-pyrimidin-5-yl]-piperazin-1-ylmethyl}-benzoylamino)-butyric acid ethyl ester;
4-(3-{4-[3-((R)-2-amino-2-phenyl-ethyl)-1-(2-fluoro-6-trifluoromethyl-benzyl)-6-methyl-2,4-dioxo-1,2,3,4-tetrahydro-pyrimidin-5-yl]-piperazin-1-ylmethyl}-benzoylamino)-butyric acid;
3-(3-{4-[3-((R)-2-amino-2-phenyl-ethyl)-1-(2-fluoro-6-trifluoromethyl-benzyl)-6-methyl-2,4-dioxo-1,2,3,4-tetrahydro-pyrimidin-5-yl]-piperazin-1-ylmethyl}-benzoylamino)-propionic acid;
(3-{4-[3-((R)-2-amino-2-phenyl-ethyl)-1-(2-fluoro-6-trifluoromethyl-benzyl)-6-methyl-2,4-dioxo-1,2,3,4-tetrahydro-pyrimidin-5-yl]-piperazin-1-ylmethyl}-benzoylamino)-acetic acid;
3-((R)-2-{3-(2-fluoro-6-trifluoromethyl-benzyl)-4-methyl-5-[4-(3-nitro-benzyl)-piperazin-1-yl]-2,6-dioxo-3,6-dihydro-2H-pyrimidin-1-yl}-1-phenyl-ethylamino)-propane-1-sulfonic acid;
3-((R)-2-{3-(2-fluoro-6-trifluoromethyl-benzyl)-4-methyl-2,6-dioxo-5-[4-(5-trifluoromethyl-furan-2-ylmethyl)-piperazin-1-yl]-3,6-dihydro-2H-pyrimidin-1-yl}-1-phenyl-ethylamino)-propane-1-sulfonic acid;
[2-((R)-1-amino-2-{3-(2-fluoro-6-trifluoromethyl-benzyl)-4-methyl-5-[4-(3-nitro-benzyl)-piperazin-1-yl]-2,6-dioxo-3,6-dihydro-2H-pyrimidin-1-yl}-ethyl)-phenoxy]-acetic acid;
3-[(R)-2-amino-2-(2-hydroxy-phenyl)-ethyl]-1-(2-fluoro-6-trifluoromethyl-benzyl)-6-methyl-5-[4-(3-nitro-benzyl)-piperazin-1-yl]-1H-pyrimidine-2,4-dione;
3-((R)-2-amino-2-phenyl-ethyl)-1-(2-fluoro-6-trifluoromethyl-benzyl)-6-methyl-5-{4-[3-(1H-tetrazol-5-yl)-benzyl]-piperazin-1-yl}-1H-pyrimidine-2,4-dione;
4-[2-((R)-1-amino-2-{3-(2-fluoro-6-trifluoromethyl-benzyl)-4-methyl-5-[4-(3-nitro-benzyl)-piperazin-1-yl]-2,6-dioxo-3,6-dihydro-2H-pyrimidin-1-yl}-ethyl)-phenoxy]-butyric acid;
3-((R)-1-amino-2-{3-(2-fluoro-6-trifluoromethyl-benzyl)-4-methyl-2,6-dioxo-5-[4-(5-trifluoromethyl-furan-2-ylmethyl)-piperazin-1-yl]-3,6-dihydro-2H-pyrimidin-1-yl}-ethyl)-benzoic acid;
4-((R)-1-amino-2-{3-(2-fluoro-6-trifluoromethyl-benzyl)-4-methyl-2,6-dioxo-5-[4-(5-trifluoromethyl-furan-2-ylmethyl)-piperazin-1-yl]-3,6-dihydro-2H-pyrimidin-1-yl}-ethyl)-benzoic acid;
((R)-2-{3-(2-fluoro-6-trifluoromethyl-benzyl)-4-methyl-2,6-dioxo-5-[4-(5-trifluoromethyl-furan-2-ylmethyl)-piperazin-1-yl]-3,6-dihydro-2H-pyrimidin-1-yl}-1-phenyl-ethylamino)-acetic acid;
3-((R)-2-{3-(2-fluoro-6-trifluoromethyl-benzyl)-4-methyl-2,6-dioxo-5-[4-(5-trifluoromethyl-furan-2-ylmethyl)-piperazin-1-yl]-3,6-dihydro-2H-pyrimidin-1-yl}-1-phenyl-ethylamino)-propionic acid;
5-((R)-2-{3-(2-fluoro-6-trifluoromethyl-benzyl)-4-methyl-2,6-dioxo-5-[4-(5-trifluoromethyl-furan-2-ylmethyl)-piperazin-1-yl]-3,6-dihydro-2H-pyrimidin-1-yl}-1-phenyl-ethylamino)-pentanoic acid;
3-((R)-2-{3-(2-fluoro-6-trifluoromethyl-benzyl)-4-methyl-5-[4-(3-nitro-benzyl)-piperazin-1-yl]-2,6-dioxo-3,6-dihydro-2H-pyrimidin-1-yl}-1-phenyl-ethylamino)-propionic acid;
1-(2-fluoro-6-trifluoromethyl-benzyl)-3-((R)-2-hydroxy-2-phenyl-ethyl)-6-methyl-5-[4-(5-trifluoromethyl-furan-2-ylmethyl)-piperazin-1-yl]-1H-pyrimidine-2,4-dione;
3-((R)-2-amino-2-phenyl-ethyl)-1-(2-fluoro-6-trifluoromethyl-benzyl)-6-methyl-5-[4-(3-trifluoromethyl-benzyl)-piperazin-1-yl]-1H-pyrimidine-2,4-dione;
(E)-4-((R)-2-{3-(2-fluoro-6-trifluoromethyl-benzyl)-4-methyl-2,6-dioxo-5-[4-(5-trifluoromethyl-furan-2-ylmethyl)-piperazin-1-yl]-3,6-dihydro-2H-pyrimidin-1-yl}-1-phenyl-ethylamino)-but-2-enic acid;
4-((R)-2-{3-(2-fluoro-6-trifluoromethyl-benzyl)-4-methyl-2,6-dioxo-5-[4-(5-trifluoromethyl-furan-2-ylmethyl)-piperazin-1-yl]-3,6-dihydro-2H-pyrimidin-1-yl}-1-phenyl-ethylamino)-2-hydroxy-butyric acid;
3-((R)-2-amino-2-phenyl-ethyl)-5-(4-benzyl-4-hydroxy-piperidin-1-yl)-1-(2-fluoro-6-trifluoromethyl-benzyl)-6-methyl-1H-pyrimidine-2,4-dione;
3-[(R)-2-amino-2-(2-methoxy-phenyl)-ethyl]-1-(2-fluoro-6-trifluoromethyl-benzyl)-6-methyl-5-[4-(5-trifluoromethyl-furan-2-ylmethyl)-piperazin-1-yl]-1H-pyrimidine-2,4-dione;
3-((R)-2-amino-2-phenyl-ethyl)-1-(2-fluoro-6-trifluoromethyl-benzyl)-5-[3-hydroxymethyl-4-(5-trifluoromethyl-furan-2-ylmethyl)-piperazin-1-yl]-6-methyl-1H-pyrimidine-2,4-dione;
4-[3-((R)-2-amino-2-phenyl-ethyl)-1-(2-fluoro-6-trifluoromethyl-benzyl)-6-methyl-2,4-dioxo-1,2,3,4-tetrahydro-pyrimidin-5-yl]-1-(3-nitro-benzyl)-piperazine-2-carboxylic acid;
3-[(R)-2-amino-2-(2-hydroxy-phenyl)-ethyl]-1-(2-fluoro-6-trifluoromethyl-benzyl)-6-methyl-5-[4-(5-trifluoromethyl-furan-2-ylmethyl)-piperazin-1-yl]-1H-pyrimidine-2,4-dione;
[2-((R)-1-amino-2-{3-(2-fluoro-6-trifluoromethyl-benzyl)-4-methyl-2,6-dioxo-5-[4-(5-trifluoromethyl-furan-2-ylmethyl)-piperazin-1-yl]-3,6-dihydro-2H-pyrimidin-1-yl}-ethyl)-phenoxy]-acetic acid;
4-((R)-2-{3-(2-fluoro-6-trifluoromethyl-benzyl)-4-methyl-2,6-dioxo-5-[4-(3-trifluoromethyl-benzyl)-piperazin-1-yl]-3,6-dihydro-2H-pyrimidin-1-yl}-1-phenyl-ethylamino)-butyric acid;
{4-[3-((R)-2-amino-2-phenyl-ethyl)-1-(2-fluoro-6-trifluoromethyl-benzyl)-6-methyl-2,4-dioxo-1,2,3,4-tetrahydro-pyrimidin-5-yl]-piperazin-1-yl}-(3-trifluoromethyl-phenyl)-acetic acid;
3-((R)-2-amino-2-phenyl-ethyl)-1-(2-fluoro-6-trifluoromethyl-benzyl)-6-methyl-5-[4-(5-methyl-2-trifluoromethyl-furan-3-ylmethyl)-piperazin-1-yl]-1H-pyrimidine-2,4-dione;
3-((R)-2-amino-2-phenyl-ethyl)-1-(2-fluoro-6-trifluoromethyl-benzyl)-6-methyl-5-[4-(2-trifluoromethyl-pyridin-3-ylmethyl)-piperazin-1-yl]-1H-pyrimidine-2,4-dione;
3-((R)-2-amino-2-phenyl-ethyl)-1-(2-fluoro-6-trifluoromethyl-benzyl)-6-methyl-5-[4-(6-trifluoromethyl-pyridin-3-ylmethyl)-piperazin-1-yl]-1H-pyrimidine-2,4-dione;
3-((R)-2-amino-2-phenyl-ethyl)-5-[4-(2-fluoro-3-nitro-benzyl)-piperazin-1-yl]-1-(2-fluoro-6-trifluoromethyl-benzyl)-6-methyl-1H-pyrimidine-2,4-dione;

4-((R)-1-(3-fluoro-5-methyl-phenyl)-2-{3-(2-fluoro-6-trifluoromethyl-benzyl)-4-methyl-2,6-dioxo-5-[4-(5-trifluoromethyl-furan-2-ylmethyl)-piperazin-1-yl]-3,6-dihydro-2H-pyrimidin-1-yl}-ethylamino)-butyric acid;

4-((R)-1-(5-fluoro-2-methoxy-phenyl)-2-{3-(2-fluoro-6-trifluoromethyl-benzyl)-4-methyl-2,6-dioxo-5-[4-(5-trifluoromethyl-furan-2-ylmethyl)-piperazin-1-yl]-3,6-dihydro-2H-pyrimidin-1-yl}-ethylamino)-butyric acid;

4-[(R)-2-{3-(2-fluoro-6-trifluoromethyl-benzyl)-4-methyl-2,6-dioxo-5-[4-(5-trifluoromethyl-furan-2-ylmethyl)-piperazin-1-yl]-3,6-dihydro-2H-pyrimidin-1-yl}-1-(2-methoxy-phenyl)-ethylamino]-butyric acid;

3-((R)-2-amino-2-phenyl-ethyl)-1-(2-fluoro-6-trifluoromethyl-benzyl)-5-[4-(4-hydroxy-3-trifluoromethyl-benzyl)-piperazin-1-yl]-6-methyl-1H-pyrimidine-2,4-dione;

4-[(R)-2-{3-(2-fluoro-6-trifluoromethyl-benzyl)-4-methyl-2,6-dioxo-5-[4-(5-trifluoromethyl-furan-2-ylmethyl)-piperazin-1-yl]-3,6-dihydro-2H-pyrimidin-1-yl}-1-(2-hydroxy-phenyl)-ethylamino]-butyric acid;

3-((R)-2-amino-2-phenyl-ethyl)-1-(2-fluoro-6-trifluoromethyl-benzyl)-6-methyl-5-[4-(5-trifluoromethyl-[1,3,4]oxadizol-2-ylmethyl)-piperazin-1-yl]-1H-pyrimidine-2,4-dione;

3-((R)-2-amino-2-phenyl-ethyl)-1-(2-fluoro-6-trifluoromethyl-benzyl)-6-methyl-5-[4-(4-trifluoromethyl-furan-2-ylmethyl)-piperazin-1-yl]-1H-pyrimidine-2,4-dione;

3-((R)-2-amino-2-phenyl-ethyl)-1-(2-fluoro-6-trifluoromethyl-benzyl)-6-methyl-5-(4-pyrimidin-4-ylmethyl-piperazin-1-yl)-1H-pyrimidine-2,4-dione;

3-((R)-2-amino-2-phenyl-ethyl)-1-(2-fluoro-6-trifluoromethyl-benzyl)-6-methyl-5-[4-(2-trifluoromethyl-thiozol-5-ylmethyl)-piperazin-1-yl]-1H-pyrimidine-2,4-dione;

3-{4-[3-((R)-2-amino-2-phenyl-ethyl)-1-(2-fluoro-6-trifluoromethyl-benzyl)-6-methyl-2,4-dioxo-1,2,3,4-tetrahydro-pyrimidin-5-yl]-piperazin-1-ylmethyl}-2-fluorobenzamide;

3-((R)-2-amino-2-phenyl-ethyl)-1-(2-fluoro-6-trifluoromethyl-benzyl)-6-methyl-5-[4-(3-oxazol-2-yl-benzyl)-piperazin-1-yl]-1H-pyrimidine-2,4-dione;

3-((R)-2-amino-2-phenyl-ethyl)-1-(2-fluoro-6-trifluoromethyl-benzyl)-6-methyl-5-[4-(6-oxo-6H-pyran-2-ylmethyl)-piperazin-1-yl]-1H-pyrimidine-2,4-dione;

3-((R)-2-amino-2-phenyl-ethyl)-5-(4-benzo[d]isooxazol-7-ylmethyl-piperazin-1-yl)-1-(2-fluoro-6-trifluoromethyl-benzyl)-6-methyl-1H-pyrimidine-2,4-dione;

acetic acid 3-{4-[3-((R)-2-amino-2-phenyl-ethyl)-1-(2-fluoro-6-trifluoromethyl-benzyl)-6-methyl-2,4-dioxo-1,2,3,4-tetrahydro-pyrimidin-5-yl]-piperazin-1-ylmethyl}-phenyl ester;

3-{4-[3-((R)-2-amino-2-phenyl-ethyl)-1-(2-fluoro-6-trifluoromethyl-benzyl)-6-methyl-2,4-dioxo-1,2,3,4-tetrahydro-pyrimidin-5-yl]-piperazin-1-ylmethyl}-2-fluorobenzonitrile;

2-{4-[3-((R)-2-amino-2-phenyl-ethyl)-1-(2-fluoro-6-trifluoromethyl-benzyl)-6-methyl-2,4-dioxo-1,2,3,4-tetrahydro-pyrimidin-5-yl]-piperazin-1-ylmethyl}-6-fluorobenzonitrile;

3-((R)-2-amino-2-phenyl-ethyl)-1-(2-fluoro-6-trifluoromethyl-benzyl)-6-methyl-5-[4-(6-trifluoromethyl-pyridin-2-ylmethyl)-piperazin-1-yl]-1H-pyrimidine-2,4-dione;

3-((R)-2-amino-2-phenyl-ethyl)-5-(4-benzofuran-4-ylmethyl-piperazin-1-yl)-1-(2-fluoro-6-trifluoromethyl-benzyl)-6-methyl-1H-pyrimidine-2,4-dione;

3-((R)-2-amino-2-phenyl-ethyl)-1-(2-fluoro-6-trifluoromethyl-benzyl)-6-methyl-5-[4-(5-methyl-furan-2-ylmethyl)-piperazin-1-yl]-1H-pyrimidine-2,4-dione;

3-((R)-2-amino-2-phenyl-ethyl)-5-[4-(5-tert-butyl-furan-2-ylmethyl)-piperazin-1-yl]-1-(2-fluoro-6-trifluoromethyl-benzyl)-6-methyl-1H-pyrimidine-2,4-dione;

3-((R)-2-amino-propyl)-1-(2-fluoro-6-trifluoromethyl-benzyl)-6-methyl-5-[4-(5-trifluoromethyl-furan-2-ylmethyl)-piperazin-1-yl]-1H-pyrimidine-2,4-dione;

3-((R)-2-amino-4-methyl-pentyl)-1-(2-fluoro-6-trifluoromethyl-benzyl)-6-methyl-5-[4-(5-trifluoromethyl-furan-2-ylmethyl)-piperazin-1-yl]-1H-pyrimidine-2,4-dione;

3-((S)-2-amino-4-methyl-pentyl)-1-(2-fluoro-6-trifluoromethyl-benzyl)-6-methyl-5-[4-(5-trifluoromethyl-furan-2-ylmethyl)-piperazin-1-yl]-1-pyrimidine-2,4-dione;

3-((S)-2-amino-3-methoxy-propyl)-1-(2-fluoro-6-trifluoromethyl-benzyl)-6-methyl-5-[4-(5-trifluoromethyl-furan-2-ylmethyl)-piperazin-1-yl]-1H-pyrimidine-2,4-dione;

3-((R)-2-amino-3-methoxy-propyl)-1-(2-fluoro-6-trifluoromethyl-benzyl)-6-methyl-5-[4-(5-trifluoromethyl-furan-2-ylmethyl)-piperazin-1-yl]-1H-pyrimidine-2,4-dione;

3-(2-amino-4-methylsulfanyl-butyl)-1-(2-fluoro-6-trifluoromethyl-benzyl)-6-methyl-5-[4-(5-trifluoromethyl-furan-2-ylmethyl)-piperazin-1-yl]-1H-pyrimidine-2,4-dione;

4-((R)-2-{3-(2-fluoro-6-trifluoromethyl-benzyl)-4-methyl-5-[4-(3-oxazol-2-yl-benzyl)-piperazin-1-yl]-2,6-dioxo-3,6-dihydro-2H-pyrimidin-1-yl}-1-phenyl-ethylamino)-butyric acid;

4-{(R)-2-[5-[4-(3-cyano-2-fluoro-benzyl)-piperazin-1-yl]-3-(2-fluoro-6-trifluoromethyl-benzyl)-4-methyl-2,6-dioxo-3,6-dihydro-2H-pyrimidin-1-yl]-1-phenyl-ethylamino}-butyric acid;

4-{(R)-2-[5-[4-(2-cyano-3-fluoro-benzyl)-piperazin-1-yl]-3-(2-fluoro-6-trifluoromethyl-benzyl)-4-methyl-2,6-dioxo-3,6-dihydro-2H-pyrimidin-1-yl]-1-phenyl-ethylamino}-butyric acid;

1-(2-fluoro-6-trifluoromethyl-benzyl)-6-methyl-3-[(R)-2-(2-oxo-pyrrolidin-1-yl)-2-phenyl-ethyl]-5-[4-(5-trifluoromethyl-furan-2-ylmethyl)-piperazin-1-yl]-1H-pyrimidine-2,4-dione;

4-[(R)-2-{3-(2-fluoro-6-trifluoromethyl-benzyl)-4-methyl-2,6-dioxo-5-[4-(5-trifluoromethyl-furan-2-ylmethyl)-piperazin-1-yl]-3,6-dihydro-2H-pyrimidin-1-yl}-1-(2-hydroxy-phenyl)-ethylamino]-butyric acid;

4-{(R)-2-[5-[4-(3-carbamoyl-2-fluoro-benzyl)-piperazin-1-yl]-3-(2-fluoro-6-trifluoromethyl-benzyl)-4-methyl-2,6-dioxo-3,6-dihydro-2H-pyrimidin-1-yl]-1-phenyl-ethylamino}-butyric acid;

2-fluoro-3-(4-{1-(2-fluoro-6-trifluoromethyl-benzyl)-6-methyl-2,4-dioxo-3-[(R)-2-(2-oxo-pyrrolidin-1-yl)-2-phenyl-ethyl]-1,2,3,4-tetrahydro-pyrimidin-5-yl}-piperazin-1-ylmethyl)-benzamide;

3-{4-[3-((R)-2-amino-2-phenyl-ethyl)-1-(2-fluoro-6-trifluoromethyl-benzyl)-6-methyl-2,4-dioxo-1,2,3,4-tetrahydro-pyrimidin-5-yl]-piperazin-1-ylmethyl}-N-methyl-benzamide;

3-{4-[3-((R)-2-amino-2-phenyl-ethyl)-1-(2-fluoro-6-trifluoromethyl-benzyl)-6-methyl-2,4-dioxo-1,2,3,4-tetrahydro-pyrimidin-5-yl]-piperazin-1-ylmethyl}-N-ethyl-benzamide;

3-((R)-2-amino-2-phenyl-ethyl)-1-(2-fluoro-6-trifluoromethyl-benzyl)-6-methyl-5-[4-(4,4,5,5,5-pentafluoro-pentyl)-piperazin-1-yl]-1H-pyrimidine-2,4-dione;

3-((R)-2-amino-2-phenyl-ethyl)-1-(2-fluoro-6-trifluoromethyl-benzyl)-6-methyl-5-{4-[2-(2,2,2-trifluoro-ethoxy)-ethyl]-piperazin-1-yl}-1H-pyrimidine-2,4-dione;

3-((R)-2-amino-2-phenyl-ethyl)-1-(2-fluoro-6-trifluoromethyl-benzyl)-6-methyl-5-[4-(6-trifluoromethyl-pyridin-2-ylmethyl)-piperazin-1-yl]-1H-pyrimidine-2,4-dione;

3-((R)-2-amino-2-phenyl-ethyl)-1-(2-fluoro-6-trifluoromethyl-benzyl)-6-methyl-5-[4-(5-trifluoromethyl-thiophen-2-ylmethyl)-piperazin-1-yl]-1H-pyrimidine-2,4-dione;

5-{4-[3-((R)-2-amino-2-phenyl-ethyl)-1-(2-fluoro-6-trifluoromethyl-benzyl)-6-methyl-2,4-dioxo-1,2,3,4-tetrahydro-pyrimidin-5-yl]-piperazin-1-ylmethyl}-1H-pyrrole-2-carboxylic acid methyl ester;

3-((R)-2-amino-2-phenyl-ethyl)-1-(2-fluoro-6-trifluoromethyl-benzyl)-6-methyl-5-[4-(7-oxo-6,7-dihydro-5H-pyrrolizin-3-ylmethyl)-piperazin-1-yl]-1H-pyrimidine-2,4-dione;

3-((R)-2-amino-2-phenyl-ethyl)-1-(2-fluoro-6-trifluoromethyl-benzyl)-5-[4-(3-methanesulfinyl-benzyl)-piperazin-1-yl]-6-methyl-1H-pyrimidine-2,4-dione;

3-[(R)-2-amino-2-(2-methoxy-phenyl)-ethyl]-1-(2-fluoro-6-trifluoromethyl-benzyl)-6-methyl-5-[4-(3-trifluoromethyl-benzyl)-piperazin-1-yl]-1H-pyrimidine-2,4-dione;

4-[(R)-2-{3-(2-fluoro-6-trifluoromethyl-benzyl)-4-methyl-2,6-dioxo-5-[4-(3-trifluoromethyl-benzyl)-piperazin-1-yl]-3,6-dihydro-2H-pyrimidin-1-yl}-1-(2-methoxy-phenyl)-ethylamino]-butyric acid;

3-((R)-2-amino-2-phenyl-ethyl)-1-(2-fluoro-6-trifluoromethyl-benzyl)-6-methyl-5-((S)-3-methyl-piperazin-1-yl)-1H-pyrimidine-2,4-dione;

3-((R)-2-amino-2-phenyl-ethyl)-1-(2-fluoro-6-trifluoromethyl-benzyl)-6-methyl-5-((R)-3-methyl-piperazin-1-yl)-1H-pyrimidine-2,4-dione;

3-((R)-2-amino-2-phenyl-ethyl)-1-(2-fluoro-6-trifluoromethyl-benzyl)-6-methyl-5-[(R)-3-methyl-4-(5-trifluoromethyl-furan-2-ylmethyl)-piperazin-1-yl]-1H-pyrimidine-2,4-dione;

3-((R)-2-amino-2-phenyl-ethyl)-1-(2-fluoro-6-trifluoromethyl-benzyl)-6-methyl-5-[(S)-3-methyl-4-(5-trifluoromethyl-furan-2-ylmethyl)-piperazin-1-yl]-1H-pyrimidine-2,4-dione;

3-((S)-2-amino-2-furan-2-yl-ethyl)-1-(2-fluoro-6-trifluoromethyl-benzyl)-6-methyl-5-[4-(5-trifluoromethyl-furan-2-ylmethyl)-piperazin-1-yl]-1H-pyrimidine-2,4-dione;

3-((S)-2-amino-2-thiophen-3-yl-ethyl)-1-(2-fluoro-6-trifluoromethyl-benzyl)-6-methyl-5-[4-(5-trifluoromethyl-furan-2-ylmethyl)-piperazin-1-yl]-1H-pyrimidine-2,4-dione;

4-((R)-2-{3-(2-fluoro-6-trifluoromethyl-benzyl)-4-methyl-5-[(R)-3-methyl-4-(5-trifluoromethyl-furan-2-ylmethyl)-piperazin-1-yl]-2,6-dioxo-3,6-dihydro-2H-pyrimidin-1-yl}-1-phenyl-ethylamino)-butyric acid;

4-((R)-2-{3-(2-fluoro-6-trifluoromethyl-benzyl)-4-methyl-5-[(S)-3-methyl-4-(5-trifluoromethyl-furan-2-ylmethyl)-piperazin-1-yl]-2,6-dioxo-3,6-dihydro-2H-pyrimidin-1-yl}-1-phenyl-ethylamino)-butyric acid;

4-((S)-2-{3-(2-fluoro-6-trifluoromethyl-benzyl)-4-methyl-2,6-dioxo-5-[4-(5-trifluoromethyl-furan-2-ylmethyl)-piperazin-1-yl]-3,6-dihydro-2H-pyrimidin-1-yl}-1-furan-2-yl-ethylamino)-butyric acid; and 4-((S)-2-{3-(2-fluoro-6-trifluoromethyl-benzyl)-4-methyl-2,6-dioxo-5-[4-(5-trifluoromethyl-furan-2-ylmethyl)-piperazin-1-yl]-3,6-dihydro-2H-pyrimidin-1-yl}-1-thiophen-3-yl-ethylamino)-butyric acid, or the stereoisomer thereof or the pharmaceutically acceptable salt thereof.

5. A pharmaceutical composition comprising the compound of one of claims 1 to 4 or a pharmaceutically acceptable salt of the compound, and a pharmaceutically acceptable carrier.

6. A pharmaceutical composition for treatment of a GnRH-related disease, comprising the compound of one of claims 1 to 4 and a pharmaceutically acceptable carrier or diluents, wherein the disease is selected from the group consisting of prostate cancer, uterine cancer, breast cancer, gonadotropin-producing pituitary adenoma, benign prostatic hyperplasia and leiomyoma.

7. A pharmaceutical composition for treatment of a GnRH-related disease, comprising the compound of one of claims 1 to 4 and a pharmaceutically acceptable carrier or diluents, wherein the disease is selected from the group consisting of endometriosis, polycystic ovarian disease, uterine fibroids and precocious puberty.

8. A pharmaceutical composition for contraception, comprising the compound of one of claims 1 to 4 and a pharmaceutically acceptable carrier or diluents.

9. A pharmaceutical composition for treatment of a GnRH-related disease, comprising the compound of one of claims 1 to 4 and a pharmaceutically acceptable carrier or diluents, wherein the disease is selected from the group consisting of systemic lupus erythematosus, irritable bowel syndrome, premenstrual syndrome, hypertrichosis, solitary kidney and sleep disturbance.

* * * * *